US007776533B2

(12) United States Patent
Agnew et al.

(10) Patent No.: US 7,776,533 B2
(45) Date of Patent: Aug. 17, 2010

(54) COMPOSITIONS AND METHODS FOR DETECTION AND ISOLATION OF PHOSPHORYLATED MOLECULES

(75) Inventors: Brian Agnew, Eugene, OR (US); Joseph Beechem, Eugene, OR (US); Kyle R Gee, Springfield, OR (US); Richard P Haugland, Olympia, WA (US); Thomas H Steinberg, Eugene, OR (US); Wayne F Patton, Newton, MA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 11/552,275

(22) Filed: Oct. 24, 2006

(65) Prior Publication Data

US 2007/0054304 A1 Mar. 8, 2007

Related U.S. Application Data

(63) Continuation of application No. 10/703,816, filed on Nov. 7, 2003, which is a continuation-in-part of application No. 10/428,192, filed on May 2, 2003, now Pat. No. 7,102,005.

(60) Provisional application No. 60/440,252, filed on Jan. 14, 2003, provisional application No. 60/407,255, filed on Aug. 30, 2002, provisional application No. 60/393,059, filed on Jun. 28, 2002, provisional application No. 60/377,733, filed on May 3, 2002.

(51) Int. Cl.
*G01N 33/53* (2006.01)

(52) U.S. Cl. .................. 435/6; 436/88; 514/7; 530/532

(58) Field of Classification Search ...... 435/4, 435/21, 17; 436/103, 104, 105
See application file for complete search history.

(56) References Cited

U.S. PATENT DOCUMENTS

| 4,339,337 | A | 7/1982 | Tricot et al. |
|---|---|---|---|
| 4,384,042 | A | 5/1983 | Miike et al. |
| 4,520,110 | A | 5/1985 | Stryer et al. |
| 4,542,104 | A | 9/1985 | Stryer et al. |
| 4,603,209 | A | 7/1986 | Tsien et al. |
| 4,647,447 | A | 3/1987 | Gries |
| 4,774,339 | A | 9/1988 | Haugland et al. |
| 4,810,636 | A | 3/1989 | Corey et al. |
| 4,812,409 | A | 3/1989 | Babb et al. |
| 4,849,362 | A | 7/1989 | Demarinis et al. |
| 4,859,582 | A | 8/1989 | Stryer et al. |
| 4,945,171 | A | 7/1990 | Haugland et al. |
| 4,978,763 | A | 12/1990 | Rocklage et al. |
| 5,049,673 | A | 9/1991 | Tsien et al. |
| 5,055,556 | A | 10/1991 | Stryer et al. |
| 5,141,852 | A | 8/1992 | Egan et al. |
| 5,187,288 | A | 2/1993 | Kang et al. |
| 5,196,306 | A | 3/1993 | Bobrow et al. |
| 5,208,148 | A | 5/1993 | Haugland et al. |
| 5,227,487 | A | 7/1993 | Haugland et al. |
| 5,242,805 | A | 9/1993 | Naleway et al. |
| 5,248,782 | A | 9/1993 | Haugland et al. |
| 5,268,486 | A | 12/1993 | Waggoner et al. |
| 5,274,113 | A | 12/1993 | Kang et al. |
| 5,316,906 | A | 5/1994 | Haugland et al. |
| 5,338,854 | A | 8/1994 | Kang |
| 5,362,628 | A | 11/1994 | Haugland et al. |
| 5,433,896 | A | 7/1995 | Kang et al. |
| 5,442,045 | A | 8/1995 | Haugland et al. |
| 5,443,986 | A | 8/1995 | Haughland et al. |
| 5,451,343 | A | 9/1995 | Neckers et al. |
| 5,453,517 | A | 9/1995 | Kuhn et al. |
| 5,459,276 | A | 10/1995 | Kuhn et al. |
| 5,464,935 | A | 11/1995 | Heavner et al. |
| 5,468,468 | A * | 11/1995 | LaRochelle et al. ........ 424/1.49 |
| 5,486,616 | A | 1/1996 | Waggoner et al. |
| 5,501,980 | A | 3/1996 | Katerinopoulos et al. |
| 5,512,486 | A | 4/1996 | Giese et al. |
| 5,516,911 | A * | 5/1996 | London et al. .............. 548/236 |
| 5,527,688 | A | 6/1996 | Malla et al. |
| 5,538,897 | A | 7/1996 | Yates, III et al. |
| 5,569,587 | A | 10/1996 | Waggoner |
| 5,569,766 | A | 10/1996 | Waggoner et al. |
| 5,576,424 | A | 11/1996 | Mao et al. |
| 5,583,001 | A | 12/1996 | Bobrow et al. |
| 5,595,915 | A | 1/1997 | Geysen et al. |
| 5,616,502 | A | 4/1997 | Hauhland et al. |
| 5,627,027 | A | 5/1997 | Waggoner |
| 5,656,554 | A | 8/1997 | Desai et al. |
| 5,686,310 | A | 11/1997 | Haystead et al. |

(Continued)

FOREIGN PATENT DOCUMENTS

EP 1156329 A2 1/2001

(Continued)

OTHER PUBLICATIONS

Stancato et al. (Electrophoresis 2001, vol. 22, p. 2120-2124).*

(Continued)

*Primary Examiner*—Jacob Cheu

(57) ABSTRACT

The present invention relates to phosphate-binding compounds that find use in binding, detecting and isolating phosphorylated target molecules including the subsequent identification of target molecules that interact with phosphorylated target molecules or molecules capable of being phosphorylated. A binding solution is provide that comprises a phosphate-binding compound, an acid and a metal ion wherein the metal ion simultaneously interacts with an exposed phosphate group on a target molecule and the metal chelating moiety of the phosphate-binding compound forming a bridge between the phosphate-binding compound and a phosphorylated target molecule resulting in a ternary complex. The binding solution of the present invention finds use in binding and detecting immobilized and solubilized phosphorylated target molecules, isolation of phosphorylated target molecules from a complex mixture and aiding in proteomic analysis wherein kinase and phosphatase substrates and enzymes can be identified.

8 Claims, 13 Drawing Sheets

U.S. PATENT DOCUMENTS

| | | | |
|---|---|---|---|
| 5,696,157 A | 12/1997 | Wang et al. | |
| 5,714,327 A | 2/1998 | Houthoff et al. | |
| 5,731,158 A | 3/1998 | Bobrow et al. | |
| 5,773,227 A | 6/1998 | Kuhn et al. | |
| 5,773,236 A | 6/1998 | Diwu et al. | |
| 5,798,276 A | 8/1998 | Haugland et al. | |
| 5,830,912 A | 11/1998 | Gee et al. | |
| 5,834,121 A | 11/1998 | Sucholeiki et al. | |
| 5,846,737 A | 12/1998 | Kang | |
| 5,847,162 A | 12/1998 | Lee et al. | |
| 5,863,727 A | 1/1999 | Lee et al. | |
| 5,981,180 A | 11/1999 | Chandler et al. | |
| 6,008,379 A | 12/1999 | Benson et al. | |
| 6,017,712 A | 1/2000 | Lee et al. | |
| 6,048,982 A | 4/2000 | Waggoner et al. | |
| 6,080,852 A | 6/2000 | Lee et al. | |
| 6,111,116 A | 8/2000 | Benson et al. | |
| 6,130,101 A | 10/2000 | Mao et al. | |
| 6,162,931 A | 12/2000 | Gee et al. | |
| 6,184,379 B1 | 2/2001 | Josel et al. | |
| 6,207,397 B1 | 3/2001 | Lynch | |
| 6,221,606 B1 | 4/2001 | Benson et al. | |
| 6,229,055 B1 | 5/2001 | Klaubert et al. | |
| 6,268,222 B1 | 7/2001 | Chandler et al. | |
| 6,316,267 B1 | 11/2001 | Bhalgat et al. | |
| 6,316,276 B1 | 11/2001 | Gregory | |
| 6,329,205 B1 | 12/2001 | Diwu | |
| 6,339,392 B1 | 1/2002 | Ashihara et al. | |
| 6,348,599 B1 | 2/2002 | Cummins et al. | |
| 6,358,684 B1 | 3/2002 | Lee | |
| 6,365,418 B1 | 4/2002 | Wagner et al. | |
| 6,372,445 B1 | 4/2002 | Davis et al. | |
| 6,372,813 B1 | 4/2002 | Johnson et al. | |
| 6,387,631 B1 | 5/2002 | Arnold et al. | |
| 6,391,937 B1 | 5/2002 | Beuhler et al. | |
| 6,399,299 B1 | 6/2002 | Bobrow et al. | |
| 6,399,392 B1 | 6/2002 | Haugland et al. | |
| 6,403,368 B1 | 6/2002 | Jan et al. | |
| 6,403,807 B1 | 6/2002 | Singh et al. | |
| 6,409,921 B1 | 6/2002 | Muller et al. | |
| 6,413,420 B1 | 7/2002 | Foy et al. | |
| 6,413,722 B1 | 7/2002 | Arnold et al. | |
| 6,444,433 B1 | 9/2002 | Plhak et al. | |
| 6,461,807 B1 | 10/2002 | Friend et al. | |
| 6,472,141 B2 | 10/2002 | Nikiforov | |
| 6,475,809 B1 | 11/2002 | Wagner et al. | |
| 6,548,266 B1 | 4/2003 | Zhang et al. | |
| 6,579,718 B1 | 6/2003 | Yue et al. | |
| 6,656,696 B2 | 12/2003 | Craig et al. | |
| 6,664,047 B1 | 12/2003 | Haugland et al. | |
| 6,670,159 B1 | 12/2003 | Savage et al. | |
| 6,680,335 B2 | 1/2004 | Tang | |
| 6,716,979 B2 | 4/2004 | Diwu et al. | |
| 6,720,162 B2 | 4/2004 | Goueli et al. | |
| 6,818,454 B2 | 11/2004 | Goshe et al. | |
| 6,972,326 B2 | 12/2005 | Haugland et al. | |
| 7,026,167 B2 | 4/2006 | Hunt et al. | |
| 7,052,915 B2 | 5/2006 | Aebersold et al. | |
| 7,070,921 B2* | 7/2006 | Huang et al. | 435/4 |
| 7,169,922 B2 | 1/2007 | Diwu et al. | |
| 7,445,894 B2* | 11/2008 | Agnew et al. | 435/6 |
| 2001/0031469 A1 | 10/2001 | Volinia | |
| 2002/0009762 A1 | 1/2002 | Flint et al. | |
| 2002/0055186 A1 | 5/2002 | Barry et al. | |
| 2002/0059684 A1 | 5/2002 | Diwu | |
| 2002/0064794 A1 | 5/2002 | Leung et al. | |
| 2002/0076727 A1 | 6/2002 | Cardone et al. | |
| 2002/0077487 A1 | 6/2002 | Leung et al. | |
| 2002/0106785 A1 | 8/2002 | Jan et al. | |
| 2002/0117451 A1 | 8/2002 | Foy et al. | |
| 2002/0137068 A1 | 9/2002 | Haugland et al. | |
| 2003/0040016 A1* | 2/2003 | Singh et al. | 435/7.1 |
| 2003/0096322 A1 | 5/2003 | Giuliano et al. | |
| 2003/0113711 A1 | 6/2003 | Blackburn et al. | |
| 2004/0038306 A1 | 2/2004 | Agnew | |
| 2004/0146950 A1 | 7/2004 | Howe | |
| 2004/0171034 A1 | 9/2004 | Agnew et al. | |
| 2005/0233307 A1 | 10/2005 | Gee et al. | |
| 2007/0054304 A1 | 3/2007 | Agnew | |
| 2007/0227974 A1 | 10/2007 | Anders et al. | |
| 2008/0044804 A1 | 2/2008 | Agnew et al. | |

FOREIGN PATENT DOCUMENTS

| | | |
|---|---|---|
| EP | 1156329 | 11/2001 |
| EP | 1215501 | 6/2002 |
| EP | 1215501 A1 | 6/2002 |
| WO | WO 97/39064 | 10/1997 |
| WO | 9939210 | 8/1999 |
| WO | WO-99/39210 | 8/1999 |
| WO | 0004380 | 1/2000 |
| WO | WO-00/04380 | 1/2000 |
| WO | 0063701 | 10/2000 |
| WO | WO-00/63701 | 10/2000 |
| WO | 0075167 | 12/2000 |
| WO | WO-00/75167 A2 | 12/2000 |
| WO | 0118545 | 3/2001 |
| WO | WO-01/18545 | 3/2001 |
| WO | 0196869 | 12/2001 |
| WO | WO-01/96869 A1 | 12/2001 |
| WO | 0225288 | 3/2002 |
| WO | WO-02/25288 | 6/2002 |
| WO | WO 2004/042347 | 5/2004 |

OTHER PUBLICATIONS

Li et al. (Analytical Biochem 1999 vol. 270, p. 9-14).*
U.S. Appl. No. 60/377,733, filed May 3, 2002, Agnew et al.
U.S. Appl. No. 60/393,059, filed Jun. 28, 2002, Agnew et al.
U.S. Appl. No. 60/407,252, filed Apr. 9, 2004, Agnew et al.
U.S. Appl. No. 60/440,252, filed Jan. 14, 2003, Agnew et al.
U.S. Appl. No. 10/703,816, filed Nov. 7, 2003, Agnew et al., publication date Dec. 13, 2007.
U.S. Appl. No. 08/868,598, filed Jun. 4, 1997, Sterman et al., publication date Sep. 17, 2002.
U.S. Appl. No. 09/557,275, filed Apr. 24, 2000, Haugland et al., publication date Dec. 16, 2003.
U.S. Appl. No. 10/005,050, filed Dec. 3, 2001, Haugland et al., publication date Aug. 25, 2005.
U.S. Appl. No. 10/661,451, filed Sep. 12, 2003, Gee et al., publication date Oct. 20, 2005.
Office Action for, U.S. Appl. No. 10/428,192, (Aug. 30, 2005).
Office Action for, U.S. Appl. No. 10/428,192, Restriction Requirement,(Jun. 15, 2005).
Office Action for, U.S. Appl. No. 10/703,816, (Mar. 7, 2007).
Office Action for, U.S. Appl. No. 10/703,816, (Mar. 16, 2007).
Office Action for, U.S. Appl. No. 10/703,816, (Oct. 4, 2007).
Office Action for, U.S. Appl. No. 10/703,816, Restriction Requirement,(Jun. 9, 2006).
Office Action for, U.S. Appl. No. 10/821,522, (Feb. 22, 2007).
Office Action for, U.S. Appl. No. 10/821,522, Restriction Requirement,(Oct. 25, 2006).
Agnew, Brian et al., "PCT/US03/13765 Search Report", (Mar. 1, 2005).
Adamczyk, M. et al., "Selective Analysis of Phosphopeptides Within a Protein Mixture by Chemical Modification, Reversible Biotinylation and mass Spectrometry", *Rapid Commun Mass Spectrom* 15(16):, (2001),1481-8.
Aebersold, R. et al., "Mass Spectrometry in Proteomics", *Chem Rev* 101(2):, (2001),269-95.
Affolter, M. et al., "Evaluation of Two-Dimensional Phosphopeptide Maps by Electrospray Ionization Mass Spectrometry of Recovered Peptides.", *Anal Biochem* 223(1):, (1994),74-81.
Ausubel, F. M., et al., "Short Protocols in Molecular Biology", John Wiley and Sons, (1997).

Bligh, et al., "A Rapid Method of Total Lipid Extraction and Purification.", *Canadian Journal of Biochemistry and Physiology 37(8):*, (1959),911-917.

Bouizar, Z. et al., "Purification and Characterization of Calcitonin Receptors in Rat Kidney Membranes by Covalent Cross-Linking Techniques.", *Eur J Biochem 155(1):*, (1986),141-7.

Browning, J. et al., "Studies on the Differing Effects of Tumor Necrosis Factor and Lymphotoxin on the Growth of Several Human Tumor Lines.", *J Immunol 143(6)*,1859-67.

Corson, D. T., et al., "Efficient Multigram Synthesis of the Bifunctional Chelating Agent (S)-1-p-isothiocyanatobenzyl-diethylenetriaminepentaacetic acid [Correction of Diethylenetetraminepentaacetic Acid].", *Bioconjug Chem 11(2):*, (2000),292-9.

Cutting, J. A., et al., "Staining of Phospho-Proteins on Acrylamide Gel Electropherograms.", *Anal Biochem 54(2):*, (1973),386-94.

Debruyne, I. "Staining of alkali-labile phosphoproteins and alkaline phosphatases on polyacrylamide gels", *Anal Biochem, 1983.,* 133(1),(1983),110-5.

Deissler, H et al., "Rapid Protein Sequencing by Tandem Mass Spectrometry and cDNA Cloning of p20-CGGBP. A Novel Protein that Binds to the Unstable Triplet Repeat 5'-d(CGG)n-e' in the Human FMR1 Gene.", *J Biol Chem 272(27):*, (1997),16761-8.

Dole, et al., "Microdetermination of Long-Chain Fatty Acids in Plasma and Tissues", *J. Biol. Chem. 235(9):*, (1960),2595-2599.

Dole, V. P., "A Relation Between Non-Esterified Fatty Acids in Plasma and the Metabolism of Glucose", *J Clin Invest 35(2):*, (1956),150-4.

Dos Remedios, C. G., et al., "Fluorescence Resonance Energy Transfer Spectroscopy is a Reliable "Ruler" for Measuring Structural Changes in Proteins. Dispelling the Problem with the Unknown Orentation Factor", *J Struct Biol 115(2):*, (1995),175-85.

Doughty, D. A., et al., "Multinuclear NMR Microscopy of Two-Phase Fluid Systems in Porous Rock", *Magn Reson Imaging,* 14(7-8):,(1996),869-73.

Eng, J. K., et al., "An Approach to Correlate Tandem Mass Spectral Data of Peptides with Amino Acid Sequences in a Protein Database", *J Am Soc Mass Spectrom 5:*, (1994),976-989.

Fadden, P. et al., "Quantitative and Selective Fluorophore Labeling of Phosphoserine on Peptides and Proteins: Characterization at the Attomole level by Capillary Electrophoresis and Laser-Induced Florescence", *Anal Biochem 225(1):*, (1995),81-8.

Figeys, D. et al., "Electrophoresis Combined with Novel Mass Spectrometry Techniques: Powerful Tools for the Analysis of Proteins and Proteomes", *Electrophoresis 19(10):*, (1998),1811-8.

Folch, et al., "A Simple Method for the Isolation and Purfication of Total Lipides from Animal Tissues", *J. Biochem. 226:*, (1957),497-509.

Fruehling, S et al., "In Vitro Assays for the Detection of Protein Tyrosine Phosphorylation and Protein Tyrosine Kinase Activities", *Methods Mol Biol 174:*, (2001),337-43.

Furniss, B. S., et al., "Vogel's Encyclopedia of Practical Organic Chemistry", *Longman Scientific and Technical Ltd. Essex,* 5th Edition,(1991),809-816.

Gay, G. R., et al., "Analysis of Cellular Phosphoproteins by Two-Dimensional Gel Electrophoresis: Applications for Cell Signaling in Normal and Cancer Cells", *Electrophoresis 15(3-4):*, (1994),417-40.

Gee, K. et al., "Site-specific labeling of affinity tags in fusion proteins", U.S. Appl. No. 10/661,451, filed Sep. 12, 2003.

Gee, Kyle R., et al., "New Ratiometric Fluorescent Calcium Indicators with Moderately Attenuated Binding Affinities", Bioorganic and Medicinal Chemistry Letters 10,(2000),1515-1518.

Goodlett, D. R., et al., "Protein Identification with a Single Accurate Mass of a Cysteine-Containing Peptide and Constrained Database Searching", *Anal Chem 72(6):*, (2000),1112-8.

Goodlett, D. R., et al., "Quantitative in Vitro Kinase Reaction as a Guide for Phosphoprotein Analysis by Mass Spectrometry", *Rapid Commun Mass Spectrom 14(5):*, (2000),344-8.

Gooley, A. A., et al., "How to find, Identify and Quantitate the Sugars on Proteins.", *Nature 385(6616):*, (1997),557-9.

Goshe, M. B., et al., "Phosphoprotein Isotope-Coded Affinity Tag Approach for Isolating and Quantitating Phosphopeptides in Proteome-Wide Analyses", *Anal Chem 73(11):*, (2001),2578-86.

Green, M. R., et al., "Differential Staining of Phosphoproteins on Polyacrylamide Gels with a Cationic Carbocyanine Dye.", *Anal Biochem 56(1):*, (1973),43-51.

Gromov, P. S., et al., "Several Small GTP-Binding Proteins are Strongly Down-Regulated in Simian Virus 40 (SV40) Transformed Human Keratinocytes and May be Required for the Maintenance of the Normal Phenotype.", *Electrophoresis 15(3-4):*, (1994),474-81.

Gygi, S. P., et al., "Measuring Gene Expression by Quantitative Proteome Analysis", *Curr Opin Biotechnol 11(4):*, (2000),396-401.

Hanash, S. M., et al., "Mining the Human Proteome: Experience with the Human Lymphoid Protein Database", *Electrophoresis 19(11):*, (1998),2004-9.

Hardie, D. G., et al., *Protein Phosphorylation: A Practical Approach*, The Practical Approach Series,(1993),ISBN 0-19-963305.

Haugland, R. "Handbook of Flourescent Probes and Research Chemicals", *9th Edition CD-ROM,* (Sep. 2002).

Hegenauer, J. L., et al., "Staining Acidic Phosphoproteins (Phosvitin) in Electrophoretic Gels.", *Anal Biochem 78(1):*, (1977),308-11.

Heller, A. "Electrical Wiring of Redox Enzymes", *Acc. Chem. Res 23:*, (1990),128-134.

Herbert, B. "Advances in Protein Solubilisation for Two-Dimensional Electrophoresis", *Electrophoresis 20(4-5):*, (1999),660-3.

Holmes, C. F., "A New Method for the Selective Isolation of Phosphoserine-containing Peptides.", *FEBS Lett 215(1):*, (1987),21-4.

Hunter, T "Signaling—2000 and Beyond.", *Cell 100(1),* (2000),113-27.

Ideker, T. et al., "Integrated Genomic and Proteomic Analyses of a Systematically Perturbed Metabolic Network.", *Science 292(5518):*, (2001),929-34.

Jensen, O. N., et al., "Mass Spectrometric Identification and Microcharacterization of Proteins from Electrophoretic Gels: Strategies and Applications.", *Proteins Suppl 2:*, (1998),74-89.

Jensen, O. N., et al., "Sample Preparation Methods for Mass Spectrometric Peptide Mapping Directly from 2-DE Gels", *Meth. Mol. Biol. 112:*, (1999),513-30.

Joshi, S. et al., "ATP Synthase complex from Bovine Heart Mitochondria. Subunit Arrangements as Revealed by Nearest Analysis and Susceptibilty to Trypsin", *J Biol Chem 265(24):*, (1990),14518-25.

Jung, S. M., et al., "Crosslinking of Platelet Glycoprotein Lb by N-Succinimidyl (4-azidophenyldithio) Propionate and 3, 3'-dithiobis (Sulfosuccinimidyl Promionate).", *Biochim Biophys Acta 761(2):*, (1983),152-62.

Kamiya, M. et al., "Staining Acidic Phosphoprotein in Polyacrylamide Gels with Acridine Orange", *Seikaqaku 45(7):*, (1973),327-35.

Kaufmann, H. et al., "Use of Antibodies for Detection of Phosphorylated Proteins Separated by Two-Dimensional Gel Electrophoresis", *Proteomics 1(2):*, (2001),194-199.

Liao, P. C., et al., "An Approach to Locate Phosphorylation Sites in a Phosphoprotein: Mass Mapping by Combining Specific Enzymatic Degradation with matrix-Assisted Laser Desorption/Ionization Mass Spectrometry", *Anal Biochem,* 219(1),(1994),9-20.

Loo, R. R., et al., "Virtual 2-D Gel Electrophoresis: Visualization and Anlaysis of the *E. coli* Proteome by Mass Spectrometry.", *Anal Chem 73(17):*, (2001),4063-70.

Malone, J. P., et al., "Practical aspects of fluorescent staining for proteomic applications.", *Electrophoresis,* 22(5):,(2001),919-32.

Marshall, P. et al., "The Determination of Protein Phosphorylation on Electrophoresis Gel Blots by Laser Ablation Inductively Coupled Plasma-Mass Spectrometry", *Analyst 127(4):*, (2002),459-61.

Matayoshi, E. D., et al., "Novel Fluoregenic Substrates for Assaying Retroviral Proteases by Resonance Energy Transfer", *Science 247(4945):*, (1990),954-8.

McCormack, A. L., et al., "Direct Analysis and Identification of Proteins in Mixtures by LC/MS/MS and Database Searching at the Low-Femtomole Level", *Anal Chem 69(4):*, (1997),767-76.

McLachlin, D. T., et al., "Analysis of Phosphorylated Proteins and Peptides by Mass spectrometry", *Curr Opin Chem Biol 5(5),* (2001),591-602.

Meyer, H. E., et al., "Quantitative Determination of Phosphoserine by High-Performance Liquid Chromatography as the Phenylthiocarbamyl-S-Ethylcysteine. Application to Picomolar Amounts of Peptides and Proteins", *J Chromatogr 397:*, (1987),113-21.

Meyer, H. E., et al., "Strategies for Nonradioactive Methods in the Localization of Phosphorylated Amino Acids in Proteins", *Faseb J 7(9):*, (1993),776-82.

Morrison, L. E., "Detection of Energy Transfer and Flourescence Quenching", in *Nonisotopic DNA Probe Techniques*, L. Kricka, ed.,(1992),311-352.

Muzio, M. et al., "FLICE, a novel FADD-Homologous ICE/CED-3Like Protease, is Recruited to the CD95 (Fas/APO-1) Death—Inducing Signaling Complex", *Cell 85(6):*, (1996),817-27.

Neville, D. C., et al., "Evidence for Phosphorylation of Serine 753 in CFTR Using a Novel Metal-ion Affinity Resin and Matrix-Assisted Laser Desorption Mass Spectrometry", *Protein Sci 6(11):*, (1997),2436-45.

Nishizuka, Y "Studies and Perspectives of Protein Kinase C.", *Science 233(4761):*, (1986),305-12.

Oda, Y. et al., "Accurate Quantitation of Protein Expression and Site-Specific Phosphorylation.", *Proc Natl Acad Sci U S A 96(12):*, (1999),6591-6.

Oda, Y. T., et al., "Enrichemnt Analysis of Phosphorylated Proteins as a Tool for Probing the Phosphoproteome-Wide Analyses.", *Anal. Chem.*, 73(110,(2001),2578-86.

Oda, Y. T., et al., "Enrichment Analysis of Phosphorylated Proteins as a Tool for Probing the Phosphoproteome", *Nat Biotechnol 19(4):*, (2001),379-82.

Ojala, P. J., et al., "Identification of Yeast Coflin Residues Specific for Actin Monomer and PIP2 Binding", *Biochemistry 40(51):*, (2001),15562-9.

Park, L. S., et al., "Characterization of the Cell Surface Receptor for a Multi-Lineage colony-Stimulating Factor (CSF-2 Alpha)", *J Biol Chem 261(1):*, (1986),205-10.

Patton, W. F., "A Thousand Points of Light: The Application of Fluorescence Detection Technologies to Two Dimensional Gel Electrophoresis and Proteomics", *Electrophoresis 21(6):*, (2000),1123-44.

Patton, W. F., "Detection Technologies in Proteome Analysis", *J Chromatogr B Analyt Technol Biomed Life Sci 771(1-2):*, (2002),3-31.

Perrin, F. "Polarisation de la Lumiere de Fluorescence. Vie Moyenne des Molecules Dans L'etat Excite", *J. Phys. Rad 1:*, (1926),390-401.

Posewitz, M. C., et al., "Immobilized Gallium (III) Affinity Chromatography of Phosphopeptides", *Anal Chem 71(14):*, (1999),2883-92.

Rando, O. J., et al., "Phosphatidylinositol-Dependent Actin Filament Binding by the SWI/SNF-like BAF Chromatin Remodeling Comlex. ", *Proc Natl Acad Sci U S A 99(5):*, (2002),2824-9.

Resing, K. A., et al., "Protein Phosphorylation Analysis by Electrospray Ionization-Mass Spectrometry.", *Methods Enzymol 283:*, (1997),29-44.

Sandler, Stanley R., et al., "Organic Functional Group Preparations", Academic Press vol. 3,(1972),5-7.

Schreiber, S. L., "Immunophilin-Sensitive Protein Phosphates Action in Cell Signaling Pathways", *Cell 70(3):*, (1992),365-8.

Selvin, P. R., "Flouresence Resonance Energy Transfer", *Methods Enzymol 246:*, Academic Press Inc.,(1995),300-34.

Shevchenko, A. et al., "Mass Spectrometric Sequencing of Proteins Silver-Stained Polyacrylamide Gels", *Anal Chem 68(5):*, (1996),850-8.

Soskic, V. C., et al., "Functional Proteomics Analysis of Signal Transduction Pathways of the Platelet-Derived Growth Factor Beta Receptor.", *Biochemistry 38(6):*, (1999),1757-64.

Stancato, L. F., et al., "Fingerprinting of Signal Transduction Pathways Using a Combination of Anti-Phosphotyrosine Immunoprecipitations and Two-Dimensional Polyacrylamide Gel Electrophoresis", *Electrophoresis 22(10):*, (2001),2120-4.

Steinberg, T. H., et al., "Rapid and Simple Single Nanogram Detection of Glycoproteins in Pllycralamide Gels and on Electroblots", *Proteomics 1(7):*, (2001),841-55.

Steinberg, Thomas H., et al., "Global Quantitative Phosphoprotein Analysis Using Multiplexed Proteomics Technology", *Proteomics*, vol. 3 (7), (Jul. 7, 2003),1128-1144.

Stensballe, A. et al., "Characterization of Phosphoproteins from Electrophoretic Gels by Nanoscale Fe(III) Affinity Chromatography with Off-Line Mass Spectrometry Analysis.", *Proteomics 1(2):*, (2001),207-22.

Tavares, A. et al., "Profile of Phosphoprotein Labelling in Organotypic Slice Cultures of Rat Hippocampus", *Neuroreport 12(12):*, (2001),2705-9.

Tyagi, S. et al., "Molecular Beacons : probes that fluorescence upon hybridization", *Nat Biotechnol 14(3):*, (1996),303-8.

Tyagi, S. et al., "Multicolor molecular beacons for allele discrimination", *Nat Biotechnol 16(1):*, Nature Publishing Group,(1998),49-53.

Vener, A. V., et al., "Mass Spectrometric Resolution of Reversible Protein Phosphorylation in Photosynthetic Membranes of *Arabidopsis thaliana*", *J Biol Chem 276(10):*, (2001),6959-66.

Wang, P. et al., "Phosphate-Specific Fluorescence Labeling of Pepsin by BO-IMI", *Anal Biochem 230(2):*, (1995),329-32.

Watty, A. et al., "The In Vitro and In Vivo Phosphotyrosine Map of Activated MuSK", *Proc Natl Acad Sci U S A 97(9):*, (2000),4585-90.

Wilbur, D. S., et al., "Evaluation of Biotin-Dye Conjugates for Use in an HPLC Assay to Assess Relative Binding of Biotin Derivatives with Avidin and Streptavidin", *Bioconjug Chem 11(4):*, (2000),584-98.

Wilkins, M. R., et al., "Progress with Proteome Projects: Why All Proteins Expressed by a Genome Should be Identified and How to Do It.", *Biotechnol Genet Eng Rev*, 1996.13,(1996),19-50.

Wu, P. et al., "Resonance Energy Transfer: Methods and Applications", *Anal Biochem 218(1):*, (1994),1-13.

Xhou, W. et al., "Detection and Sequencing of Phosphopeptides Affinity Bound to Immobilized Metal Ion Beads by Matrix-Assisted Laser Desorption/Ionization mass Spectrometry", *J Am Soc Mass Spectrom 11(4):*, (2000),273-82.

Yan, J. X., et al., "Protein Phosphorylation: Technologies for the Identification of Phosphoamino Acids", *J Chromatogr A*, 808(1-2),(1998),23-41.

Yates, J. R., et al., "Method to Correlate Tandem Mass Spectra of Modified Peptides to Amino Acid Sequences in the Protein Database", *Anal. chem.*, 67(8),(1995),1426-36.

Zarling, D. A., et al., "Mapping of Lymphocyte Surface Polypeptide Antigens by Chemical Cross-Linking with BSOCOES.", *J Immunol 124(2):*, (1980),913-20.

Zhou, H. et al., "A Systematic Approach to the Analysis of Protein Phosphorylation.", *Nat Biotechnol 19(4):*, (2001),375-8.

U.S. Appl. No. 10/703,816, Office Action mailed Mar. 7, 2007.
U.S. Appl. No. 10/703,816, Office Action mailed Mar. 16, 2007.
U.S. Appl. No. 10/703,816, Office Action mailed Oct. 4, 2007.
U.S. Appl. No. 10/703,816, Office Action mailed Jul. 17, 2008.
U.S. Appl. No. 10/703,816, Response to Mar. 16, 2007 Office Action, Filed Jul. 16, 2007.
U.S. Appl. No. 10/703,816, Response to Jun. 9, 2006 Restriction Requirement, Filed Jun. 26, 2006.
U.S. Appl. No. 10/703,816, Response to Oct. 4, 2007 Office Action, Filed Apr. 4, 2008.
U.S. Appl. No. 10/713,670, Office Action mailed Mar. 31, 2006.
U.S. Appl. No. 10/713,670, Office Action mailed Nov. 7, 2005.
U.S. Appl. No. 10/719,990, Office Action mailed Feb. 6, 2008.
U.S. Appl. No. 10/719,990, Office Action mailed Apr. 20, 2006.
U.S. Appl. No. 10/719,990, Office Action mailed Aug. 9, 2007.
U.S. Appl. No. 10/719,990, Office Action mailed Aug. 29, 2005.
U.S. Appl. No. 10/719,990, Office Action mailed Dec. 18, 2006.
U.S. Appl. No. 10/821,522, Notice of Allowance mailed Jun. 27, 2008.
U.S. Appl. No. 10/946,786, Office Action mailed Jun. 1, 2007.
U.S. Appl. No. 10/946,786, Office Action mailed Nov. 2, 2006.
U.S. Appl. No. 11/697,103, Office Action mailed Jul. 1, 2008.
U.S. Appl. No. 60/407,255, "Novel BAPTA-based Chelator Compositions and Methods for Detection and Isolation of Phosphophorylated Biomolecules", Agnew, Aug. 30, 2002.

Ahn, Natalie G. et al., "Toward the phosphoproteome", *Nature Biotechnology*, 19, 2001, 317-318.

Beck, Alexander et al., "Alkaline Liquid Chromatography/Electrospray Ionization Skimmer Collision-Induced Dissociation Mass Spectrometry for Phosphopeptide Screening", *Rapid Communicaitons in Mass Spectrometry*, 2001,2324-2333.

Byford, Michael F., "Rapid and Selective Modification of Phosphoserine Residues Catalysed by Ba2+ ions for their Detection during Peptide Microsequencing", *Biochem J.*, 280, 1991, 261-265.

Capps, G. G. et al., "A Double-Labeling Method for Measuring Induction of Protein Phosphorylation", *BioTechniques*, 8 (1), 1990, 62-69.

De Silva, A. P. et al., "Signaling Recognition Events with Fluorescent Sensors and Switches", *Chem Rev.*, vol. 97, 1997, 1515-1566.

Fages, Frederic et al., "Fluorescent, Siderophore-Based Chelators. Design and Synthesis of a Trispyrenyl Trishydroxamate Ligand, and Intramolecular Excimer-Forming Sensing Molecule Which Responds to Iron (III) and Gallium (III) Metal Cations", *J. Org. Chem.*, 61, 1996, 3956-3961.

Ficarro, Scott B. et al., "Phosphorproteome analysis by mass spectrometry and its application to *Saccharomyces cerevisiae*", *Nature Biotechnology*, 20, Apr. 2002, 301-305.

Gast, Rainer et al., "Method for Determining Protein Kinase Substrate Specificities by the Phosphorylation of Peptide Libraries on Beads, Phosphate-Specific Staining, Automated Sorting, and Sequencing", *Analytical Biochemistry*, vol. 276, 1999, 227-241.

Hedberg, Karen K. et al., "Sensitive Fluorescent Quantitation of myo-inositol 1,2-cyclic phosphate and myo-inositol 1-phosphate by high-performance thin-layer chromatography", *Journal of Chromatography B*, 2001, 317-324.

Larsen, Martin R. et al., "Phospho-proteomics: Evaluation of the use of enzymatic de-phosphorylation and differential mass spectrometric peptide mass mapping for site specific phosphorylation assignment in proteins separated by gel electrophoresis", *Proteomics*, 1, 2001, 223-238.

Muszynska, Grazyna et al., "Selective Adsorption of Phosphoproteins on Gel-Immobilized Ferric Chelate", *Biochemistry*, 25, 1986, 6850-6853.

Myers, Jody M. et al., "A Method for Enhancing the Sensitivity and Stability of Stains-All for Phosphoproteins Separated in Sodium Dodecycl Sulfate-Polyacrylamide Gels", *Analytical Biochemistry*, 240, 1996, 300-302.

O'Farrell, Patrick H. et al., "High Resolution Two-Dimensional Electrophoresis of Proteins", *Journal of Biological Chemistry*, vol. 250, No. 10, May 25, 1975, 4007-4021.

Patton, Wayne F., "Proteome analysis II. Protein subcellular redistribution: linking physiology to genomics via the proteome and separation technologies involved", *Journal of Chromatography B*, 1999, 203-223.

Patton, Wayne F. et al., "Rainbow's end: the quest for multiplexed fluorescence quantitative analysis in proteomics", *Current Opinion in Chemical Biology*, 2001, 63-69.

Pierce Product Literature, "GelCode Phosphoprotein Staining Kit", Pierce Biotechnology, Inc., Oct. 2006, 1-2.

Reynolds, Eric C. et al., "A Selective Precipitation Purification Procedure for Multiple Phosphoseryl-Containing Peptides and Methods for Their Identification", *Analytical Biochemistry*, 217, 1994, 277-284.

Sato, Moritoshi et al., "A Fluorescent Indicator for Tyrosine Phosphorylation-Based Insulin Signaling Pathways", *Anal. Chem.*, 71, 1999, 3948-3954.

Seikagaku, "Staining of Phosphoproteins in Polyacrylamide Gels with Acridine Orange", 45(7), 1973, 327-35. (Translation of Abstract Included).

Sickmann, Albert et al., "Phosphoamino acid analysis", *Proteomics*, vol. 1, 2001, 200-206.

Steen, Hanno et al., "Detection of Tyrosine Phosphorylate Peptides by Precursor Ion Scanning Quadrupole TOF Mass Spectrometry in Positive Ion Mode", *Analytical Chemistry*, vol. 73, No. 7, Apr. 1, 2001, 1440-1448.

Tsien, Roger Y., "New Calcium Indicators and Buffers with High Selectivity against Magnesium and Protons: Design, Synthesis, and Properties of Prototype Structures", *Biochemistry*, 19, 1980, 2396-2404.

U'Prichard, David C. et al., "Guanyl Nucleotide Influences on 3H-ligand Binding to a-Noradrenergic Receptors in Calf Brain Membranes", *The Journal of Biological Chemistry*, 253 (10), 1978, 3444-3452.

Vallorani, Luciana et al., "Reversed-Phase High-Performance Liquid Chromatographic Amino Acid Analysis of Phosphoproteins Electroblotted onto a Polyvinylidene Difluoride Membrane Using Dimethylaminoazobenzene Sulfonyl Chloride as Derivatizing Reagent", *Analytical Biochemistry*, 258, 1998, 376-379.

Walters, John D. et al., "Terbium as a Luminescent Probe of Metal-binding Sites in Protein Kinase C", *Journal of Biological Chemistry*, 1990, 4223-4226.

Wilbur, Steven et al., "Determination of Trace Levels of Phosphorus in Environmental Samples with the 7500c ICP-MS System", Agilent Technologies, Inc., Nov. 19, 2001, 1-4.

WO 2003/013765, PCT ISR, Dec. 23, 2002.

WO 2004/042347, PCT ISR, Mar. 1, 2005.

WO 2005/047901, PCT ISR, Jun. 6, 2005.

Zhou, Wei et al., "Detection and Sequencing of Phosphopeptides Affinity Bound to Immobilized Metal Ion Beads by Matrix-Assisted Laser Desorption/Ionization Mass Spectrometry", *J Am Soc Mass Spectrom*, vol. 11, 2000, 273-282.

Non-Final Office Action mailed on Mar. 4, 2009 in U.S. Appl. No. 10/703,816.

Response to Office Action mailed Jan. 20, 2009 in U.S. Appl. No. 10/703,816.

Response to Office Action mailed May 22, 2007 in U.S. Appl. No. 10/821,522.

Li, S. et al., "Iron(III)-Immobilized Metal Ion Affinity Chromatography and Mass Spectrometry for the Purification and Characterization of Synthetic Phosphopeptides", *Analytical Biochem.*, vol. 270, 1999, pp. 9-14.

Wang, Lijuan, "Synthesis of Hydroxyl Substituted Benzoxazol Hemicyanine and asym-Cyanine Dyes", (*Chinese Version*) *Journal of Wuhan Univ.*, No. 2, Feb. 1991, pp. 73-77, Abstract Only.

* cited by examiner

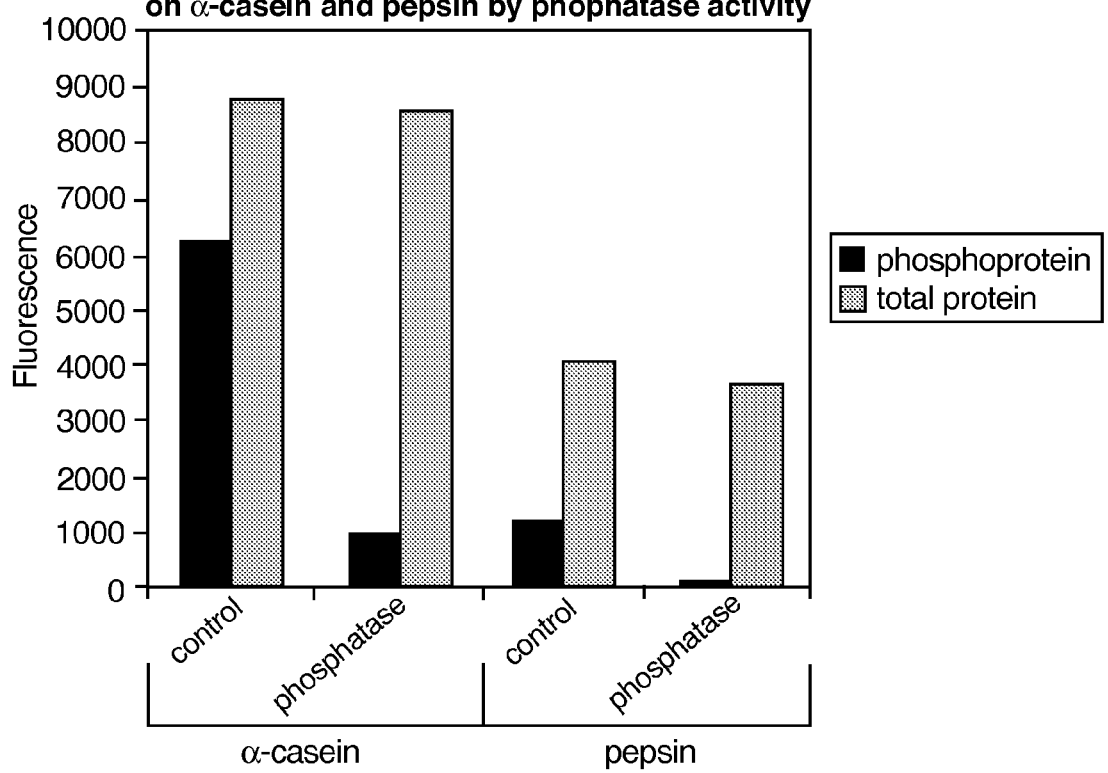
Figure 4  Detection of the removal of phosphate groups on α-casein and pepsin by phophatase activity

US 7,776,533 B2

COMPOSITIONS AND METHODS FOR DETECTION AND ISOLATION OF PHOSPHORYLATED MOLECULES

CROSS-REFERENCE TO RELATED APPLICATIONS

This application is a continuation of U.S. Ser. No. 10/703,816, filed on Nov. 7, 2003, which is a continuation-in-part of U.S. Ser. No. 10/428,192, filed May 2, 2003 now U.S. Pat. No. 7,102,005 which claims priority to U.S. Ser. No. 60/377,733, filed May 3, 2002; U.S. Ser. No. 60/393,059, filed Jun. 28, 2002; U.S. Ser. No. 60/407,255, filed Aug. 30, 2002; and U.S. Ser. No. 60/440,252, filed Jan. 14, 2003, which disclosures are herein incorporated by reference.

STATEMENT REGARDING FEDERALLY SPONSORED RESEARCH

This invention was made in part with government support under grant number 1 R33 CA093292-01, awarded by the National Cancer Institute. The United States Government may have certain rights in this invention.

FIELD OF THE INVENTION

The present invention relates to metal-chelating compositions and methods for use in the detection and isolation of phosphorylated target molecules. The invention has applications in the fields of proteomics, molecular biology, high-throughput screening and diagnostics.

BACKGROUND OF THE INVENTION

Phosphorylation and dephosphorylation are processes by which phosphate groups are added or removed from a target molecule, typically a protein. The process of reversible phosphorylation is a key feature of cellular regulation, including signal transduction, gene expression, cell cycle regulation, cytoskeletal regulation and apoptosis. See, e.g., PROTEIN PHOSPHORYLATION (Marks F. ed., 1996); Hunter, "Signaling—2000 and beyond," *Cell* 100:113-127 (2000). Principally, two classes of enzymes (kinases and phosphatases) modulate reversible protein phosphorylation, adding phosphate groups and removing phosphate groups, respectively, from molecules. Phosphorylation reactions are key features of protein function, and thus phosphorylated proteins must be able to be identified if the proteome is to be fully understood; however, to date no practical methods exist for the systematic parallel analysis of the phosphorylation status of large sets of proteins involved in the regulatory circuitry of cells and tissues. See, Wilkins et al., *Genetic Eng. Rev.* 13:19 (1995).

Signal transduction is an example of a process involving protein phosphorylation that is critical for cellular regulation. After an extracellular stimulatory factor binds to its recognized cell surface receptor, signal transduction is initiated, often by a specific set of cellular protein kinases. These kinases subsequently phosphorylate the target molecule, resulting in an altered activity and a continued cellular response to the signal. See, e.g., Nishizuka, "Studies and perspectives of protein kinase C," *Science* 233:305-312 (1986). It is not enough for researchers to simply identify whether a protein is a phosphorylated protein or not. It has become additionally essential for researchers to identify the sites of phosphorylation on proteins and to determine the stoichiometry of phosphorylation. Serine, threonine and tyrosine amino acid residues are the most common sites of phosphorylation in eukaryotic cells. See, e.g., Guy et al. "Analysis of Cellular Phosphoproteins by Two-Dimensional Gel Electrophoresis: Applications for Cell Signaling in Normal and Cancer Cells," *Electrophoresis* 15:417-440 (1994). Thus, the focus for researchers in understanding protein phosphorylation events occurs at two levels. The first level of analysis requires a determination of whether a protein is a phosphoprotein, including identifying molecules responsible for phosphorylation, and the second level of analysis requires the identification of which amino acid is phosphorylated and how many amino acids are phosphorylated. The present invention provides materials and methods for both levels of analysis. The present invention also provides materials and methods for analysis of certain other phosphate and thiophosphate-containing materials including esters of carbohydrates, nucleotides and lipids.

Currently, phosphoproteins are most often detected by autoradiography after incorporation of $^{32}P$ or $^{33}P$ into cultured cells or after incorporation into subcellular fractions by protein kinases. See, e.g., Yan et al., "Protein Phosphorylation: Technologies for the Identification of Phosphoamino Acids," *J. Chromatogr. A.* 808:23-41 (1998); Guy, G., Phillip, R. and Tan, Y. Electrophoresis 15:417-440 (1994). Such approaches are restricted to a limited range of biological materials, such as tissue culture samples and analysis of clinical samples would require in vivo labeling of patients, which is not feasible. Several alternatives to radiolabeling have also been developed over the years.

Phosphoproteins can also be detected by immunoblotting and immunoprecipitation. See, e.g., Soskic et al., "Functional Proteomics Analysis of Signal Transduction Pathways of the Platelet-Derived Growth Factor Beta Receptor," *Biochemistry* 38:1757-1764 (1999); Watty et al., "The In Vitro and In Vivo Phosphotyrosine Map of Activated MuSK," *Proc. Natl. Acad. Sci. USA.* 97:4585-4590 (2000). Immunoblotting is best performed after blocking unoccupied sites on the solid-phase support with protein solutions, which interferes with microchemical analysis. Removal of the antibody and stain require relatively harsh treatments (i.e., heating to 65° C., incubation with 0.1% SDS and 1 mM DTT). This also poses problems with subsequent use of the protein for sequencing and mass spectrometry. For immunoprecipitation, only the anti-phosphotyrosine antibodies display binding that is tight enough to allow effective isolation. Though high-quality antibodies to phosphotyrosine are commercially available, antibodies that specifically recognize phosphoserine and phosphothreonine residues have been more problematic, often being sensitive to amino acid sequence context. The reliability of these antibodies has been questioned because of potential steric hindrances between the interaction of these antibodies and the phosphoproteins. Moreover, when phosphoproteins are not enriched prior to detection with the antibody, the presence of unrelated proteins co-migrating with the protein of interest may lead to false positive signals. Therefore, identification of phosphorylated proteins using immunoblotting and immunoprecipitation techniques is effectively limited to proteins containing phosphorylated tyrosine residues. See McLachlin & Chait, supra.

Alternatively, phosphorylated proteins can be identified using chromogenic dyes, but with limited success. The cationic carbocyanine dye "Stains-All" (1-ethyl-2-[3-(3-ethyl-naphtho[1,2d]thiazolin-2-ylidene)-2-methylpropenyl]-naph-tho[1,2d]thiazolium bromide) stains RNA, DNA, phosphoproteins and calcium-binding proteins blue while unphosphorylated proteins are stained red. See, e.g., Green et al., "Differential Staining of Phosphoproteins on Polyacrylamide Gels with a Cationic Carbocyanine Dye," *Anal. Bio-* chem. 56:43-51 (1973); Hegenauer et al., "Staining Acidic Phosphoproteins (Phosvitin) in Electrophoretic Gels," *Anal. Biochem.* 78:308-311 (1977); Debruyne, "Staining of Alkali-Labile Phosphoproteins and Alkaline Phosphatases on Polyacrylamide Gels," *Anal. Biochem.* 133:110-115 (1983); "Staining of phosphoproteins in polyacrylamide gels with acridine orange", *Seikagaku* 45:327-35 (1973). Stains-All is not routinely used to detect phosphoproteins due to poor specificity and low sensitivity. Stains-All is at least 10 times less sensitive than Coomassie Brilliant Blue as a general protein stain and several orders of magnitude less sensitive than $^{32}$P-autoradiography or the techniques described in this patent. Another chromogenic method, the GelCode™ Phosphoprotein detection kit (Pierce Chemical Company, Rockford, Ill.), is designed to detect phosphoproteins in gels; however, this method has many limitations. According to this method, phosphoproteins are detected in gels through alkaline hydrolysis of phosphate esters of serine or threonine, precipitation of the released inorganic phosphate with calcium ions, formation of an insoluble phosphomolybdate complex and then visualization of the complex with a dye such as methyl green, malachite green or rhodamine B [as described in Cutting and Roth (1973)]. The detection sensitivity of the staining method is considerably poorer than Coomassie Blue staining, with 80-160 ng of phosvitin, a protein containing roughly 100 phosphoserine residues, being detectable by the commercialized kit. The staining procedure is quite complex (involving seven different reagents) and alkaline hydrolysis requires heating gels to 65° C., which causes the gel matrix to hydrolyze and swell considerably. Since phosphotyrosine residues are not hydrolyzed by the alkaline treatment, proteins phosphorylated at this amino acid residue escape detection by the method. Dyes for the phosphate-selective fluorescence labeling in which a BODIPY dye is covalently attached to a reactive imidazole group has been developed for the detection of pepsin phosphorylation. See, U.S. Pat. No. 5,512,486; Wang & Giese, "Phosphate-Specific Fluorescence Labeling of Pepsin by BO-IMI," *Anal. Biochem.* 230:329-332 (1995).

In addition to detecting phosphoproteins, two methods for the chemical derivatization and enrichment of phosphopeptides resulting in isolation of phosphopeptides from complex mixtures exist. See, e.g. Goshe et al., "Phosphoprotein Isotope-Coded Affinity Tag Approach For Isolating and Quantitating Phosphopeptides in Proteome-Wide Analyses," *Anal. Chem.* 73:2578-2586 (2001). The first method involves oxidation of cysteine residues with performic acid, alkaline hydrolysis to induce β-elimination of phosphate groups from phosphoserine and phosphothreonine residues, addition of ethanedithiol, coupling of the resulting free sulfhydryl residues with biotin, purification of phosphoproteins by avidin affinity chromatography, proteolytic digestion of the eluted phosphoproteins, a second round of avidin purification and then analysis by mass spectrometry (Oda, Y., Nagasu, T., and Chait, B. *Nature Biotechnol.* 19:379 (2001)). The first method uses β-elimination to remove phosphate groups that are replaced with a tag, as exemplified with biotinylated thiol groups wherein the peptides could then be isolated by chromatography on avidin resins. An alternative method requires proteolytic digestion of the sample, reduction and alkylation of cysteine residues, N-terminal and C-terminal protection of the peptides, formation of phosphoramidate adducts at phosphorylated residues by carbodiimide condensation with cystamine, capture of the phosphopeptides on glass beads coupled to iodoacetate, elution with trifluoroacetic acid and evaluation by mass spectrometry (Zhou et al., "A Systematic Approach to the Analysis of Protein Phosphorylation," *Nat. Biotechnol.* 19:375-378 (2001). These methods are time consuming, require purified phosphopeptides, and are limiting in what can be isolated. Both procedures identified the monophosphorylated trypsin peptide fragment from the test protein β-casein, but both failed to detect the tetraphosphorylated peptide fragment.

Alternatively, a method for combining chemical modification and affinity purification has been shown for the characterization of serine and threonine phosphopeptides in proteins based on the conversion of phosphoserine and phosphothreonine residues to S-(2-mercaptoethyl)cysteinyl or β-methyl-S-(2-mercaptoethyl)cysteinyl residues by β-elimination/1,2-ethanedithiol addition, followed by reversible biotinylation of the modified proteins. After trypsin digestion, the biotinylated peptides are affinity-isolated and enriched, followed by their subsequent structural characterization by liquid chromatography/tandem mass spectrometry (LC/MS/MS). See Adamczyk et al., "Selective Analysis of Phosphopeptides Within a Protein Mixture by Chemical Modification, Reversible Biotinylation and Mass Spectrometry," *Rapid. Commun. Mass Spectrom.* 15:1481-1488 (2001).

Fluorescence detection methods appear to offer the best solution to global protein quantitation in proteomics. However, currently, there is no satisfactory method for the specific and reversible fluorescent detection of gel-separated phosphoproteins from complex samples. Derivatization and fluorophore labeling of phosphoserine residues by blocking free sulfhydryl groups with iodoacetate or performate, alkaline β-elimination of the phosphate residue, addition of ethanedithiol, and reaction of the resulting free sulfhydryl group with 6-iodoacetamidofluorescein has been demonstrated in capillary electrophoresis using laser-induced fluorescence detection and similar reactions have been performed on protein microsequencing membranes. However, neither method has been shown to be suitable for detection of phosphoproteins directly in gels. One problem with the approach is that a delicate balance must be struck between the base and the ethanedithiol in order to achieve elimination of the phosphate group from the serine residue and addition of the ethanedithiol to the resulting dehydroalanine residue without hydrolysis of the peptide backbone.

Several instrument-based methods are also available for the determination of protein phosphorylation such as $^{31}$P-NMR, mass spectrometry [See, e.g., Resing & Ahn, "Protein Phosphorylation Analysis by Electrospray Ionization-Mass Spectrometery," *Methods Enzymol.* 283:29-44 (1997); Aebersold and Goodlett, "Mass Spectrometry in Proteomics," *Chem. Rev.* 101:269-295 (2001). Affolter, M., Watts, J., Krebs, D., and Aebersold, R. *Anal. Biochem.* 223:74 (1994); Liao, P., Leykam, J., Andrews, P., Gage, D., and Allison, *J. Anal. Biochem.* 219:9 (1994); Oda, Y., Huang, K., Cross, F., Cowburn, D., and Chait, B. *Proc. Natl. Acad. Sci. USA* 96:6591 (1999)) and protein sequencing. Mass spectrometry has been used to provide the molecular mass of an intact phosphorylated protein by comparing the mass of the unphosphorylated protein to that of the phosphorylated protein. See, e.g., McLachlin & Chait, "Analysis of Phosphorylated Proteins and Peptides by Mass Spectrometry," *Current Opin. Chem. Biol.* 5:591-602 (2001). This is limiting in that researchers must have purified amounts of both proteins. While these procedures accurately characterize the phosphorylation status of proteins and peptides, they are unsuitable for high-throughput screening of phosphorylated substrates. The techniques are generally used after a phosphoprotein has been identified by autoradiography or immunoblotting with an anti-phosphotyrosine antibody. Though methods have recently been introduced to directly quantify the relative abundance of phosphoproteins in two different samples by mass spectrometry through culturing different cell populations in $^{15}$N-enriched and $^{14}$N-enriched medium, the linear dynamic range of such methods has explicitly been demonstrated over only a 10-fold range. Ion suppression phenomena associated with mass spectrometry prevents stoichiometric comparison of different phosphoproteins by such techniques.

For analysis of the site(s) of phosphorylation on molecules, a more detailed analysis of the sites of phosphate attachment and stoichiometry often requires the examination of peptide fragments of the phosphoprotein of interest. Such fragments are usually generated by digestion of the phosphoprotein with proteases such as trypsin. However, mass spectroscopic analysis of proteolytic digests of proteins rarely provides full coverage of the protein sequence and regions of interests often go undetected. In addition, protein phosphorylation is often sub-stoichiometric, such that the phosphoproteins are present in lower abundance than other peptides from the protein of interest. Therefore, the identification and characterization of phosphoproteins would be improved greatly by highly selective methods of enriching phosphopeptides prior to analysis with mass spectrometry. It would be particularly useful to detect phosphoproteins by reagents that do not chemically alter the structure or mass of the phosphoproteins.

Currently, selective enrichment of phosphopeptides from complex mixtures is performed using immobilized metal affinity chromatography, known as IMAC. Using this technique, metal ions such as $Fe^{3+}$ or $Ga^{+3}$ are bound to a chelating support prior to the addition of a complex mixture of peptides or proteins. See, e.g., Posewitz & Tempst, "Immobilized Gallium(III) Affinity Chromatography of Phosphopeptides," *Anal. Biochem.* 71:2883-2892 (1999). Phosphopeptides that bind to the column can be released using high pH or phosphate buffer, though the latter step usually requires a further desalting step before analysis with mass spectrometry. Resins with iminodiacetic acid and nitrilotriacetic acid chelators are known and are available commercially. See, e.g., Neville et al., "Evidence for Phosphorylation of Serine 753 in CFTR Using a Novel Metal-Ion Affinity Resin and Matrix-Assisted Laser Desorption Mass Spectrometry," *Protein Sci.* 6:2436-2445 (1997). However, there are several complications using current techniques, including loss of phosphopeptides that do not bind to the column (low affinity), difficulty in the subsequent elution of phosphorylated peptides, and background from non-phosphorylated peptides that have affinity for immobilized metal ions (low specificity).

Mass spectrometry-based detection of separated peptides and direct matrix-assisted laser desorption/ionization (MALDI) analysis of phosphopeptides bound to an IMAC support has been demonstrated. See Zhou et al., "Detection and Sequencing of Phosphopeptides Affinity Bound to Immobilized Metal Ion Beads by Matrix-Assisted Laser Desorption/Ionization Mass Spectrometry," *J. Am. Soc. Mass. Spectrom.* 11:273-283 (2000). IMAC has also been coupled directly to mass spectrometry instruments on-line, or with superseding separation techniques, such as HPLC and capillary electrophoresis (CE), for the detection and analysis of phosphopeptides.

The present invention overcomes the limitations of the current methods by utilizing a cationic transition metal and a compound that comprises a metal-chelating moiety and a chemical moiety, typically a reactive group or label such as a fluorophore, or a combination thereof, to detect phosphoproteins and phosphopeptides. There are a variety of chelating moieties that use poly-carboxylate binding sites to selectively bind monovalent and divalent metal cations, and these are often used in fluorescent calcium ion indicators. Examples of these indicators are, for example, quin-2, fura-2, indo-1 (U.S. Pat. No. 4,603,209); fluo-3 and rhod-2 (U.S. Pat. No. 5,049,673), and FURA RED™ (U.S. Pat. No. 4,849,362). A family of BAPTA-based indicators that are selective for calcium ions are described in HAUGLAND, HANDBOOK OF FLUORESCENT PROBES AND RESEARCH CHEMICALS (9$^{th}$ edition, CD-ROM, September 2002). Examples of BAPTA-based metal-chelators are also described in U.S. Pat. Nos. 5,773,227; 5,453,517; 5,516,911; 5,501,980; 6,162,931 and 5,459,276.

Indicators of free calcium concentrations are based upon selective calcium binding to fluorescent dyes. Though it is well known that BAPTA compounds bind certain divalent cations, such as calcium, as analogs of the common EGTA chelator, the BAPTA compounds are also known to bind almost all inorganic polyvalent cations with an affinity that may be higher or lower than that of the compound for calcium ions. Their selectivity and utility for measuring calcium in biological cells results from the general absence or low abundance of these other polycations in living systems. The affinity and selectivity of the BAPTA-based indicators for polycations, including gallium and similar metals of utility to this invention, can be modified by shifts in pH, solvent composition, ionic strength and other experimental variables. This shift in cation selectivity and affinity is critical to all aspects of the disclosed invention, including both detection and isolation of phosphorylated targets.

The present invention overcomes the limitations and disadvantages of currently disclosed methods for identifying, isolating, analyzing and quantitating phosphorylated proteins and thus provide methods, compounds and compositions to alleviate long-felt needs for rapid and effective high-throughput methods for detecting and isolating phosphoproteins for further analysis. The present invention can accurately identify phosphopeptides and phosphoproteins comprising as few as one phosphate group and in a simple method that does not require multiple steps or pre-treatment of the sample. Importantly, the present invention is the first known method to provide a means for accurately identifying the phosphorylated proteome and allows for the quantitative identification of increased phosphorylation of proteins. The present invention is an important tool for identifying novel phosphorylated proteins in the proteome. The technology has unsurpassed quantitative characteristics, particularly when used in combination with reagents for the detection of total proteins. In addition, as will be described below, the materials and methods of the present invention are not limited to the detection and/or separation of phosphorylated proteins.

SUMMARY OF THE INVENTION

The present invention provides phosphate-binding compounds and methods for specifically detecting, isolating and/or quantitating phosphorylated target molecules. These compounds, when in a moderately acidic environment, and in the presence of an appropriate metal ion will selectively bind phosphate groups on phosphorylated target molecules that are either immobilized, such as in a gel, or adsorbed on a solid or semisolid matrix, or are dissolved or suspended in a mostly aqueous solution to form a ternary complex.

The phosphate-binding compounds comprise a metal chelating moiety that is optionally bonded to a label or a chemically reactive group. Thus, in one aspect the phosphate-binding compounds have the formula (A)m(L)n(B), wherein A is a chemical moiety, L is a linker, B is a metal-chelating moiety, m is an integer from 1 to 4 and n is an integer from 0 to 4. Without being bound by theory, it appears that the metal-chelating moiety of these particular phosphate-binding compounds simultaneously binds a trivalent metal ion and a phosphate group on a target molecule in a reaction that forms a ternary complex. In this way, the metal ion provides a bridge between the phosphate group and the metal-chelating moiety wherein the chemical moiety A is effectively bound to the phosphate target molecule by ionic interactions. Thus, it is a requirement of the present invention that the metal-chelating moiety bind a metal ion that has simultaneous affinity for the phosphorylated target molecule, under appropriate conditions.

The utility of the compositions and methods of this invention is principally the result of the chemical moieties A that are covalently attached to the metal-chelating moieties by a linker to form the phosphate binding compounds of the present invention. Typically, chemical moieties A are a reactive group or a label. The reactive groups function to covalently attach another natural or synthetic substance to the metal-chelating moieties or alternatively covalently bind the phosphorylated target molecule after the metal-chelating moiety and metal ion has brought the reactive group in close proximity to the phosphorylated target molecule. Particularly useful substances that the reactive group A covalently binds to the metal chelating moiety of formula (A)m(L)n(B) include without limitation particles, polymers, peptides and proteins. In this way, a particle could have many phosphate-binding compounds attached.

For detection purposes, A is typically a detectable label that is a dye including pigments, chromophores and fluorophores, haptens, enzymes, or radioactive isotopes, although an extensive assortment of other detectable labels that fall within the scope of this invention is known. For isolation purposes of phosphate containing targets, A is typically a label or a reactive group that is bound to a polymer such as agarose, a surface, a magnetic particle or a microsphere. The polymer, in combination with the metal chelating moiety and a metal ion is selected to form a soluble or insoluble ternary complex with the phosphorylated target molecule. Such ternary complexes are particularly useful for the selective isolation of phosphorylated targets from complex mixtures or as components of various detection schemes. In a further aspect of the invention, A is a chemical moiety that alters the solubility of the ternary complex or alternatively comprises an amine-reactive group used to form a covalent bond with an amine-containing molecule, including polymers and phosphate target molecules.

The "binding solution" of the invention (which we define to include true solutions, suspensions, emulsions, dispersions and immobilized variants thereof) of the present invention comprises a phosphate-binding compound, typically having the formula (A)m(L)n(B), a salt comprising selected metal ions, and an acid. The preferred salt and metal ion composition and concentration of the binding solution or suspension will depend to some extent on the metal-chelating moiety of the compound. A particularly useful binding solution is the combination of a BAPTA-based chelating moiety of the phosphate-binding compound and a gallium salt. Unexpectedly, we have determined that trivalent gallium ions simultaneously bind BAPTA moieties and phosphorylated target molecules to form a ternary complex with a useful affinity only in the presence of a moderately acidic environment. However we have also shown, other metal-chelating moieties such as DTPA, IDA and phenanthroline to simultaneously bind gallium trivalent ions and phosphate groups. Thus, one requirement of the binding solution is the presence of an acid, wherein the binding solution preferably has a pH of about 3 to about 6; typically the pH is about 3 to about 4. The nature of the acid used to obtain this pH appears to be irrelevant; however, a phosphoric acid, phosphonic acid or polyphosphoric acid should not be used to obtain this pH, as they could reduce the stability of the ternary complex. Typically, the phosphate-binding compound is free in the binding solution or suspension; however, the phosphate-binding compound can be immobilized on a solid or semi-solid matrix such that when the metal ion and acid are added a binding solution is formed and a ternary complex of the invention is subsequently formed if a phosphorylated target is present in a sample.

The methods of the invention comprise contacting a sample with a binding solution comprising the phosphate-binding compound, the metal ion and the acid, incubating the sample and the binding solution for sufficient time to allow the compound of the binding solution to associate with said phosphorylated target molecule whereby said phosphorylated target molecule forms a ternary complex.

Typically, for detection purposes, the resulting ternary complex that comprises the compound is illuminated to measure a detectable optical property of the chemical moiety A, whereby the presence of the phosphorylated target molecules is detected. The phosphorylated target molecules can be detected in solution or when immobilized on a solid or semi-solid matrix. The compositions and methods of this invention can be used to detect phosphorylated target molecules present in a complex sample of phosphorylated and nonphosphorylated target molecules or to detect a change in the number of phosphate groups on a target molecule. Differences in the degree of phosphorylation can be due to intrinsic differences in the degree of phosphorylation of the biopolymer, which can cause differences in folding of proteins, or to an in vivo process such as a disease state or in conjunction with an in vitro assay to identify specific kinases and phosphatases.

Alternatively, when the method is utilized to selectively isolate phosphorylated target molecules from solution, visualizing the complex may not be necessary. To isolate the phosphorylated target molecules, the ternary complex can be precipitated, immobilized, separated by a chromatographic or electrophoretic technique or by a magnetic field or remain in solution. In some cases, organic extraction can be used to separate the metal-chelating moiety from the phosphorylated target molecule. When the ternary complex is precipitated or otherwise immobilized, the phosphorylated target molecules can be separated from the nonphosphorylated target molecules and other components of the sample by affinity chromatography, such as by simple washing with an aqueous, organic or mixed aqueous/organic wash solution. In some cases, it is advantageous to further analyze the extracted phosphorylated target molecules while they are still immobilized on a matrix. Isolation of phosphorylated target molecules is useful for further analysis of the target molecules, such as by liquid chromatography/mass spectrography, an electrophoretic separation technique, by detection of the bound target molecules by an antibody to any part of the target molecule or by a variety of other techniques. In particular, isolation of the phosphorylated target molecules simplifies the subsequent analysis of the sample by removing interfering components of the original sample.

μg and contained nine total proteins, one of which was a phosphoprotein (ovalbumin) that contains two phosphate groups. The figure demonstrates selective detection of ovalbumin against a background of very low or no staining of eight proteins known to be non-phosphorylated.

Figure 1A:
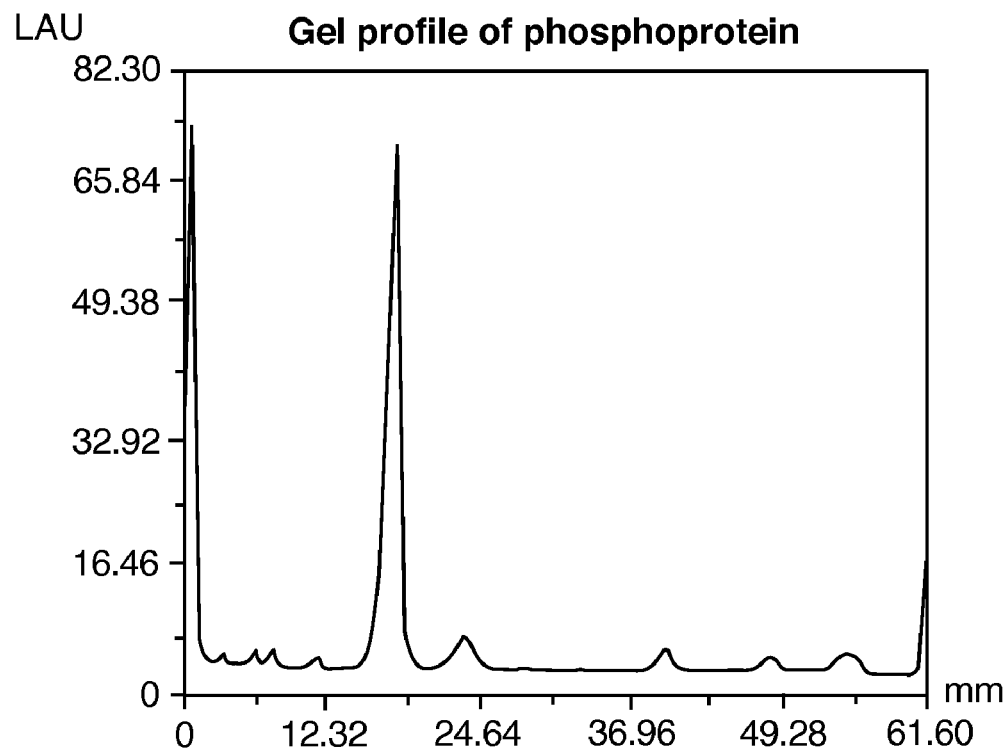
FIG. 1: Shows the selective detection of a phosphorylated target molecule (ovalbumin) (1A) in a polyacrylamide gel using a binding solution comprising gallium chloride and Compound 2 compared to the same gel post-stained with a total protein stain (1B) (SYPRO® Ruby protein gel stain) (See, Example 2). The protein mixture was loaded at ca. 500
Figure 1B:
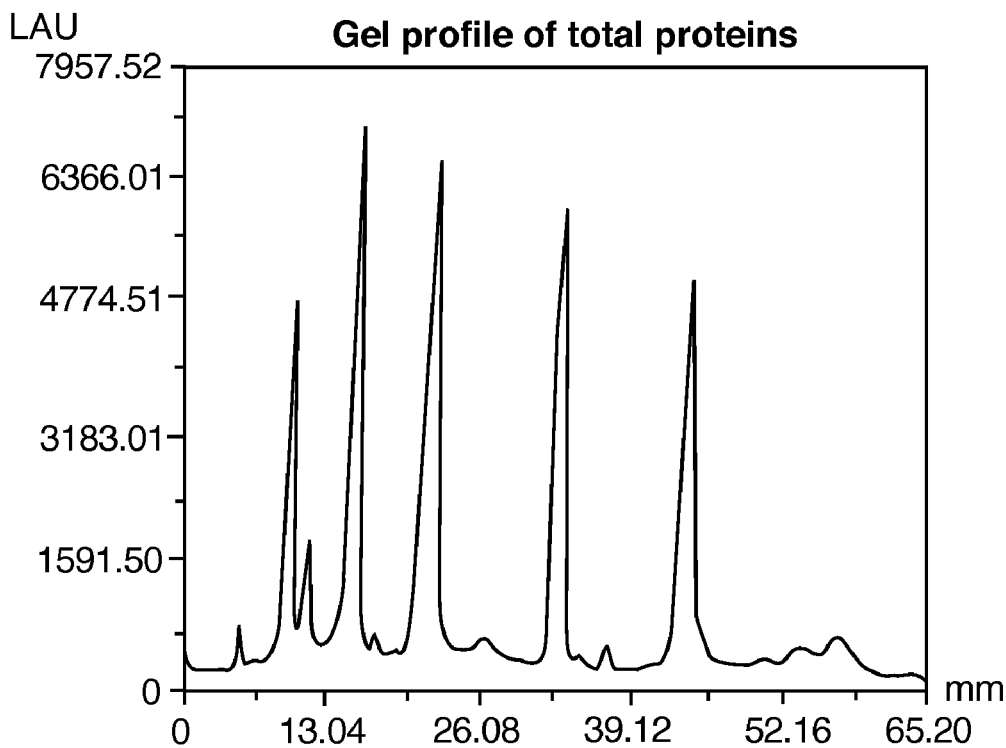
Figure 2A:
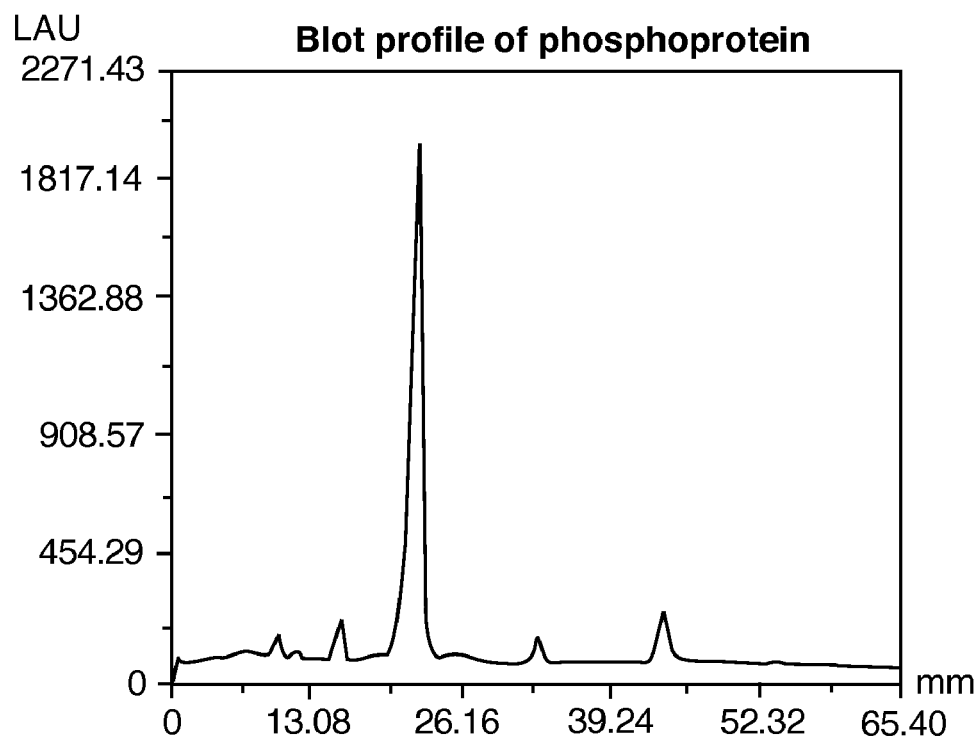
Figure 2B:
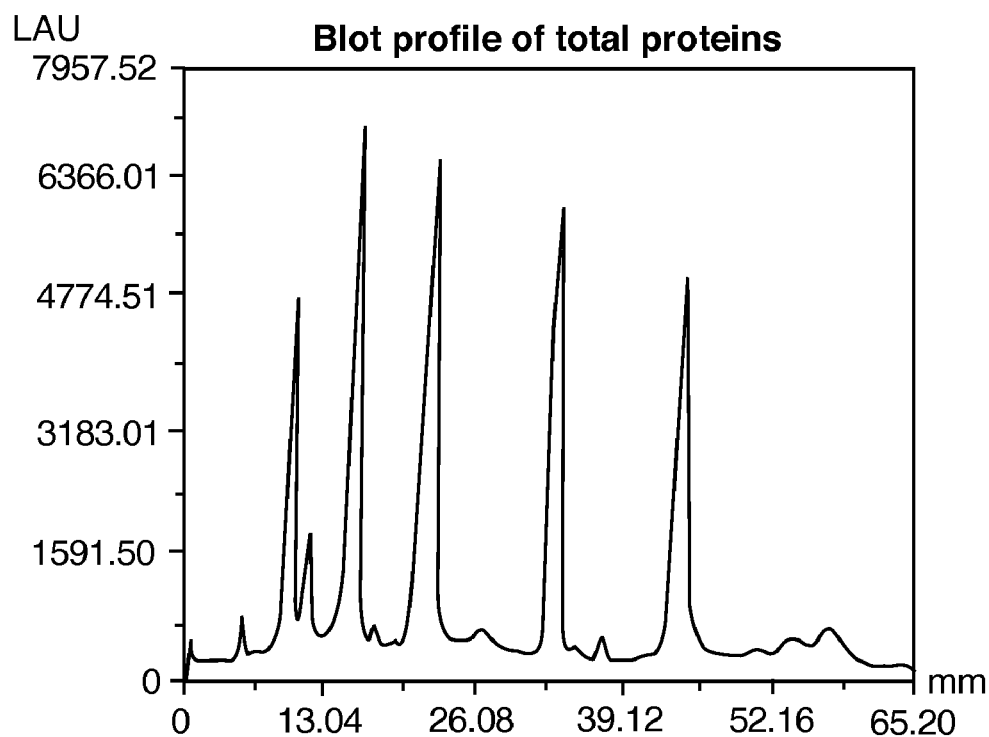

FIG. 2: Shows the selective detection of a phosphorylated target molecule (ovalbumin) (2A) on a PVDF membrane using a binding solution comprising gallium chloride and Compound 1 compared to the same membrane post-stained with a total protein stain (2B) (SYPRO® Ruby protein blot stain) (See, Example 8). The figure demonstrates selective detection of ovalbumin against a background of very low or no staining of five non-phosphorylated proteins.

Figure 3A:
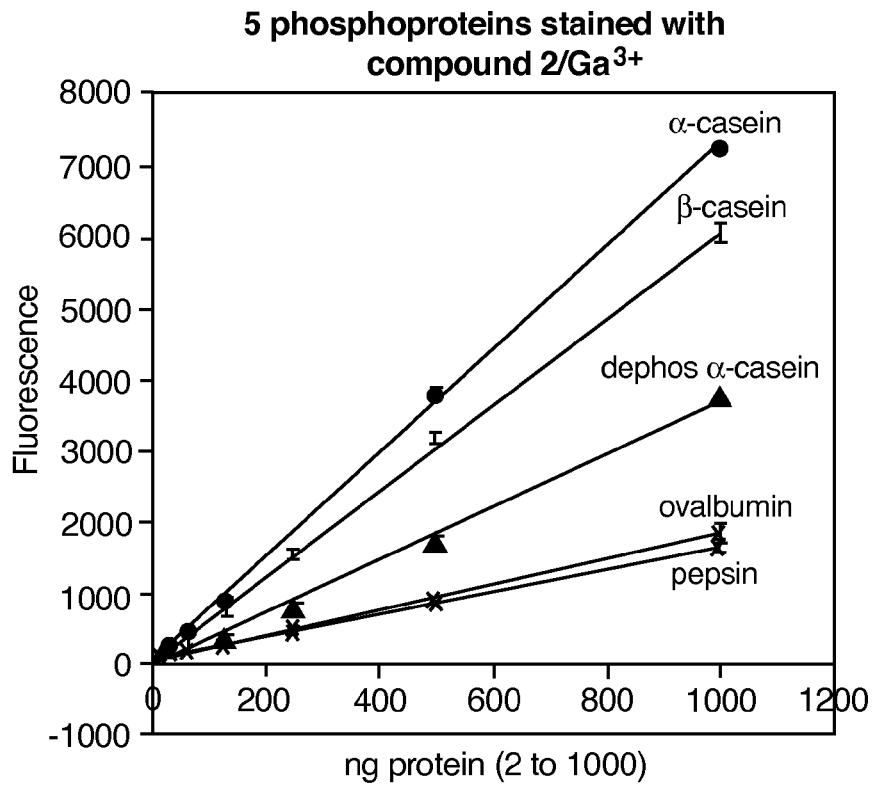
Figure 3B:
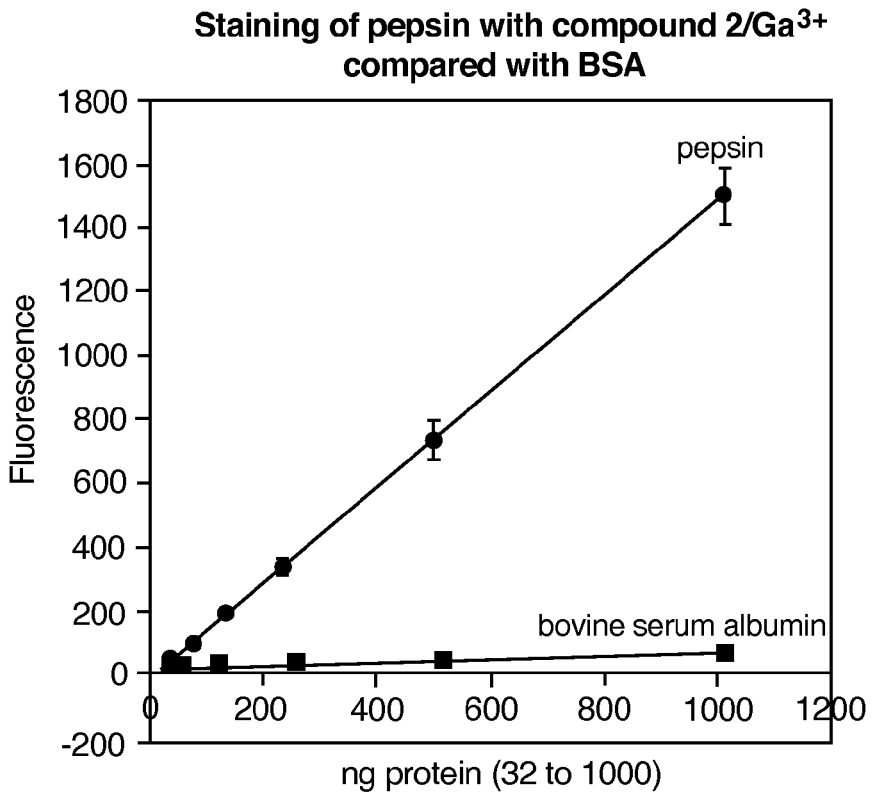

FIG. 3: Shows the sensitivity and linear dynamic range of detecting phosphorylated proteins in a gel using a binding solution comprising gallium chloride and Compound 2 (See, Example 2); (3A) is a comparison of five proteins with different ratios of phosphate groups and (3B) compares pepsin to bovine serum albumin (BSA). Proteins were loaded in two-fold dilution series on SDS polyacrylamide mini-gels from 2 ng-1000 ng; each protein sample was done in series in four replicate gels. The phosphoproteins were α-casein (7 or 8 phosphates); dephosphorylated α-casein (1 or 2 phosphates); β-casein (5 phosphates); ovalbumin (2 phosphates) and pepsin (1 phosphate). BSA contains no phosphates and was used as a negative control. The results demonstrate that the methods and binding solution of the present invention can detect as little as 1-2 ng of a pentaphosphorylated protein (β-casein), and 8 ng of a monophosphorylated protein (pepsin).

FIG. 4: Shows the detection of protein phosphatase activity wherein α-casein and pepsin were used as a phosphatase substrate. The gels were incubated with a binding solution comprising gallium chloride and Compound 2 to demonstrate a reduction in phosphate groups, compared to a control, after the substrates were incubated with a protein phosphatase, See example 6.

Figure 5:
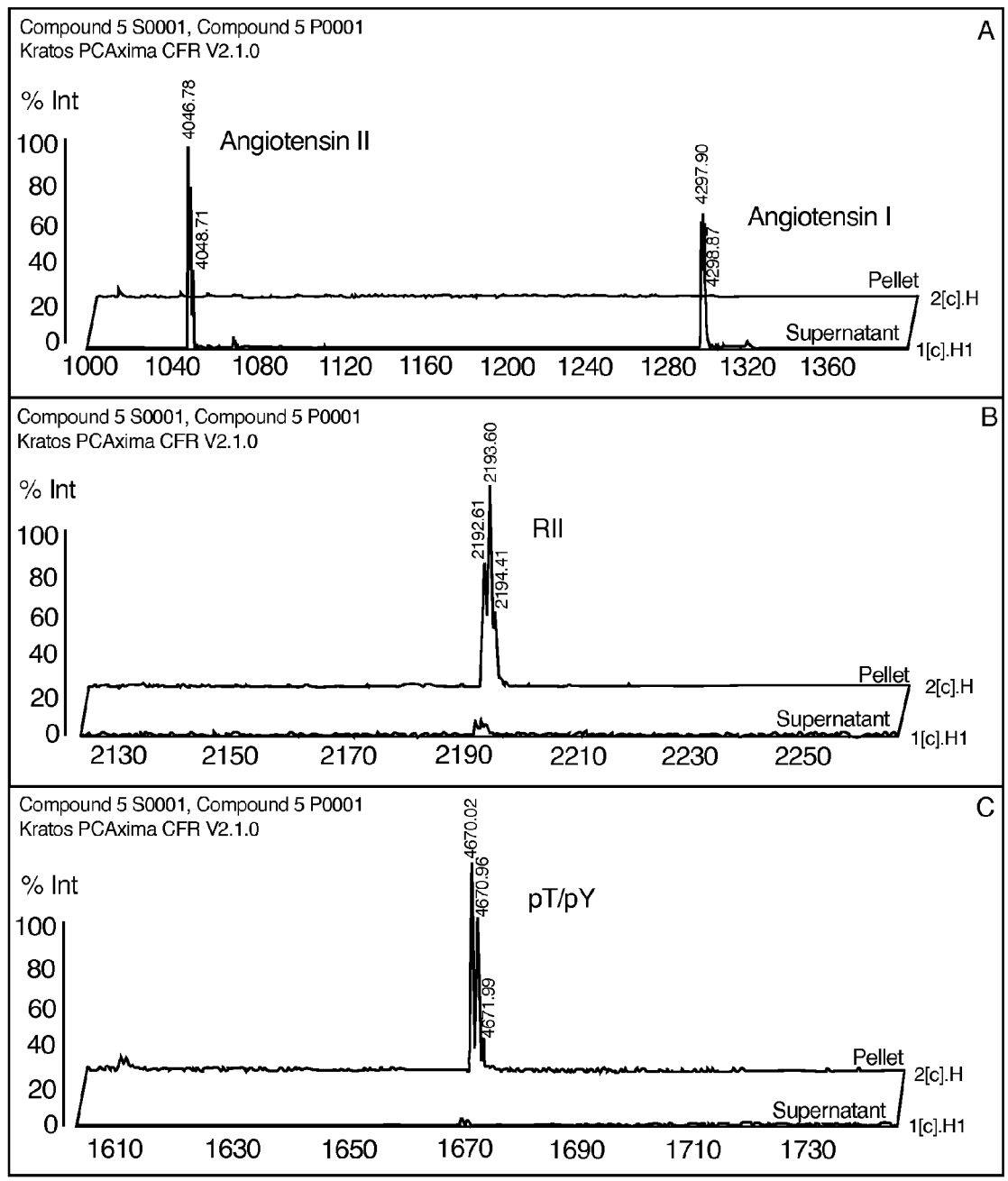

FIG. 5: Shows the isolation of phosphopeptides (pT/pY and RII; MWs 1670 and 2193) (Panel B and C) from a solution containing non-phosphorylated peptides (angiotensin I and II, MWs 1297 and 1046) (Panel A) when the solution of peptides was incubated with a binding solution comprising gallium chloride and Compound 5. The mixture was incubated for 1 hour and centrifuged for 5 minutes. The resulting supernatants (bottom spectra in all panels) and pellet precipitates (top spectra in all panels) were analyzed by MALDI-TOF mass spectrometry. Panel A shows the non-phosphorylated peptides exclusively in the supernatants, while figures B and C show the two phosphopeptides of greater than 95% purity in the pellets.

Figure 6:
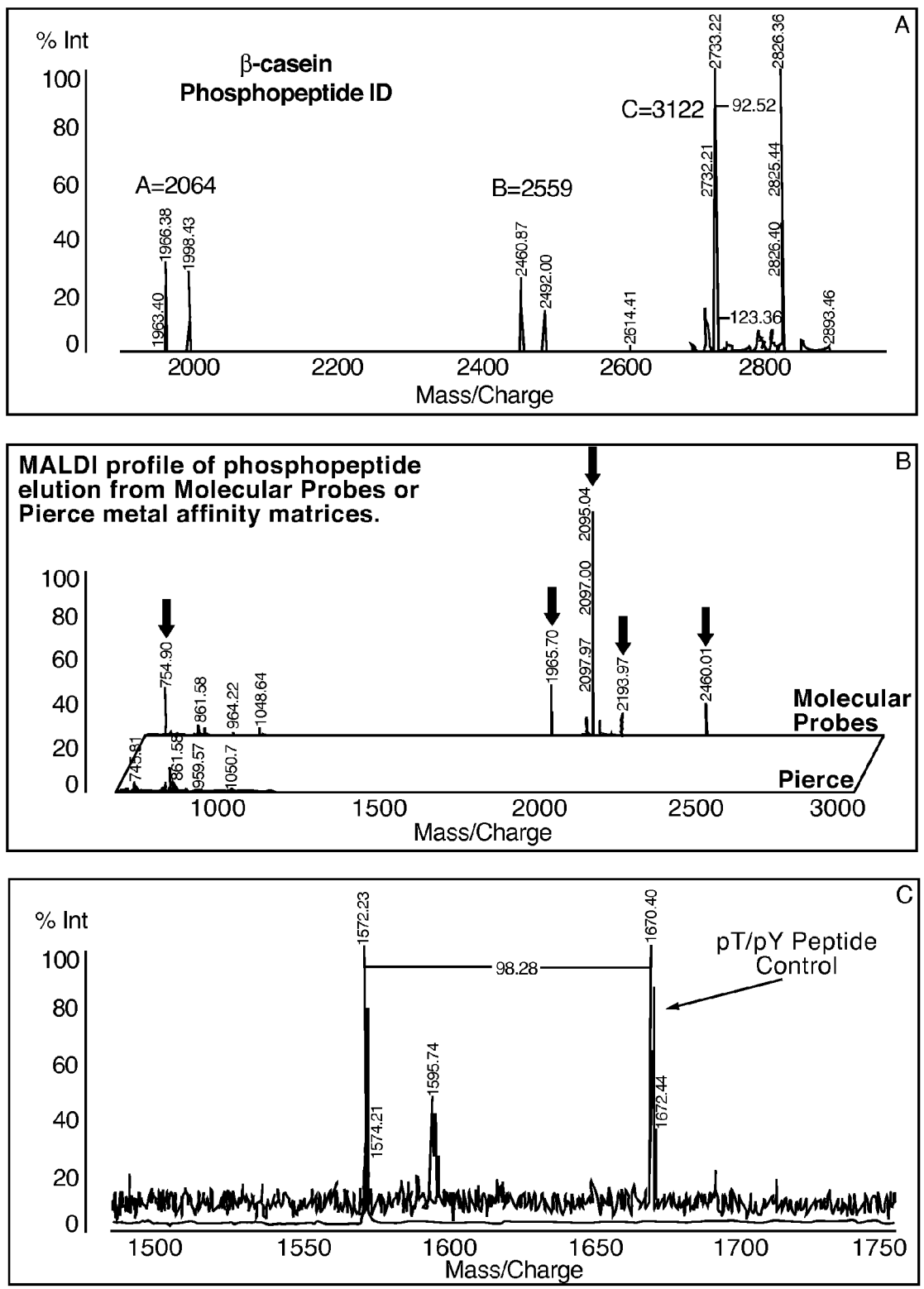

FIG. 6: Shows the analysis of phosphorylated peptides α-casein) eluted from an affinity chromatography matrix column containing Compound 13 or Compound 14 that had been charged with gallium ions. Panel A shows differential MALDI-TOF MS analysis of purified α-casein phosphoserine peptides after dephosphorylation (left peaks in pairs) and subsequent derivatization with methylamine (right peaks in pairs). Results show that all three peptides are phosphoserine derivatives by methylamine addition. A and B of Panel A were monophosphorylated (+31 amu for methylamine) and C was triphosphorylated (+93 amu for 3 methylamines). Panel B shows a MALDI-TOF MS profile of eluted phosphopeptides from a BAPTA-agarose (Compound 13 or Compound 14) column versus commercially available metal affinity columns (Pierce Chemical Co.). Under the conditions used, the BAPTA-agarose column shows all expected phosphopeptides (arrows) purified from a complex peptide mix. Panel C shows the Control peptide (MW=1870) with one phosphothreonine and one phosphotyrosine residue after treatment with strong base (−98 amu) and methylamine. Results show elimination of a single phosphate only (−98 amu from threonine) with no subsequent addition of methylamine (+32 amu), confirming a single phosphothreonine residue. Phosphotyrosine is determined by a lack of modification under these elimination conditions.

Figure 7:
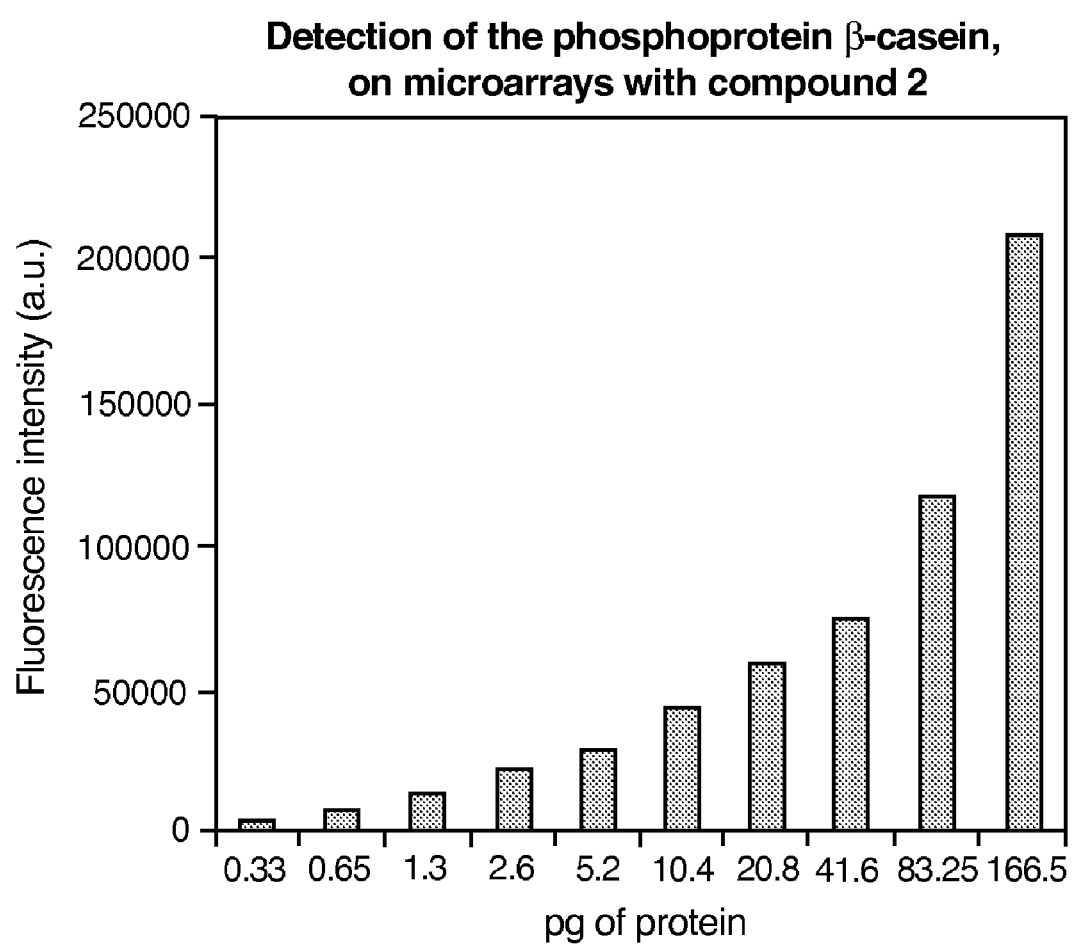

FIG. 7: Shows the detection of a phosphoprotein (β-casein) on a HydroGel microarray (Perkin Elmer, Foster City, Calif.) when the microarray was incubated with a binding solution comprising Compound 2 and gallium chloride, see Example 18. The protein was loaded in a two-fold dilution series from 166 pg-0.324 pg on the microarray. The results show the detection of 0.65 pg of a pentaphosphorylated protein on a HydroGel microarray.

Figure 8:
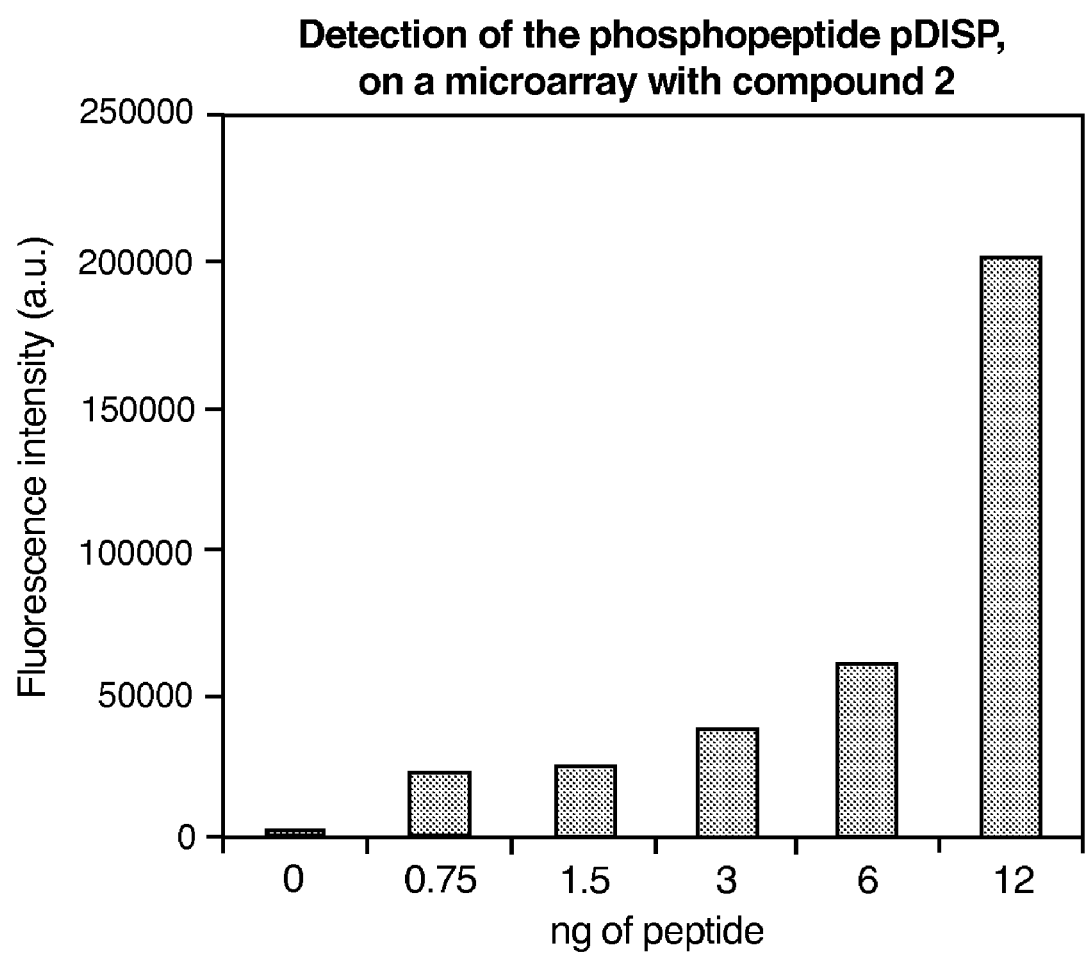

FIG. 8: Shows the detection of a phosphopeptide (PDISP) on a HydroGel microarray (Perkin Elmer) when the microarray was incubated with a binding solution comprising Compound 2 and gallium chloride, see Example 19. The peptide was loaded in a two-fold dilution series from 12 pg-0.18 pg on the microarray. The results demonstrate that as little as 300 fg of a monophosphorylated peptide can be detected on a HydroGel microarray.

Figure 9A:
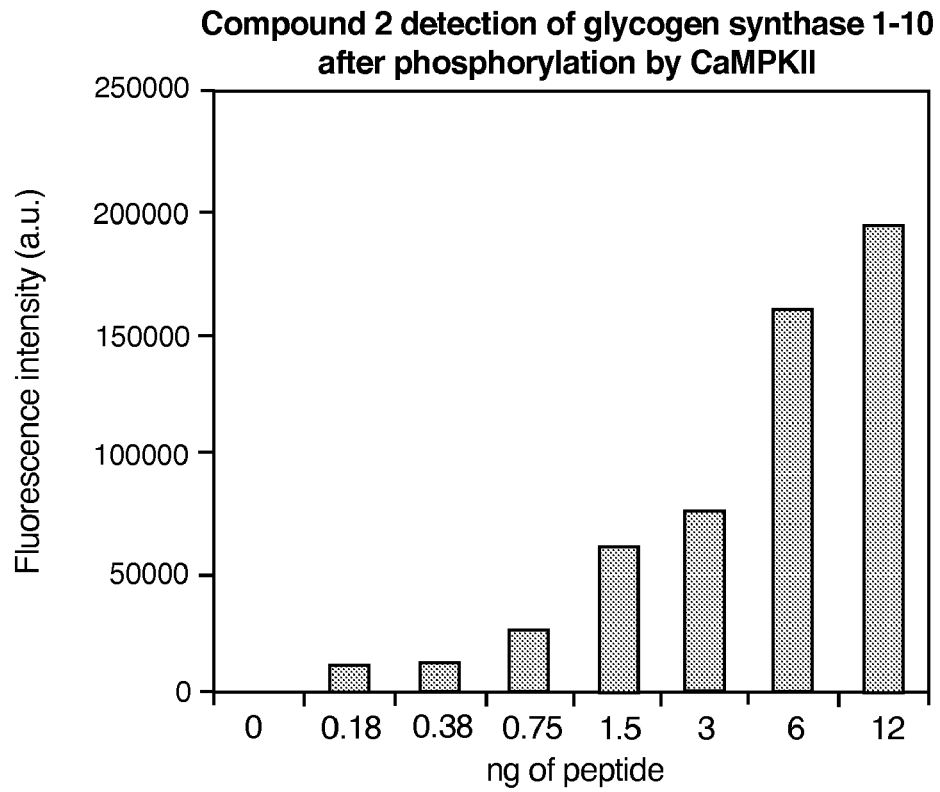
Figure 9B:
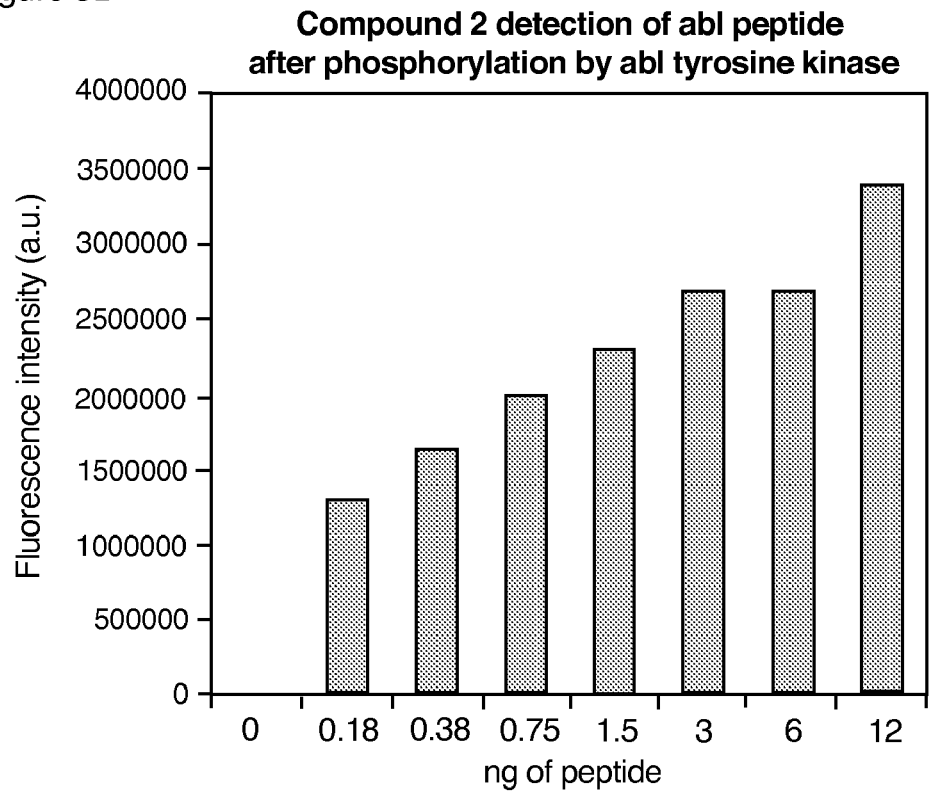

FIG. 9: Shows the detection of protein kinase activity (9A; CaMPKII) and (9B; Abl tyrosine kinase) by the detection of peptides that were phosphorylated on a HydroGel microarray (Perkin Elmer) that was incubated with a binding solution comprising Compound 2 and gallium chloride, see Examples 20 and 21. The peptide glycogen synthase 1-10 was detected to demonstrate the kinase activity of CaMPKII and the peptide Abl was detected to demonstrate the kinase activity of Abl tyrosine kinase.

Figure 10A:
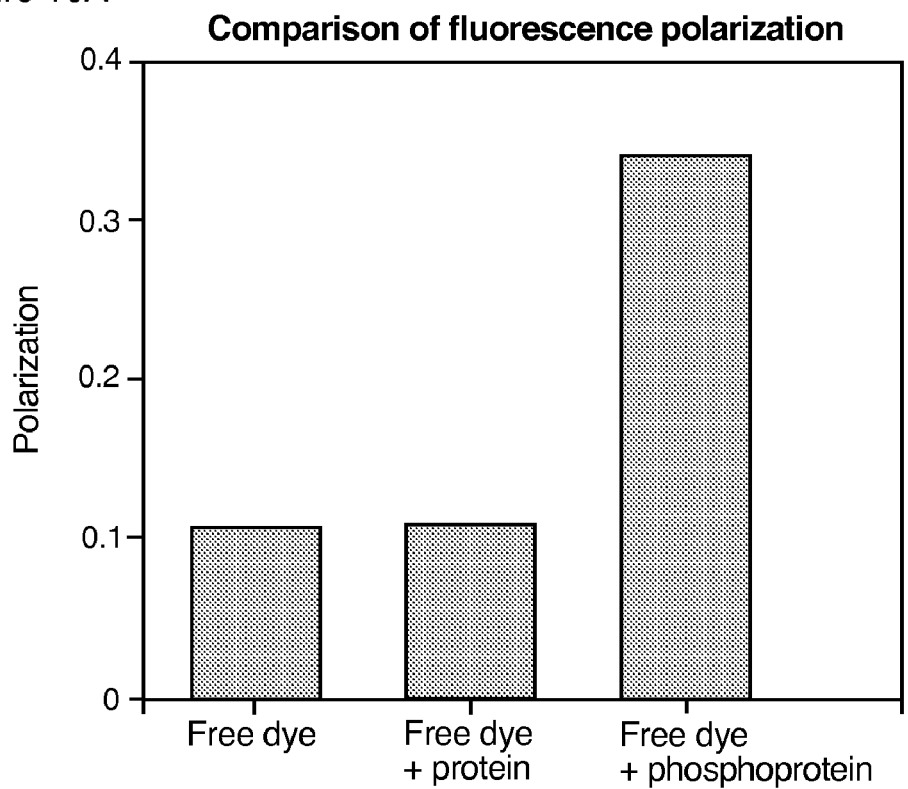
Figure 10B:
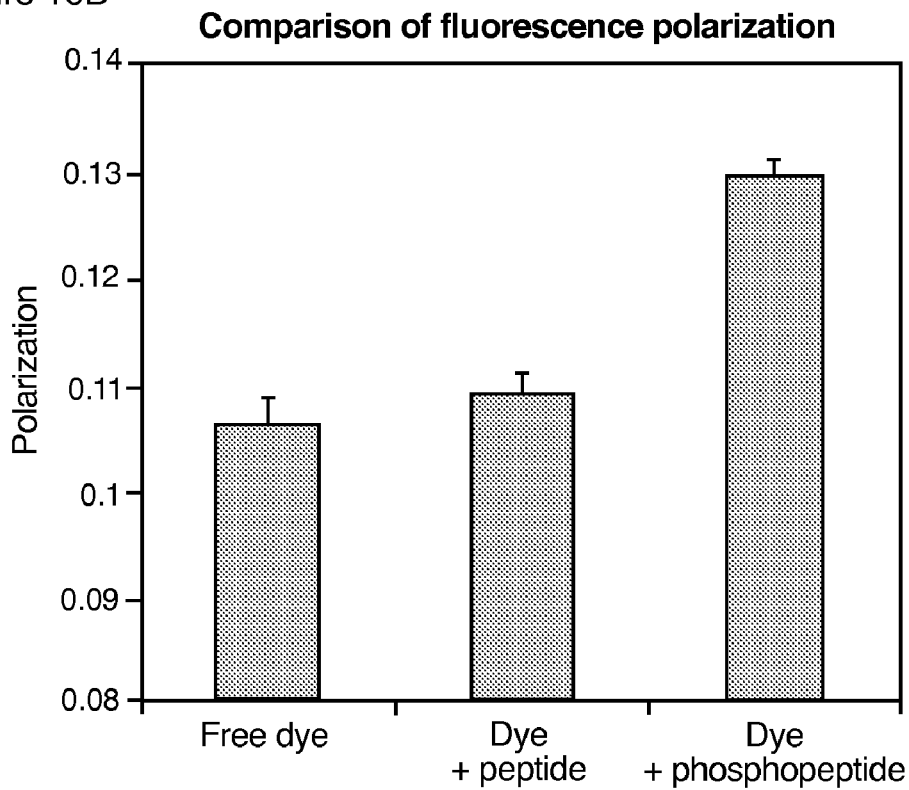

FIG. 10: Shows the detection of a (10A) phosphoprotein and (10B) phosphopeptide in solution by comparison of the polarization values with binding solution alone and binding solution with phosphorylated and non-phosphorylated protein or peptide, ovalbumin and delta sleep-inducing peptide, see Example 14. The binding solution alone and binding solution in the presence of non-phosphorylated protein or peptide demonstrates very similar fluorescence polarization and anisotropies. However, in the presence of the phosphoprotein or phosphopeptide, there is a significant increase in the fluorescence polarization values. This result demonstrates selective binding of the phosphoprotein and phosphopeptide to the Compound 2—$Ga^{3+}$ complex in solution but not to the non-phosphorylated protein or peptide.

Figure 11A:
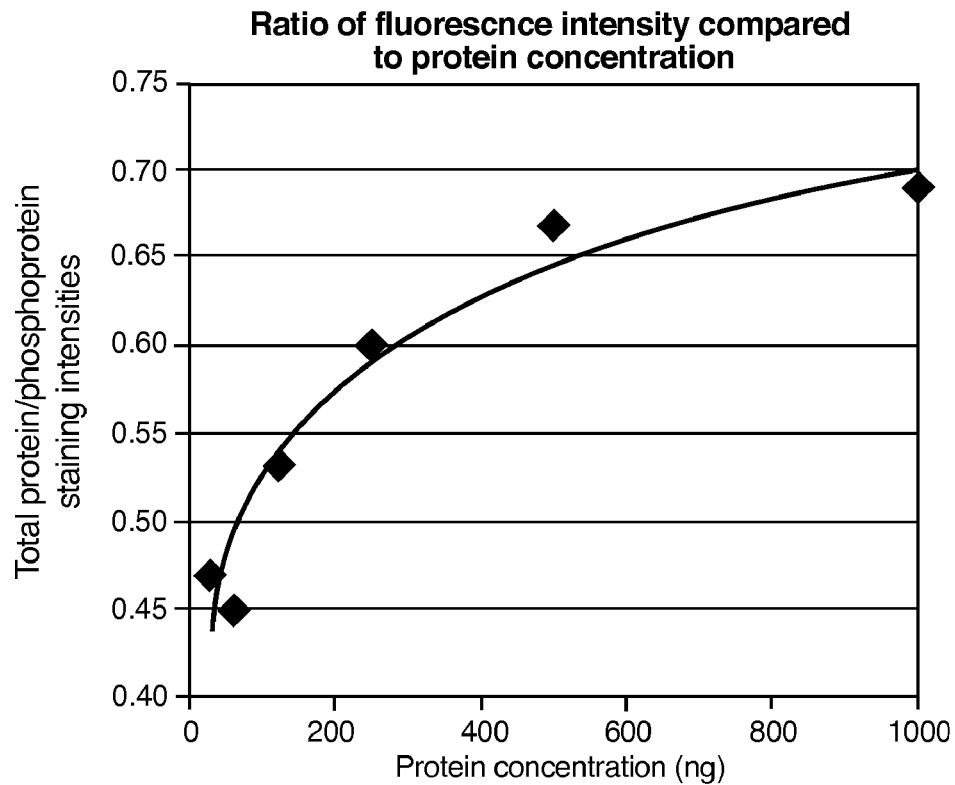
Figure 11B:
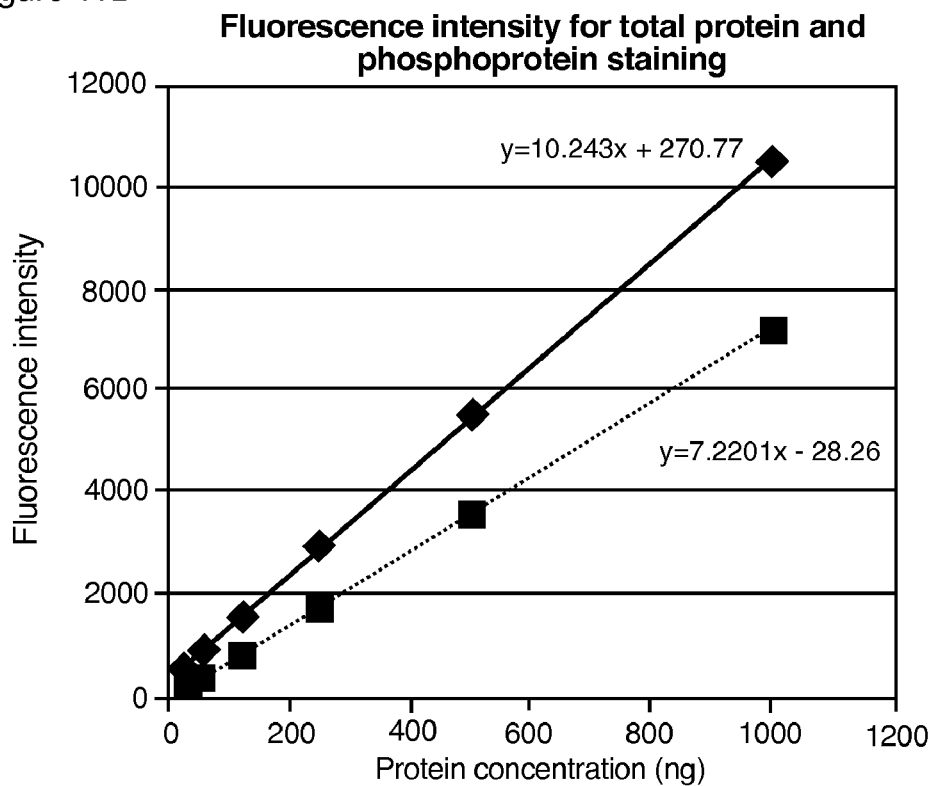
Figure 11C:
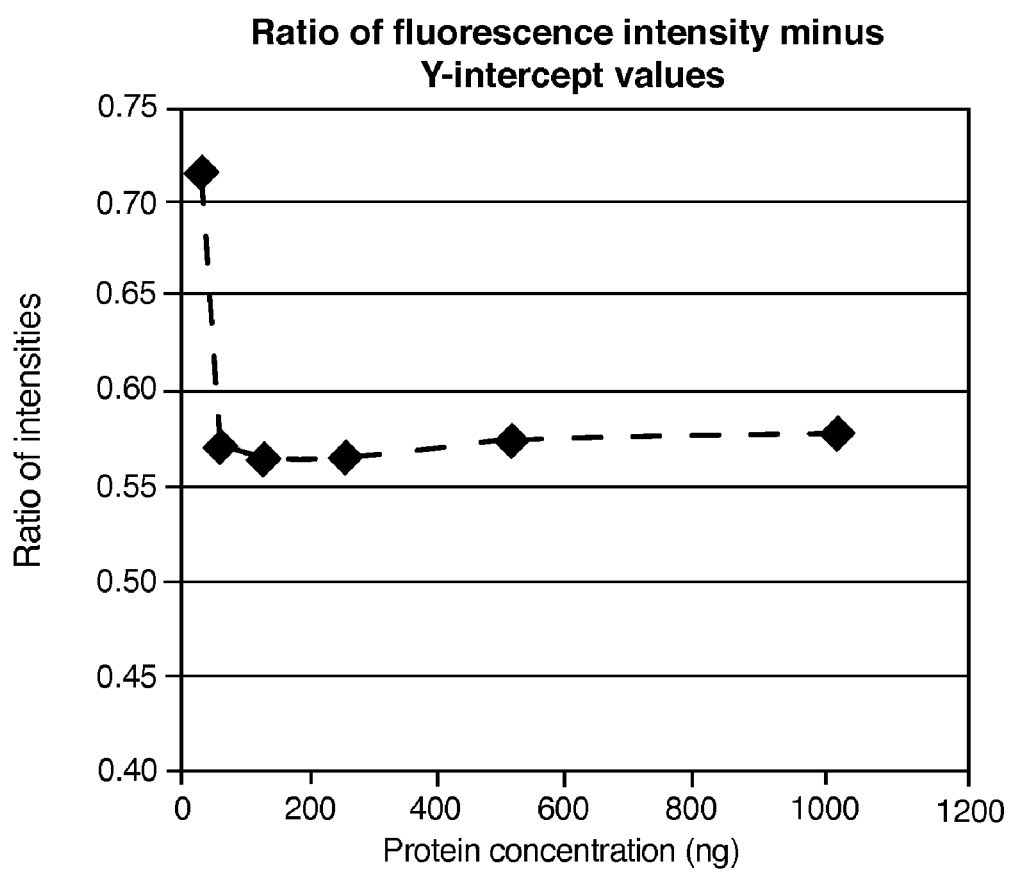

FIG. 11: Shows the ratiometric analysis of proteins labeled with a binding solution of the present invention and the SYPRO® Ruby protein gel stain, demonstrating that non-specific staining and low-abundance phosphoproteins can be distinguished from non-phosphorylated proteins, see Example 22. A protein mixture containing phosphorylated and non-phosphorylated proteins was separated on a polyacrylamide gel and the phosphoproteins were detected with a binding solution comprising Compound 2 and gallium chloride. All the proteins were detected when the gel was post-stained with SYPRO® Ruby protein gel stain. FIG. 11A) shows the ratio of fluorescence intensities for ternary complexes of phosphorylated proteins compared to total proteins. FIG. 11B) shows the fluorescence intensities of the phosphorylated protein complexes and total proteins plotted against the protein concentration, resulting in a constant Y-intercept value. FIG. 11C) shows the ratio of the Y-intercept values when plotted against the protein concentration resulting in phosphoproteins with a ratio value 50-100 times greater than that of the non-phosphorylated proteins.

Figure 12:
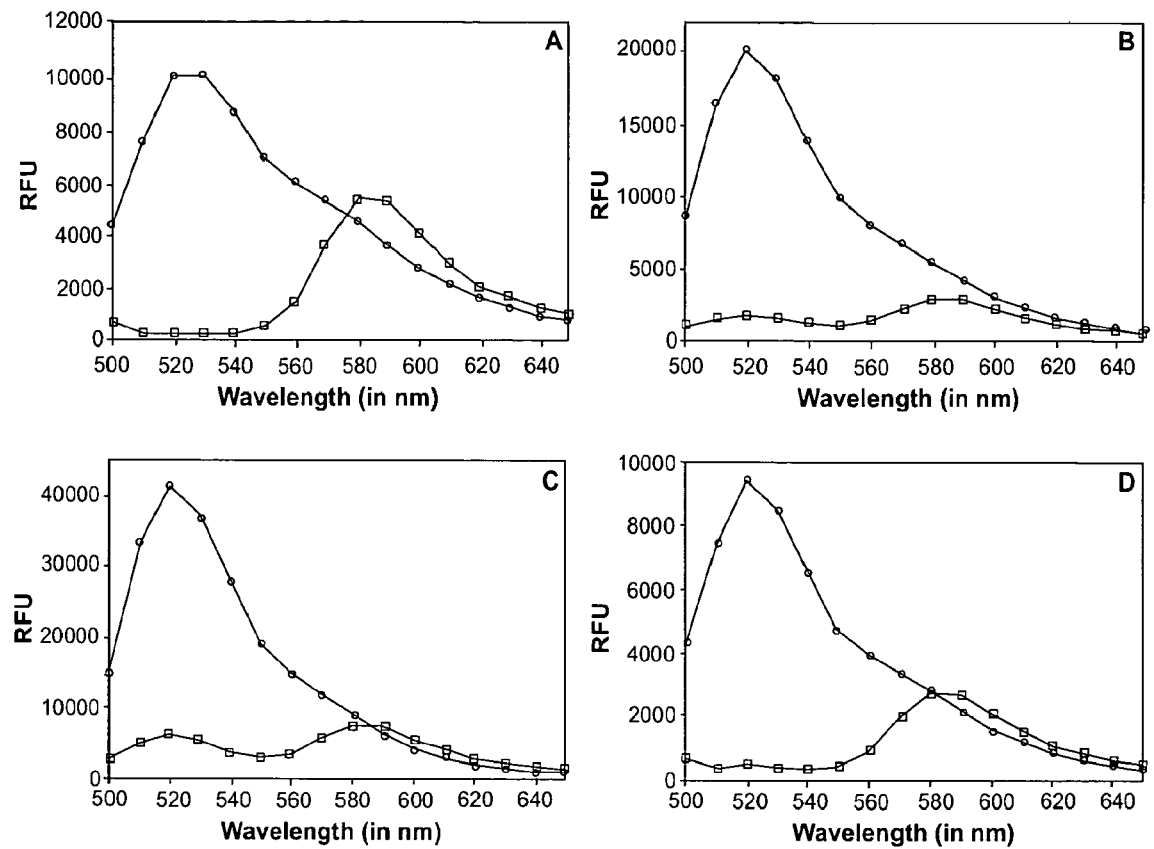

FIG. 12: Shows the ability to detect phosphorylated kinase substrate in solution when the kinase substrate is conjugated to either Oregon Green dye label or Alexa Fluor 488 dye label using Compound 2 as the phosphate-binding compound wherein the dye labels on the substrate are quenched when a ternary complex is formed with Compound 2 and $GaCl_3$. FIG. 12A, is pp60-Oregon Green 488 dye (OG); B, p-Abl-Oregon Green dye; C, pp60-Alexa Fluor 488 dye (A488); D, pStat3-Oregon Green dye label wherein the circles represent samples without $GaCl_3$ addition, and the squares represent samples with $GaCl_3$ addition.

DETAILED DESCRIPTION OF THE INVENTION

Introduction

The present invention provides phosphate-binding compounds, a phosphate-binding solution and methods for selectively detecting and/or isolating phosphorylated target molecules. The phosphate-binding compounds of the present invention, when present in the binding solution, selectively bind to phosphorylated target molecules and permit detection and/or isolation of the target molecules. The binding solution comprises three critical components for binding phosphorylated target molecules: 1) phosphate-binding compounds; 2) a salt comprising a metal ion and 3) an acid. The phosphate-binding compounds comprise a metal chelating moiety that is capable of binding the metal ion. Typically the phosphate-binding compounds are represent, but not limited, by the formula (A)m(L)n(B) wherein A is a chemical moiety, L is a linker, B is a metal-chelating moiety, m is an integer from 1 to 4 and n is an integer from 0 to 4.

The binding solution typically includes a buffering agent to maintain the acidic pH, which is ideally about pH 3 to about pH 6, and an organic solvent, wherein the use and solvent depends on the application and will be discussed below. The ternary complex that comprises the phosphate-binding compound, metal ion and phosphorylated target molecule is stable in an acidic environment but when the pH approaches neutral (pH 7) or basic (pH>7.0) the complex becomes increasingly unstable.

The binding solution is typically used to noncovalently attach a phosphate-binding compound, of the present invention to exposed phosphate groups on phosphorylated target molecules, wherein the phosphate-binding compound typically comprises a label. Alternatively, the binding solution is used to covalently attached a phosphate-binding compound to a phosphorylated target molecule wherein the present phosphate-binding compound comprises a reactive group that will form a covalent bond when brought within proximity to the phosphorylated target molecule. Because this is a highly directed covalent attachment, the reactive group is typically a photoactivatable group. These bound target molecules can be subsequently detected using one of the detection methods described herein or isolated by a number of methods described below. The metal ions of the binding solution simultaneously have affinity for both phosphate groups and the metal-chelating moiety of the phosphate-binding compounds of the invention when in an acidic environment.

Thus, a method of the present invention for the binding of phosphorylated target molecules by a phosphate-binding compound comprises the following steps:
  i) contacting the sample with a binding solution, and;
  ii) incubating the sample and the binding solution for sufficient time to allow said compound to associate with said phosphorylated target molecules, whereby said phosphorylated target molecule is bound.

The methods of the present invention can be used in unlimited assay formats, provided that there is sufficient contact between the sample and the binding solution. Therefore, this method is intended to cover an unlimited number of assays, in any format, wherein the binding solution of the present invention has contact with an exposed phosphate group on a target molecule, regardless of the intent of the assay. Thus, the methods of the present invention contemplate, without limit, the identification of phosphorylated target molecules, identification of dephosphorylated molecules, identification of enzymes responsible for phosphorylation or dephosphorylation, directly or indirectly, identification of molecules that interact with phosphorylated target molecules and isolation of phosphorylated target molecules. Detection includes—where practical—quantitation, discrimination and subsequent analysis and identification of the phosphorylated target molecules, with the use of standards and controls, as appropriate.

Definitions

Before describing the present invention in detail, it is to be understood that this invention is not limited to specific compositions or process steps, as such may vary. It must be noted that, as used in this specification and the appended claims, the singular form "a", "an" and "the" includes plural referents unless the context clearly dictates otherwise. Thus, for example, reference to "a phosphorylated protein" includes a plurality of proteins and reference to "a compound" includes a plurality of compounds and the like.

Unless defined otherwise, all technical and scientific terms used herein have the same meaning as commonly understood by one of ordinary skill in the art to which this invention is related. The following terms are defined for purposes of the invention as described herein.

The term "affinity" as used herein refers to the strength of the binding interaction of two molecules, such as a metal-chelating compound and a metal ion.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, Acc. Chem. Res. 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty-five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally be quaternized. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently.

The term "heteroaryl" as used herein refers to an aryl group as defined above in which one or more carbon atoms have been replaced by a non-carbon atom, especially nitrogen, oxygen, or sulfur. For example, but not as a limitation, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolinyl, indolizinyl, indazolyl, quinolizinyl, qunolinyl, isoquinolinyl, cinnolinyl, phthalazinyl, quinazolinyl, quinoxalinyl, pteridinyl, quinuclidinyl, carbazolyl, acridinyl, phenazinyl, phenothizinyl, phenoxazinyl, purinyl, benzimidazolyl and benzthiazolyl and their aromatic ring-fused analogs. Many fluorophores are comprised of heteroaryl groups and include, without limitations, xanthenes, oxazines, benzazolium derivatives (including cyanines and carbocyanines), borapolyazaindacenes, benzofurans, indoles and quinazolones.

The above heterocyclic groups may further include one or more substituents at one or more carbon and/or non-carbon atoms of the heteroaryl group, e.g., alkyl; aryl; heterocycle; halogen; nitro; cyano; hydroxyl, alkoxyl or aryloxyl; thio or mercapto, alkyl- or arylthio; amino, alkyl-, aryl-, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or arylsulfonyl; hydroximinyl, or aryl- or alkoximinyl. In addition, two or more alkyl substituents may be combined to form fused heterocycle-alkyl ring systems. Substituents including heterocyclic groups (e.g., heteroaryloxy, and heteroaralkylthio) are defined by analogy to the above-described terms.

The term "heterocycloalkyl" as used herein refers to a heterocycle group that is joined to a parent structure by one or more alkyl groups as described above, e.g., 2-piperidylmethyl, and the like. The term "heterocycloalkyl" refers to a heteroaryl group that is joined to a parent structure by one or more alkyl groups as described above, e.g., 2-thienylmethyl, and the like.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R, R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR' or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R', R', R" and R'" are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

The term "amino" or "amine group" refers to the group —NR'R" (or NRR'R") where R', R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "attachment site" as used herein refers to a site on a moiety or a molecule, e.g. a quencher, a fluorescent dye, an avidin, or an antibody, to which is covalently attached, or capable of being covalently attached, to a linker or another moiety.

The term "aqueous solution" as used herein refers to a solution that is predominantly water and retains the solution characteristics of water. Where the aqueous solution contains solvents in addition to water, water is typically the predominant solvent.

The term "BAPTA" as used herein refers to a metal-chelating compound that is 1,2-bis(2-aminophenoxy)ethane-N,N,N',N'-tetraacetic acid or its analogs, derivatives, ring-fused variants and conjugates, and all metallic and nonmetallic salts, partial salts and hydrates thereof, including any corresponding compounds disclosed in U.S. Pat. Nos. 4,603,209; 4,849,362; 5,049,673; 5,453,517; 5,459,276; 5,516,911; 5,501,980; 6,162,931 and 5,773,227 (supra). When used generically, "BAPTA" refers to two benzene rings that are joined by a C$_1$-C$_3$ hydrocarbon bridge terminated by oxygen atoms, including methylenedioxy (—OCH$_2$O—), ethylenedioxy (—OCH$_2$CH$_2$O—) or propylenedioxy (—OCH$_2$CH$_2$CH$_2$O—) bridging groups, where each benzene ring is optionally substituted by one or more substituents that adjust the metal ion-binding affinity, solubility, chemical reactivity, spectral properties or other physical properties of the compound. In a preferred embodiment of the present invention "BAPTA" is covalently attached to a chemical moiety A that, in combination with an appropriate trivalent metal ion and an acid, permits detection or isolation of phosphorylated target molecules as a ternary complex. BAPTA derivatives additionally include compounds in which the benzene rings of the BAPTA structure are substituted by or fused to additional aromatic, or heteroaromatic rings.

The term "biotin" as used herein refers to any biotin derivative, including without limitation, substituted and unsubstituted biotin, and analogs and derivatives thereof, as well as substituted and unsubstituted derivatives of caproylamidobiotin, biocytin, desthiobiotin, desthiobiocytin, iminobiotin, and biotin sulfone.

The term "biotin-binding protein" as used herein refers to any protein that binds selectively to biotin, including without limitation, antibodies to biotin, substituted or unsubstituted avidin, and analogs and derivatives thereof, as well as substituted and unsubstituted derivatives of antibodies, streptavidin, ferritin avidin, nitroavidin, nitrostreptavidin, Neutravidin™ avidin (a de-glycosylated modified avidin having an isoelectric point near neutral) and their dye-, enzyme-, or polymer-modified variants and immobilized forms of the biotin-binding proteins.

The term "buffer" as used herein refers to a system that acts to minimize the change in acidity or basicity of the solution against addition or depletion of chemical substances.

The term "carbonyl" as used herein refers to the functional group —(C=O)—. However, it will be appreciated that this group may be replaced with other well-known groups that have similar electronic and/or steric character, such as thiocarbonyl (—(C=S)—); sulfinyl (—S(O)—); sulfonyl (—SO$_2$—), phosphonyl (—PO$_2$—).

The term "carboxy" or "carboxyl" refers to the group —R' (COOR$^{13}$) where R' is alkyl, substituted alkyl, aryl, substituted aryl, arylalkyl, substituted arylalkyl, heteroaryl, or substituted heteroaryl. R$^{13}$ is hydrogen or a salt.

The term "chemical moiety A" or "chemical moiety" as used herein refers to the moiety that is covalently attached to the metal chelating compound according the Formula (A)m (L)n(B) to form a phosphate-binding compound of the present invention. The "chemical moiety A" includes a label, as defined below, that is a detectable moiety used to facilitate detection and isolation of phosphorylated target molecules. The term "chemical moiety A" is a natural or syntheic moiety that is typically a label but can also be, without limitation, a reactive group, typically a photoactivatable group or an amine reactive group such as succinimidyl ester that functions to covalently bind a polymer including agarose, acrylamide, microparticles, a protein such as an antibody or an antigen, a phosphate target molecule and a ligand, including those well known to one skilled in the art, to the phosphate-binding compounds of the present invention. In addition, the chemical moiety A can also be a metal-chelating moiety of the present invention, typically if a metal chelating moiety is attached to a phosphate-binding compound of the present invention it will be through a reactive group (conjugation reaction) however the metal chelating moiety could be covalently attached wherein a reactive group was not used and is connected by a linker to the phosphate-binding compound of the present invention.

The term "complex" as used herein refers to the association of two or more molecules, usually by non-covalent bonding, e.g., with a metal ion-chelator and a metal ion complexed with (i.e., noncovalently bound to) a protein or, for instance, of an antibody and antigen, enzyme and enzyme substrate, ligand and receptor (e.g. biotin and avidin), nucleic acid and its complementary strand, a protein with another protein or with a nucleic acid having affinity for the first protein, and the like.

The term "detectable response" as used herein refers to an occurrence of, or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of these parameters. Alternatively, the detectable response is an occurrence of a signal wherein the dye is inherently fluorescent and does not produce a change in signal upon binding to a metal ion or phosphorylated target molecule. Alternatively, the detectable response is the result of a signal, such as color, fluorescence, radioactivity or another physical property of the detectable label becoming spatially localized in a subset of a sample such as in a gel, on a blot, or an array, in a well of a micoplate, in a microfluidic chamber, or on a microparticle as the result of formation of a ternary complex of the invention that comprises a phosphorylated target molecule.

The term "directly detectable" as used herein refers to the presence of a detectable label or the signal generated from a detectable label that is immediately detectable by observation, instrumentation, or film without requiring chemical modifications or additional substances. For example, a fluorophore produces a directly detectable response.

The term "DTPA" as used herein refers to a metal chelating moiety diethylenetriamine pentaacetic acid or derivatives thereof and any corresponding moieties disclosed in U.S. Pat. Nos. 4,978,763 and 4,647,447. DTPA is represented by the formula (CH$_2$CO$_2$R$^{13}$)$_Z$N[(CH$_2$)$_S$N(CH$_2$CO$_2$R$^{13}$)]$_T$(CH$_2$)$_S$N(CH$_2$CO$_2$R$^{13}$)$_Z$ wherein the linker is attached to a methine carbon or nitrogen atom and Z is 1 or 2, S is 1 to 5, T is 0 to 4 and R$^{13}$ is hydrogen or a salt.

The term "dye" as used herein refers to a compound that emits light to produce an observable detectable signal. "Dye" includes fluorescent and nonfluorescent compounds that include without limitations pigments, fluorophores, chemiluminescent compounds, luminescent compounds and chromophores. The term "fluorophore" as used herein refers to a composition that is inherently fluorescent or demonstrates a change in fluorescence upon binding to a biological compound or metal ion, or metabolism by an enzyme, i.e., fluorogenic. Fluorophores may be substituted to alter the solubility, spectral properties or physical properties of the fluorophore. Fluorophores of the present invention are not sulfonated. Numerous fluorophores are known to those skilled in the art and include, but are not limited to benzofurans, quinolines, quinazolinones, indoles, benzazoles, borapolyazaindacenes and xanthenes, with the latter including fluoresceins, rhodamines and rhodols as well as other fluorophores described in RICHARD P. HAUGLAND, MOLECULAR PROBES HANDBOOK OF FLUORESCENT PROBES AND RESEARCH CHEMICALS (9$^{th}$ edition, including the CD-ROM, September 2002).

The term "energy transfer" as used herein refers to the process by which the excited state energy of an excited group, e.g. fluorescent reporter dye, is conveyed through space or through bonds to another group, e.g. a quencher moiety or fluorescer, which may attenuate (quench) or otherwise dissipate or transfer the energy to another reporter group or emit the energy at a longer wavelength. Energy transfer typically occurs through fluorescence resonance energy transfer (FRET).

The term "energy transfer pair" as used herein refers to any two moieties that participate in energy transfer. Typically, one of the moieties acts as a fluorescent reporter, i.e. donor, and the other acts as an acceptor, which may be a quenching compound or a compound that absorbs and re-emits energy in the form of a fluorescent signal ("Fluorescence resonance energy transfer." Selvin P. (1995) Methods Enzymol 246: 300-334; dos Remedios C. G. (1995) J. Struct. Biol. 115:175-185; "Resonance energy transfer: methods and applications." Wu P. and Brand L. (1994) Anal Biochem 218:1-13). Fluorescence resonance energy transfer (FRET) is a distance-dependent interaction between two moieties in which excitation energy, i.e. light, is transferred from a donor to an acceptor without emission of a photon. The acceptor may be fluorescent and emit the transferred energy at a longer wavelength, or it may be non-fluorescent and serve to diminish the detectable fluorescence of the reporter molecule (quenching). FRET may be either an intermolecular or intramolecular event, and is dependent on the inverse sixth power of the separation of the donor and acceptor, making it useful over distances comparable with the dimensions of biological macromolecules. Thus, the spectral properties of the energy transfer pair as a whole change in some measurable way if the distance between the moieties is altered by some critical amount. Self-quenching probes incorporating fluorescent donor-non-fluorescent acceptor combinations have been developed primarily for detection of proteolysis (Matayoshi, (1990) Science 247:954-958) and nucleic acid hybridization ("Detection of Energy Transfer and Fluorescence Quenching" Morrison, L., in Nonisotopic DNA Probe Techniques, L. Kricka, Ed., Academic Press, San Diego, (1992) pp. 311-352; Tyagi S. (1998) Nat. Biotechnol. 16:49-53; Tyagi S. (1996) Nat. Biotechnol 14:303-308). In most applications, the donor and acceptor dyes are different, in which case FRET can be detected by the appearance of sensitized fluorescence of the acceptor or by quenching of donor fluorescence.

The term "enzyme" as used herein refers to a protein molecule produced by living organisms, or through chemical modification of a natural protein molecule, that catalyzes a chemical reaction of other substances without itself being destroyed or altered upon completion of the reactions. Examples of other substances, include, but are not limited to chemiluminescent, chromogenic and fluorogenic substances or protein-based substrates.

The term "IDA" as used herein refers to imidodiacetic acid metal chelating moieties having the formula —N(CH$_2$CO$_2$R$^{13}$)$_2$ wherein R$^{13}$ is hydrogen or a salt and the linker is attached to the nitrogen atom provided that the linker is not a single covalent bond attached to an aromatic ring of a fluorophore.

The term "isolated" as used herein with reference to the subject peptides, proteins and protein complexes, refers to a preparation of a peptide, protein or protein ternary complex that is essentially free from contaminating nonphosphorylated peptides, proteins or other associated target molecules that normally would be present in association with the peptide, protein or complex, e.g., in a cellular mixture or milieu in which the protein or complex is found endogenously. In addition, in some embodiments, "isolated" also refers to the further separation from reagents of the invention used to isolate the peptide, protein or complex from cellular mixture. Thus, an isolated protein or protein complex is separated (isolated) from other components of the sample and optionally from the phosphate-binding compounds of the invention (including polymeric matrices) that normally would "contaminate" or interfere with the study or further processing of the complex in isolation, such as by mass spectrometry. The term "isolated" can also refer to phosphorylated target molecules that are spatially or temporally separated from each other such as by different physical locations on a gel or array or by having different passage times through a detector such as in a column or capillary.

The term "kit" as used herein refers to a packaged set of related components, typically one or more compounds or compositions, optionally comprising buffers, separation media, standards, software and other components.

The term "label" as used herein refers to a detectable moiety that is used to facilitate detection and isolation of phosphorylated target molecules in combination with the metal-chelating moieties of the present invention. Illustrative labels include labels that can be directly observed or measured or indirectly observed or measured such as fluorophores, radioactive and enzyme reporter labels (Patton, W., et al, J. Chromatography B: Biomedical Applications (2002) 771:3-31; Patton, W., et al, Electrophoresis (2000) 21:1123-1144). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example or metal particles, e.g. gold or silver particles or metallic bar codes that can be detected by their optical or light-scattering properties. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag", hapten or other ligand that can bind selectively to a labeled molecule such that the labeled molecule, when added subsequently, is used to generate a detectable signal. For example, one can use biotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex® Red reagent (Molecular Probes, Inc.) to detect the presence of HRP. Numerous labels and tags and methods for their selective detection are known by those of skill in the art and include, but are not limited to, particles, fluorophores, haptens, enzymes and their chromogenic, fluorogenic and chemiluminescent substrates and other labels that are described in the MOLECULAR PROBES HANDBOOK, supra. In addition, present labels can be substituted with substitutents that alter the ion-binding affinity of the phosphate binding compound, solubility, chemical reactivity, spectral properties or other physical properties of the label provided that the label is not sulfonated.

The term "Linker" or "L", as used herein, refers to a single covalent bond or a series of stable covalent bonds incorporating 1-30 nonhydrogen atoms selected from the group consisting of C, N, O, S and P that covalently attach the phosphate-binding compounds to another moiety such as a chemically reactive group or a phosphorylated target molecule. Exemplary linking members include a moiety that includes —C(O) NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a label or phosphorylated target molecule, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

The term "metal chelator" or "metal-chelating moiety" as used herein refers to a chemical moiety that combines with a metal ion to form a chelate ring structure. For the purposes of the present invention the metal chelator has affinity for a metal ion that has simultaneous affinity for the metal chelator and a phosphate target molecule in a moderately acidic environment. Examples of metal-chelating moieties include, but are not limited to, BAPTA, IDA, DTPA and phenanthroline. The metal chelators are optionally substituted by substituents that adjust the ion-binding affinity, solubility, chemical reactivity, spectral properties or other physical properties of the compound provided that the metal chelator is not sulfonated.

The term "metal ion" as used herein refers to any trivalent metal ion that has simultaneous affinity for a phosphate group of a target molecule and a metal-chelating compound of the invention at pH 3 to 6 and that can be used to form a ternary complex of the phosphate-binding compound and the phosphorylated target molecule. Such metal ions include, without limitation, $Al^{3+}$, $Fe^{3+}$ and $Ga^{3+}$. For purposes of the present invention, the metal ion must have simultaneous affinity for both the metal-chelating moiety and phosphate groups of the target molecule and, as such, confers affinity to the metal-chelating moiety for the phosphate groups of the target molecule that would not be present without the metal ion.

The term "phosphate-binding compound" or "binding compound" as used herein refers to a compound that is capable of binding a metal ion wherein the metal ion has simultaneous affinity for a phosphorylated target molecule. Such phosphate-binding compounds are typically represented by, but not limited to, the formula $(A)m(L)n(B)n$ wherein A is a chemical moiety, L is a linker, B is metal-chelating moiety, m is an integer from 1 to 4 and n is an integer from 0 to 4. These compounds effectively, but non-covalently, attach a label to a phosphorylated target molecule when the metal-chelating moiety indirectly binds phosphate groups on the target molecule.

The terms "phosphorylated target molecule" or "phosphate target molecule" as used herein refers to a molecule possessing one or more phosphate or phosphate analog moieties each attached to such molecule by a single ester bond or inorganic phosphate. Phosphate analogs include, without limitation, thiophosphate, boraphosphate, phosphoramide, H-phosphonate, alkylphosphonate, phosphorothioate, phosphorodithioate and phosphorofluoridate. Phosphorylated target molecules include, but are not limited to, phosphoproteins, phosphopeptides, phospholipids, phosphoglycans, phosphocarbohydrates, phosphoamino acids, pyrophosphate and inorganic phosphate and their thiophosphate analogs. Most known phosphate compounds, and subsequently the phosphorylated target molecules, can be categorized into one of three groups; 1) individual phosphate groups (e.g., inorganic phosphate or a phosphate group ($PO_3$) on a protein or peptide); 2) multiple-linked phosphate group (e.g., pyrophosphate or a nucleotide such as ATP); or 3) bridging phosphate group (i.e., nucleic acids). For the purposes of the present invention, phosphorylated target molecules do not include molecules in the third group, e.g., DNA or RNA. Typically, phosphoproteins and phosphopeptides are phosphorylated post-translationally on the tyrosine, serine or threonine amino acid residues. Other phosphorylated amino acid residues in peptides and proteins include 1-phospho-histidine, 3-phospho-histidine, phospho-aspartic acid, phospho-glutamic acid and less commonly $N^{\epsilon}$-phospho-lysine, $N^{\omega}$-phospho-arginine and phospho-cysteine (Kaufmann, et al (2001) Proteomics 1: 194-199; Yan, J., Paxker, N., Gooley, A. and Williams, K. (1998) J. Chromatograph. A 808: 23-41). Thus, a phosphorylated protein or peptide typically comprises at least one of these amino acid residues. Phosphorylated target molecules also include phosphorylated proteins that incorporate other non-peptide regions such as lipids or carbohydrates, e.g., lipoproteins and lipopolysaccharides. In addition, the lipid or carbohydrate residues of the proteins can be phosphorylated instead or in combination with the tyrosine, serine or threonine amino acid residues of the proteins and peptides such as a phosphomannose-modified or N-acetylglucosamine-1-phosphate modified protein. Other modifications include a pyridoxal phosphate Schiff base to the epsilon-amino group of lysine, and an O-pantetheine phosphorylation of serine residue. The gamma phosphate of nucleotide triphosphates is also detectable using the methods of this invention, making photolabeled proteins and peptides detectable by this procedure. For the purposes of the present invention phosphorylated target molecules include phosphorylated lipids and carbohydrates.

The term "photoactivatable reactive group" as used herein refers to a chemical moiety that becomes chemically active by exposure to an appropriate wavelength, typically a UV wavelength. Once activated the reactive group is capable of forming a covalent bond with a proximal moiety on a biological or non-biological component. In the instant case, the phosphate-binding compounds may contain a photoactivatable group that can form a covalent bond with a phosphorylated target molecule when brought within proximity by the formation of the ternery complex and activated by an appropriate wavelength. Photoactivatable groups include, but are not limited to, benzophenones, aryl azides and diazirines.

The terms "protein" and "polypeptide" are used herein in a generic sense to include polymers of amino acid residues of any length. The term "peptide" is used herein to refer to polypeptides having less than 100 amino acid residues, typically less than 15 amino acid residues. The terms apply to amino acid polymers in which one or more amino acid residues is an artificial chemical analogue of a corresponding naturally occurring amino acid, as well as to naturally occurring amino acid polymers. The peptide or protein may be further conjugated to or complexed with other moieties such as dyes, haptens, radioactive isotopes, natural and synthetic polymers (including microspheres), glass, metals and metallic particles, proteins and nucleic acids.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as a photoactivatable group, carboxylic acid or succinimidyl ester, on the compounds of the present invention that is capable of chemically reacting with a functional group on a different compound to form a covalent linkage resulting in a phosphate-binding labeled component. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "sample" as used herein refers to any material that may contain phosphorylated target molecules, natural or synthetic, as defined above, or contains components that directly interact with phosphate or phosphorylated target molecules, such as enzymes. Typically, the sample comprises purified or semi-purified phosphorylated target molecules and endogenous host cell proteins. The phosphorylated target molecules can be made synthetically or obtained in a purified or semi-purified form from cells (eukaryotic and prokaryotic, without limitation) cell extracts, cell homogenates, subcellular components as natural or recombinant molecules. Alternatively, phosphorylated target molecules can be obtained from tissue homogenate, bodily and other biological fluids, or synthesized proteins, all of which comprise a sample in the present invention. The sample may be in an aqueous or mostly aqueous solution, a viable cell culture or immobilized on a solid or semi solid surface such as a polymer gel, a membrane, a microparticle, an optical fiber or on a microarray. In addition "sample" as use herein also refers to substrates for kinases or phosphatases or molecules that bind phosphorylated target molecules that may or may not be phosphorylated. In this way the sample comprises components that interact with phosphate and phosphorylated target molecules, particularly including antibodies to either the phosphorylated target molecules or to other regions of the target molecule or, for instance, complexes of biotinylated target molecules with an avidin derivative.

The term "ternary complex" as used herein refers to a composition that simultaneously comprises a phosphate-binding compound, a trivalent metal ion of the present invention and a phosphate target molecule, wherein the metal ions simultaneously have affinity for both the metal-chelating moiety of the compound and the phosphate group on the molecule, and wherein the metal ion forms a bridge between the two molecules. Unless limited by the context of their use, the terms "binding" and "complex formation" in this invention mean the process of formation of this ternary complex.

The Phosphate-Binding Compounds

In general, for ease of understanding the present invention, the phosphate-binding compounds and components of the binding solution will first be described in detail, followed by the many and varied methods in which the phosphate-binding compounds and metal ions find uses, which is followed by exemplified methods of use and synthesis of certain novel compounds that are particularly advantageous for use with the methods of the present invention.

The phosphate-binding compounds of the present invention are characterized as being capable of binding to a trivalent metal ion that has simultaneously affinity for a phosphorylated target molecule to form a ternary complex. Thus, any metal chelating moiety that is capable of binding a trivalent metal ion wherein the metal ion has affinity for a phosphorylated target molecule is contemplated and considered part of the present invention. For detection, isolation and quantification purposes the metal chelating moiety is typically covalently attached to a reactive group or a label that typically a dye, a hapten or an enzyme, wherein the reactive group or label are collectively defined herein as "chemical moiety A".

Thus, the present phosphate-binding compounds are typically represented by, but not limited to, the formula (A)(B) wherein A is the chemical moiety and B is the metal chelating moiety. More typically, the present phosphate-binding compounds are represented by the formula (A)m(L)n(B), wherein A is a chemical moiety and L is a linker that covalently attaches the chemical moiety to the metal-chelating moiety (B) and m and n are individually integers between 0 and 4. The metal-chelating moiety is dictated by metal ions that have affinity for phosphate and phosphate analog groups; such ions include, but are not limited to, $Ga^{3+}$, $Fe^{3+}$ and $Al^{3+}$. It was found that for purposes of the present invention trivalent gallium ions when in a moderately acidic environment, e.g. between about pH 3 and about pH 6, have affinity for phosphate groups on target molecules and certain chelating groups such as BAPTA, IDA, DTPA and phenanthroline; BAPTA chelating moieties are the most preferred.

Metal Chelating Moieties

The metal-chelating moieties are moieties characterized as being capable of simultaneously binding metal ions that have affinity for exposed phosphate groups on target molecules, wherein a ternary complex is formed between the metal-chelating moiety, the metal ion and the phosphorylated target molecule. Metal ions that have been found to bind phosphate groups include, without limitation, trivalent gallium, iron and aluminum. Metal-chelating moieties that bind these ions, under certain conditions, include, without limitation, BAPTA, IDA, DTPA and phenanthrolines. Thus, the metal-chelating moieties must 1) bind metal ions that have affinity for phosphate groups, 2) not interfere with the binding of the metal ion for the phosphate groups and 3) maintain a stable ternary complex. Exemplary metal-chelating moieties that fit these three criteria include BAPTA, IDA, DTPA and phenanthrolines.

BAPTA, as used herein, refers to analogs, including fluorescent and nonfluorescent derivatives, of the metal-chelating moiety (1,2-bis(2-aminophenoxy)ethane-N,N,N'N'-tetraacetic acid) and salts thereof including any corresponding compounds disclosed in U.S. Pat. Nos. 4,603,209; 4,849,362; 5,049,673; 5,453,517; 5,459,276; 5,516,911; 5,501,980; and 5,773,227. These BAPTA-based metal-chelating moieties are well known to those skilled in the art, primarily as calcium indicators due to their ability to bind divalent calcium ions under physiological conditions, i.e. a pH of about 7 and free calcium ion concentrations near the micromolar and submicromolar range. As calcium indicators these compounds are typically used in live cells wherein the indicators are derivatized on a carboxylic group to comprise at least one lipophilic group or specifically an acetoxymethyl (AM) ester group, wherein AM ester is represented as —$CH_2OCOCH_3$, to produce cell permeant derivatives of the indicators.

However, we found that calcium is a totally ineffective metal ion for practice of the methods of the present invention to detect phosphorylated target molecules described in this invention with these indicators.

For the sake of clarity the following structure represents preferred present BAPTA metal-chelating moieties having Formula IV:

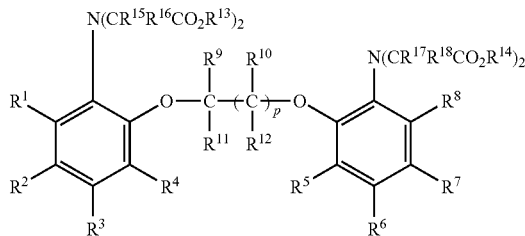

Preferably the two rings are linked by a hydrocarbon bridge between two oxygen atoms in which p is 0, 1 or 2 and the ring substituents ($R^1$—$R^3$) are selected independently from the group consisting of hydrogen, halogen, hydroxyl, alkoxy, alicyclic, heteroalicyclic, alkyl, aryl, amino, aldehyde, carboxyl, nitro, cyano, thioether, sulfinyl and linker (L). Alternatively, two adjacent ring substituents in combination constitute a cyclic substituent that is cycloalkyl, cycloheteroalkyl, aryl, fused aryl, heteroaryl or fused heteroaryl. Preferably, the BAPTA metal-chelating moieties have at least two substituents that are not hydrogen, a most preferred BAPTA metal-chelating moiety is substituted by a fluorine atom as one of the substituents, most preferably substituted at the $R^6$ or $R^3$ position (e.g., Compounds 1, 2, 5, 7, 8 and 12). Typically the linker attaching the chemical moiety to the BAPTA is at the $R^3$ or $R^6$ position. Equally preferred are BAPTA metal-chelating moieties that comprise a carbonyl group as a substituent, preferably at the $R^7$ position, e.g., Compounds 9 and 12. Without being bound by a particular theory, it appears that an electron withdrawing group such as fluorine or carbonyl substituted at the $R^3$, $R^4$, $R^6$ or $R^7$ position results in BAPTA chelating moieties that are particularly advantageous for chelating trivalent gallium ions that also allows for the simultaneous interaction of the chelated gallium ion with an exposed phosphate group on the phosphorylated target molecules, resulting in a stable ternary complex.

The bridge substituents $R^9$, $R^{10}$, $R^{11}$ and $R^{12}$, are independently selected from the group consisting of hydrogen, lower alkyl, or adjacent substituents $R^9$ and $R^{10}$, taken in combination, constitute a 5-membered or 6-membered alicyclic or heterocyclic ring. $R^{15}$, $R^{16}$, $R^{17}$ and $R^{18}$ are independently H or lower alkyl; preferably $R^{15}$, $R^{16}$, $R^{17}$ and $R^{18}$ are all hydrogen. $R^{13}$ and $R^{14}$ are independently hydrogen or a salt.

It is understood that the chemical moieties of the present invention are attached to the BAPTA metal-chelating moiety by a linker at any of $R^1$—$R^{12}$ or alternatively the dye label comprises one of the aromatic rings of the metal-chelating moieties wherein no linker is present. Therefore, two adjacent substituents of $R^1$—$R^{12}$, when taken in combination with each other, and with the aromatic ring to which they are bound, comprise a fluorophore or chromophore label. However, a phosphate-binding compound could have more than one linker, such that a dye label is attached with no linker and four other linkers are present on the metal chelating compound to attach other labels or reactive groups. In one aspect of the invention, two adjacent ring substituents ($R^1$—$R^4$ or $R^5$—$R^3$) taken in combination form the dye label that is a fused benzofuran or heteroaryl- or carboxyheteroaryl-substituted benzofuran fluorophore. Where the dye label is fused to the compound of the invention, it is preferably fused between $R^2$ and $R^3$, or between $R^5$ and $R^7$.

Xanthene derivative dyes are particularly useful dyes of the present invention wherein, either or both of the benzene rings of the BAPTA or substituted BAPTA metal-binding compound is bonded to a xanthene ring through a single chemical bond, as in the common $Ca^{2+}$ indicators fluo-3, fluo-4 and rhod-2 (U.S. Pat. No. 5,049,673, supra) or through the intermediacy of a phenyl or substituted phenyl spacer as in the Oregon Green® BAPTA indicators (U.S. Pat. No. 6,162,931, supra). The xanthene rings are typically bonded to the BAPTA at positions para to the nitrogen functions of the BAPTA. Particularly preferred are xanthene-containing BAPTA derivatives whose fluorophore is a rhodamine or a halogenated fluorescein. Particularly preferred are fluorescent BAPTA derivatives in which the 5-position of the BAPTA chelator is substituted by F, including rhod-5F and fluo-5F.

DTPA, as used herein, refers to diethylenetriamine pentaacetic acid chelating moieties and derivatives thereof, including any corresponding compounds disclosed in U.S. Pat. Nos. 4,978,763 and 4,647,447. DTPA metal-chelating moieties are represented by Formula V comprising $(CH_2CO_2R^{13})_Z N[(CH_2)_S N(CH_2CO_2R^{13})]_T (CH_2)_S N(CH_2CO_2R^{13})_Z$, wherein a linker is attached to a methine carbon or nitrogen atom, Z is 1 or 2, S is 1 to 5, T is 0-4 and $R^{13}$ is independently a hydrogen or a salt.

IDA, as used herein, refers to iminodiacetic acid compounds and derivatives thereof and is represented by Formula VI comprising -(L)-$N(CH_2CO_2R^{13})_2$ wherein $R^{13}$ is independently a hydrogen or a salt and provided that said linker is not a single covalent bond. The IDA metal-chelating moieties must be attached by a linker to a chemical moiety wherein the linker comprises at least one nonhydrogen atom. Without wishing to be bound by a theory, it appears that the linker increases the stability of the ternary complex and possibly tunes the affinity of the metal-chelating moiety for a metal ion of the present invention.

In addition to the above mentioned specific metal chelating moieties we have also found that phenanthroline based chelators also form ternary complex with metal ions and phosphate target molecules in a moderately acidic environment.

Phenanthroline, as used herein, refers to 1,10-phenanthroline compounds and derivatives thereof and is represented by the structure

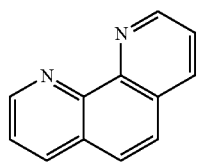

Any of the aromatic carbon atoms may be substituted with substituents well known to one skilled in the art, including those substituents disclosed in U.S. Pat. No. 6,316,267, supra. Alternatively, a linker can be attached to any of the aromatic carbon atoms to covalently attach a chemical moiety A to the phenanthroline moiety to form the phosphate-binding compounds of the present invention.

Labels

In certain embodiments, the present phosphate-binding compounds comprise a label that is covalently bonded to a present metal chelating moiety. The present labels are characterized as being any label known to one skilled in the art and when the label is either covalently linked to a metal-chelating moiety or comprises part of the metal-chelating moiety wherein no linker is present, forms a present phosphate-binding compound. Labels include, without limitation, a chromophore, a fluorophore, a fluorescent protein, a phosphorescent dye, a tandem dye (energy transfer pair), a microparticle, a polymer, a hapten, an enzyme and a radioisotope. Preferred labels include dyes, fluorescent proteins, haptens, and enzymes. The covalent linkage can be a single covalent bond or a combination of stable chemical bonds. The covalent linkage binding the label to the metal-chelating moiety is typically a single covalent bond, but can also be a substituted alkyl chain that incorporates 1-30 nonhydrogen atoms, or a substituted cycloalkyl, selected from the group consisting of C, N, O, S and P.

A dye of the present invention is any chemical moiety that exhibits an absorption maximum beyond 280 nm, that when part of a phosphate-binding compound retains its unique spectral properties to provide a detectable signal. The preferred dyes are fluorophores or chemiluminescence precursors that are directly detectable or that upon action of an additional reagent or reagents yield fluorescence or chemiluminescence.

Dyes of the present invention include, without limitation; a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine including any corresponding compounds in U.S. Ser. Nos. 09/968,401 and 09/969,853 and U.S. Pat. Nos. 6,403,807 and 6,348,599), a carbocyanine (including any corresponding compounds in U.S. Ser. No. 09/557,275 and U.S. Pat. Nos. 5,486,616; 5,268,486; 5,569,587; 5,569,766; 5,627,027 and 6,048,982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896, supra), a xanthene (including any corresponding compounds disclosed in U.S. Pat. Nos. 6,162,931; 6,130,101; 6,229,055; 6,339,392; 5,451,343 6,221,606; 6,358,684; 6,008,379; 6,111,116; 6,184,379; 6,017,712; 6,080,852; 5,847,162 and U.S. Ser. No. 09/922,333) an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including any corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the dye is a xanthene, the dye is optionally a fluorescein, a rhodol (including any corresponding compounds disclosed in U.S. Pat. Nos. 5,227,487 and 5,442,045), a rhodamine (including any corresponding compounds in U.S. Pat. Nos. 5,798,276 and 5,846,737). As used herein, rhodamine and rhodol dyes include, among other derivatives, compounds that comprise xanthenes with saturated or unsaturated "julolidine" rings. As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171).

Preferred dyes of the present invention include benzofurans, quinolines, quinazolinones, xanthenes, indoles, benzazoles and borapolyazaindacenes. Preferred xanthenes include julolidine-containing xanthenes, as well as fluoresceins, rhodols, rhodamines and rosamines. Xanthenes of this invention comprise both compounds substituted and unsubstituted on the carbon atom of the central ring of the xanthene by substituents typically found in the xanthene-based dyes such as phenyl and substituted-phenyl moieties. It is an important aspect of the current invention that none of the preferred fluorescent dyes are sulfonated.

Alternatively, the dye is a xanthene that is bound via an L that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Typically the dye contains one or more aromatic or heteroaromatic rings that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on dyes known in the art.

In one aspect of the invention, the dye has an absorption maximum beyond 480 nm. In a particularly useful embodiment, the dye absorbs at or near 488 nm to 514 nm (particularly suitable for excitation by the output of the argon-ion laser excitation source) or near 546 nm (particularly suitable for excitation by a mercury arc lamp). As is the case for many dyes, they can also function as both chromophores and fluorophores, resulting in compounds that simultaneously act both as colorimetric and fluorescent labels for phosphorylated target molecules. Thus, the described fluorescent dyes are also the preferred chromophores of the present invention.

In addition to dyes, enzymes also find use as labels for the phosphate-binding compounds having the formula $(A)_m(L)_n(B)$. Enzymes are desirable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, calorimetric or luminescent signal. Enzymes amplify the detectable signal because one enzyme on a labeling compound can result in multiple substrate molecules being converted to a detectable signal. This is advantageous where there is a low quantity of phosphorylated target molecules present in the sample or a fluorophore does not exist that will give comparable or stronger signal than the enzyme. Fluorophores are most preferred because they do not require additional assay steps that can lead to an unstable ternary complex. The enzyme substrate is selected to yield the preferred measurable product, e.g. color, fluorescence or chemiluminescence. Such substrates are extensively used in the art, many of which are described in the MOLECULAR PROBES HANDBOOK, supra.

A preferred calorimetric or fluorogenic substrate and enzyme combination uses oxidoreductases such as horseradish peroxidase (HRP) and a substrate such as 3,3'-diaminobenzidine (DAB) or 3-amino-9-ethylcarbazole (AEC), which yield a distinguishing color (brown and red, respectively). Other calorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid and 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042) and reduced dihydroxanthenes, including dihydrofluoresceins (U.S. Pat. No. 6,162,931) and dihydrorhodamines, including dihydrorhodamine 123. Peroxidase substrates that are tyramides (U.S. Pat. Nos. 5,196,306; 5,583,001 and 5,731,158) represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

Another preferred colorimetric (and in some cases fluorogenic) substrate and enzyme combination uses a phosphatase enzyme such as an acid phosphatase or a recombinant version of such a phosphatase in combination with a colorimetric substrate such as 5-bromo-4-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912), fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates (U.S. Pat. Nos. 5,316,906 and 5,443,986).

Glycosidases, in particular β-galactosidase, β-glucuronidase and β-glucosidase, are additional suitable enzymes. Appropriate colorimetric substrates include, but are not limited to, 5-bromo-4-chloro-3-indolyl β-D-galactopyranoside (X-gal) and similar indolyl galactosides, glucosides, and glucuronides, o-nitrophenyl β-D-galactopyranoside (ONPG) and p-nitrophenyl β-D-galactopyranoside. Preferred fluorogenic substrates include resorufin β-D-galactopyranoside, fluorescein digalactoside (FDG), fluorescein diglucuronide and their structural variants (U.S. Pat. Nos. 5,208,148; 5,242, 805; 5,362,628; 5,576,424 and 5,773,236), 4-methylumbelliferyl β-D-galactopyranoside, carboxyumbelliferyl β-D-galactopyranoside and fluorinated coumarin β-D-galactopyranosides (U.S. Pat. No. 5,830,912).

Additional enzymes include, but are not limited to, hydrolases such as cholinesterases and peptidases, oxidases such as glucose oxidase and cytochrome oxidases and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful. Several chemiluminescent substrates for phosphatase enzymes are known, including the BOLD APB chemiluminescent substrate (Molecular Probes, Inc.).

In addition to enzymes, haptens such as biotin, digoxigenin and 2,4-dinitrophenyl are also preferred labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently, a peroxidase substrate is added to produce a detectable signal. For isolation purposes, a protein such as avidin that has affinity for biotin is conjugated to agarose beads. The biotin-labeled metal-chelating moiety, after contacting a phosphorylated target molecule, is then incubated with the avidin beads, on a column, bound to a magnetic particel or in solution, to separate and/or concentrate the phosphorylated target molecules. A preferred form of biotin is the desthiobiotin analog, which can be easily adsorbed and released from avidin-based affinity matrices. A preferred form of avidin for some applications is CaptAvidin biotin-binding protein (Molecular Probes), which permits facile release of biotinylated compounds.

Haptens also include, among other derivatives, hormones, naturally occurring and synthetic drugs, pollutants, allergens, affector molecules, growth factors, chemokines, cytokines, lymphokines, amino acids, peptides, chemical intermediates, nucleotides and the like.

Fluorescent or lumescent proteins also find use as labels for the phosphate-binding compounds of the present invention. Examples of fluorescent proteins include green-fluorescent protein (GFP), acquorin and the phycobiliproteins and the derivatives thereof. The fluorescent proteins, especially phycobiliproteins, are particularly useful for creating tandem dye-labeled labeling reagents or for indirect detection of hapten-labeled labeling compounds or phosphorylated target molecules that are immobilized on a matrix, such as a microsphere or an array. These tandem dyes comprise a fluorescent protein and a fluorophore for the purposes of obtaining a larger Stokes shift, wherein the emission spectra are farther shifted from the wavelength of the fluorescent protein's absorption spectra. This property is particularly advantageous for detecting a low quantity of a target molecule in a sample wherein the emitted fluorescent light is maximally optimized; in other words, little to none of the emitted light is reabsorbed by the fluorescent protein. For this to work, the fluorescent protein and fluorophore function as an energy transfer pair wherein the fluorescent protein emits at the wavelength that the acceptor fluorophore absorbs and the fluorophore then emits at a wavelength farther from the fluorescent proteins than could have been obtained with only the fluorescent protein. Alternatively, the fluorophore functions as the energy donor and the fluorescent protein is the energy acceptor. Particularly useful fluorescent proteins are the phycobiliproteins disclosed in U.S. Pat. Nos. 4,520,110; 4,859, 582; 5,055,556 and the fluorophore bilin protein combinations disclosed in U.S. Pat. No. 4,542,104. Alternatively, two or more fluorophore dyes can function as an energy transfer pair wherein one fluorphore is a donor dye and the other is the acceptor dye (including any dye compounds disclosed in U.S. Pat. Nos. 6,358,684; 5,863,727; 6,372,445 and 5,656,554).

Reactive Groups

Selected phosphate-binding compounds of the invention include one or more reactive groups within their structure. The reactive group provides a locus for attaching a metal chelating moiety to another species, generally referred to herein as a "component" of a conjugate. Exemplary components include biological or non-biological molecules, linkers, solid supports, phosphorylated target molecules and the like. The reactive group reacts with a functional group of complementary reactivity at the "attachment site" of the component of the conjugate. The reaction leads to the formation of a covalent linkage between the metal chelating moiety of the phosphate-binding compound and the component of the conjugate.

Therefore, these reactive groups function to attach a biological or non-biological component to the metal chelating moiety or are used to form a covalent attachment between the present chelating moieties and the phosphorylated target molecules. Such components include solid and semi-solid matrices such as polymeric particles (in particular polystyrene microspheres of a diameter less that about 16 microns), magnetic particle, polymeric membranes and glass. These substances are particularly useful when an assay is utilized wherein the phosphate-binding compound is immobilized, such as for isolation purposes or when a further assay is conducted directly on an immobilized phosphorylated target molecules, as described in this invention.

In addition, any biological component can be covalently attached by way of reactive groups to the phosphate-binding compound; these include but are not limited to, proteins, peptides, saccharides and polysaccharides, nucleic acids (including nucleotides and nucleosides), amino acids, organelles, cells and cellular extract components.

Therefore, the phosphate-binding compounds of the present invention can also comprise reactive groups, such as an amine-reactive group, for the covalent attachment of the phosphate-binding compound to a matrix, microparticle, a phosphate target molecule or directly to a biological component. Thus, when the ternary complex comprising the phosphate-binding compound, metal ion and phosphorylated target molecules forms, the reactive groups can form an additional covalent bond with the phosphorylated target molecule. This effectively increases the complex's stability and allows for more stringent isolation and analysis of phosphorylated target molecules, including being able to maintain the complex's integrity above the moderately acidic pH range.

Typically, covalent attachment of the phosphate-binding compound to a molecule is the result of a chemical reaction between an electrophilic group and a nucleophilic group. However, in a preferred embodiment, when a reactive group is used that is photoactivated, the covalent attachment results when the binding solution is illuminated. This is particularly advantageous to ensure that only phosphorylated target molecules form a covalent attachment to the binding compounds of the present invention. Photoactivatable reactive groups include, without limitation, benzophenones, aryl azides and diazirines. Exemplary phosphate-binding compounds comprising a photoactivatable group include Compounds 34, 36, 39, 42 and 44.

Typically, the conjugation reaction between the reactive group and the component to be conjugated results in one or more atoms of the reactive group to be incorporated into a new linkage attaching the compound or reagents of the invention to the biological or non-biological component. Selected components include, without limitation, these other molecules include without limitation, labels, biological components (proteins, nucleic acid,), non-biological components including microparticles, plastic such as microplate wells, polymers such as PVDF, nitrocellulose, polysaccharides in particular agarose, dextrans and cellulose including any compounds disclosed in U.S. Pat. No. 5,453,517.

Selected examples of nucleophile, electrophiles and resulting covalent linkages are shown in Table 1.

TABLE 1

Examples of some routes to useful covalent linkages with electrophile and nucleophile reactive groups

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Preferred reactive groups incorporated into the compounds of the invention react with an amine, a thiol or an alcohol. In one embodiment, the reactive group is a photoactivatable group, an acrylamide, an activated ester of a carboxylic acid, an acyl azide, an acyl nitrile, an aldehyde, an alkyl halide, an amine, an anhydride, an aniline, an aryl halide, an aryl azide, an azide, an aziridine, a benzophenone, a boronate, a carboxylic acid, a diazoalkane, a diazirine, a haloacetamide, a halotriazine, a hydrazine, an imido ester, an isocyanate, an isothiocyanate, a maleimide, a phosphoramidite, a sulfonyl halide, or a thiol group.

Where the reactive group is an activated ester of a carboxylic acid, the resulting compound is particularly useful for preparing conjugates of proteins, nucleic acids, e.g., nucleotides and oligonucleotides, or haptens. Where the reactive group is a maleimide or haloacetamide the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation or forms the substrate of a microarray or biochip. Where the reactive group is a photoactivatable group (benzophenone, aryl azide or diazirine) the resulting phosphate-binding compound is particularly useful for conjugation to phosphorylated target molecules, See Example 50.

Preferably, the reactive group is a photoactivatable group, a succinimidyl ester of a carboxylic acid, a haloacetamide, a hydrazine, an isothiocyanate, a maleimide group, an aliphatic amine, a silyl halide, or a psoralen. More preferably, the reactive group is a photoactivatable group, a succinimidyl ester of a carboxylic acid, a maleimide, an iodoacetamide, or a silyl halide.

Linkers

In an exemplary embodiment, the compounds of the present invention that include a reactive group or label further comprise a linker. The linker serves to covalently attach the reactive group or label to the metal chelating moiety of the phosphate-binding compound. When present, the linker is a single covalent bond or a branched- or straight-chain, saturated or unsaturated chain of atoms. Examples of L include substituted or unsubstituted polyalkylene, arylene, alkylarylene, arylenealkyl, or arylthio.

In certain embodiments, no linker is present when the phosphate-binding compounds comprise a label. In this instance the label and the metal-chelating moiety share an aromatic ring, e.g., benzofuran and BAPTA. Thus, when the label and chelating moiety share an aromatic ring no linker is present and n of the formula (A)m(L)n(B) is 0. A preferred embodiment, when the metal chelating moiety comprise a label, is phosphate-binding compounds wherein no linker is present; however, linkers as single covalent bonds are equally preferred.

Thus, the label or reactive group may be directly attached (where Linker is a single bond) to the present compounds or attached through a series of stable bonds. When the linker is a series of stable covalent bonds the linker typically incorporates 1-30, more preferably 1-20, and most preferred 1-15 non-hydrogen atoms selected from the group consisting of C, N, O, S and P. In addition, the covalent linkage can incorporate a platinum atom, such as described in U.S. Pat. No. 5,714,327.

The linker may be any combination of chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Exemplary components of the linker include ether, thioether, thiourea, amine, ester, carboxamide, sulfonamide, hydrazide bonds and aromatic or heteroaromatic bonds.

An exemplary linker is a combination of single carbon-carbon bonds and carboxamide, sulfonamide or thioether bonds. The bonds of the linker typically result in the following moieties being in the linker: ether, thioether, carboxamide, thiourea, sulfonamide, urea, urethane, hydrazine, alkyl, aryl, heteroaryl, alkoxy, cycloalkyl and amine moieties.

Any combination of linkers may be present in the present phosphate-binding compounds. An exemplary compound of the present invention, when attached to more than one label, reactive group or a combination thereof will have one or two linkers attached that may be the same or different. The linker may also be substituted to alter a physical property of the present compounds, such as affinity, hydrophilicity, solubility and spectral properties of the compound.

Selected examples of phosphate-binding compounds incorporate the following three (I, II and III) Linker formulas: Formula (I) $-(CH_2)_eC(X)NH(CH_2)_e(NHC(X)(CH_2)_e)_d-$ and Formula (II) $-((C_6R''_4)O)_d(CH_2)_e(C(X)NH(CH_2)_e)_g(NH)_dC(X)NH(C_6R''_4)(CH_2)_e-$, Formula (III) $-(NHC(X)(NH)_d(CH_2)_e(NH)_dC(X)(NH)_d(CH_2)_e(NHC(X)(CH_2)_e)_d)-$, wherein X is O or S, d is 0-1, e is 0-6, g is 1-4 and R'' is independently H, halogen, alkoxy or alkyl. It is understood that X, d, e and g are independently selected within a linker.

Thus, a selected embodiment of the present invention is the following phosphate-binding compound formulas (VII, VIII, IX, X and XI): Formula (VII) (A)(B), no linker; Formula (VIII) (A)-(n)(B), linker is a single covalent bond; Formula (IX) (A)-$[(CH_2)_eC(X)NH(CH_2)_e(NHC(X)(CH_2)_e)_d]$-(B); Formula (X) (A)-$[(C_6R''_4)O)_d(CH_2)_e(C(X)NH(CH_2)_e)_g(NH)_dC(X)NH(C_6R''_4)(CH_2)_e]$-(B) and Formula (XI) (A)-$[NHC(X)(NH)_d(CH_2)_e(NH)_dC(X)(NH)_d(CH_2)_e(NHC(X)(CH_2)_e)_d]$—(B), wherein A is a chemical moiety and B is a metal-chelating moiety.

Any combination of linkers may be used to attach the chemical moiety and the metal-chelating moiety together. In addition, a metal-chelating moiety may have more than one linker that is used to attach either another label, such as an energy transfer pair, or an additional substance such as agarose, a microparticle or a reactive group that functions to attach the linker to the additional substance or to the phosphorylated target molecule. A preferred embodiment includes a metal-chelating moiety attached to a label, with or without a linker, and also attached to a reactive group, a phosphorylated target molecule, a non-biological component or a biological component. The linker may also be substituted to alter the physical properties of the phosphate-binding compound, such as binding affinity of the metal-chelating moiety and spectral properties of the dye, or substituted with an amine- or thiol-reactive group.

Another important feature of the linker is to provide an adequate space between the chemical moiety A and the chelating moiety B so as to prevent the chemical moiety from providing a steric hindrance to the binding of the metal ion for the binding domain of the metal-chelating moiety and the binding of the metal ion for the phosphorylated target molecule. It is appreciated that not all chemical moieties will provide a steric hindrance, as a preferred embodiment of the present invention is a metal-chelating moiety that comprises a dye label without a linker. However, some labels such as biotin and reactive groups are typically attached to the metal-chelating moiety by a linker. Therefore, the linkers of the present phosphate-binding compounds are important for (1) attaching the chemical moiety A to the metal-chelating moiety, (2) providing an adequate distance between the chemical moiety and the metal-chelating moiety so as not to sterically hinder the affinity of the metal-chelating moiety and a phosphate group on a target molecule and (3) for altering the affinity of the metal-chelating moiety for the phosphorylated target molecule either by the choice of the atoms of the linker or indirectly by addition of substituents to the linker.

The metal-chelating moieties of the present invention typically contain 1) no linker, 2) a single covalent bond as a linker, 3) a linker of Formula I, 4) a linker of Formula II, 5) a linker of Formula III or a combination thereof. However, it is appreciated that a wide variety of linkers that do not fall within the scope of these formulas are also useful as linkers of the phosphate-binding compounds. These options can be present individually or in any combination, as embodied by the formula (A)m(L)n(B), on the metal-chelating moiety to attach chemical moieties A such as labels or reactive groups to form the phosphate-binding compounds of the present invention.

Synthesis

The synthetic strategy of phosphate-binding compounds that provide optimal signals after formation of a ternary complex involves selection of appropriate chemical linkages between the chemical moieties A and the metal-chelating moiety, and also selection of appropriate substituents on the metal-chelating moiety. These selections are made such that the resulting phosphate-binding compound retains optimal simultaneous binding affinity for both the metal and of the metal for the phosphorylated target molecules and sufficient solubility to promote a persistent ternary complex. Improper selections result in phosphate-binding compounds that do not have sufficient binding affinity and do not produce a persistent ternary complex. Improper selections also result in excessive non-selective binding of the phosphate-binding compound to analytes other than the phosphorylated target compounds, resulting in a high background and thus a low signal-to-noise ratio. Compounds that are suitable for practice of the invention are best screened by the method in Example 1D.

We have discovered that BAPTA derivatives are particularly suitable for practice of the various aspects of the invention, although other metal chelating moieties under appropriate conditions are equally preferred. The novel phosphate-binding compounds of the present invention whose synthesis and use is illustrated in examples include BAPTA chelating moieties with a quinazolinone fluorescent dye (Compounds 6, 7 and 23), BAPTA chelating moieties with a borapolyazaindacene fluorescent dye (Compounds 8, 24 and 27a-f), BAPTA chelating moieties with a xanthene based dye (Compounds 11, 19, 26 and 25) BAPTA chelating moieties with a biotin label, wherein the biotin is attached by a linker (Compounds 9, 12, 15 and 18), BAPTA chelating moieties with a benzothiazole label (Compound 17), BAPTA chelating moieties with agarose covalently attached (Compounds 13 and 14), BAPTA compounds comprising an aniline attached by a linker to the BAPTA compound (Compound 10) and BAPTA chelating moieties with a label and a photoactivatable reactive group (Compounds 34, 36, 39, 42 and 44). Novel compounds also include borapolyazaindacene fluorophore labels attached by a linker to DTPA chelating moieties (Compounds 20, 21 and 22). These novel phosphate-binding compounds find use in the detection and isolation of phosphorylated target molecules. Synthesis of these compounds is exemplified in Examples 30-48 and 52-56.

The phosphate-binding compounds of the present invention exhibit sufficient noncovalent binding affinity for the gallium (III)-phosphorylated target molecule complex to allow for rinsing away of excess reagents from the persistent ternary complex. Additionally, it was found that certain phosphate-binding compounds provided optimal signal after formation of the ternary complex and are thus more environmentally sensitive. This high signal appears to be a function of well-tuned hydrophobicity of the phosphate-binding compound-gallium (III)-phosphorylated target molecule complex. Therefore, when a detectable response is desirable, e.g., labeling phosphorylated target molecules in solution, and where the detectable response is a fluorescence response, it is typically a change in fluorescence, such as a change in the intensity, excitation or emission wavelength distribution of fluorescence, fluorescence lifetime, fluorescence polarization, or a combination thereof. Typically this change in fluorescence is a result of energy transfer between a first and second fluorophore wherein an energy transfer pair is employed, one attached to the chelating moiety and the other attached to a phosphorylated molecule, resulting in a shifted wavelength or quenching of the fluorescent signal. Preferably, when energy transfer is not employed, the detectable optical response upon binding the gallium ion and the phosphorylated target molecule to the chelator is a change in fluorescence intensity that is greater than approximately 2-fold.

However, for applications wherein the phosphorylated target molecule or phosphate-binding compound is immobilized—resulting in an immobilized ternary structure—an increase in detectable fluorescence response due to the chelation of the metal-chelating moiety and subsequent ternary complex formation may not be necessary. This is due to the stable ternary complex, which allows for washing and removal of unbound phosphate-binding compounds wherein the fluorescence response from the phosphate-binding compound is sufficient to visualize the phosphorylated target molecule. Therefore, a preferred embodiment in this situation is a phosphate-binding compound that undergoes little or no change in fluorescence when bound to a metal ion of the present invention and a phosphorylated target molecule.

The combination of metal-chelating moieties, labels and or reactive groups provides phosphate-binding compounds that are either environmentally sensitive (i.e., that produce a fluorescence change upon simultaneously binding a metal ion and the phosphorylated target molecules to form a ternary complex) or insensitive (i.e., that produces no change in fluorescence signal). The most preferred fluorescent dyes of the present invention for generating a strong detectable signal and facilitating formation of the ternary complex include benzofuran, quinoline, quinazolone, xanthene, benzazole, and borapolyazaindacene compounds including various derivatives thereof. These fluorescent dyes produce a strong detectable signal when the dye comprises a metal-chelating moiety. It is an important aspect of the current invention that none of the preferred fluorescent dyes are sulfonated.

TABLE 2

| Compound number | Phosphate-binding compound | Properties |
|---|---|---|
| Compound 1 | 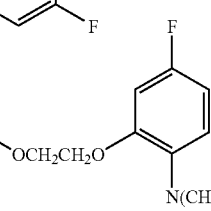 | The fluorophore is a fluorinated xanthene (fluorescein) derivative and the metal-chelating moiety is a BAPTA compound (Formula IV) that is fluorinated at the $R^6$ position. The linker is a single covalent bond. The counterion is $K^+$. |
| Compound 2 | 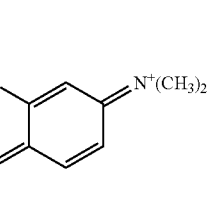 | The fluorophore is a xanthene (rhodamine) derivative and the metal-chelating moiety is a BAPTA compound (Formula IV) that is fluorinated at the $R^6$ position. The linker is a single covalent bond. The counterion is $K^+$. |
| Compound 3 | 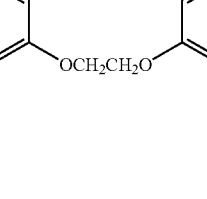 | The fluorophore is a xanthene (rhodamine) derivative and the metal-chelating moiety is a BAPTA compound (Formula IV). The linker is a single covalent bond. The counterion is $K^+$. |
| Compound 4 | 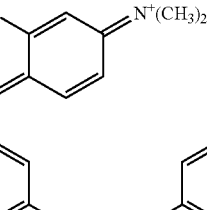 | The fluorophore is a benzofuran that shares an aromatic ring with the metal-chelating moiety (Formula IV) and comprises a substituted heteroaryl moiety. The metal-chelating moiety, BAPTA, is fluorinated at the position. The phosphate-binding compound does not comprise a linker. The counterion is $K^+$. |

TABLE 2-continued

| Compound number | Phosphate-binding compound | Properties |
|---|---|---|
| Compound 5 | 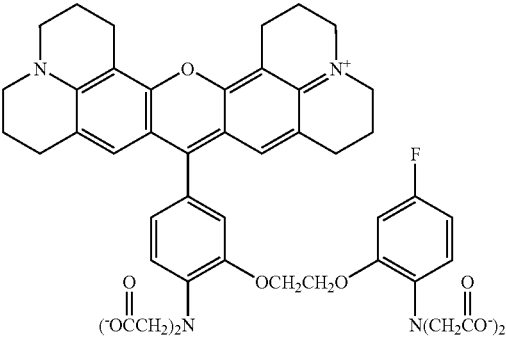 | The fluorophore is a xanthene (rhodamine) derivative and the metal-chelating moiety is a BAPTA compound (Formula IV) that is fluorinated at the $R^6$ position. The linker is a single covalent bond. The counterion is $K^+$. |
| Compound 6 | 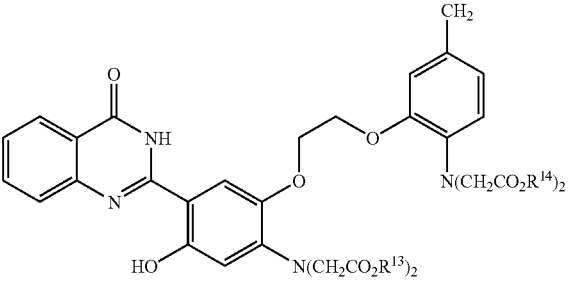 | The fluorophore is a quinazolinone with an adjacent hydroxyl group on the metal-chelating moiety (BAPTA, Formula IV). $R^{13}$ and $R^{14}$ are independently hydrogen or a salt and the linker is a single covalent bond. |
| Compound 7 | 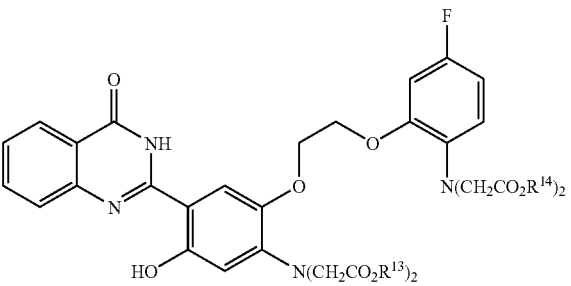 | The fluorophore is a quinazolinone with an adjacent hydroxyl group on the metal-chelating moiety (BAPTA, Formula IV). The metal-chelating moiety is fluorinated at the $R^6$ position and $R^{13}$ and $R^{14}$ are independently hydrogen or a salt. The linker is a single covalent bond. |
| Compound 8 | 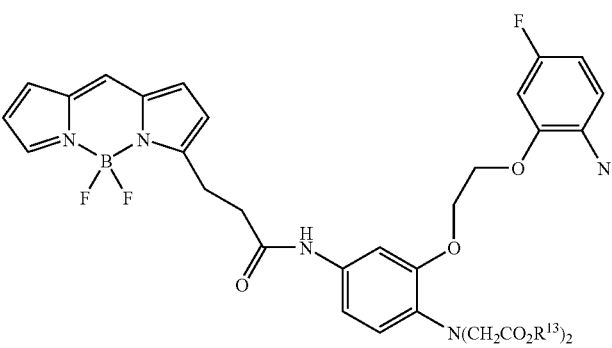 | The fluorophore is a borapolyazaindacene and the metal-chelating moiety is a BAPTA compound (Formula IV). The metal-chelating moiety is fluorinated at the $R^6$ position and $R^{13}$ and $R^{14}$ are independently hydrogen or a salt. The linker is represented by Formula I. |

TABLE 2-continued

| Compound number | Phosphate-binding compound | Properties |
|---|---|---|
| Compound 9 | 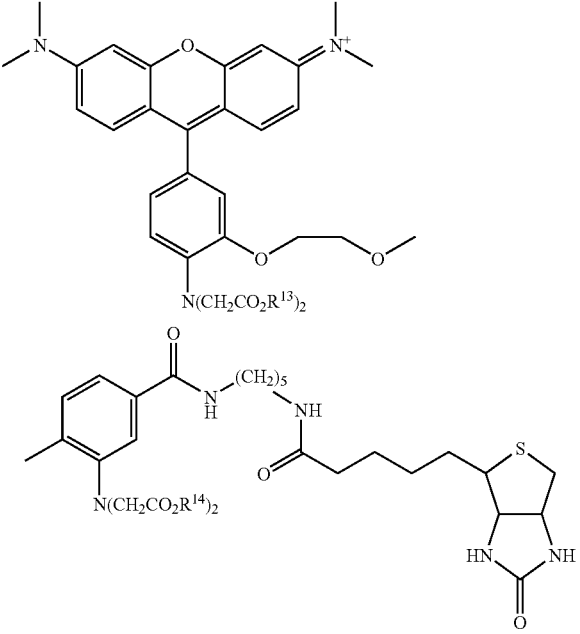 | The fluorophore is a xanthene (rhodamine) derivative and the metal chelating moiety is a BAPTA compound (Formula IV), wherein $R^{13}$ and $R^{14}$ are independently hydrogen or a salt. The linker attaching the fluorophore to the BAPTA compound is a single covalent bond. A second linker at $R^7$ (Formula I) covalently attaches a biotin label to the phosphate-binding compound. |
| Compound 10 | 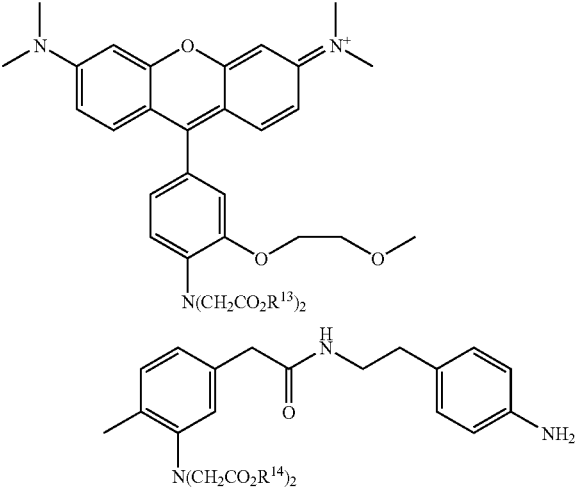 | The fluorophore is a xanthene (rhodamine) derivative that is attached by a single covalent bond linker to the metal-chelating moiety (BAPTA, Formula IV), wherein $R^{13}$ and $R^{14}$ are independently hydrogen or a salt. A second linker (Formula I) at $R^7$ attaches an aniline moiety. |
| Compound 11 | 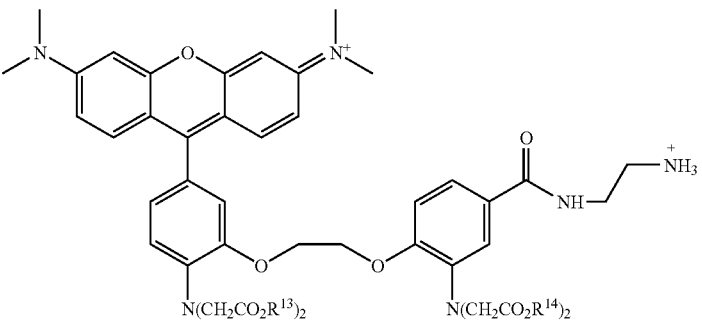 | The fluorophore is a xanthene (rhodamine) derivative that is attached to the metal-chelating moiety (BAPTA, Formula IV) by a single covalent bond, wherein $R^{13}$ and $R^{14}$ are independently hydrogen or a salt. A second linker (Formula I) at $R^7$ attaches an amine group. |

TABLE 2-continued

| Compound number | Phosphate-binding compound | Properties |
|---|---|---|
| Compound 12 | 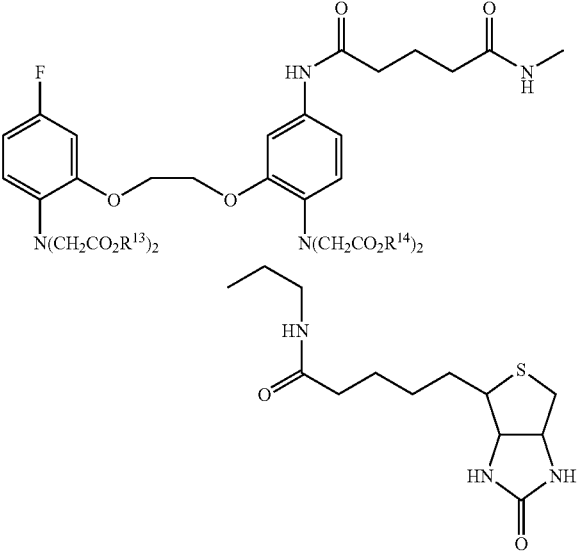 | The label is a biotin that is attached to the metal-chelating moiety (BAPTA, Formula IV) by a linker (Formula III). The metal-chelating moiety is fluorinated at the $R^3$ position and $R^{13}$ and $R^{14}$ are independently hydrogen or a salt. |
| Compound 13 | 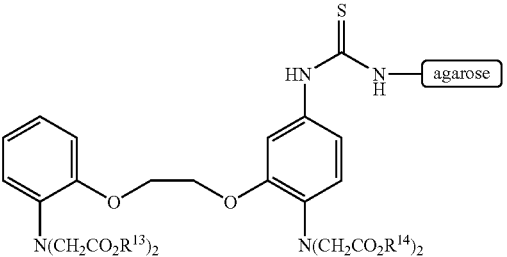 | The metal-chelating moiety (BAPTA, Formula IV) is attached to agarose by a linker, wherein $R^{13}$ and $R^{14}$ are independently hydrogen or a salt. |
| Compound 14 | 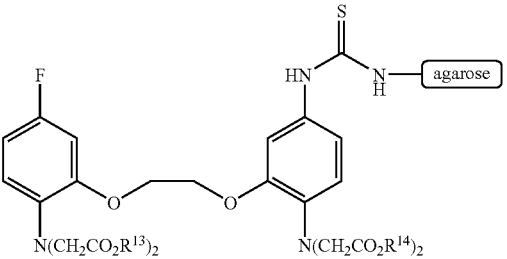 | The metal-chelating moiety (BAPTA, Formula IV) is attached to agarose by a linker, wherein $R^{13}$ and $R^{14}$ are independently hydrogen or a salt and the metal-chelating moiety is fluorinated at the $R^3$ position. |

TABLE 2-continued

| Compound number | Phosphate-binding compound | Properties |
|---|---|---|
| Compound 15 | 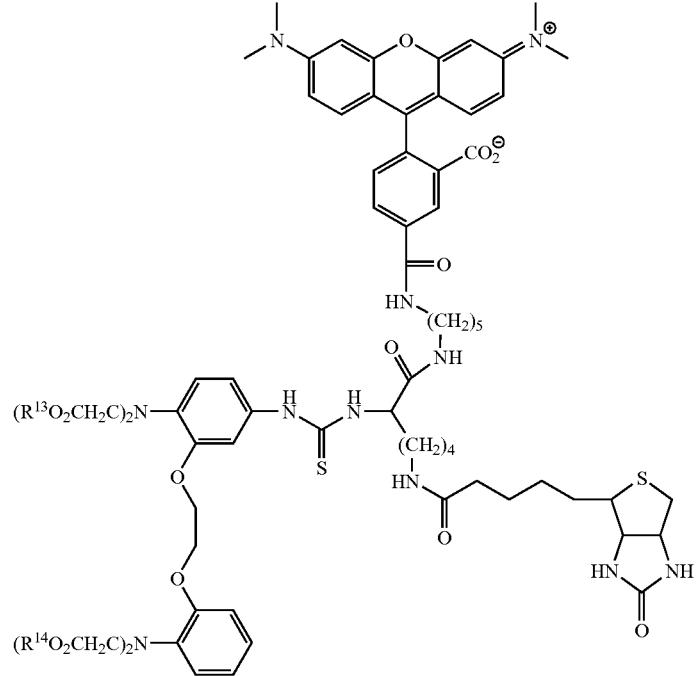 | The metal-chelating moiety (BAPTA, Formula IV) is simultaneously attached to biotin and a xanthene (rhodamine) derivative fluorophore, both by a linker represented by Formula III. $R^{13}$ and $R^{14}$ are independently hydrogen or a salt. |
| Compound 16 | 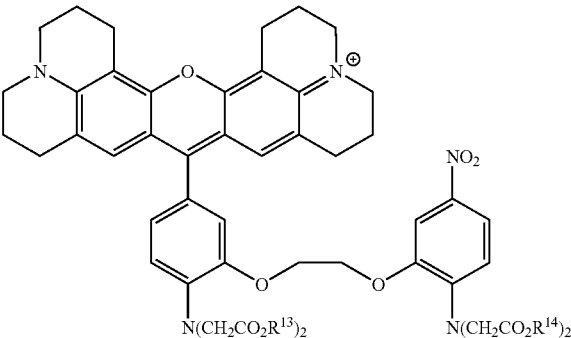 | The metal-chelating moiety (BAPTA, formula IV) is attached by a single covalent bond to a xanthene (rhodamine) derivative. $R^{13}$ and $R^{14}$ are independently hydrogen or a salt. |

TABLE 2-continued

| Compound number | Phosphate-binding compound | Properties |
|---|---|---|
| Compound 20 | 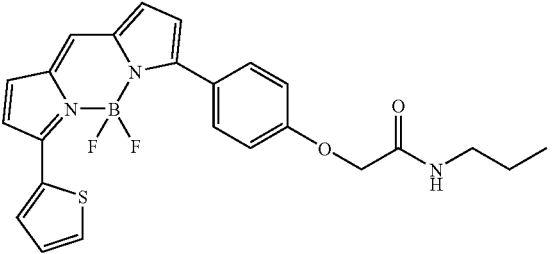 | The dye is a borapolyazaindacene that is attached to the metal-chelating moiety (DTPA, Formula V) by a linker (Formula II). The dye is substituted by a thienyl group. The counterion is K⁺. |
| Compound 21 | 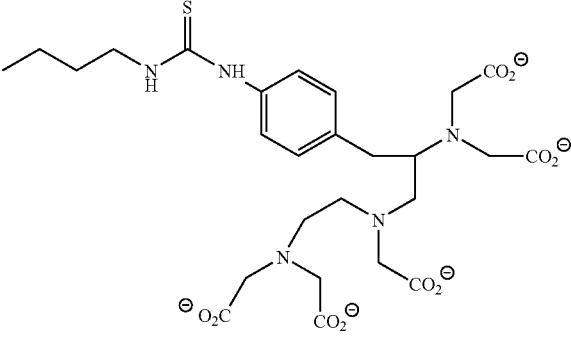 | The dye is a borapolyazaindacene that is attached to a metal-chelating moiety (DTPA, Formula V) by a linker (Formula II). The counterion is K⁺. |

TABLE 2-continued

| Compound number | Phosphate-binding compound | Properties |
|---|---|---|
| Compound 22 | 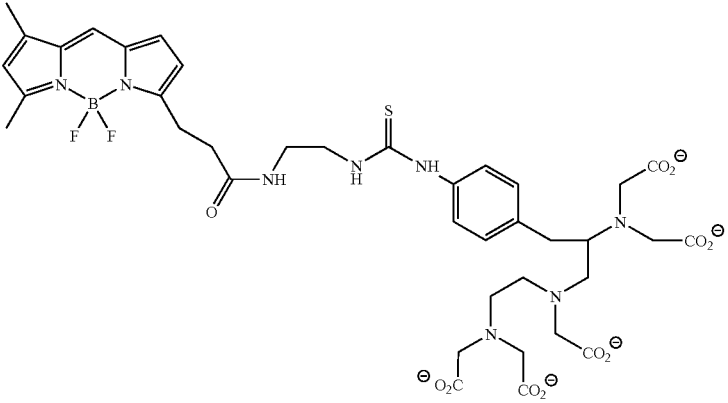 | The dye is a borapolyazaindacene that is attached to the metal-chelating moiety (DTPA, Formula V) by a linker represented by Formula II. The counterion is $K^+$. |
| Compound 29 | 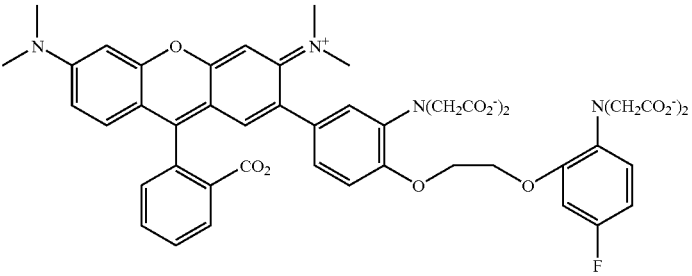 | The dye is a xanthene derivative that is attached to the metal-chelating moiety (Formula IV) by a linker that is single covalent bond. The counter ion is $K^+$. |

Binding Solution

The present binding solution comprising:
a) a metal chelating moiety;
b) a salt comprising trivalent metal ions, wherein said metal ion is capable of simultaneously binding said metal chelating moiety and a phosphorylated target molecule; and,
c) an acid.

The metal chelating moiety is optionally attached to a label, a reactive group or a combination thereof wherein the metal chelating moiety is typically selected from the group consisting of BAPTA, IDA, DTPA and phenanthrolines. However, any metal chelating moiety described above, specifically or generically, is considered part of the invention to be used in the present binding solution. The label is typically a member selected from the group consisting of a dye, an enzyme and a hapten and the reactive group is preferably a photoactivatable group. In a preferred embodiment the dye is selected from the group consisting of a benzofuran, a quinazolinone, a xanthene, an indole, a benzazole and a borapolyazaindacene provided that said dyes are not sulfonated.

Thus, in a preferred embodiment, the binding solution of the present invention comprises the following components:
a) a phosphate-binding compound having formula (A)m (L)n(B) wherein A is a chemical moiety, L is a linker, B is a metal-chelating moiety, m is an integer from 1 to 4 and n is an integer from 0 to 4;
b) a salt comprising metal ions; and,
c) an acid.

The binding solution can be prepared in a variety of ways, which are dependent on the method and the medium in which the sample is present, as described below. In a preferred embodiment, the binding solution comprises a phosphate-binding compound having formula (A)m(L)n(B), a salt comprising a metal ion and acid in an aqueous solution sufficient to adjust the pH of the binding solution to 3-6; optionally the binding solution comprises an organic solvent or a mixture of organic solvents and additional ionic or nonionic components, e.g. sodium chloride. Any of the components of the binding solution can be added together or separately and in no particular order and, as will become evident, the phosphate-binding compound may be immobilized on a solid or semi-solid matrix, wherein the metal ion and acid are added to the matrix to form the binding solution of the present invention. Therefore, the phosphate-binding compounds do not need to be free in the binding solution to form the solution but may be immobilized on a solid or semi-solid matrix surface. We have found that depending on the method, i.e. detection and isolation, that the concentration of metal ion and phosphate-binding compound needs to be adjusted.

Soluble phosphate-binding compounds are prepared by dissolution in a solvent, such as water, DMSO, DMF or methanol, usually at a final concentration of about 0.1 μM to 10 μM; preferably, the phosphate-binding compound is present in the binding solution at a concentration of about 0.5 μM to 5 μM and most preferably at a concentration of about 1.0 μM. However, in applications in which the binding solution is used to precipitate phosphorylated target molecules from solution, a higher concentration of phosphate-binding compounds in the binding solution is desired—preferably about 0.05 mM to 1 mM. For precipitation purposes that concentration is increased but the ratio of phosphate-binding compound to metal ion is comparable to the ratio of the binding solution used for detection purposes.

The metal ion-containing salt preferably contains trivalent gallium ions, such as is prepared from gallium chloride, but can be any gallium salt known to those skilled in the art. Alternatively iron and aluminum ions also find use in the binding solution of the present invention. Gallium salts that can be used with the present invention include, without limit, acetylacetonate, arsenide, bromide, chloride, fluoride, iodide, nitrate, nitride, perchlorate, sulfate and sulfide. The gallium salt is typically present in the binding solution at a concentration of about 10 nM to about 1 mM; preferably the concentration of the gallium salt is about 0.5 µM to 10 µM. However, for precipitation purposes, the gallium salt is preferably present at a slightly higher concentration of about 0.1 mM to about 0.5 mM.

Analysis of the stability and specificity of the phosphate-binding compounds for gallium ions and the gallium ions for the phosphorylated target molecules was evaluated as a function of pH (Example 1). Based on these results, it was determined that a preferred binding solution comprises an acid to provide a moderately acidic environment for the binding reaction. In fact, an important and unexpected aspect of the present invention is that metal-chelating groups bind trivalent cations such as gallium in a moderately acidic environment, resulting in a titration of fluorescent signal with an increase in pH level approaching neutral pH. An acidic environment is defined as a solution having a pH less than 6.9. Typical suitable acidic components include without limitation acetic acid, trichloroacetic acid, trifluoroacetic acid, perchloric acid, or sulfuric acid. The acidic component is typically present at a concentration of 1%-20% and is buffered to the appropriate pH by a base. The pH of the binding solution is preferably about pH 3-6 and most preferred is about pH 4.0. Acetic acid is a preferred acid for use at or near pH 4. The optimal pH for each compound used may vary slightly depending on the compound used; for Compound 2, pH 4.0 is preferred.

The pH of the binding solution is optionally modified by the inclusion of a buffering agent in addition to the acidic component. In particular, we have shown that the presence of a buffering agent unexpectedly improves binding of phosphorylated target molecules immobilized in electrophoresis gels, provided that an alcohol is also included in the formulations. Any buffering agent that maintains an acidic environment and is compatible with the phosphorylated target molecules in the sample is suitable for inclusion in the binding solution.

Useful buffering agents include salts of formate, acetate, 2-(N-morpholino)ethanesulfonic acid, imidazole, N-(2-hydroxyethyl)piperazinylethanesulfonic acid, tris-(hydroxymethyl)aminomethane acetate, or tris(hydroxymethyl)aminomethane, hydrochloride, wherein the buffering agent does not chelate gallium ions. An exemplified buffering agent is sodium acetate. The buffering agent is typically present in the binding solution at a concentration of about 20 mM to 500 mM; preferably the concentration is about 50 mM to 200 mM.

Inclusion of a water-miscible organic solvent, typically an alcohol, in the binding solution is recommended when the binding solution contains a pH-buffering agent and a salt. Although the use of highly polar solvents such as formamide is permitted, typically, the polar organic solvent is an alcohol having 1-6 carbon atoms, or a diol or triol having 2-6 carbon atoms. A preferred alcohol is 1,2-propanediol. The polar organic solvent, when present, is typically included in the binding solution at a concentration of 5-50%. The presence of a polar organic solvent is particularly advantageous when binding sodium dodecyl sulfate (SDS)-coated proteins, as is typically the case when binding phosphorylated proteins or peptides that have been electroblotted from SDS-polyacrylamide gels. Typically, in the preferred procedure, SDS is removed from a gel or blot prior to addition of the binding solution by fixing and washing; however, some SDS may remain and can interfere with the binding methods of the present invention. Without wishing to be bound by any theory, it appears that the presence of an alcohol improves luminescent labeling of phosphorylated proteins or peptides by removing any SDS that was not removed by washing or fixing the sample.

However, nitrocellulose membranes may be damaged by high concentrations of alcohol (for example, greater than about 20%), and so care should be taken to select solvent concentrations that do not damage the membranes upon which the phosphorylated proteins or peptides are immobilized.

Methods of Use

The phosphate-binding compounds of the present invention can be used without limitation for the analysis and monitoring of phosphorylated target molecules. In this way, phosphorylated target molecules can be detected in unlimited assay formats that provide information about the number of phosphate groups on the target molecule, the identification of enzymes involved in phosphorylation and dephosphorylation, the role that such target molecules have in the proteome and—with further analysis—the site of attachment of phosphate groups on the target molecules. Further analysis can be carried out after the compounds of the present invention are used to selectively detect and/or isolate phosphorylated target molecules.

The methods of the present invention can be carried out on samples that are immobilized, on samples in which the phosphate-binding compound is immobilized or where both the sample and phosphate-binding compounds are in solution. The binding solution is combined with the sample in such a way as to facilitate contact between the phosphate-binding compound, trivalent metal ion and any phosphorylated target molecules present in the sample, wherein formation of a ternary complex effectively binds a chemical moiety A to the phosphorylated target molecules that are present. When the sample is immobilized on a solid or semi-solid support, the binding solution is typically incubated with the sample under conditions that maximize contact, such as gentle mixing or rocking.

The methods of the present invention for detecting phosphorylated target molecules that have been immobilized on a gel comprise the following steps:

i) immobilizing the sample on a gel;
ii) optionally contacting the gel of step i) with a fixing solution;
iii) contacting the gel of step ii) with a binding solution of the present invention
iv) incubating the gel of step iii) and the binding solution for sufficient time to allow said compound to associate with said phosphorylated target molecule;
v) visualizing the phosphate-binding compound whereby said phosphorylated target molecule is detected; and,
vi) optionally, a second (or third) stain is added to the gel to detect either total protein or proteins of another class, such as glycoproteins, or both.

Typically, immobilizing the sample on a gel comprises electrophoretically separating the sample. The gel, without limit, includes any gel known to one of skill in the art for separating target molecules from each other, including polymer-based gels such as agarose and polyacrylamide wherein an electrical current is passed through the gel and the target molecules migrate based on charge and size. Thus, gels (reduced and native) also include both one and two-dimensional gels, and isoelectric focusing gels. Capillary electrophoresis may be employed using gels, solutions containing polymers, or solutions alone.

Optionally, a sample separated on a gel may be transferred to a polymeric membrane, using techniques well known to one skilled in the art, wherein the membrane is then contacted with a binding solution of the present invention to selectively detect phosphorylated target molecules. A method of the present invention for detecting phosphorylated target molecules immobilized on a membrane comprises the following steps:

i) electrophoretically separating the sample on a gel;
ii) transferring the separated sample to a membrane;
iii) optionally contacting the membrane of step ii) with a fixing solution;
iv) contacting the membrane of step iii) with a binding solution;
v) incubating the membrane of step iv) and the binding solution for sufficient time to allow the compound to associate with the phosphorylated target molecule; and,
v) visualizing the compound, whereby said phosphorylated target molecule is detected.
vi) Optionally, a second (and/or third) stain is added to the membrane to detect either total protein or proteins of another class, such as glycoproteins.

Protein gel electrophoresis is typically performed using SDS as a component of either the sample preparation or in the running buffer. However, SDS interferes with the binding solution of the present invention and therefore must be removed from the gel or membrane prior to addition of the binding solution. Gels and membranes are fixed and washed, which results in the removal of most or all of the SDS from the gels or blots. A preferred fixing solution for gels and membranes comprises methanol and acetic acid; optionally the fixing solution comprises glutaraldehyde. The methanol is present at a concentration of about 35-50% and the acetic acid is present at about 0-15% and the glutaraldehyde is present at about 0-2%. Typically, washing the gels or membranes with 100% water follows fixing.

However, for purposes of the invention, the binding solution also detects phosphorylated target molecules that have been separated on a native or non-reduced gel. Therefore, for methods utilizing these gels that do not contain SDS, the fixing solution step is not necessary.

After samples have been separated on a gel or transferred to a polymeric membrane, optionally fixed, and washed, the gel or blot is incubated with a binding solution (Examples 2-9). The phosphorylated proteins or peptides are incubated with the binding solution for a time sufficient for the phosphate-binding compound/metal ion complex to bind to the phosphorylated proteins or peptides that are present. Preferably, this time is not more than 24 hours, more preferably this time is less than 8 hours and most preferably this incubation time is less than 2 hours, but not less than 5 minutes. After incubation with the binding solution the gels or membranes are typically washed with a mixture that preferably comprise an acidic buffering agent and acetonitrile; useful buffering agents to be used with the present invention include, without limitation, NaOAc, formate and 2-(N-morpholino)ethanesulfonic acid. Typically, the buffering agent is present in the washing solution at a concentration of about 25 mM to about 100 mM. In addition, it has been found that optional inclusion of acetonitrile in the washing solution usually reduces non-specific labeling. Preferably, acetonitrile is present at a concentration from 1-7%, more preferably 3-4%. An alternative washing solution is comprised of 10-20% 1,2-propanediol.

Thus, following binding of the phosphate-binding compound and washing, the ternary complex can be illuminated directly when the phosphate-binding complex comprises a fluorophore or chromophore label, as described above, to visualize the phosphorylated target molecules. Alternatively the presence and location of the phosphorylated target molecule on the blot can be detected using antibodies to the label, such as anti-BAPTA antibody, an anti-fluorophore antibody, an anti-hapten antibody or an avidin (when the label is a biotin derivative), which is then detected by standard means used to detect proteins on Western blots such as by fluorescence, chemiluminescence or radioactivity, indicating labeling of the phosphorylated target molecules.

The phosphate-binding compounds of the binding solution are chosen depending upon their ability to bind phosphorylated target molecules in different media. Therefore, preferred phosphate-binding compounds for binding phosphorylated target molecules in a gel include compounds 1-4 and 7-11 of the present invention. Preferred compounds for binding phosphorylated target molecules on a membrane include compounds 1, 4 and 7 of the present invention.

A particular advantage to identifying phosphorylated proteins or peptides in a 2-D gel is the ability to correctly identify the phosphoproteome, as well as to quantitate post-translational modification of proteins for the addition or subtraction of phosphate groups. Specifically, labeling of phosphorylated proteins or peptides while doing concurrent, or subsequent, total protein staining identifies the phosphorylated proteome, while the intensity of the signal can be correlated to the level of phosphorylation, when compared to the total protein stain (see, Examples 6, 7 and 13). Any fluorescent dye specific for total proteins can be used to stain total proteins in the gel; a preferred stain is SYPRO® Ruby dye for gels or any dye disclosed in U.S. Pat. No. 6,316,276 B1. Other fluorescent dyes such as MDPF and CBQCA could also be used for detection on membranes. Because SDS is removed by washing prior to staining with the staining mixture of the present invention, total protein stains such as SYPRO® Ruby dye are preferred because SDS is not critical for their staining function. However, protocol changes can be made when using a stain that requires SDS for staining sensitivity, such as SYPRO® Orange dye, SYPRO® Red dye and SYPRO® Tangerine dye, by adding SDS back to the gel prior to a total protein stain step and including SDS in the staining solution for the total protein stain (Malone et al. *Electrophoresis* (2001) 22(5):919-32). A preferred mixture for returning SDS back to a gel is 2% acid/0.0005% SDS, and optionally above 40% ethanol, wherein the gel is incubated for at least one hour. Alternatively, the total protein stain can be performed prior to the phosphorylated target molecules staining of the present invention; therefore, in this case, it is not necessary to add back the SDS to the gel, but simply to remove the SDS prior to the phosphorylated target molecule staining step, as contemplated by the present invention. Therefore, alternative preferable total protein stains for gels include but are not limited to, SYPRO® Orange dye, SYPRO® Tangerine dye and SYPRO® Red dye or any dye disclosed in U.S. Pat. No. 5,616,502 or U.S. Ser. No. 09/632,927. Alternative, but less preferred, total protein stains for gels include Coomassie Blue or silver staining, which utilize staining techniques well known to those skilled in the art. Alternative total proteins stains useful for staining blots are SYPRO® Rose Plus dye and DyeChrome™ dye or any dye solution disclosed in U.S. Pat. No. 6,329,205 B1 and U.S. Ser. No. 10/005,050.

Another very important advantage when labeling phosphorylated target molecules in a 2-D gel is to include a stain for glycoproteins, wherein a 3-way analysis of the proteome could be accomplished (Steinberg et al., "Rapid and Simple Single Nanogram Detection of Glycoproteins in Polyacrylamide Gels and on Electroblots," *Proteomics* 1:841-855 (2001)). A preferred glycoprotein stain is Pro-Q™ Emerald 300 dye or Pro-Q™ Emerald 488 dye, Pro-Q™ Fuchsia dye or any other dye disclosed in U.S. Ser. No. 09/970,215. In addition, if the sample comprises fusion proteins with oligohistidine affinity peptides, Pro-Q™ Sapphire 365 or 488 dye can be used to simultaneously detect these proteins or peptides.

Thus, it is particularly advantageous that the parallel determination of both protein expression levels and functional attributes of the proteins such as phosphorylation of proteins can be achieved with the present invention within a single 2-D gel electrophoresis experiment. Analysis can be accomplished by using image analysis software, e.g., Compugen's Z3 program or Phoretix Progenesis software. Any two images can be re-displayed, allowing visual inspection of the differences between the images, and quantitative information can be readily retrieved in tabular form with differential expression data calculated.

Alternatively, single-dimension polyacrylamide and corresponding blots can be simultaneously or subsequently stained for total proteins or glycoproteins using staining techniques and dyes described above. A particular advantage for counterstaining a gel or blot that has been labeled using methods of the present invention is the ability to distinguish between nonspecific labeling and labeling of phosphorylated target molecules with a low number of phosphate groups. This is important for accurately identifying phosphorylated target molecules that have undergone a small change in the degree of phosphorylation. Counterstaining a blot or gel with a total protein stain such as SYPRO® Ruby permits a ratiometric analysis of the fluorescent signal generated from the dyes of the present invention compared to the fluorescent signal generated from a total protein stain (see, FIG. 11 and Example 22). This ratiometric analysis also permits the stoichiometry determination of the phosphorylated target molecule relating to the overall phosphorylation state of the molecule as well as the addition or subtraction of phosphate groups.

Another particular advantage for staining phosphorylated proteins or peptides separated in polyacrylamide gels is for the analysis of proteins of interest by combining spot detection with the compounds of this invention with mass spectrometry techniques for further analysis. For example, because phosphoproteins may co-migrate in a gel, further analysis may be essential or desired to specifically identify and analyze the phosphoprotein of interest. This further analysis can be achieved by measurement of a set of peptide masses derived from a protein, i.e., by peptide mapping with mass spectrometry (MS), or by obtaining amino acid sequence information from individual peptides, i.e., protein sequencing by MS/MS or by Edman degradation. Thus, a protein band or spot, once identified using the compositions and methods of the present invention, may be excised from the gel, rinsed, optionally reduced and S-alkylated, and then digested in situ in the gel with a sequence-specific protease, e.g., trypsin, using standard protocols. See Shevchenko et al., "Mass Spectrometric Sequencing of Proteins from Silver Stained Polyacrylamide Gels," *Anal. Chem.* 68:850-58 (1996). The peptide mixture thus generated may be extracted from the gel and analyzed by MS, using standard protocols. Peptide mapping by matrix-assisted laser desorption/ionization (MALDI) mass spectrometry is often most sensitive. Methods for the in-gel digestion of proteins are described in Jensen et al., "Mass Spectrometric Identification and Microcharacterization of Proteins From Electrophoretic Gels: Strategies and Applications," *PROTEINS: Structure, Function, and Genetics Suppl.* 2:74-89 (1998).

DNA-binding proteins are key to the regulation and control of gene expression, replication and recombination. The electrophoretic mobility shift assay (or gel shift assay) is considered an essential tool in modern molecular biology for the study of protein-nucleic acid interactions. Nucleic acids could be detected with SYBR® Green II dye, while phosphoproteins are subsequently detected by methods described in this invention. All fluorescence staining steps would be performed after the entire gel-shift experiment is completed, so there is no need to pre-label either the DNA or the protein and no possibility of the fluorescent reagents interfering with the protein-nucleic acid interactions. A third total protein stain might be employed as well, such as SYPRO® Ruby dye. In this way the influence of protein phosphorylation on DNA-binding may be measured. The ability to independently quantify each molecular species allows more rigorous data analysis methods to be applied, especially with respect to the mass of phosphoprotein bound per nucleic acid.

The present invention is also contemplated to be used in a wide range of microarray formats, including but not limited to the methods and arrays disclosed in US Patent Application 2002/0076727; US Patent Application 2002/0106785; US Patent Application 2002/0055186; WO 99/39210; WO 00/63701; WO 02/25288; WO 01/18545, WO 00/04380 and U.S. Pat. Nos. 6,403,368; 6,475,809; 6,365,418; 6,409,921; 5,595,915; 6,461,807; 6,399,299. Phosphorylated target molecules immobilized on an array such as a HydroGel-coated slide including those disclosed in U.S. Pat. Nos. 6,372,813; 6,391,937; 6,387,631; 6,413,722 and those manufactured by Perkin Elmer; can also be detected using the methods and compositions of the present invention (Examples 18 and 19). Alternatively, phosphate-binding compounds can be immobilized on these arrays.

The methods of the present invention for detecting phosphorylated target molecules on an array typically comprise the steps of:
  i) immobilizing said sample on an array;
  ii) contacting said array of step i) with a binding solution,
  iii) incubating said array of step ii) and said binding solution for sufficient time to allow said compound to associate indirectly with said phosphorylated target molecule; and,
  iv) illuminating said compound with a suitable light source whereby said phosphorylated target molecule is detected.

The sample is immobilized on the array using techniques well known to one skilled in the art, including but not limited to, using a piezo array printer, contact printer or other array printer technology, immobilizing a phosphorylated target molecule, binding molecule such as an antibody and then added the sample to non-covalently bind the phosphorylated target molecules to the array. Typically the array comprises molecules that covalently attach the sample, or a protein that selectively binds the sample, such as an amine-reactive group.

The array is incubated with a binding solution for sufficient time to form a ternary complex between a phosphate-binding compound, the metal ion (typically gallium) and phosphorylated target molecule. Alternatively, the array may comprise phosphate-binding compounds complexed with the metal ions immobilized on the surface of the array, wherein a sample is incubated with the array and detection of phosphorylated target molecules occurs when the target molecules bind the metal ion/phosphate-binding complex and are typically illuminated, unbound sample is washed away. In this way, an assay to detect phosphatases or kinases is performed with an appropriate peptide or protein substrate and the resulting phosphorylated or dephosphorylated peptides or proteins are spotted or synthesized on the array, wherein phosphate groups on the peptides bind the phosphate-binding compounds/metal-ion complex on the array. Alternatively, a kinase and/or phosphatase substrate is spotted or synthesized on the array and then the enzyme, kinase (and ATP) or phosphatase, is added to the array. After removing the enzyme, the array is then contacted with the binding solution. In this way, the array is used to detect and/or isolate phosphorylated target molecules and to identify the enzymes responsible for adding and/or removing phosphate groups from target molecules and their efficiency in doing so.

Typically phosphatase and kinase peptide substrates are immobilized on an array by spotting or synthesis using standard protocols, the phosphates or kinase enzymes, either comprise an unknown sample or are isolated enzymes, are added and subsequent presence of phosphate groups is detected using a binding solution of the present invention. Thus, the methods and binding solution of the present invention are useful, for example, with arrays of protein substrates for various protein kinases (e.g., myosin light chain, MARCKS, myelin basic protein, casein, src-supressed C kinase substrate, insulin Receptor Substrate 1, Nuclear factor 90, Rap1, transcription factor stat5a). A sample comprising phosphatase or kinase enzymes is incubated with the array comprising enzyme substrate; following incubation under appropriate conditions and with appropriate reaction additives for the enzymes the phosphorylated products can be detected with a binding solution of the present invention. When the detectable label is a fluorophore, for example, the coordinates of the fluorescent signals provides a read-out of the kinases present in the fluid and their activity against the various enzyme substrates (peptides or proteins) on the array. Detection of phosphorylated target molecules with an array offers many possibilities and the above description is not meant to limit how the present invention can be used in combination with array technology.

Current commercial kinase assays are often time-consuming and require many steps such as electrophoresis, centrifugation, ELISA or immunoprecipitation. The present invention provides methods for the rapid, sensitive, and non-radioactive detection of a variety of selected kinases and phosphatases and provides, in addition, methods that are well suited for high-throughput screening. The kinase and phosphatase assays of the present invention also permit the screening of inhibitors and activators of, for example, tyrosine kinases and, in addition, also permit the monitoring and the purification of kinase and phosphatase enzymes. Moreover, detection of the enzyme substrate on the array makes the methods of the invention far more sensitive than any known solution-based assays for kinases and phosphatases and use of fluorescence or chemiluminescence for detection on the array permits a higher density of labeling than is possible with radiochemical detection.

As described above, a kinase substrate is covalently or non-covalently attached to a surface, solid or semisolid matrix including a microwell plate, polymeric beads or an array such as a HydroGel array slide (or amine microarray substrate, aldehyde microarray substrate, an epoxy microarray substrate, a poly-L-lysine microarray substrate or other polyacrylamide microarray substrates) and the assay is performed in a non-continuous heterogeneous manner. The kinase substrate comprises a kinase consensus phosphorylation site, preferably a peptide or a random polymer (poly(Glu:Tyr), poly(Glu:Ala:Tyr). Optionally the kinase substrate comprises a fluorophore. A sample suspected of containing a kinase is combined with the kinase substrate, along with ATP, wherein an active kinase enzyme will add phosphates to the kinase substrate. The addition of phosphate groups is measured after removal of the kinase solution and adequate washing, wherein a binding solution, as described above, is added to the kinase substrate. Typically the phosphate-binding compound comprises a fluorophore and the kinase activity is measured by illuminating the fluorophore. Alternatively, the phosphate-binding compound comprises an enzyme such as peroxidase, wherein the kinase activity would be measured after addition of the appropriate enzyme substrate and detection with a fluorometers or an instrument to measure color or chemiluminescence. In addition, using an inhibitor of the selected kinase or phosphatase in the assay, for example, by using sodium orthovanadate may enhance the specificity of the kinase. Furthermore, the assay methods of this invention can be used to screen for inhibitors or activators of kinases and/or phosphatases. Alternatively, the assay is easily adaptable to measure phosphatase activity wherein the phosphatase substrate, phosphorylated peptides or proteins, would be bound to a solid or semi-solid matrix such as a microwell plate, polymeric particle or a hydrogel.

The materials and methods of the present invention may also be used to detect and/or quantitate kinases or phosphatases by employing a FRET-based assay. For example, a peptide labeled with a fluorophore can be combined with the phosphate-binding compound/metal-ion (typically gallium) complex derivatized with a phycoerythrin or other dye label. When the peptide is phosphorylated, the peptide binds the dye labeled phosphate-binding compound and the emission maximum shifts in the assay. Time-resolved fluorescence can be achieved, for example, by employing a europium-based chelate on the peptide and the phosphate-binding compound/metal ion complex derivatized with allophycocyanin. The donor fluorophore can be excited, in this example, at 335 nm and an emission shift from 620 nm to 665 nm indicates peptide interaction with the metal-chelator and gallium complex.

Thus, in one aspect of the invention, numerous enzymes, including nitrogenase, phosphoribosyl-pyrophosphate synthetase, undecaprenyl pyrophosphate synthase, DNA polymerases, RNA polymerases, farnesyltransferase, nucleoside triphosphate pyrophosphohydrolases, pyrophosphate-fructose 6-phosphate 1-phosphotransferase (PFPPT), sulfate adenyltransferase, UTP-glucose 1-phosphate uridinyltransferase (UGPP), asparagine synthetase, and UDP-glucose pyrophosphorylase involve the metabolism of inorganic pyrophosphate and thus are potential targets for quantitation by the disclosed invention.

In addition, the methods and materials of the present invention are also useful for studying functional proteomics involving ligand overlay methodology. For example, arrayed proteins would be detected after incubation with phosphatidylinositol 4,5-bisphosphate (PIP2) micelles, followed by incubation with the binding solution. The differences in labeling would highlight an important class of phosphatidylinositide-binding proteins. Proteins such as SWI/SNF-like BAF, a chromatin remodeling complex and cofilin/ADF, a ubiquitous actin-binding protein, are likely to be identified using the methods of the present invention (Rando et al. *Proc Natl Acad Sci USA* 99(5):2824-9 (2002); Ojala et al. *Biochemistry* 40(51):15562-9 (2001)). Another example of a ligand overlay assay would be GTP-binding proteins, wherein the small GTP-binding proteins can be separated by high-resolution 2-D gel electrophoresis and subsequently transferred under renaturing conditions to a nitrocellulose or PVDF membrane and probed with GTP. The bound GTP would then be subsequently bound with the binding solution of the present invention, resulting in identification of GTP-binding proteins. A variety of other membrane overlay nucleotide-binding assays could be preformed using the binding solution of the present invention, wherein potentially any ligand and binding protein, wherein at least one of the pair contains phosphate group(s), could be used to identify novel binding proteins (Gromov et al. *Electrophoresis* (1994) 3-4: 478-81).

In contrast to having either the phosphorylated target molecules or the phosphate-binding compound immobilized, the compositions and methods of the present invention are also useful for binding, detecting and isolation of phosphorylated target molecules that are free in a solution. A sample suspected of containing phosphorylated target molecules is incubated with the binding solution comprising fluorescent dye-labeled phosphate-binding compounds wherein phosphorylated target molecules are detected by fluorescence polarization (Example 14) or energy transfer (Example 51).

Fluorescence polarization is based upon the finding that the emission of light by a fluorophore may be depolarized by rotational diffusion, or the rate at which a molecule tumbles in solution (*J. Phys. Rad.* 1:390-401 (1926)). Polarization is the measurement of the average angular displacement of the fluorophore, which occurs between the absorption and subsequent emission of a photon. This angular displacement of the fluorophore is, in turn, dependent upon the rate and extent of rotational diffusion during the lifetime of the excited state, which is influenced by the viscosity of the solution and the size and shape of the diffusing fluorescent species. If viscosity and temperature are held constant, for example, then fluorescence polarization is directly related to the molecular volume or size of the fluorophore. Thus, when detecting phosphorylated target molecules in solution, the compounds and methods of the present invention contemplate taking advantage of fluorescent polarization, as described in U.S. Pat. No. 6,207,397. The detection of phosphorylated target molecules would be based upon the observation that changes in polarization occur when a fluorescent dye-labeled phosphate-binding compound undergoes a molecular weight change due to the binding of a phosphorylated target molecule, for example, a phosphoprotein. The solution containing the sample and binding solution are irradiated with plane-polarized light of a wavelength that is sufficient to excite the fluorophore. The light subsequently emitted by the fluorescent phosphorylated target molecule is polarized to varying degrees, depending on the molecular size of the fluorescent dye. In the unbound state in solution, low molecular weight labeled phosphate-binding compounds will rotate rapidly, and give low polarization readings. The degree of polarization of the emission can be measured without the necessity to separate the components in the solution. See, FIG. 10.

As discussed above for the kinase assay, FRET or energy transfer between a first dye label and a second dye label can be employed for the detection of phosphorylated target molecules in solution. A first dye label is employed on the phosphate-binding compound and a second dye label is added to the sample as part of a phosphorylated or phosphorylatable molecule. When the phosphate-binding compound binds the dye-labeled molecule then the first and second dye label are brought within proximity that facilitates energy transfer. The first dye label has a first absorption and emission spectra and the second dye label has a second absorption and emission spectra. Energy transfer occurs between the two dye labels when overlap between the emission of the first dye label and the absorption of the second dye label is present wherein the absorbed energy by the second dye label is either quenched or re-emitted at a longer wavelength. It is understood that the first dye label is present either as part of the phosphate-binding compound or as part of a phosphorylated or phosphorylatable target molecule; the same is also the case for the second dye label.

In this instance, a method for detecting phosphorylated target molecules in a solution sample comprises:
   a) contacting said sample with a binding solution to form a combined mixture, wherein said binding solution comprises a phosphate-binding compound, a salt comprising trivalent metal ions and an acid, wherein said combined mixture comprises a first dye label that has a first absorption and emission spectra and a second dye label that has a second absorption and emission spectra;
   b) incubating said phosphate binding compound and said sample for a sufficient amount of time for said phosphate binding compound to bind a phosphorylated target molecule; and,
   c) illuminating said sample with an appropriate wavelength whereby said phosphorylated target molecule is detected by a change in fluorescence signal.

This method is particularly useful when the sample contains ATP, as is the case for many kinase assays, due to the ability to discriminate between bound ATP and the kinase substrate. This method is also useful when a phosphate-binding compound is employed that does not result in an increase in signal intensity when a phosphorylated target molecule is bound compared to when no target molecule is bound. Thus, the use of energy transfer allows for a homogenous assay system that does not require separation or additional detection reagents for the detection of phosphorylated target molecules in solution. For the detection of immobilized target molecules this is not an issue because unbound phosphate-binding compounds or unused ATP is washed away, leaving only the bound phosphate-binding compounds and a resulting detectable signal. However, we have found that for solution-based assays both fluorescence polarization and FRET are preferred for the detection of phosphorylated target molecules.

Thus in an aspect of the invention, the detection of kinase enzymes in a solution based assay comprises a dye-labeled kinase substrate, enzyme and ATP combined with a present binding solution wherein the phosphate-binding compound comprises a metal chelating moiety that is covalently bonded to a dye label. The phosphate-binding compound may still bind the free ATP but there will be no shift in signal, in this instance, a shift only occurs when a phosphate-binding compound binds a phosphorylated dye-labeled kinase substrate. This same methodology can be applied to phosphatase substrates wherein the removal of phosphate groups from the substrate results in a signal from the first and second dye label as would be observed without energy transfer. It is advantageous that this assay be observed at several set time intervals to observe the change in fluorescent signal and for a baseline signal. See, FIG. 12.

In a further aspect of the invention, the phosphate-binding compounds that comprise a reactive group can be used to covalently attach a present phosphate-binding compound to a phosphorylated target molecule. The phosphate-binding compounds may further comprise a present label. In this instance, a binding solution is incubated with a phosphorylated target molecule for a sufficient amount of time for the phosphate-binding compound to bind the target molecule. The covalent bond forms when an appropriate reactive group is brought into proximity with a compatible reactive group on the target molecule. In a preferred embodiment, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix.

Thus, a preferred method for specifically covalently labeling phosphorylated target molecules in a sample comprises:
i) contacting said sample with a binding solution comprising a phosphate binding compound that is covalently bonded to a label and a photoactivatable chemically reactive group; a salt comprising trivalent metal ions and an acid;
ii) incubating said sample and said binding solution for sufficient time to allow said phosphate binding compound and said metal salt to associate with said phosphorylated target molecule;
iii) illuminating said phosphate binding compound with an appropriate wavelength where said photoactivatable reactive group specifically forms a covalent bond with said phosphorylated target molecule whereby said phosphorylated target molecule is labeled.

This method is particularly useful when a stronger association is needed than can be obtained with the non-covalent binding of the present ternary complex. In certain aspects, it is desirable that after the formation of the ternary complex that the pH be raised to about 7.0 instead of an acidic pH. This method facilitates that process due to the stable formation of the covalent bond between the chelating moiety and the target molecule. In addition, a covalent bond is also desirable for isolation purposes wherein perturbation of the system may lead to unstable ternary complexes. Preferred compounds for covalently labeling phosphorylated target molecules includes Compounds 34, 36, 39, 42 and 44.

Unexpectedly, phosphorylated target molecules, typically peptides, can also be isolated from a complex solution by taking advantage of the insoluble nature of the ternary complex when higher concentrations of the more hydrophobic phosphate-binding compounds, such as Compound 5, are used in a moderately acidic environment with essentially equimolar metal ion concentrations.

Methods of the present invention for isolating phosphorylated target molecules from solution comprise the following steps:
i) contacting the sample with a binding solution of the present invention;
ii) incubating the sample of step i) and the binding solution for sufficient time to allow said compound to associate with the phosphorylated target molecule to form a ternary complex; and,
iii) separating said complex from said sample, whereby said phosphorylated target molecules are isolated.

Hydrophobic phosphate-binding compounds of the invention when present in a binding solution at a concentration up to a hundred times higher than a binding solution for detection purposes typically form insoluble aggregates when the ternary complex forms. This property of the certain hydrophobic phosphate-binding compounds was taken advantage of to develop a method for isolation of phosphopeptides. Thus, when a binding solution comprising certain hydrophobic phosphate-binding compounds is incubated with a sample in a way to facilitate formation of the ternary complex, the complex can be precipitated out of solution by centrifugation (Example 13). Therefore, typically the binding mixture and sample solution is vortexed, or mixed in a manner well known to those skilled in the art, to simultaneously facilitate binding (formation of aggregates) and prevent precipitation of the ternary complexes. Following formation of the ternary complex, the solution is treated in such a way as to isolate the precipitated complexes, wherein a preferred method is centrifugation. The resulting pellet comprises phosphorylated target molecules that can be further analyzed, by methods such as MS. This method takes advantage of the affinity "pull-down" of phosphopeptides or phosphoproteins from a complex solution (e.g., a cell extract protein digest), whereby at an acidic pH phosphate-binding compounds can complex with metal (typically gallium) ions and the phosphopeptides or phosphoproteins to form a precipitate. In addition, for the methods used to precipitate phosphorylated target molecules from solution, aluminum ions and ferric chloride comprising iron ions can be also used for the formation of the ternary complex.

The present invention also contemplates further isolation, after aggregated, of the phosphorylated target molecules, wherein the phosphate-binding compounds are removed from the phosphorylated target compounds, resulting in a solution free of phosphate-binding compounds. This is accomplished when the phosphate-binding compounds optionally comprises a tag label such as a hapten, wherein the tag label functions as a handle by which the phosphate-binding compounds can be pulled away from the phosphorylated target molecules. A preferred tag label is biotin wherein a matrix comprising biotin-binding proteins would be used as the medium to separate the phosphate-binding compounds from the phosphorylated target molecules. Specifically, the resulting precipitation pellet is resuspended in a solvent that disassociates the metal ion, phosphate-binding compound and phosphorylated target molecule complex, such as a basic solution, about pH 7-10, or through use of a chelator such as EDTA or EGTA. The solution is then added to a matrix, such as a column containing Sepharose beads bound to a biotin-binding protein, wherein the phosphate-binding compounds comprising biotin bind to the beads and the phosphorylated target molecules pass through the column. The resulting eluant contains phosphorylated target molecules free from phosphate-binding compounds that may be desirable for certain applications. Alternatively, the dissociated mixture of phosphate-binding compounds, metal ions and phosphorylated target molecules can be incubated with beads comprising biotin-binding proteins as a slurry, wherein removal of the beads by gravity, such as by size exclusion or centrifugation, results in a solution of phosphorylated target molecules without phosphate-binding compounds. Preferred compounds for the formation of a precipitable ternary complex include compounds 2, 5, 9, 12, 20, 21 and 22.

In some cases, phosphate-binding compounds can be removed from phosphorylated target molecules without the need for affinity purification. In this way, the aggregated ternary complex is contacted with an organic extraction buffer (Example 27). Mixing of the pellet with an organic solvent, such as acetonitrile, chloroform and water results in the phosphorylated peptide entering in the aqueous phase and the phosphate-binding compound dissolving in the organic phase.

The isolated phosphorylated target molecules can be analyzed by a number of methods, including but not limited to, gel electrophoresis, MALDI-TOF MS, or LC-MS/MS. Additionally, as described below, the phosphopeptides can be derivatized using β-elimination, with subsequent addition of nucleophiles to aid in identification of the site of phosphorylation.

In addition to isolation of phosphorylated target molecules from a complex sample in solution, the present invention also contemplates the isolation of target molecules by capturing the phosphorylated target molecules using immobilized phosphate-binding compounds (Example 15, 25 and 26). This can be done in a number of ways and the method is exemplified using an affinity column, ferrofluid beads and membranes; however, the methods illustrated are not intended to be a limitation of the method.

The methods of the present invention for isolating phosphorylated target molecules from solution using immobilized phosphate-binding compounds typically comprise the following steps:

i) charging a matrix comprising an immobilized phosphate-binding compound, wherein a metal-chelating moiety comprises Formula IV, with a salt comprising metal ions;

ii) equilibrating the matrix with a moderately acidic binding buffer, iii) adding the sample to the matrix, wherein the phosphorylated target molecules are bound to the matrix of step ii); and iv) eluting the phosphorylated target molecules from the matrix, whereby said phosphorylated target molecules are isolated.

The matrix can be any matrix known to one skilled in the art, including polymeric membranes, polymeric particles such as agarose, latex, magnetic or Sepharose beads, and glass, such as slides, beads or optical fibers. The beads can be present in slurry or as a packed column through which the sample passes and the membranes capture the phosphorylated target molecules. An example of such a column is an affinity matrix comprising phosphate-binding compounds bound to agarose (for instance, Compounds 13 and 14) or a resin (immobilized affinity column (IMAC)). Other compounds that find use in this method include, among others, Compounds 15, 20, 21 and 22.

Unlike the precipitation method, where an affinity column or organic extraction buffer can be used to remove phosphate-binding compounds from the isolated phosphorylated target molecules, the matrix in this method can optionally comprise just the metal-chelating moiety component of the phosphate-binding compound, which is subsequently bound with metal (preferably gallium) ions following the addition of the metal salt. However, a phosphate-binding compound represented by formula (A)m(L)n(B) can form the matrix wherein A is a reactive group that is used to attach B by way of L to the matrix material. Thus, the matrix is charged with the metal ion, prior to addition of the sample. The matrix is then equilibrated with a moderately acidic binding buffer; alternatively, the metal ion and acidic binding buffer would be present in one solution. The acidic binding buffer typically uses the same components as the binding solution. A sample in an acidic binding buffer is then added to the mixture, where phosphorylated target molecules will bind the metal ions complexed to the metal-chelating moiety. Isolation of the phosphorylated target molecules is accomplished by an addition of a solution, which dissociates the ternary complex of the phosphate-binding compound (metal-chelating moiety), metal ion and phosphorylated target molecules. Preferably, the elution solution comprises a base and a basic pH-buffering agent. Useful bases include, without limitation, barium hydroxide, sodium hydroxide and ammonium hydroxide. Alternatively, basic amine solutions are also useful elution agents. Any base that is compatible with the sample and metal ion phosphorylated target molecule complex that dissociates the complex is preferred. In addition, organic solvents such as acetonitrile is useful in eluting phosphorylated target molecules from the phosphate-binding compound matrix, and may be preferable, depending on the subsequent analysis of the phosphorylated target molecules, such as with MS.

As many phosphorylated target molecules often exist only in low abundance, the isolation methods of the present invention are especially useful for the purification and enrichment of such phosphorylated target molecules. These methods are useful for purifying phosphorylated peptides from crude peptide mixtures, which is advantageous for methods that subsequently analyze the peptides by MALDI, MS or nanoelectrospray tandem mass spectrometry (MS/MS). It is contemplated that a wide variety of methods can be used to prepare samples purified and/or enriched by the affinity matrix or separated from a complex solution. For example, dried separated phosphopeptides can be resuspended in water for LC-MS analysis.

The IMAC of the present invention is also readily adaptable to microfluidics applications, such as the CD technology developed by Gyros AB (Uppsula, Sweden), wherein high-throughput screening of samples for proteomic analysis, such as peptide mapping with MALDI-TOF, can be accomplished. Briefly, the Gyros AB technology comprises a CD microlaboratory with hundreds of microstructures (columns), wherein samples are run through the columns based on centrifugation speeds and the eluted sample is analyzed on the CD, permitting the entire process from a protein digest to MS analysis to be conducted on the CD. The columns can be packed with particles that comprise BAPTA compounds (Compounds 13 or 14); samples can be then run through the columns and either analyzed for phosphorylated peptide concentration, by fluorescent or chemiluminescent signal, or applied to a matrix on the CD for MALDI-TOF analysis. Thus, the methods of the present invention are amenable to microfluidics for high-throughput screening of samples, which is advantageous for proteomic studies.

Thus, the invention provides analytical reagents and methods for use with mass spectrometry-based methods for the rapid, and quantitative analysis of phosphoproteins or phosphopeptides in a mixture. The reagents and methods can be applied to the detection and identification of proteins in sample mixtures of proteins, where the peptides isolated by the method are characteristic of the presence of a protein in the mixture. Isolated peptides or proteins can be characterized by mass spectrometric (MS) techniques, and by application of sequence database searching techniques for identifying the protein from which the sequenced peptide originates.

The following references are examples of mass spectrometric techniques for protein identification, and can be used with the materials and methods of the present invention: Ideker et al., "Integrated Genomic and Proteomic Analyses of a Systematically Perturbed Metabolic Network," *Science* 292:929-934 (2001); Gygi & Aebersold, "Measuring Gene Expression by Quantitative Proteome Analysis," *Curr. Opin. Biotechnol.* 11:396-401 (2000); Goodlett et al., "Protein Identification with a Single Accurate Mass of a Cysteine-containing Peptide and Constrained Database Searching," *Anal. Chem.* 72:1112-8 (2000); Goodlett et al., "Quantitative In Vitro Kinase Reaction as a Guide for Phosphoprotein Analysis by Mass Spectrometry," *Rapid. Commun. Mass. Spectrom.* 14:344-8 (2000); McLachlin & Chait, "Analysis of Phosphorylated Proteins and Peptides by Mass Spectrometry," *Current Opin. Chem. Biol.* 5:591-602 (2001); Aebersold & Goodlett, "Mass Spectrometry in Proteomics," *Chem. Rev.* 101:269-295 (2001); Vener et al., "Mass Spectrometric Resolution of Reversible Protein Phosphorylation in Photosynthetic Membranes of *Arabidopsis thaliana*," *J. Biol. Chem.* 276:6959-66 (2001); Zhou et al., *Nature Biotechnol.* 19:375-8 (2001). Those of skill in the art will recognize these currently available mass spectrometry methods as compatible with the materials and methods of the present invention. However, the present invention also contemplates that the materials and methods can be used with mass spectrometry techniques yet to become available that achieve the same or similar results. In addition, it is contemplated by the present invention that, prior to detection, phosphopeptides can be subjected to reverse phase, normal phase or ion-exchange columns to remove undesired materials from the phosphopeptide sample.

The present invention also contemplates alternative methods of detection, purification and/or enrichment. For example, the materials and methods of the present invention may be used with Luminex technology, which involves the labeling of latex microbeads with two fluorophores (U.S. Pat. No. 5,981,180 and U.S. Pat. No. 6,268,222). Using precise ratios of the two fluorophores, many different bead sets can be created, each one being unique and distinguishable in a laser beam, based on the color code that results from the ratio of the two dyes. Instead of a capture antibody for a specific molecule coupled to a specific bead set, the metal-chelators of the present invention may be used, i.e., phosphate-binding compound and metal ion complex or biotin-binding protein that would bind biotin-labeled phosphate-binding compounds. However, antibodies that bind the sample could be used and the phosphorylated target molecule could be detected with the binding solution of the present invention. For example, after an analyte is bound to the metal-chelator complex on the bead, a detector antibody coupled to phycoerythrin may be used as a reporter. The end result is an antibody/metal-chelator sandwich assay on the color-coded microbead. The beads and the reporter molecule may be read on a Luminex 100 instrument using a dual laser system as they pass through a flow cell. One laser detects the beads (the color code for an assay) and the other laser detects the reporter signals. Thus, it is contemplated by the present invention that instead of a detector antibody, the metal-chelating complex may be used in accordance with the bead detection for the separation and detection of phosphorylated target molecules.

In the alternative, magnetic bead separation for automated bead and particle capture systems, for example, LifeSep magnetic beads by Dexter Magnetic Technologies or Captivate ferrofluid (Molecular Probes, Inc), may be used with the materials and methods of the present invention (U.S. Pat. No. 6,413,420; U.S. Ser. No. 08/868,598; US Application 20020117451; U.S. Pat. No. 4,339,337; and U.S. Pat. No. 5,834,121) or ferrofluid beads (Example 27). Magnetic separation works by means of specific affinity coatings attached to tiny magnetic beads, such as the phosphate-binding compounds. Beads are mixed with a sample containing phosphorylated target molecules such that the phosphorylated target molecules have the opportunity to bind tightly to the metal ion/phosphate-binding compound on the bead. Once attached, the bead and the ternary complex can be separated using a strong magnetic field. Depending on the process, the phosphorylated target molecule may either be left bound to the bead or released by washing in a suitable solvent or a basic buffer. Thus, efficient and rapid isolation is possible and, therefore, it is contemplated by the present invention, that the phosphate-binding compound/metal ion complex may be used with well-known methods of magnetic bead separation.

Thus, a wide variety of materials and methods are provided for the separation, purification and enrichment of phosphorylated target molecules, including the novel use of an immobilized affinity matrix.

The present invention provides compounds and methods for the differential isolation and identification of phosphorylated serine, threonine or tyrosine amino acids. The materials and methods described above for the labeling and isolation of phosphorylated target molecules, absent mass spectrometry or other similar techniques, are generally used for detecting protein phosphorylation, but do not give information on the specific location of the phosphate on the protein or polypeptide. The present invention contemplates further analyzing isolated phosphorylated proteins or peptides obtained by immobilized affinity matrix or precipitation methods described above to differentially identify phosphorylated peptides. Isolated phosphorylated proteins are subjected to proteolytic digestion, followed by acid hydrolysis or alkaline hydrolysis and analyzed.

A base such as barium hydroxide or sodium hydroxide catalyzes the dephosphorylation of the peptides, forming activated dehydroalanine derivatives, which are vulnerable to attack by amine or thiol-containing compounds, resulting in the formation of stable derivatives of the original phosphopeptide. These derivatives are more hydrophobic and are therefore more amenable to identification by HPLC, mass spectrometry, or by Edman sequencing. Under the conditions used, phosphoserine residues undergo elimination and addition, phosphothreonine residues undergo elimination but not addition and phosphotyrosine residues are unaltered by the treatment. Thus, differential identification can be accomplished based on this knowledge. In Edman degradation, during the acid or base delivery the phosphate is β-eliminated and the resulting dehydro-amino acids rapidly form a dithiothreitol (DTT) adduct. See Meyer et al., *FASEB J.* 7:776 (1993). In contrast, O-Hex-N—Ac on serine and threonine is stable in Edman degradation. See Gooley & Williams, *Nature* 358:557 (1997). Thus, the present invention may be used to differentiate between serine or threonine phosphorylation and glycosylation.

Edman degradation is thus an effective method for quantitating serine and threonine, following β-elimination and derivatization. See Yan et al., "Protein Phosphorylation: Technologies for the Identification of Phosphoamino Acids", *J. Chromatogr.* 808:23-41 (1998)). These modified products also survive acid hydrolysis, and can be quantitated by reversed-phase HPLC analysis. See, e.g., Meyer et al., *J. Chromatogr.* 397:113 (1987) and Holmes, *FEBS Lett.* 215:21 (1987). Using a similar approach, characterization by capillary zone electrophoresis and laser-induced fluorescence has also been used to quantitate the phosphoserine content of peptides and proteins. See, Fadden & Haystead, *Anal. Biochem.* 225:81 (1995).

Nanoelectrospray MS/MS is used for phosphopeptide sequencing for exact determination of phosphorylation sites. See Stensballe et al., "Characterization of Phosphoproteins From Electrophoretic Gels by Nanoscale Fe(III) Affinity Chromatography With Off-Line Mass Spectrometry Analysis," *Proteomics* 1:207-222 (2001). In-gel digestions can be achieved as described in Shevchenko et al., *Anal. Chem.* 68:850-58 (1996) and Jensen et al., *Meth. Mol. Biol.* 112:513-30 (1998). The present invention also contemplates that the materials and methods can be used with mass spectrometry techniques yet to become available that achieve the same results.

The sequence of phosphopeptides and the identification of the site(s) of phosphorylation can also be determined by a combination of tandem mass spectrometry and computer-assisted database search programs, such as SEQUEST (Trademark, University of Washington, Seattle Wash.) (Mc-Cormack et al., "Direct Analysis and Identification of Proteins in Mixtures by LC/MS/1\4S and Database Searching at the Low-Femtomole Level," *Anal. Chem.* 69:767-776 (1996);

Eng et al., "An Approach to Correlate Tandem Mass Spectral Data of Peptides with Amino Acid Sequences in a Protein Database," *J. Amer. Soc. Mass. Spectrom.* 5:976-989 (1994); U.S. Pat. No. 5,538,897. While a variety of MS methods are available and may be used in these methods, MALDI/MS and Electrospray Ionization MS (ESI/MS) methods are typically used.

Sample Preparation

The sample is defined to include any material that may contain phosphorylated target molecules, substrates that interact with kinases and phosphatases, substances that interact with kinase and phosphatase substrates and any substance that binds phosphorylated target molecules. Typically the sample is biological in origin and comprises tissue, a cell or a population of cells, cell extracts, cell homogenates, purified or reconstituted proteins, recombinant proteins, fusion proteins, bodily and other biological fluids, viruses or viral particles, prions, subcellular components, or synthesized peptides or proteins. Possible sources of cellular material used to prepare the sample of the invention include, without limitation, plants, animals, fungi, bacteria, archae, or cell lines derived from such organisms. The sample can be a biological fluid such as whole blood, plasma, serum, nasal secretions, sputum, saliva, urine, sweat, transdermal exudates, cerebrospinal fluid, or the like. Alternatively, the sample may be whole organs, tissue or cells from an animal. Examples of sources of such samples include muscle, eye, skin, gonads, lymph nodes, heart, brain, lung, liver, kidney, spleen, solid tumors, macrophages, mesothelium, and the like.

Prior to combination with the binding solution of the present invention, the sample is prepared in a way that makes the phosphorylated target molecules or enzyme substrates in the sample accessible to the phosphate-binding compounds. Alternatively, the sample may comprise enzymes or binding proteins that interact with phosphorylated target molecules. Typically, the samples used in the invention comprise tissue, cells, cell extracts, cell homogenates, purified or reconstituted proteins, peptides, recombinant proteins, biological fluids, lipids, amino acids, nucleic acids and carbohydrates or synthesized proteins. However, the desired target (target molecule comprising exposed phosphate groups) may require purification or separation prior to addition of the binding solution due to the presence of other discrete biological components. The desired phosphorylated target molecules and other discrete biological components can be optionally separated from each other or from other components in the sample by mobility (e.g., electrophoretic gel or capillary) by size (e.g., centrifugation, pelleting or density gradient), or by binding affinity (e.g., to a filter membrane or affinity resin) in the course of the present methods. For example, when the sample is to be separated on an SDS-polyacrylamide gel, the sample is first equilibrated in an appropriate buffer, such as an SDS-sample buffer containing Tris, glycerol, DTT, SDS, and bromophenol blue. For certain aspects of the invention it is preferred that the phosphorylated target molecules not be separated before analysis.

When starting with a sample source that is not appropriate for separation, e.g., whole cells or tissue homogenate, the sample needs to first be prepared, using techniques well known to those skilled in the art. Preparation of the sample will depend on how the phosphorylated target molecules are contained in the sample (see e.g., Current Protocols in Molecular Biology; Herbert, *Electrophoresis* 20:660-663 (1999)). For example, an optional way of preparing samples for 2-D gel electrophoresis followed by labeling with the compositions and methods of the present invention includes lysing cells using a lysis buffer that ensures that the proteome, in addition to post-translational modifications, of a sample remain in their in vivo state throughout the entire procedure. Examples of such buffers include ones derived from a urea/NP-40/2-mercaptoethanol mixture. Therefore, the lysis buffer might additionally contain phosphatase inhibitors such as sodium orthovanadate, sodium fluoride or β-glycerophosphate in addition to a protease inhibitor cocktail.

Typically the phosphorylated peptides and proteins in the sample have a molecular weight greater than about 500 daltons. More typically the phosphorylated peptides and proteins are more than 800 daltons. In one aspect of the invention, the phosphorylated proteins comprise a mixture of phosphorylated proteins with different molecular weights that fall within a range of molecular weights, wherein the phosphorylated proteins are used as molecular weight standards so that labeled phosphorylated proteins or peptides can be accurately analyzed. Samples comprising phosphorylated peptides subjected to the methods of the present invention can be generated from natural or synthetic samples and may be the result of chemical, physical or enzymatic digestion of phosphorylated protein samples. Proteins can be digested using any appropriate enzymatic method, such as trypsin digestion. Peptides in the digest may be preferably sized to facilitate peptide sequencing using tandem mass spectrometric methods, and are typically in the size range from about 10 to about 50 amino acids in length. Alternatively, these peptides can also function as phosphatase substrates in a method of the invention to identify such enzymes and to measure their quantity and/or enzymatic activity.

Samples comprising phospholipids, wherein the phospholipids are the target molecules, are prepared with modifications compared to samples comprising phosphoproteins prior to applying to solid or semi-solid matrix due to their hydrophobic nature. Most samples typically require some sort of extraction treatment prior to binding with the compositions and methods of the present invention. Where the phosphorylated target molecule of interest come from tissue samples or samples from organisms having cell walls, mechanical or chemical disruption may be required. Suitable means are well known in the art and include, but are not limited to, the use of a tissue homogenizer or a French pressure cell in conjunction with, for example, organic solvent extractions. Methods of cell disruption and fractionation are described in Ausubel et al., CURRENT PROTOCOLS IN MOLECULAR BIOLOGY (John Wiley & Sons 1997). Samples may be extracted with solvents possessing varying hydrophobic properties, and the optimal solvent is contingent upon the nature of the phosphorylated target molecule of interest. Extraction techniques conventional in the art that result in a sample suitable for detection are contemplated by the present invention.

The following references describe various extraction techniques: Dole et al., *J. Clin. Invest.* 35:150-54 (1956); Dole et al., *J. Biol. Chem.* 235:2595-99 (1960); Bligh et al., *Canadian J. Biochem. Physiol.* 37:914-17 (1959); Folch et al., *J. Biochem.* 226:497-509 (1957). The Dole et al. references describe an extraction method that involves extractions of the sample with an isopropyl alcohol/heptane/sulfuric acid mixture, followed by several heptane extractions. The organic phase is dried with nitrogen for use in subsequent steps. The Folch et al. reference describes the extraction of lipids from biological tissue homogenates or body fluids. Samples are extracted with chloroform/methanol, filtered and reverse-extracted with 0.1 M KCl. The Bligh et al. reference describes the organic extraction of lipids from biological tissue homogenates or fluids. Samples are extracted with methanol/chloroform and chloroform, and then filtered and reverse-extracted with water.

Typically, the phosphorylated target molecules (proteins, peptides, carbohydrates or lipids) are present on or in a solid or semi-solid matrix. In one aspect of the invention, this matrix comprises an electrophoresis medium, such as a polyacrylamide gel, agarose gel, linear polyacrylamide solution, polyvinyl alcohol gel or a hydrogel. The solid or semi-solid matrix can also comprise a membrane, such as a filter membrane, a nitrocellulose, poly(vinylidene difluoride) (PVDF) membrane, or nylon membrane wherein the phosphorylated target molecules are immobilized on the membrane by blotting, spotting, electroblotting (tank and semi-dry), capillary blotting or other methods of application well known to those skilled in the art. In accordance with the present invention, a solid and semisolid matrix also includes a glass slide, a plastic matrix (e.g., multi-well plate or pin), a glass or polymeric bead or fiber or a semiconductor material. The phosphorylated target molecules may be arrayed on the support in a regular pattern or randomly. A preferred array of the present invention is a hydrogel glass slide support, wherein the phosphorylated target molecules of the sample are arrayed in a regular pattern. The present invention contemplates that the phosphorylated target molecules can be phosphorylated after immobilization on a matrix material, wherein an enzyme substrate is immobilized and the appropriate enzyme and phosphate is incubated with the immobilized substrate. For certain aspects of the invention it is preferred that the phosphorylated target molecules be free from a solid or semi-solid matrix, i.e. not immobilized and present in an aqueous solution as solubilized molecules.

Illumination

In a typical detection method, at any time after or during binding with the phosphate-binding compounds of the present invention, the sample is visualized whereby the phosphorylated target molecule is detected. Visualization can comprise different methods and is dependent on the chemical moiety A that is covalently attached to the metal-chelating moiety of the phosphate-binding compound. When the chemical moiety A is a label, visualization typically comprises illumination with a wavelength of light capable of exciting the reagent to produce a detectable optical response, as defined above, and observed with a means for detecting the optical response. Equipment that is useful for illuminating the phosphate-binding compounds of the invention includes, but is not limited to, hand-held ultraviolet lamps, mercury arc lamps, xenon lamps, lasers and laser diodes. These illumination sources are optionally integrated into laser scanners, fluorescence-based microplate readers, standard or minifluorometers, or chromatographic detectors. The degree and/or location of binding, compared with a standard or expected response, indicates whether and to what degree the sample possesses a given characteristic, i.e., phosphorylated target molecules.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, fluorescence-based microplate readers, or by a means for amplifying the signal such as photomultiplier tubes.

The detectable optical response can be quantified and used to measure the degree of phosphorylation of the phosphorylated target molecule in the sample mixture. Quantification is typically performed by comparison of the optical response to a prepared standard or to a calibration curve. Typically, the measured optical response is compared with that obtained from a standard dilution of a known concentration of the phosphorylated target molecule in an electrophoretic gel, HydroGel or on a membrane. Generally, a standard curve must be prepared whenever an accurate measurement is desired. Alternatively, the standard curve is generated by comparison with a reference dye or dyed particle that has been standardized versus the reagent-target conjugate desired.

Alternatively, stained electrophoretic gels are used to analyze the composition of complex sample mixtures and additionally to determine the relative amount of a particular phosphorylated target molecule in samples. This can be accomplished, for instance, in conjunction with determination of the number of phosphate groups on a molecule and a total protein stain to differentiate between an increase in the amount of protein versus an increase in phosphate groups on a particular protein or peptide.

Inductively coupled plasma mass spectrometry (ICP-MS) is a useful technology for the trace elemental analysis of environmental, biological, and pharmaceutical samples. Recently, the feasibility of directly measuring phosphorous as m/z 31 signal liberated from β-casein using laser ablation ICP-MS has been demonstrated on electroblot membranes (Marshall, P., et al. *Analyst* 127: 459-461 (2002)). Though 16 pmole of the pentaphosphorylated protein was detectable on blots, the technique was not successfully performed on polyacrylamide gels due to very high background signal. This was undoubtedly due to the presence of isobaric species and overlap from adjacent species generated from the polyacrylamide gel matrix and electrophoresis buffer components. The detection of low concentrations of phosphorous presents several analytical challenges for ICP-MS due to its poor ionization in the argon ICP and the presence of interfering polyatomic species directly at mass 31 ($^{15}N^{16}O$ and $^{14}N^{16}O^{1}H$) and indirectly at mass 32 ($^{16}O_2$ and $^{32}S$). ICP-MS could be used to detect phosphoproteins stained with the methods of this invention. The detection procedure is envisioned to involve the following steps. First, proteins separated by gel electrophoresis are fixed to remove the SDS. A typical fixative would be 40% methanol/10% acetic acid. Next, gels would be stained for phosphoproteins using the methods of the invention. Next, the gels would be washed to remove excess stain. The more prominent phosphoproteins could be visualized by fluorescence imaging at this point and background staining can be minimized by inspection and adjustment of wash times as appropriate. Gels are then dried down and the gel is subjected to laser ablation ICP-MS by methods similar to those described in Marshall et al, 2002. Sampling can be performed by single or multi-spot analysis, straight-line scans or rastering. In the case of rastering, virtual gels can be constructed from the data obtained as described by Loo R R, et al., *Anal Chem.* 73:4063-70 (2001)). Using the ruthenium-containing SYPRO® Ruby dye staining technology, gallium (aluminum or iron) signal from the phosphoprotein stain, as well as ruthenium for the total protein stain could be independently quantified.

Thus, it is contemplated by the present invention that a wide variety of instrumentation may be used to detect the phosphorylated target molecules, e.g., electrospray ionization (ESI) tandem mass spectrometry (MS/MS). A series of different techniques, including automated high performance liquid chromatography (HPLC)-MS/MS, capillary-HPLC-MS/MS, and solid phase extraction (SPE)-capillary zone electrophoresis (CZE)-MS/MS, are described in Figeys et al., *Electrophoresis* 19:1811-1818 (1998).

When measuring fluorescence polarization, many forms of automation may be used and are known by those skilled in the art. As one example, any standard fluorometer equipped for polarization experiments or measurements may be used in practicing this embodiment of the invention to both irradiate the mixture and measure the polarization. Wavelengths suitable to excite the fluorophore depend on the nature of the fluorophore, as described above. Typically, one uses cut-off filters to define a wavelength range, which is determined by the excitation and emission wavelengths of the fluorophore. For example, for fluorescein-labeled peptides, one would typically use an excitation cutoff filter of 485 nm. Standard fluorometers can be used, or, for example, a fluorescence-based plate reader. Thus, in addition, one of skill in the art of automation may use various instruments to measure fluorescence polarization in accordance with the materials and methods of the invention.

The use of 1,2-bis(2-amino-5,6-difluorophenoxy)ethane-N,N,N',N'-tetraacetic acid (TF-BAPTA) or any of the fluoride-containing phosphate-binding molecules described in this invention with gallium for binding to the phosphorylated target molecule could be detected using $19_F$-NMR spectroscopy (Doughty D A, Tomutsa L. Magn Reson Imaging 1996; 14(7-8):869-73). Additionally, radioactive gallium-67 (half-life: 78 hr), gallium-68 (half-life: 1.13 hr) or gallium-72 (half-life: 14.1 hr) could be employed with any of the phosphate-binding compounds of the invention to generate a detectable signal by autoradiography or scintigraphy.

As described above, while a wide variety of methods of detection are used with the present invention, a preferred method includes the use of fluorescence. Fluorescence from the phosphate-binding compound metal (preferably gallium) ion complex simultaneously binding to the phosphorylated target molecule can be visualized with a variety of imaging techniques, including ordinary light or fluorescence microscopy.

Kits

Suitable kits for labeling, isolating and identifying enzymes that interact with phosphorylated target molecules also form part of the invention. Such kits can be prepared from readily available materials and reagents and can come in a variety of embodiments. The contents of the kit will depend on the design of the assay protocol or reagent for detection or measurement. All kits will contain instructions, appropriate reagents and phosphate-binding compounds, separation media, and solid supports, as needed. Typically, instructions include a tangible expression describing the reagent concentration or at least one assay method parameter such as the relative amounts of reagent and sample to be added together, maintenance time periods for reagent/sample admixtures, temperature, buffer conditions and the like to allow the user to carry out any one of the methods or preparations described above.

A kit for binding phosphorylated target molecules comprises a binding reagent that is typically prepared in solution, wherein the binding solution is identical to what was described above. Optionally, the kit would comprise any one of the following; molecular weight markers for both phosphorylated and non-phosphorylated target molecules, a total protein stain and a staining solution for glycoproteins. When the kit is used to detect phosphorylated proteins or peptides in a gel or on a blot, molecular weight markers are typically part of the kit. Alternatively, when the kit is used to stain phosphorylated target molecules in a solution or on an array, molecular weight markers would typically not be part of the kit.

Another kit in the present invention finds use in identifying kinases or phosphatases or measuring their activity and/or evaluating the effect of inhibitors and activators on these enzymes. Typically this kit would comprise appropriate substrate immobilized on matrix material, binding solution and appropriate controls. Alternatively the phosphate-binding compounds would be immobilized on the matrix and the end user would supply both substrate and enzyme. This kit would comprise a solution containing a metal ion salt and an acid or appropriate buffer that when added to the immobilized phosphate-binding compounds would form the binding solution of the present invention.

Another kit of the present invention finds use in isolating phosphorylated proteins or peptides from a complex sample mixture, wherein the ternary complex is pulled out of solution. The kit would optionally comprise a binding solution, elution buffer and optionally a protein or hapten-binding support, wherein the support could be a multiwell plate, agarose resin, polymeric microbeads or magnetic beads, containing an appropriate affinity reagent, e.g. a biotin- or hapten-binding protein, an antibody, a lectin, a protein-binding nucleic acid or other biopolymer covalently attached to the support. The kit would further optionally contain one or more of a spin column, standard peptide mixture and nucleophilic derivatization compound.

Another kit of the invention that finds use in isolating phosphorylated proteins or peptides from a complex sample mixture comprises a matrix containing phosphate-binding compounds that are covalently attached to the matrix, typically in the form of a column. The kit would typically comprise, in addition to the phosphate-binding compounds immobilized on the matrix, a metal salt, a wash buffer, a moderately acidic binding buffer, and an elution buffer. The metal salt is preferably gallium chloride and the elution buffer preferably comprises barium hydroxide.

Those skilled in the art will appreciate that a wide variety of additional kits and kit components can be prepared according to the present invention, depending upon the intended user of the kit, and the particular needs of the user.

Applications

The present invention is useful for a wide variety of applications in a wide variety of areas including, but not limited to, basic research applications, high-throughput screening, proteomics, microarray technology, diagnostics, and medical therapeutics. Those skilled in the art will appreciate that the invention can be used in a wide variety of assay formats in a wide variety of diagnostic applications. The foregoing description seeks merely to illustrate the many applications of the materials and methods of the present invention, and does not seek to limit the metes and bounds of the invention as described in the above sections.

The materials and methods of the present invention are useful for a number of applications. The present invention may be used to generate data that are used as a reference point for a human patient or animal sample for the diagnosis of disease, progression of disease, and/or predisposition for disease. By way of example, if a disease is associated with changes in protein composition in certain cells, e.g., protein phosphorylation in different organ systems, cell sources or tissue types, a patient sample may be used to generate a protein profile according to the materials and methods of the invention, and compared with profiles of corresponding samples of normal or non-diseased samples and/or diseased origin to determine the presence or absence of, progression of, and/or predisposition to the particular disease in question. It is contemplated by the present invention that many diseases may be diagnosed with data or images generated by the materials and methods of the present invention, including diseases for which particular aberrations in protein expression are either known or not known. Such disease states include, but are not limited to, metabolic diseases that are associated with the lack of certain enzymes, proliferative diseases that are associated with aberrant expression of certain genes, e.g., oncogenes or tumor suppressors, or developmental diseases that are associated with aberrant gene expression. Thus, if it is known that a given disease of interest is associated with certain changes of a particular type of cell, tissue, cell source, or organ system, a human patient or animal may be diagnosed simply based on its individual expression profile generated by 2-D gel electrophoresis or another appropriate separation and analysis technique such as bead-based analysis technology developed by Luminex, or others, or evaluations done on microarrays in accordance with any aspect of the present invention. In another aspect, expression profiles generated by one of these methods may be used to analyze a diseased organ, tissue or cell type and compared with the corresponding profile counterpart obtained from a non-diseased sample.

Moreover, the information generated by the materials and methods of the present invention may be used to "backtrack" or identify and/or associate novel or known genes and their corresponding products that are involved in the manifestation of, progression of, or predisposition to a disease of interest, and with the development of symptoms of a particular disease, by generating the amino acid sequence of a phosphoprotein or phosphopeptide of interest based on the materials and methods of the present invention. For example, ESTs are partial nucleotide sequences obtained from cDNA derived from mRNA from any given cell line. Thus, the present invention may be used to generate amino acid sequence data, and from the amino acid sequence data, extrapolate potential DNA sequences that can be used to search EST databases. For example, MS/MS sequence data in the form of a peptide sequence tag, may be used to query EST databases if a protein is not identified by searching the conventional full length sequence databases. If an EST is retrieved, then the corresponding DNA clone can be ordered and sequenced. The apoptotic protease FLICE/Caspase-8 and the trinucleotide repeat binding protein p20-CGGBP was identified and cloned by this approach. See Muzio et al. "FLICE, a Novel FADD-homologous ICE/CED-3-like Protease, is Recruited to the CD95 (Fas/APO-1) Death-Inducing Signaling Complex," *Cell* 85:817-827 (1996) and Deissler et al., "Rapid Protein Sequencing by Tandem Mass Spectrometry and cDNA Cloning of p20-CGGBP. A Novel Protein that Binds to the Unstable Triplet Repeat 5'-d(CGG)$_n$-3' in the Human FMR1 Gene," *J. Biol. Chem.* 272:16761-16768 (1997). During analysis of protein components isolated from the human spliceosome, a relatively large number of ESTs were retrieved by MS/MS data. In the alternative, it may be necessary to generate amino acid sequence data for sequence homology searching, e.g., by BLAST algorithm searching. If the sequence is significantly related to a characterized protein from another species, then its function may be directly deduced. If no related proteins exist, however, then the amino acid sequence data may be used to design oligonucleotide probes for cloning of the cognant gene. Complete sequence determination of the protein can then be performed at the DNA level by established genetic and molecular biology techniques.

The phosphorylated target molecules can be from many different sources, including cell types, cell conditions, genetic background, states of perturbation or of different developmental states. Cell sources for analysis may be transgenic or non-transgenic, transfected or non-transfected, virus-or prion-infected or non-infected. "Perturbation" refers to experimental manipulation of the sources, i.e., cells, such as treatment with a particular compound or drug compared to non-treatment of a drug. Alternatively, it can refer to treatment with a particular compound or drug compared to treatment of a source or cell with a different dosage of a particular compound or drug.

For example, cells can be subjected to a candidate drug regimen to generate a phosphoprotein expression profile in accordance with the present invention. The images of 2-D gels generated in accordance with the present invention may be stored on a database, and the database may be later queried for a cell source representing a different treatment, e.g., protein expression profiles generated by a response to a different drug or where no drug is present, or where the candidate drug is used in a different way. Moreover, the candidate drug may bind specifically to a particular protein, permitting analysis of cells or other sources, which express that protein. The database query may derive information about cell sources that express a particular protein.

Thus, the materials and methods of the present invention could be used to gain valuable information of the effects of various drugs and compounds on the cellular phosphoprotein status. For example, it was demonstrated that the compounds FK-506, cyclosporin and rapamycin, used to suppress tissue rejection, inhibit certain protein phosphatases. Schreiber et al., *Cell* 70:365-68 (1992). A database of lymphoid proteins detected by 2-D polyacrylamide gel electrophoresis has also been generated. The database contains 2-D patterns and derived information pertaining to polypeptide constituents of unstimulated and stimulated mature T cells and immature thymocytes, cultured T cells and cell lines that have been manipulated by transfection with a variety of constructs or by treatment with specific agents, single cell-derived T and B cell clones, cells obtained from patients with lympoproliferative disorders and leukemia, and a variety of other relevant cell populations. See Hanash & Teichroew, "Mining the Human Proteome: Experience with the Human Lymphoid Protein Database," *Electrophoresis* 19:2004-2009 (1998). Thus, in accordance with the present invention, cells treated with a suspected drug compound can be compared to untreated cells to generate a 2-D gel electrophoresis profile. Furthermore, it may be observed, for example, that certain drug compounds induce the activation of different sets of kinases or phosphatases. Such evidence could lead to the elucidation of the mechanism by which many drug compounds work and manifest their effects.

A 2-D gel electrophoresis study was performed to generate a phosphoprotein profile in cultures that were subjected to the effect of oxygen/glucose deprivation. The results suggested that this model could be a good method to observe the development of the tissue and its response to an ischaemic lesion. See Tavares et al., "Profile of Phosphoprotein Labeling in Organotypic Slice Cultures of Rat Hippocampus," *Neurochemistry* 12:2705-2709 (2001).

The materials and methods of the present invention can also be used to study biological phenomena, such as, for example, signal transduction, mitosis, cell proliferation, cell motility, cell shape, gene regulation, and many other cellular processes. The mechanism of action of kinases and phosphatases and the physiological relevance of site-specific phosphorylation of substrate proteins can be explored with the materials and methods of the present invention. The materials and methods of the present invention offer the advantage of high-resolution 2-D gel electrophoresis to simultaneously resolve hundreds of cellular polypeptides. Using the materials and methods of the present invention, the potential for the identification of proteins and the expression of their genes at various stages of cell growth, differentiation, or disease, is extensive. Thus, the invention provides methods and materials for the detection and quantitation of phosphorylation of specific cellular proteins that may provide insight into the mechanisms by which phosphorylation is employed for the regulation in cells.

It is well known that the critical events in the cell cycle are controlled by a complex interplay of kinases and phosphatases. Thus, the status of phosphorylation of different protein isoforms during different phases of the life cycle is important to researchers. Thus, in accordance with the materials and methods of the present invention, the phosphorylation of different proteins related to the stage of the cell cycle related to the activity of certain kinases or phosphatases may be explored using the materials and methods of the present invention. By way of example, a global analysis of phosphoproteins in cells can be used to analyze the primary signals of, for example, mitogenesis in selected cells, or in G1 or S phase cells. Thus, the materials and methods of the present invention may be useful in investigating the phosphorylation status of various proteins during the cell cycle.

Those of skill in the art will recognize that a database can be generated using the materials and methods of the present invention to produce a record that may show the correlation between gene expression at the RNA and protein level to the function of the cell. For examples, in situations where the cells under study are obtained in both cancerous and normal conditions, comparison of the relative gene expression can be used to identify genes that can serve either as diagnostic markers of pathology or as sites for the pharmacological intervention or treatment of, for example, cancer. Similarly, other diseases can be analyzed merely by substituting the source of cells for analysis.

Thus, the present invention may be used to generate a comprehensive phosphoprotein expression profile from any cell type or biological fluid of interest. A cell type of interest may be any cell, or portion thereof with genetic material. A reference cell can be of any cell type in which the difference in protein expression patterns and levels is desired to be measured. Preferably, the cells are maintained as similar to their native state as possible and culture techniques, incubation times etc., are performed identically between the two to minimize any non-naturally occurring differences. For example, development of a comprehensive protein profile of pre-cancerous, and/or malignant test cells and a normal reference cell can be achieved according to the invention. Such expression profiles can be used to characterize molecular events, for example, related to tumor development and the cellular mechanisms involved.

In accordance with the present invention, a cell of interest and a reference cell could be obtained from the same patient to get an individual phosphoprotein expression profile that can be used to diagnose or treat that patient for those diseases that involve protein phosphorylation. For example, when a tumor is excised, a margin of non-transformed cells is typically removed as well. Phosphoprotein expression profiles can help to ensure that the cells removed all had similar profiles to normal cells rather than the metastatic cells from the same patient for those cancers that involve, or are thought to involve, protein phosphorylation.

One example of cell lines that may be analyzed using the materials and methods of the present invention includes human tumor cell lines. For example, human tumor cell lines representing a broad spectrum of human tumors and exhibiting acceptable properties and growth characteristics may be grown according to standard methods for cell line expansion, cryopreservation and/or characterization for use with the present invention. If phosphorylation is implicated in cellular aging, the materials and methods of the present invention may be used to analyze test and reference cells, i.e., to develop phosphoprotein expression profiles associated with aging, such as different stages of ontogenesis, for example, protein profiles of embryonic liver-derived hematopoietic stem cells. Thus, the invention contemplates a comparison of any diseased state to a normal reference state.

In addition, studying the effects of various ligands added to cells can assess the effects of various agonists on the reversible phosphorylation on multiple cellular proteins. Thus, for example, the in vivo substrates of a kinase of interest could be determined by treating cells with suspected substrates and comparing the resulting gel images of 2-D separated proteins with untreated controls. As an increasing number of cytokines are being discovered and characterized, many or all of which will activate protein kinases or phosphatases as they manifest their effects on target cells, the materials and methods of the present invention may be especially useful for exploring such mechanisms. For example, the identity of some of these proteins may suggest assays to be formulated for the location and characterization of kinases and phosphatases induced by lymphokines or cytokines and lead to a better understanding of autoimmune diseases. Methods for identifying phosphoproteins upregulated in response to the cytokines IL-2 or IFN-γ were described using both silver staining and Western blotting for protein detection and identification. The silver-stained profile served as a "fingerprint" for phosphorylation events that occur in response to cytokine treatment. See Stancato & Petricoin III, "Fingerprinting of Signal Transduction Pathways Using a Combination of Anti-Phosphotyrosine Immunoprecipitations and Two-Dimensional Polyacrylamide Gel Electrophoresis," *Electrophoresis* 22:2120-2124 (2001).

The materials and methods of the present invention can also be used to map kinase and phosphatase substrates in vitro. For example the identification of substrates for various kinases can be determined by processing extracts from cells and allowing a purified kinase to phosphorylate its substrate proteins. One skilled in the art could compare all the cytosolic proteins as candidate substrates for the kinase under investigation to identify major substrates for a kinase of interest. Similar to in vitro assays for kinases, it is possible to use the advantages offered by 2-D separation and assays on microarrays, in multiwell plates, in microfluidics devices, on microbeads and using other high-throughput assay technologies and the invention to isolate and characterize the phosphatases that catalyze the removal of phosphate from phosphorylated substrates. Thus, the activity of kinases and phosphatases responsible for phosphorylating and dephosphorylating individual proteins can be analyzed. See, e.g., Fruehling & Longnecker, "In Vitro Assays for the Detection of Protein Tyrosine Phosphorylation and Protein Tyrosine Kinase Activities," *Methods in Mol. Biol.* 174(Ch. 36):337-343 (2001).

The applications described herein are provided merely to illustrate a wide variety of potential uses of the invention, and are in no way intended to limit the scope of the invention. A detailed description of the invention having been provided above, the following examples are given for the purpose of illustrating the invention and shall not be construed as being a limitation on the scope of the invention or claims.

EXAMPLES

Generally, the nomenclature as used herein, and the laboratory procedures in cell culture, molecular genetics, and protein chemistry described below are those well known and commonly employed in the art. Generally, enzymatic reactions and purification steps are performed according to the manufacturer's specifications. Units, prefixes, and symbols may be denoted in their SI accepted form. Numeric ranges are inclusive of the number defining the range and include each integer within the defined range.

Example 1

Determination of BAPTA Selectivity for Gallium and Gallium Ions for Phosphorylated Target Molecules and a Screening Method for Phosphate-binding Compounds (A) BAPTA with Trivalent Gallium Ions Selectively Detects Phosphoproteins.

A comprehensive search of metal-chelating compounds was performed to identify fluorescent reagents that when combined with a gallium salt (gallium chloride) would selectively detect phosphorylated target molecules (particularly phosphopeptides and phosphoproteins) in a mixture of phosphorylated and nonphosphorylated target molecules. The compounds were tested in a fluorescence spectrophotometer for their ability to bind gallium (III) ion and selectively detect the phosphoprotein ovalbumin. Binding to gallium (III) ion was determined by a fluorescence increase of the same compound in the presence of up to 5 µM gallium chloride in 75 mM NaOAc (pH 4.0) and 140 mM NaCl. Ovalbumin detection was also judged by a fluorescence increase; however, the compounds were placed in a solution containing 75 mM NaOAc (pH 4.0), 140 mM NaCl, 1-4 µM ovalbumin, and 0.5 µM gallium chloride. Selectivity of phosphoprotein detection was evaluated by virtual elimination of the fluorescence increase in the presence of the same solution lacking gallium chloride.

Using compound 1, a variety of metal ions, including iron and gallium, were screened to determine which ion(s) were best suited for phosphoprotein detection. Metal ions were assayed for binding to compound 1, phosphoprotein detection, and general protein staining by monitoring a fluorescence increase at 530 nm in 75 mM NaOAc (pH 4.0), 140 mM NaCl, 0.5-5 µM metal ion, with or without 4 µM ovalbumin or 1 µM lysozyme. Only trivalent cations that bound to compound 1 resulted in a fluorescence increase at 530 nm and only gallium (III) ion was capable of selectively indicating phosphoproteins when bound to compound 1. Therefore, gallium (III) ion is the most preferred metal ion for phosphoprotein detection. This methodology was extrapolated to identify other compounds wherein a different dye was attached to the metal-chelating moiety.

(B) Differential Binding Affinity of Compound 1 for Phosphate Compounds.

Compound 1 complexed with gallium (III) ion has differential affinities for various phosphate substrates in 75 mM NaOAc (pH 4.0) and 140 mM NaCl. Some of the phosphate-containing compounds studied were inorganic phosphate, phosphate attached to a protein, a peptide or an amino acid, pyrophosphate, ATP, and DNA. The affinities for these phosphate-based substrates for the Compound 1/gallium (III) ion reagent were determined to be ~50 µM for inorganic phosphate and phosphate attached to a protein, a peptide or an amino acid, ~200 nM for pyrophosphate and ATP, and no binding was detected for DNA. Compare these values to the affinity of compound 1 for gallium (III) ion of 2.5 µM. Most known phosphate compounds should fall into one of these three categories with respect to how it will bind to BAPTA gallium (III) ion; 1) single phosphate group (i.e., inorganic phosphate or phosphate on a protein), 2) multiple linked phosphate group (i.e., pyrophosphate or ATP), or 3) bridging phosphate group (i.e. nucleic acids).

(C) Compound 4 Displays Dual-emission Wavelengths Upon Simultaneously Binding to Gallium (III) Ion and Phosphate.

Concentrations of 0.1-1.0 µM of compound 4 in a solution of 75 mM NaOAc (pH 4.0) and 140 mM NaCl display a single emission peak centered at 410 nm (excitation 350 nm). Addition of 10 nM to 1 mM gallium chloride results in a decrease in the 410 nm emission and a concomitant increase in emission at 490 nm, with an isosbestic point of 475 nm. The half-maximal response for this transition from the blue to green emitting state occurs at approximately 1.8 µM gallium chloride. Therefore, 0.1 µM compound 4 with 1.7 µM gallium chloride in 75 mM NaOAc (pH 4.0) and 140 mM NaCl display both the 410 nm and 490 nm emission peaks. The addition of phosphate can alter the equilibrium between the emission peaks in favor of the longer wavelength 490 nm peak.

(D) Screening for Phosphate-binding Compounds that Simultaneously Bind Gallium and Immobilized Phosphorylated Target Molecules.

A panel of test proteins was loaded on a denaturing SDS polyacrylamide gel, separated by electrophoresis, and the gels were fixed with 45% methanol, 5% acetic acid. Typically the test gels contained 500-600 ng each of myosin, β-galactosidase, phosphorylase b, ovalbumin (2 phosphates), carbonic anhydrase, soybean trypsin inhibitor, lysozyme, aprotinin, $\alpha_2$-macroglobulin, phosphorylase b, glucose oxidase, bovine serum albumin, $\alpha_1$ acid glycoprotein, carbonic anhydrase, avidin, and lysozyme. The gels also contained a 4-fold dilution series of α-casein (8 phosphates), 500 ng to 2 ng loaded. Thus the gels contained a range of proteins with different physicochemical properties, such as proteins with hydrophobic binding pockets (e.g. BSA), glycosylated proteins (e.g. $\alpha_2$-macroglobulin, glucose oxidase and avidin), acidic proteins (e.g. soybean trypsin inhibitor), basic proteins (e.g. lysozyme and aprotonin), and two different phosphoproteins (ovalbumin, α-casein). The dilution series of α-casein yielded an estimate of phosphoprotein staining sensitivity. A selection of phosphate-binding compounds comprising different dye labels and different chelating moieties was initially screened in minimal binding buffers of pH 3.0 to 7.0, with a variety of metal ions, in the presence or absence of metal ion. Dye and metal ion concentrations ranged from 0.1 to 10 µM, typically 0.3 to 3 µM, and most frequently at 1.0 µM. Binding conditions that produced preferential staining of phosphoproteins typically were at pH 3.0 to 5.5, in the presence of certain trivalent metal ions. Under these conditions, optimal preferential phosphoprotein staining was obtained with certain dye labels and the BAPTA chelating moiety with an equimolar concentration of $Ga^{3+}$. Further evaluation of the successful dyes revealed that the pH optimum was 4.0, and that addition of salt (e.g. 250-750 mM NaCl) improved staining specificity chiefly by decreasing intensity of staining of non-phosphoproteins. A broadened screen of dyes was undertaken with 1 µM candidate dye, 1 µM of $Ga^{3+}$ in 50 mM sodium acetate, pH 4.0, 500 mM sodium chloride.

(E) Binding Solution Formulation

The binding solution comprises a phosphate-binding compound with a metal ion in molar ratios of 1:2 to 2:1 and a buffer at about pH 3.0 to 6.0. Typically, the binding solution comprises a pH 3.0 to 5.5 buffer (50 to 100 mM), salt (e.g. 100 to 1000 mM NaCl, or 100 to 300 mM $MgCl_2$) and equimolar concentrations of $Ga^{3+}$ and of a phosphate-binding compound (e.g Compound 2), typically 1 to 10 µM each for detection purposes.

Concentrations of the metal ion and phosphate-binding compound are typically at least 100 times higher concentration for isolation purposes than is present in the binding solution for detection purposes (see, Example 13). An optimal binding solution for a gel stain was prepared as follows: 500 µg of compound 2 was dissolved in 873 µl water for a 1 mM stock solution. Five g of $GaCl_3$ were dissolved in 28.4 mL water for a 1 M solution, from which 1 mL was combined with 9 mL water to make a 0.1 M solution, from which 10 µL was added to 990 µL water for a 1 mM stock solution. One liter of a 1 M stock solution of sodium acetate, pH 4.0 was prepared by dissolving 136 g of sodium acetate trihydrate in ca. 800 ml water, adjusting pH to 4.0 by adding ca. 23.5 mL 12 M HCl and bringing volume to 1 liter. One liter of a 4 M stock solution of sodium chloride was prepared by dissolving 233.8 NaCl in ca. 800 mL water and bringing the volume to 1 liter with water. The sodium acetate and sodium chloride stock solutions were filtered through a 0.45 µM filter. For 100 mL of binding solution, 5 ml of 1 M sodium acetate, pH 4.0, 12.5 ml of 4 M sodium chloride, and 20 mL of 1,2 propanediol were combined with water to a final volume of 100 mL, to which was added while stirring 100 µL of 1 mM $GaCl_3$ and 100 µl of 1 mM Compound 2 to obtain a final binding solution of 1 µM Compound 2, 1 µM $Ga^{3+}$, 20% 1,2-propane diol, 500 mM NaCl, 50 mM sodium acetate, pH 4.0.

Example 2

Detection of Phosphoproteins in SDS-Polyacrylamide Gels

Phosphoproteins were separated by SDS-polyacrylamide gel electrophoresis utilizing a 4% T, 2.6% C stacking gel, pH 6.8 and 13% T, 2.6% C separating gel, and pH 8.8, according to standard procedures. % T is the total monomer concentration (acrylamide+crosslinker) expressed in grams per 100 mL and % C is the percentage crosslinker (e.g., N,N'-methylene-bis-acrylamide, N,N'-diacryloylpiperazine or other suitable agent). The separating gels were 8 cm wide by 5 cm high and 0.75 cm in thickness. After electrophoresis, the gels were fixed by immersing them in 100 mL 45% methanol and 5% acetic acid for 90 minutes. The gels were washed twice in water for a total of 30 minutes. The gels were then added to a binding solution of the invention (Example 1E) and incubated for 120 minutes at room temperature with gentle orbital shaking, typically 50 rpm. The binding buffer contained 50 mM NaOAc (pH 4.0), 250 mM sodium chloride, 20% v/v 1,2-propanediol, 1 µM gallium chloride. To prepare the binding solution, 120 µL of a 1 mM stock solution of Compound 2 and 120 µL of a 1 mM stock solution of gallium chloride were added to 1080 µL water. This mixture was then added to 59 mL of the binding buffer to yield the binding solution. Alternatively, the phosphate-binding compound and the gallium chloride can be added separately, directly to 60 mL of the binding diluent. Binding solutions that utilize other phosphate-binding compounds of the present invention can be prepared and similarly tested for gel staining. After incubation in binding solution, the gel was washed with 75 mL of 50 mM NaOAc (pH 4.0) and subjected to two washes of 30 minutes each.

For Compound 2 and other dyes that can be excited at 532 nm, images were acquired on a Fujifilm FLA 3000 laser scanner using 532 nm excitation and 580 nm bandpass emission filters. For fluorescent phosphate-binding compounds that absorb in the ultraviolet or at visible wavelengths below 532 nm, excitation was performed using 300 nm and detection was via Roche Lumi-Imager or Fujifilm FLA 3000 laser scanner using 473 nm excitation and 580 nm bandpass emission. The data were displayed using Image Gauge Analysis software. Images of phosphoproteins were displayed as dark bands. Proteins not containing phosphate were not labeled or were very lightly stained relative to the phosphoproteins. When gels were labeled as above but with gallium chloride omitted from the binding solution, phosphoproteins were not selectively stained, and could not be distinguished from background or had very light nonspecific staining. Gels were washed overnight with 50 mM NaOAc (pH 4.0) and images were acquired as above. The background and nonspecific staining was further reduced relative to phosphoprotein staining. Replacement of gallium chloride by other gallium salts gave comparable results with all indicators tested; however, replacement by other metals, including $Fe^{3+}$ and $Al^{3+}$ typically gave inferior results in staining of phosphoproteins.

Fixation of the gels in methanol/acetic acid can be done overnight or the gels can be left in fixative for several days. Other salts can be used instead of sodium chloride, including magnesium chloride, magnesium sulfate, and ammonium sulfate. Sodium chloride concentration is preferably between 100 mM to 1000 mM. If salt is not included in the binding solution, nonspecific staining of nonphosphoproteins is increased. Nonspecific staining is reduced to low levels by extensive washing with ~50 mM NaOAc (pH 4.0). Buffers other than NaOAc may be used, including formate and 2-(N-morpholino)ethanesulfonic acid. If 1,2-propanediol is omitted, the background staining of the gel is increased but phosphoproteins are still selectively stained. The most effective pH ranges of the acidic buffers are in the range of 3.0 to 6.0.

Example 3

Serial Dichromatic Detection of Phosphoproteins and Total Protein in SDS Polyacrylamide Gels After detection of the phosphoproteins as in Example 2, the gel was incubated overnight with 60 ml SYPRO® Ruby protein gel stain (Molecular Probes, Eugene, Oreg.) with gentle orbital shaking, typically 50 rpm. The gel was then incubated in 7% acetic acid, 10% methanol for 30 minutes, also at 50 rpm. The orange signal from the phosphorylated and non-phosphorylated proteins was collected with a standard CCD camera-based imaging system with 300 nm UV light excitation and a 600 nm bandpass filter.

Example 4

Detection of Phosphopeptides in a Polyacrylamide Gel

Peptides generated by a trypsin digestion of bovine milk β-casein were separated by electrophoresis in a Novex® Tricine gel (16% polyacrylamide, Invitrogen™ life technologies). After electrophoresis the gel was fixed for 1 hour in 100 mL 40% methanol, 10% acetic acid, and then fixed for 1 hour in 100 mL of 40% methanol, 0.82 M NaOAc, 0.5% glutaraldehyde. The gel was washed with three changes of water, and then incubated for 100 minutes in 30 mL staining solution containing 50 mM NaOAc, pH 4.0, 500 mM sodium chloride, 1 µM compound 2, 1 µM gallium chloride. The gel was then washed with three changes of 50 mM NaOAc in 75 minutes. Images were acquired on a Fujifilm FLA 3000 laser based scanner with 532 nm excitation and 580 nm bandpass emission filter and data displayed using the Image Gauge Analysis software. The two known phosphopeptides that result from a trypsin digest of β-casein were visible as prominent bands on the gel. The gel was then stained with 60 mL SYPRO® Ruby protein gel stain by incubating the gel overnight in the stain, and then incubating the gel in 7% acetic acid, 10% methanol for 30 minutes.

Example 5

Detection of Phosphoproteins in Isoelectric Focusing Gels

Isoelectric focusing (IEF) can be performed utilizing a variety of pre-cast and laboratory prepared gels that employ different chemistries to generate a pH gradient. In this instance, Ampholine PAG plates were run horizontally for 1500 volt-hours using a Multiphor II electrophoresis unit (Amersham-Pharmacia Biotech, Uppsala, Sweden) per the manufacturer's instructions. The gels were fixed in 100 mL of 45% methanol, 5% acetic acid overnight. The gels were then washed with several changes of equal volumes of water, and incubated for 130 minutes in 50 mL of staining solution containing 50 mM 2-(N-morpholino)ethanesulfonic acid (pH 3.0), 1000 mM NaCl, 1 µM compound 2, and 1 µM gallium chloride. The gels were washed with 50 mL of 50 mM 2-(N-morpholino)ethanesulfonic acid (pH 3.0), 1 M NaCl twice for 30 minutes per wash, and then in 50 mM 2-(N-morpholino) ethanesulfonic acid (pH 3.0). Images were acquired as described in Example 2.

Example 6

Detection of Phosphoproteins in Two-Dimensional Gels

A human MRC-5 lung fibroblast cell lysate protein mixture (150 µg) was diluted into urea buffer (7 M urea, 2 M thiourea, 2% CHAPS, 1% Zwittergent 3-10, 0.8% carrier ampholytes (3-10), 65 mM DTT) and applied on a first dimension IPG strip (3-10 nonlinear, 18 cm). After overnight rehydration, the strips were covered with mineral oil and the proteins were focused for 75,000 volts total. IPG strips were then laid on top of 1 mm thick, 20 cm×20 cm, 12.5% T, 2.6% C polyacrylamide gels containing 375 mM Tris base, pH 8.8 and SDS-polyacrylamide gel electrophoresis was performed according to standard procedures, except that the cathode electrode buffer was 50 mM Tris, 384 mM glycine, 4% SDS, pH 8.8 while the anode electrode buffer was 25 mM Tris, 192 mM glycine, 2% SDS, pH 8.8. After the second dimension electrophoresis, gels were fixed in 750 mL 45% methanol, 5% acetic acid for 20 hours. Gels were washed twice, 75 minutes per wash, with water and then put in 500 ml staining solution. The staining solution contained 50 mM NaOAc, pH 4.0, 250 mM sodium chloride, 20% v/v 1,2-propanediol, 1 µM compound 2, 1 µM gallium chloride. 500 µL of compound 2, in stock solution at 1 mM and 500 µL of gallium chloride, in stock solution at 1 mM were added to 9 mL water. This mixture was then added to 490 mL of the staining buffer. The gel was incubated for 8 hours in the binding solution; the solution was decanted and the gels were washed with 3 changes of 800 mL 50 mM NaOAc, pH 4.0, 30 to 40 minutes per wash, and then washed overnight in 1 liter 50 mM NaOAc, pH 4.0. Images were acquired on a Fujifilm FLA 3000 laser scanner with 532 nm excitation and 580 nm bandpass emission filter and data displayed using Image Gauge Analysis software. Images of phosphoproteins were displayed as dark spots. Proteins not containing phosphate were not stained or were very lightly stained relative to the phosphoproteins. When gels were stained as above but with $GaCl_3$ omitted from the staining solution phosphoproteins were not selectively stained, and could not be distinguished from background or light nonspecific staining. In addition, staining of phosphoproteins resulted in a trail of spots that correlated with different percentage of phosphorylation of the same protein, i.e., the protein had the same molecular weight but the charge was different due to the addition or removal of a phosphate group. Thus, 2-D gel analysis is a useful tool for identify phosphoproteins using methods of the present invention and allows for identification of changes in phosphorylation of a single protein.

Example 7

Serial Dichromatic Detection of Phosphoproteins and Total Protein in 2-D Gels

Electrophoresis and phosphoprotein detection was performed as in Example 6. After detection of the phosphoproteins, the gel was stained with 500 mL SYPRO® Ruby protein gel stain by incubating the gel overnight in the stain, and then washing the gel in 7% acetic acid, 10% methanol for two changes, at 30 minutes each wash. Images were acquired as described in Example 2. Alternatively, the orange signal from the phosphorylated and nonphosphorylated proteins is collected with a standard CCD camera-based imaging system with 300 nm UV light excitation and a 600 nm bandpass filter.

Example 8

Detection of Phosphoproteins Electroblotted to PVDF or Nitrocellulose Membranes

Proteins of interest were separated by SDS-polyacrylamide electrophoresis and transferred to PVDF membrane using standard procedures, and the membrane was allowed to air dry. The PVDF membrane was quickly dipped in 100% methanol, washed with a solution of 40% methanol, 5% acetic acid for 15 minutes, and with two changes of water for 10 minutes each. The blot was then added to a binding solution and incubated for 80 minutes at room temperature with gentle orbital shaking. The binding solution contained 50 mM NaOAc, pH 4.0, 500 mM sodium chloride, 1 µM Compound 1 or Compound 4, and 1 µM gallium chloride. Typically, 60 µL of the phosphate-binding compound, in stock solution at 1 mM and 60 µL of gallium chloride, in stock solution at 1 mM were added to 540 µL water. This mixture was then added to 29.5 mL of the staining buffer. Alternatively the phosphate-binding compounds and the gallium chloride may be added separately, directly to 30 mL of the staining diluent. After incubation in staining solution, the gel was washed with 50 mL of 50 mM NaOAc; pH 4.0, 2 washes of 30 to 50 minutes each.

Images were acquired with a standard CCD camera imaging system (BioRad FluorS Max) with a reflective 300 nm UV light source, and a 465 nm bandpass emission filter for Compound 4. Proteins not containing phosphate were not labeled or were very lightly stained relative to the phosphoproteins. When the blot was stained as above but with GaCl₃ omitted from the staining solution, phosphoproteins were not selectively stained, and could not be distinguished from background or light nonspecific staining. For imaging with Compound 1, the wet blots were placed face down in the Fujifilm FLA 3000 laser scanner with a 473 nm excitation laser and 520 nm bandpass emission filter, and data displayed using the Image Gauge Analysis software.

Example 9

Dichromatic Detection of Phosphoproteins and Total Protein Electroblotted to PVDF Membrane Serial dichromatic detection of phosphoprotein and total protein on PVDF membrane was accomplished by post-staining the blot labeled and imaged to detect phosphoprotein as in Example 8 (above) with SYPRO® Ruby protein blot stain to detect total protein. The blot was floated face down on a solution of 10% methanol, 7% acetic acid for 15 minutes followed by face staining with SYPRO® Ruby dye for 15 minutes. The blot was washed face down on water, 3 changes in 10 minutes. The membrane was allowed to air dry. The fluorescent signal from total proteins was acquired with a standard CCD camera imaging system (BioRad FluorS Max) with a reflective 300 nm UV light source and a 610 nm longpass filter.

Dichromatic staining was achieved by image acquisition with a standard CCD camera imaging system (BioRad FluorS Max) with a reflective 300 nm UV light source and a 465 nm bandpass emission filter as in Example 8. The signal from the phosphoprotein stained with Compound 4/Ga (III) could be distinguished from the signal from total protein stained with SYPRO® Ruby, not detected with the 465 nm bandpass filter.

For Compound 1, SYPRO® Ruby staining and image acquisition as above reveals fluorescent signal from total protein, revealing the phosphoproteins as a subset when the SYPRO® Ruby image is compared to the fluorescent image obtained as in Example 6, above.

Example 10

Detection of Phosphatase Activity

Phosphoproteins and non-phosphorylated proteins were incubated with commercially available calf intestinal alkaline phosphatase at 37° C. for 30 minutes under standard conditions. Control digests were done under the same conditions with no enzyme. Suitable test proteins include bovine α-casein, ovalbumin, and pepsin as phosphoproteins; and bovine serum albumin, chicken egg white lysozyme, and soybean trypsin inhibitor as non-phosphorylated proteins. Electrophoresis was performed as per Example 2, with control (undigested) and phosphatase-treated samples loaded pairwise, 1250 ng protein per lane. Phosphoprotein detection was performed as per Example 2 above, with images taken 90 minutes after labeling and again after overnight washing. An additional gel was labeled as per Example 2 but with no gallium chloride in the binding solution. For the gel labeled with the full binding solution, comparisons of the control, undigested sample proteins showed that the phosphoproteins appeared as dark bands according to the software display and the nonphosphoproteins were not labeled or were only very lightly stained. For the gel labeled with the formulation lacking gallium chloride, phosphoproteins showed the same degree of no labeling or only very light staining as the nonphosphoproteins, and this level of signal was the same as the nonphosphoproteins in the gels labeled with the full formulation including gallium chloride. Comparison of the pairwise phosphoproteins in the fully labeled gel showed that the signal from the alkaline phosphatase-treated sample was significantly less than the signal from the undigested control. The very light signal from the nonphosphoproteins, if detectable, was virtually the same for the control and enzyme-treated samples.

After detection of the phosphoproteins, the gel was stained for total protein with SYPRO® Ruby protein gel stain as per Example 2 and images of SYPRO® Ruby staining were acquired as per Examples 3 and 7. The signal for total protein staining was similar for the pairwise control and digested samples for both gels, indicating that the reduced signal from alkaline phosphatase-treated phosphoprotein samples was not due to protein degradation.

Example 11

Detecting Kinase Activity

Bovine muscle myosin light chain was incubated with commercially available cloned calmodulin-dependent protein kinase 11 (New England BioLabs) according to the manufacturer's instructions, with 100 mM adenosine triphosphate (ATP) and the supplied buffer components. A parallel, control incubation was done with no enzyme. A sample of each reaction mixture was loaded in adjacent lanes and analyzed by electrophoresis as in Example 2. The gels were fixed in 100 mL of 45% methanol, 5% acetic acid for 60 minutes. The gels were then washed with several changes of water. One gel was incubated for 110 minutes in 30 mL of binding solution containing 50 mM 2-(N-morpholino)ethanesulfonic acid, pH 3.0, 1000 mM NaCl, 1 µM compound 2, 1 µM gallium chloride. The other gel was incubated in an identical solution, minus gallium chloride. The gels were washed with 50 mL 50 mM 2-(N-morpholino)ethanesulfonic acid, pH 3.0, 1000 mM NaCl twice for 30 minutes per wash, and then in 50 mM 50 mM 2-(N-morpholino)ethanesulfonic acid, pH 3.0. Image acquisition for phosphoprotein detection was done as in Example 2 and serial dichromatic detection of phosphoproteins and total protein was done as in Example 3.

Staining for total protein revealed identical profiles of 3 major bands in both lanes. Staining for phosphoprotein revealed one major band in both lanes, with the signal from the band in the lane corresponding to the reaction containing the enzyme 3.4-fold greater than the no-enzyme control.

Example 12

TRAIL/Apo2L Detection

To determine the cell signaling factors involved in TRAIL/Apo2L mediated apoptosis, a proteomics approach involving 2-D gel electrophoresis and mass spectrometry is used. This approach involves comparing 2-D gels of colon cancer cells (Colo205) treated and not treated with a soluble fragment of TRAIL/Apo2L (amino acids 114-281) for various lengths of time ranging from several seconds to several hours. To assist in comparison of 2-D gels, compound 7 bound to gallium ions is used in conjunction with the SYPRO® Ruby total protein stain. Since cell signaling often involves protein phosphorylation, the use of compound 7 highlights spots likely to be involved in death receptor signaling or apoptotic signaling. Protein spots that are significantly different between the TRAIL/Apo2L treated and untreated Colo205 cells are identified by subsequent mass spectrometry analysis.

Example 13

Precipitation of Phosphopeptide

Mixtures of two non-phosphorylated peptides (Angiotensin I and II) and two phosphorylated peptides (pT/pY and RII) were combined (5 µL each) in a final volume of 100 µL containing 100 mM NaOAc, pH 4.0, 0.2 mM $GaCl_3$ and 0.1 mM compound 9. The mixtures were vigorously vortexed for 1 hour at room temperature and then centrifuged in a microfuge at full speed for 5 minutes. The supernatants were removed and stored. The pellets were resuspended by triturating with a micropipet tip in 100 µL wash buffer (100 mM NaOAc, pH 4.0, 0.2 mM $GaCl_3$). The samples were again centrifuged for 5 minutes and the supernatant wash components were saved for analysis. The pellets were dissolved in 100 µL 50% acetonitrile, 0.1% TFA for further analysis by HPLC or MALDI mass spectrometry. Pellets can also be dissolved in various different basic solutions of choice.

If phosphate-binding compound removal is required after precipitation, extraction with chloroform can be used. Also, any biotinylated phosphate-binding compound, such as compound 9, can be used in the precipitation procedure. After separation of the pellet, phosphopeptides from the phosphate-binding compound/gallium complex using organic or base treatment, the phosphate-binding compound can be removed using an immobilized streptavidin support (e.g., streptavidin-agarose or streptavidin magnetic beads.)

Example 14

Detection of a Phosphopeptide in Solution by Fluorescence Polarization using Compound 2-$Ga^{3+}$ To demonstrate complexation of Compound 2-$Ga^{3+}$ to phosphoproteins and phosphopeptides, fluorescence polarization of free dye was examined and compared to the complex (compound 2-$Ga^{3+}$) in the presence of a phosphorylated and non-phosphorylated protein and peptide.

First, an assay was conducted with a (1) phosphoprotein (ovalbumin) and a (2) control non-phosphorylated protein (lysozyme). A modified binding solution containing 1.0 µM Compound 2 was incubated in 50 mM 2-(N-morpholino) ethanesulfonic acid (pH 3.0 to 3.5), 500 mM NaCl at room temperature in parallel to solutions containing, in addition, (a) 1 µM gallium chloride, (b) 100 µM lysozyme plus 1 µM gallium chloride, or (c) and 100 µM ovalbumin plus 1 µM gallium chloride. The fluorescence polarization of the resulting solutions was then measured in a fluorescence spectrophotometer with excitation at 530 nm and emission at 545 to 700 nm. The integrated polarized emission spectra yielded anisotropy "r values" of: r=0.10+/−0.003+/−0.02 (Compound 2 plus gallium); r=0.10+/−0.002 (Compound 2 plus lysozyme non-phosphorylated control); r=0.34+/−0.002 (Compound 2 plus gallium plus ovalbumin), indicating phosphorylation-dependent binding of the Compound 2 to this phosphoprotein (see FIG. 10A)

Second, an assay was conducted with a (1) phosphopeptide, (2) non-phosphorylated peptide and (3) control with no peptide. Phosphorylated and non-phosphorylated delta sleeping inducing peptide DSIP (Typ-Ala-Gly-Gly-Asp-Ala-Ser($PO_3$)-Gly-Glu) were purchased from SynPep Corporation (Dublin, Calif.) Ovalbumin (Cat. A-7641) and lysozyme (Cat. L-7651) were purchased from Sigma Chemical Company (St. Louis, Mo.). For the assay 100 µM of each peptide and a peptide-free control in binding solution (50 mM NaOAc pH 4.0, 500 mM NaCl, 1 µM Compound 2 and 1 µM $GaCl_3$) were incubated for 30 minutes at room temperature. The fluorescence polarization and anisotropy measurements were made using an Aminco-Bowman Series-2 Spectrometer (Spectronic Instruments, Inc., Rochester, N.Y.) using wavelength settings excitation 555±4 nm and emission wavelength setting 580 nm±4 nm. Alternatively, fluorescence was measured with the Wallac 1420 Multilabel Counter (PerkinElmer Life Sciences) using wavelength settings excitation 535±17.5 nm and emission wavelength setting 590 nm±17.5 nm. The binding solution alone and binding solution in the presence of non-phosphorylated peptide demonstrates very similar fluorescence polarization and anisotropies. However, in the presence of the phosphopeptide there is a significant increase in the fluorescence polarization and the anisotropy values. This result demonstrates specific binding of the phosphopeptide to the Compound 2-$Ga^{3+}$ complex in solution but not the non-phosphorylated peptide. See FIG. 10B.

This assay also provides a method for screening compounds that will bind trivalent gallium ions and label phosphorylated peptides and for solution based kinase assays.

Example 15

Isolation and Characterization of Phosphopeptides from Complex Protein Digests with a Matrix-Immobilized Phosphate-binding Compound A phosphate-binding compound-agarose column (compound 13 or 14) (typically 200 µL of medium) was charged with 0.1 M $GaCl_3$ and washed with de-ionized $H_2O$ until the pH of the flow-through material approached 7.0. The column was then equilibrated with 5 column volumes of binding buffer (100 mM NaOAc buffer (pH 3.0)). The phosphopeptide mixture was vacuum dried in the SpeedVac (Savant) or similar instrument and dissolved in binding buffer. If the final pH of the peptide mixture is not 3.0, then it can be adjusted with 1-10 M acetic acid as appropriate. The protein digest (1-5 mg/mL) was applied in 1 column volume or less (but no less than half the column volume) and followed with 2 column volumes of binding buffer. Flow-through (FT) fractions were combined and stored for further analysis. The column was washed with 2 column volumes of 100 mM NaOAc (pH 7.0), 500 mM NaCl, 10% acetonitrile followed by 1 column volume of NaOAc (pH 7.0). The FT fractions were combined and stored for further analysis. Bound peptides were eluted with 3 separate column volumes of saturated Ba(OH)$_2$ that are collected in a single tube. The pH of the resulting elution fraction was greater than pH 11.0, and when it was not, it was immediately adjusted with saturated Ba(OH)$_2$. The elution fraction was incubated for 90 minutes at 30° C. After incubation, the sample was divided into 2 portions, one of which was neutralized to pH 5.0-7.0 with glacial acetic acid and stored frozen. One-half volume of de-ionized water is added to the other tube followed by the addition of a concentrated nucleophilic thiol or amine (methylamine, cystamine or β-mercaptoethylamine) to achieve a final concentration of 0.1-0.5 M in a volume not exceeding ⅙ of the starting sample/$H_2O$ volume. The reaction mix was incubated for an additional 60 minutes at 30° C., then neutralized to pH 5.0-7.0 with glacial acetic acid. For MALDI-TOF mass spectrometry analysis, peptides were purified from samples using C18 ZipTips (Millipore) using standard protocols, vacuum dried in a SpeedVac dryer and dissolved in 50% acetonitrile and 0.1% TFA. An equal volume of 10 mg/mL MALDI matrix (α-cyano-5-hydroxycinnamic acid) in the same solvent was added. The solution was mixed thoroughly and 1 μL was spotted onto the MALDI target.

Differential mass weight analyses of both peptide fractions resulted in the determination of the number of phosphorylation sites on the peptides, as well as the nature of the phosphoamino acids. Under the conditions used, only phosphoserine residues undergo elimination and nucleophilic addition (loss of phosphoric acid −98 amu, +mass weight of nucleophilic addition reagent). Phosphothreonine residues undergo elimination only (loss of phosphoric acid only, −98 amu) and phosphotyrosine residues remain unchanged, as phosphotyrosine is stable in strong base.

Example 16

Quantitating the Number of Phosphates on Ovalbumin

Solutions of 1 μM and 4 μM ovalbumin were incubated in 75 mM NaOAc (pH 4.0), 140 mM NaCl, 0.1 μM Compound 4, and 1.7 μM gallium chloride at room temperature for 5-10 minutes. The fluorescence intensity of the resulting solution was then measured at 410 nm in a fluorescence spectrophotometer and compared to a standard phosphate calibration curve to determine the number of phosphates on ovalbumin. The standard phosphate calibration curve was produced by equilibrating known concentrations (1, 2, 4, 6, 8, and 10 μM) of a 19 amino acid phosphoserine-containing peptide in 75 mM NaOAc (pH 4.0), 140 mM NaCl, 0.1 μM compound 4, and 1.7 μM gallium chloride and measuring the fluorescence intensity at 410 nm. Next the fluorescence intensity was graphed versus the known concentration of phosphopeptide. The fluorescence intensity from the solution containing ovalbumin was compared to the standard curve to reveal ~2 μM and ~8 μM phosphate. Finally, accounting for the protein's concentration resulted in the determination of two phosphate groups per molecule of ovalbumin.

Example 17

Phospholipid Detection

To test the detection of phospholipids with the present invention, different phospholipids were spotted onto a nitrocellulose membrane. The phospholipids were obtained from Echelon Research Labs in a format called a PIP Array™, which contains 8 different phosphoinositides (PtdIns) at 7 different concentrations. PIP Arrays™ were used for determining the sensitivity limits of the invention for detecting phospholipids.

PIP Array™

1. PtdIns 100 50 25 12.5 6.3 3.2 1.6 pmol
2. PtdIns (3) P
3. PtdIns (4) P
4. PtdIns (5) P
5. PtdIns (3,5) P2
6. PtdIns (4,5) P2
7. PtdIns (3,4) P2
8. PtdIns (3,4,5,) P3

One PIP Array™ was washed in 50 mM NaOAc (pH 4.0) for 15 min. After the wash, the PIP Array™ was incubated in 50 mM NaOAc (pH 4.0), 20% 1,2-propanediol, 500 mM NaCl, 1 μM compound 1, and 1 μM GaCl₃ for 1 hour, by incubating the array at 100-150 RPM on an orbital shaker.

After incubating the PIP Array™ the array was washed 3 times in 50 mM NaOAc (pH 4.0) for 15 minutes each at 100-150 RPM on an orbital shaker to remove unbound dye and reduce the background fluorescence. An image of the PIP Array™ was generated using a laser based scanner (Fuji FLA 3000) with an excitation wavelength of 473 nm and an emission filter of 520 nm. Of the eight phosphoinositides, four gave a strong positive signal. These included phosphatidic acid, phosphoinositide (4,5) $P_2$, phosphoinositide (3,4) $P_2$ and phosphoinositide (3,4,5) $P_3$. The strongest signal was obtained with phosphoinositide (3,4) $P_2$ followed by phosphoinositide (4,5) $P_2$ and then phosphoinositide (3,4,5) $P_3$.

Example 18

Phosphoprotein Detection on Microarrays

Four specific, purified proteins including β-casein, ovalbumin, pepsin and bovine serum albumin were arrayed from a source plate (384 well plate) at a concentration of 0.975 μg/mL-0.5 mg/mL in water, onto HydroGel coated slides (Perkin Elmer), using the BioChip Arrayer™ (Packard Instrument Co., Meriden, Conn.). The BioChip Arrayer™ utilizes a PiezoTip™ Dispenser consisting of 4 glass capillaries. Proteins were dispensed from the PiezoTip™ by droplets 333 pL in volume to create array spots 175 microns in diameter with a 500 micron horizontal and vertical pitch (pitch=center to center spacing of spots). Proteins were arrayed in duplicate in four rows, with 10 dilution points, resulting in an array of 160 spots. The resulting concentration range of the array was 166.5 pg/spot-0.325 pg/spot. For detection of phosphoproteins, slides were incubated for 1 hour on a rotator in 1 μM of Compound 2, in buffer containing 0.5 M NaCl, 20% 1,2-propanediol, 1 μM GaCl₃, and 0.05 M NaOAc, pH 4.0. Slides were then washed for 1 hour on a rotator in 0.05 M NaOAc, pH 4.0, containing 10% methanol followed by a 15 minute water wash. Slides were then spun briefly in a microarray high-speed centrifuge affixed with a rotor with a slide holder (Telechem) at ~6000 rpm to remove excess liquid. After the slides were dry, the arrays were imaged using the ScanArray® 5000 XL Microarray Analysis System (Packard Instrument Co., Meriden, Conn.) using the 543.5 nm laser and either 570 nm or 592 nm emission filter. Phosphate content per protein was determined to be as follows: β-casein, five phosphates; ovalbumin, two phosphates; pepsin, one phosphate; and BSA, no phosphates.

Example 19

Phosphopeptide Detection on Microarrays

Two peptides, Kemptide and pDSIP, were arrayed on to HydroGel coated slides (Perkin Elmer) from a source plate (384-well) with a concentration of 0.03125 to 2 mg/mL peptide in water. The amino acid sequence of Kemptide is Leu-Arg-Arg-Ala-Ser-Leu-Gly (MW 771.9). The amino acid sequence of pDSIP is Trp-Ala-Gly-Gly-Asp-Ala-Ser(PO₃H)-Gly-Glu (MW 929.5). Arrays were spotted using a manual glass slide arrayer (V & P Scientific, San Diego, Calif.) fixed with 4 rows of 8 pins (32 total), ~500 micron diameter spot size, 1.125 micron horizontal pitch and 750 micron vertical pitch (pitch=center to center spacing of spots). The hand arrayer collected 6 nL of peptide from the source plate and transferred ~6 nL to the array surface by direct contact. The resultant peptide concentration was 0.18 to 12 ng/spot. Peptides were arrayed in replicates of 6, resulting in an array of 84 spots. For specific detection of pDSIP, the phosphopeptide, slides were incubated for 1 hour on a rotator in 1 µM dye of compound 2 in buffer containing 0.5 M NaCl, 20% 1,2-propanediol, 1 µM GaCl$_3$, and 0.05 M NaOAc, pH 4.0. Slides were then washed for 1 hour on a rotator in 0.05 M NaOAc, pH 4.0, containing 10% methanol followed by a 15-minute water wash. Slides were then spun briefly in a microarray high-speed centrifuge affixed with a rotor with a slide holder (Telechem) at ~6000 rpm to remove excess liquid. After the slides were dry, the arrays were imaged using the ScanArray® 5000 XL Microarray Analysis System (Packard Instrument Co., Meriden, Conn.) using the 543.5 nm laser and either 570 nm or 592 nm emission filter.

Example 20

Detection of Immobilized Kinase Substrates in Microarray Format; Selective Detection of Glycogen Synthase 1-10

Two specific peptides, Abl peptide and glycogen synthase 1-10, were arrayed from a source plate (384-well plate) concentration of 0.03-2 mg/mL in water, onto HydroGel coated slides (Perkin Elmer). Abl peptide (New England Biolabs) is a substrate for Abl tyrosine kinase and its amino acid sequence is E-A-I-Y-A-A-P-F-A-K-K-K (MW 1336). Glycogen synthase 1-10 (Calbiochem) is a substrate for Calcium-Calmodulin-Dependent protein Kinase II and its amino acid sequence is P-L-S-R-T-L-S-V-S-S (MW 1045.2). Arrays were spotted using a manual glass slide arrayer (V&P Scientific, San Diego, Calif.) fixed with 4 rows of 8 pins (32 total), ~500 micron diameter spot size, 1.125 micron horizontal pitch and 750 micron vertical pitch (pitch=center-to-center spacing of spots). The handarrayer collected 6 nL of peptide from the source plate and transferred ~6 nL to the hydrogel coated slide by direct contact. The resultant peptide concentration is 0.18 to 12 ng/spot. Peptides were arrayed in replicates of 6, resulting in array of 96 spots (12 spots, of which were 0 ng/spot). Slides were left overnight after arraying in a humidity chamber. Slides were then blocked for 1 hour in 100 mM HEPES, 1% BSA while rotating (Barnstead/Thermolyne Labquake rotisserie). After blocking, the slides were spun briefly in a small microarray high-speed (max ~6000 rpm) centrifuge affixed with a rotor with a slide holder (Telechem) to remove excess liquid. Next, kinase reactions were performed by attaching a Grace Biolabs Hybriwell™ hybridization sealing system (40×22×0.25 mm) to the hydrogel coated slide to enclose the area containing the hydrogel polyacrylamide pad. The reaction was carried out in an 80 µL reaction volume containing 20,000 U/mL or 1600 units enzyme (Calmodulin-Dependent protein Kinase II, NEB) using buffer, CaCl$_2$, calmodulin, and ATP supplied with the enzyme. 1× CamKII buffer included 50 mM Tris-HCl, 10 mM MgCl$_2$, 2 mM dithiothreitol, 0.1 mM Na$_2$EDTA, pH 7.5. CaCl$_2$, calmodulin and ATP working concentrations were 2 mM, 1.2 µM and 0.10 mM. The reaction solution with enzyme was pipetted into the Hybriwell™ through 1 of 2 ports on the seal cover. Ports were then sealed with seal-tabs, placed in a CMT-hybridization chamber (VWR Scientific) and incubated on a nutator (Clay Adams) in a 37° C. incubator. The kinase reaction was carried out for 3 hours. After incubation, the slides were removed from the hybridization chamber and washed 2 times for 5 minutes in 10% SDS followed by 5-7 times for 5 minutes in water while rotating. Slides were then transferred immediately to binding solution comprising 1 µM of compound 2 in 50 mM NaOAc, pH 4.0; 500 mM NaCl; 20% 1,2-propanediol; and 1 µM GaCl$_3$ for 45 minutes while rotating. Slides were then washed 3 times for 15 minutes each time in 50 mM NaOAc, pH 4.0, 10% methanol followed by a 15-minute water wash. Slides were then dried and imaged using the ScanArray® 5000 XL Microarray Analysis System (Packard Instrument Co., Meriden, Conn.) using the 543.5 nm laser and either 570 nm or 592 nm emission filters. Calmodulin-dependent kinase 11 specifically phosphorylates glycogen synthase 1-10 peptide. Using the 543.5 nm excitation and 570 nm emission filter, glycogen synthase peptide is the only fluorescently labeled peptide on the array. Sensitivity of detection after kinase reaction is at least 0.375 ng or 0.35 pmol.

Example 21

Detection of Immobilized Kinase Substrates in Microarray Format; Specific Detection of Abl Peptide Substrate The following experiment was performed essentially as described in Example 20 with the following differences. Two specific peptides, Abl peptide and Kemptide, were arrayed from a source plate (384-well plate) concentration of 0.03 to 2 mg/mL in water, onto hydrogel-coated slides (Perkin Elmer). Kemptide (New England Biolabs) is a substrate for cAMP-dependent Protein Kinase (PKA) catalytic subunit and its amino acid sequence is L-R-R-A-S-L-G (MW 771). Arrays were spotted as described in Example 20 and kinase reactions performed as described previously. The reaction was carried out in a 80 µL reaction volume containing 3,750 U/mL or 300 units enzyme (Abl Protein Tyrosine Kinase, NEB) using buffer and ATP supplied with the enzyme. 1× Abl buffer included 50 mM Tris-HCl, 10 mM MgCl$_2$, 1 mM EGTA, 2 mM dithiothreitol, 0.01% Brij 35, pH 7.5. Labeling of slides and imaging were performed as previously described. Using the 543.5 nm excitation and 570 nm emission filter, Abl peptide substrate is the only fluorescently labeled peptide on the array. Sensitivity of detection after kinase reaction is at least 0.18 ng or 0.14 pmol.

Example 22

Ratiometric Analysis of Phosphorylated Target Molecules Using a Binding Solution of the Present Invention and the Total Protein Stain SYPRO® Ruby Gel Stain SDS-polyacrylamide gels were loaded with serial dilutions of phosphoproteins and non-phosphoproteins and gels stained as described in Example 2. The gels were illuminated and fluorescence signal quantified (intensity) for each protein concentration and each stain (phosphoprotein and total protein). The ratio of these fluorescence intensities was then graphed, phosphoprotein and total protein, against the amount of protein loaded in the well (ng). The fluorescence intensity for each stain was next plotted against the protein concentration, this graph allows for the calculation of a constant number for each of the two stains, the Y-intercept value. The Y-intercept value is then subtracted from the fluorescence intensity values and the resulting rations (phosphoprotein to total protein) are again graphed against the protein concentration. This resulting graph produces numbers wherein stained phosphoproteins have ratio values 50-100 times greater than nonphosphorylated proteins, thus nonspecific staining and low abundance phosphoproteins can be distinguished from non-phosphorylated proteins. See, FIG. 10.

Example 23

Incorporation of ATP-γ-S During Phosphorylation of Immobilized Peptides on Microarrays and Subsequent Detection of the Phosphorothioate Group with a Binding Solution of the Present Invention Three specific peptides including Abl peptide, Kemptide and Glycogen Synthase 1-10 were arrayed from a source plate (384-well plate) concentration of 0.03 μg/mL to 0.5 mg/mL in water, onto hydrogel-coated slides (Perkin Elmer). Proteins were spotted using the BioChip Arrayer™ (Packard Instrument Co., Meriden, Conn.) that utilizes a PiezoTip™ Dispenser consisting of 4 glass capillaries. Proteins were dispensed from the PiezoTip™ by droplets 333 pL in volume to create array spots 175 microns in diameter with a 500 micron horizontal and vertical pitch (pitch=center to center spacing of spots). Each peptide was arrayed in quadruplicate from a 2-fold dilution series consisting of 15 dilution points, resulting in an array of 240 spots (including 60 water spots=0 pg/spot protein). The resultant peptide concentration was 0.01 pg/spot to 166.5 pg/spot. Slides were left overnight after arraying in a humidity chamber. Slides were then blocked for 1 hour in 100 mM HEPES, 1% BSA, pH 7.5, while rotating (Barnstead/Thermolyne Labquake rotisserie). After blocking, the slides were spun briefly in a small microarray high-speed (max ~6000 rpm) centrifuge affixed with a rotor with a slide holder (Telechem) to remove excess liquid. Next, kinase reactions were performed by attaching a Grace Biolabs Hybriwell™ hybridization sealing system (40×22×0.25 mm) to the hydrogel-coated slide to enclose the area containing the hydrogel acrylamide pad. The reaction was carried out in a 80 μL reaction volume containing 3750 U/mL or 300 units enzyme (Abl Protein Tyrosine Kinase, NEB) using buffer supplied with the enzyme. 1× Abl buffer included 50 mM Tris-HCl, 10 mM $MgCl_2$, 1 mM EGTA, 2 mM dithiothreitol, 0.01% Brij 35, pH 7.5. ATP-γ-S (Sigma Chemical Company) was substituted in place of ATP at a working concentration of 0.10 mM. A control reaction was run simultaneously on a second slide using ATP itself, supplied with the enzyme, at a working concentration of 0.10 mM. The reaction solution containing the enzyme was pipetted into the Hybriwell™ through 1 of 2 ports on the seal cover. Ports were then sealed with seal-tabs, placed in a CMT-hybridization chamber (VWR Scientific) and incubated on a nutator (Clay Adams) in a 37° C. incubator. The kinase reaction was carried out for 3 hours. After incubation, the slides were removed from the hybridization chamber and washed 2 times for 5 minutes in 10% SDS followed by 7 times for 5 minutes in water while rotating. Slides were transferred immediately to 1 μM compound 2 in 50 mM NaOAc, pH 4.0, 500 mM NaCl, 20% 1,2-propanediol, 1 μM $GaCl_3$ for 45 minutes while rotating. Slides were washed 3 times for 15 minutes each time in 50 mM NaOAc, pH 4.0, 4% acetonitrile, followed by a 15 minute water wash. Slides were dried and imaged using the Scan Array® 5000 XL Microarray Analysis System (Packard Instrument Co., Meriden, Conn.) using the 543.5 nm laser and either 570 nm or 592 nm emission filters. Abl Protein Tyrosine Kinase phosphorylates the tyrosine residue of the Abl peptide substrate with the phosphorothioate (or phosphate as in control). Using the 543.5 nm excitation and 570 nm emission filter, Abl peptide substrate is the only fluorescently labeled peptide on the array. Sensitivity of detection after kinase reaction was 2.6 pg of the peptide labeled using ATP-γ-S. By contrast, 0.325 pg of Abl peptide, in the control reaction using ATP, was labeled and detected with binding solution containing Compound 2.

Example 24

Isolation of Phosphopeptides via Immobilized Streptavidin or Phosphate-Binding Compound on Membranes Immunodyne membranes, purchased from Pall, were labeled by adding enough 5-10 mg/mL streptavidin or BAPTA-amine to wet the membrane (approximately 15 μL per $cm^2$). After air-drying for 15-30 minutes the membranes were washed 3 times for 5 minutes with 50% Acetonitrile/0.1% TFA, then twice for 5 minutes with water. Experiments were performed using 6 mm diameter circles of membrane. Streptavidin-labeled membranes were charged by soaking in 200 μL of 40 μM Compound 9/250 μM $GaCl_3$, and the BAPTA labeled membranes were charged by soaking in 200 μL 250 uM $GaCl_3$. After washing once with 10% acetonitrile/400 mM NaCl, 100 mM NaOAc, pH 4, then twice with water, the membranes were soaked in 100 μL of peptide mixture containing 2 μg each of 2 non-phosphopeptides and 3 phosphopeptides (approximately 6 nanomoles of total peptide) for 15 min. The membranes were washed once with 10% acetonitrile/400 mM NaCl/100 mM NaOAc, pH 4, then twice with 100 mM NaOAc, pH 4, for 5 min per wash. Finally the membranes were eluted with 100 μL of 50% acetonitrile/0.1% TFA. The eluates and peptide supernatants (peptide solution after incubation of membranes) were prepared for MALDI analysis.

Example 25

Isolation of Phosphopeptides with Immobilized Streptavidin on Ferrofluid Beads

A. Isolation of Phosphopeptides Using Streptavidin Ferrofluid Magnetic Particles in Conjunction with BAPTA-biotin Dyes Streptavidin ferrofluid magnetic particles were used in conjunction with BAPTA-biotin compounds to isolate phosphopeptides from a complex mixture. The magnetic particles were labeled with Compound 9 and two versions of rhodamine-biotin dyes (Compound 15 and Compound 25) due to the binding between biotin and streptavidin. After washing away phosphate-binding compounds, the particles were charged with 0.1 M $GaCl_3$, then washed with 0.1 M NaOAc, pH 4.0. Fifty μL of the magnetic particle slurry (4 mg/mL) was added to the phosphopeptide mix in a total volume of 100 μL. The particles were incubated with gentle vortexing for 20 minutes and the particles were isolated using a magnetic separator. The supernatants were removed and the beads were washed 2× with 100 μL 100 mM NaOAc, pH 4.0. The phosphopeptides were eluted with 100 μL 50% acetonitrile, 0.1% TFA. The isolated peptides were analyzed by MALDI and demonstrated that only phosphorylated peptides were isolated.

B. Quantitative Binding of Phosphopeptides Using Streptavidin Ferrofluid Particles Quantitative binding of phosphopeptides was accomplished using labeled ferrofluid particles. Streptavidin ferrofluid particles were labeled with Compound 9 until saturated. After washing away unbound dye, the particles were charged with 0.1 M GaCl$_3$, then washed with 0.1 M NaOAc, pH 4.0. 100 µL of magnetic particles (4 mg/mL) was added with standard peptide mix containing 550 picomoles of phosphopeptides. The mixture was incubated for 20 min while gently vortexing. The particles were isolated using a magnetic separator and the resulting supernatant was removed. The beads were washed 2× with 100 µL 100 mM NaOAc, pH 4.0 and the phosphopeptides were eluted with 0.15 M ammonium hydroxide. Greater than 95% of the phosphopeptides (550 pmoles) were isolated.

C. Ferrofluid Particle Isolation of Phosphopeptides Coupled with Base Elimination/addition Streptavidin ferrofluid (StFF) particles labeled with Compound 9 were used for phosphopeptide isolation and coupled with base elimination/addition. Phosphopeptides were isolated on StFF and the phosphopeptides eluted with 50 µL of 0.15 M Ba(OH)$_2$. Subsequently, 3 µL methylamine was added to the eluate and peptides were incubated at 37° C. for 1 hour. The reaction was neutralized with glacial acetic acid to pH 4.0 and the eluted peptides were desalted with ZipTips. The use of streptavidin-labeled ferrofluid beads allows for a strong interaction between avidin and biotin that facilitates isolation of larger phosphorylated target molecules.

Example 26

Precipitation of Phosphopeptides with DTPA Compounds

Phosphate-binding compounds comprising DTPA (Compounds 20, 21 and 22) were used in a precipitation reaction for the isolation of phosphopeptides from complex solutions. Precipitation reactions contained 100 µM Compound 20, 21 or 22, 200 µM GaCl$_3$, 100 mM NaOAc, pH 4.0 and 5 µL of an 8-peptide mix (250 ng/µL each). The samples were vigorously vortexed for 20 minutes then centrifuged at 14,000 rpm for 5 minutes. The supernatants were removed and stored and the pellets were washed 2× in 100 mM NaOAc, pH 4.0 by resuspension with a pipet tip and re-centrifuging. The final pellets were dissolved in 100 µL of 50% acetonitrile, 0.1% TFA. Supernatants and pellet fractions were diluted 1:100 in 50% acetonitrile, 0.1% TFA and then mixed 1:1 with MALDI matrix and then spotted onto a MALDI target. The MALDI analyses demonstrated the selective isolation of phosphorylated peptides.

Example 27

Serial detection of total phosphopeptide content with a binding solution of the present invention followed by specific detection of phosphotyrosine residues in peptides using a phosphotyrosine specific monoclonal antibody and (A) Alexa Fluor® 647 goat anti-mouse or (B) Zenon™ One Alexa Fluor® 647 mouse IgG labeling reagent, both in microarray format.

(A) Three pairs of peptides, the phosphorylated and the non-phosporylated forms of Kemptide, pp60 c-src and DSIP, were arrayed on to HydroGel coated slides (Perkin Elmer) from a source plate (384-well) with a concentration of 0.95 µg/ml- 0.5 mg/ml peptide in water, using the BioChip Arrayer™ (Perkin Elmer) as described in Example 20. For specific detection of the phosphopeptides on the array, the slides were incubated for 45 minutes on a rotisserie in a binding solution comprising 1 µM Compound 2, in buffer containing 0.5 M NaCl, 20% 1,2 propanediol, 1 µM GaCl$_3$, and 0.05 M sodium acetate, pH 4.0. Slides were then washed three times for 15 minutes on a rotisserie in 0.05 M sodium acetate, pH 4.0, containing 4% acetonitrile followed by a 15 minute water wash. Slides were then spun briefly in a microarray high-speed centrifuge affixed with a rotor with a slide holder (Telechem) at ~6000 rpm to remove excess liquid. After slides were dry, the arrays were imaged using the ScanArray® 5000 XL Microarray Analysis System (Packard Instrument Co., Meriden, Conn.) using the 543.5 nm laser and 570 nm emission filter. The binding solution specifically labeled 1.3-2.6 pg pDSIP, 2.6-5.2 pg pKemptide and 10.4-20.8 pg pp60 c-src (pY). Following phosphopeptide detection, the slides were immediately placed in blocking buffer containing 50 mM Tris, pH 7.5, 150 mM NaCl, 0.2% Tween-20, 0.25% MOWIOL-488, 0.5% BSA and incubated while rotating for 3-5 hours. Slides were then transferred to blocking buffer (described above) containing a 1:1000 dilution (final concentration of 1.5 µg/mL) of phosphotyrosine monoclonal antibody (supplied at 1.5 mg/mL; P-Tyr-100; Cell Signaling Tech.) and incubated overnight at 4° C. while rotating. After overnight incubation with the primary antibody, the slides were washed three times for 10 minutes in blocking buffer and then incubated for 45 minutes, while rotating, in blocking buffer containing a 1:5000 dilution (final concentration of 0.4 µg/mL) of Alexa Fluor® 647 goat anti-mouse (supplied at 2 mg/mL). Finally, slides were washed two times for 10 minutes in blocking buffer followed by two 5 minute washes in 50 mM Tris, pH 7.5, 150 mM NaCl and spun briefly in a microarray high-speed centrifuge. After the slides were dry, the arrays were imaged using the ScanArray® 5000 XL Microarray Analysis System (Packard Instrument Co., Meriden, Conn.) using two protocols with a 543.5 nm laser/570 nm emission filter set and a 632.8 nm laser/670 nm emission filter set. Using the 543.5 nm excitation and 570 nm emission filter, there was no signal detected. Using the 632.8 nm excitation and 670 nm emission filter, pp60 c-src (pY) was specifically detected to a sensitivity of 5.2 pg.

(B) After overnight incubation with the primary antibody, the slides were washed three times for 10 minutes in blocking buffer and then incubated for 45 minutes, while rotating, in blocking buffer containing a 1:100 dilution (final concentration of 2 µg/mL) of Zenon™ One Alexa Fluor® 647 mouse IgG labeling reagent (supplied at 200 µg/mL). Finally, slides were washed once for 5 minutes in blocking buffer, once for 5 minutes in 50 mM Tris, pH 7.5, 150 mM NaCl and spun briefly in a microarray high-speed centrifuge. After the slides were dry, the arrays were imaged using the ScanArray® 5000 XL Microarray Analysis System (Packard Instrument Co., Meriden, Conn.) using two protocols with a 543.5 nm laser/ 570 nm emission filter set and a 632.8 nm laser/670 nm emission filter set. Using the 543.5 nm excitation and 570 nm emission filter, there was no signal detected. Using the 632.8 nm excitation and 670 nm emission filter, pp60 c-src (pY) was specifically detected to a sensitivity of 0.65 pg.

Example 28

Size Exclusion Column (SEC) and Reverse Phase (RP) HPLC Analysis of Phosphopeptides Using a Binding Solution of the Present Invention 10-40 µL of sample containing 2-60 µM phosphopeptide (or a control of 100 µm non-phosphopeptide), 20 µM Compound 2, 40 µM GaCl$_3$, 100 mM sodium acetate pH 4 and 0-20% ethyl alcohol or isopropyl alcohol was injected onto a size exclusion column (Superdex 30, 10×300 mm or Superdex Peptide 3.2×300 mm). Mobile phase was 50 mM sodium acetate pH 4, 500 mM NaCl plus 20% ethyl alcohol or isopropyl alcohol. The runtime was 45 min. UV and fluorescence signal was monitored at 214 nm and 555ex/580em, respectively.

SEC results demonstrated an enhanced fluorescent signal in the presence of a binding solution of the present invention and a phosphopeptide (60 μM) compared to a non-phosphopeptide.

The same sample was also analyzed by reverse phase HPLC with a Vydac 238TP52, 2.1×250 mm $C_{18}$ column. Solvent A=100 mM sodium acetate pH 4, 0-20% ethyl alcohol. Solvent B=100 mM sodium acetate pH 4, 20% ethyl alcohol, 60% methanol. A gradient separation was performed, 0-55% solvent B over 30 min at 0.2 mL/min. UV (214 nm) and fluorescence (ex 555/em 580) signals were monitored.

RP results demonstrated an enhanced fluorescent signal in the presence of a binding solution of the present invention and a solution without gallium chloride. Samples were analyzed containing a mono-phosphotyrosine, mono-phosphothreonine and mono-phosphoserine containing peptide, with comparable results.

Example 29

Detection of Phosphopeptides on Streptavidin-polystyrene Beads Using a Binding Solution of the Present Invention Streptavidin-polystyrene beads (4.0-4.9 μM) were charged with either one of two biotinylated synthetic peptides, a phosphopeptide or a non-phosphopeptide. The phosphopeptide had a molecular weight of 1812 g/mol and the amino acid sequence was biotinyl-α-aminocaproyl-Glu-Pro-Gln-Tyr ($PO_3H_2$)-Glu-Glu-Ile-Pro-Ile-Tyr-Leu-OH. The non-phosphopeptide had a molecular weight of 2342.55 g/mol and the amino acid sequence was biotinyl-Glu-Gly-Pro-Trp-Leu-Glu-Glu-Glu-Glu-Glu-Ala-Tyr-Gly-Trp-Met-Asp-Phe-$NH_2$. Beads were charged in 100 mM Tris, 100 mM NaCl, pH 7.5 and washed several times in the same buffer, following charging, before staining. Both sets of beads were then stained with 1 μM Compound 2 in buffer containing 0.05 M sodium acetate, pH 4.0, 1 μM $GaCl_3$, 0.5 M NaCl, and 20% 1,2 propanediol for 45 minutes. Following staining, beads were washed in 0.05 M sodium acetate, pH 4.0, 4% acetonitrile and mixed in different ratios of phosphopeptide-charged beads with non-phosphopeptide charged beads. All steps were performed with rotation and rigorous sonication and vortexing. The mixed bead populations were then imaged using a Nikon Eclipse 800 Epi-Fluorescent Microscope using Omega Optical, Inc. filter set XF102-2 (Exciter: 560AF55; Dichroic: 595DRLP; Emitter: 645AF75). The fluorescent signal of the phosphopeptide charged beads was found to be 6-fold higher, on average, than the non-phosphopeptide charged beads.

Example 30

Detection of Kinase-mediated Phosphorylation of Peptide Substrates Bound to Streptavidin-Polystyrene Particles Using a Binding Solution of the Present Invention Streptavidin-polystyrene beads (4.0-4.9 μM) were charged with a biotinylated synthetic peptide called crosstide. Crosstide is a peptide substrate for the serine/threonine kinase Akt/Protein Kinase B and is a 1808 g/mol peptide with the following amino acid sequence, Gly-Arg-Pro-Arg-Thr-Ser-Ser-Phe-Ala-Glu-Gly. Beads were charged in 100 mM Tris, 100 mM NaCl, pH 7.5 and washed several times in the same buffer, following charging, before staining. The crosstide peptide on the streptavidin polystyrene particle was then phosphorylated using 500 ng of Akt/PKB kinase in 40 μL of 15 mM MOPS, pH 7.2, 18.75 mM β-glycerol phosphate, 3.75 mM EGTA, 0.75 mM sodium orthovanadate, 0.75 mM DTT supplemented with 200 μM ATP. A control reaction was performed in which all reaction components were added, including ATP, except the kinase enzyme. Phosphorylation was carried out for 60 minutes at 30° C. with continuous rotation and stopped by incubating beads and kinase at 100° C. for 5 minutes. Beads were then washed again by incubating in 100 mM Tris, 100 mM NaCl, pH 7.5 followed by staining with 1 μM Compound 2 in buffer containing 0.05 M sodium acetate, pH 4.0, 1 μM $GaCl_3$, 0.5 M NaCl, and 20% 1,2 propanediol for 45 minutes. Following staining, beads were washed in 0.05 M sodium acetate, pH 4.0, 4% acetonitrile and imaged using a Nikon Eclipse 800 Epi-Fluorescent Microscope using Omega Optical, Inc. filter set XF102-2 (Exciter: 560AF55; Dichroic: 595DRLP; Emitter: 645AF75). The fluorescent signal of the peptide charged beads exposed to Akt/PKB kinase was found to be 2.2-fold higher, with no overlap in standard deviation, than the control peptide charged beads not exposed to enzyme.

Example 31

Synthesis of Compound 2

A solution of 3-dimethylaminophenol (0.47 g, 3.5 mmol) and 5-fluoro-5'-formyl BAPTA tetramethyl ester (1.00 g, 1.7 mmol) in 20 mL propionic acid was heated at 110° C. for 2 hours, cooled and poured into 120 mL aqueous NaOAc. The resulting purple gum was rinsed with water, dissolved in ethyl acetate, and evaporated to give 1.20 g dihydro-Rhod-5F tetramethyl ester as a red foam.

To dihydro-Rhod-5F tetramethyl ester (1.2 g, 1.5 mmol) in 1:1 chloroform/methanol (40 mL) was added chloranil (0.51 g, 2.0 mmol). The solution was stirred overnight at room temperature then evaporated. The residue was purified by flash chromatography using chloroform/methanol/acetic acid (50:5:1) as eluant to give 0.54 g of Rhod-5F tetramethyl ester as a red foam.

To Rhod-5F tetramethyl ester (0.48 g, 0.55 mmol) in dioxane (25 mL) was added 1 M KOH (4.4 mL, 4.4 mmol). The solution was stirred overnight, then evaporated. The residue was dissolved in 10 mL water and 50 mL of 5% HCl was added. A precipitate was filtered and dried to give 275 mg of Rhod-5F free acid as a red powder. This product was converted to the potassium salt with aqueous KOH, followed by column chromatography with water on Sephadex LH-20 to give tripotassium salt Compound 2 as a red powder.

Example 32

Synthesis of Compound 5 (Rhodamine BAPTA Compound)

8-Hydroxyjulolidine (0.76 g, 4.1 mmol), 5-fluoro-5'-formyl BAPTA tetramethyl ester (1.16 g, 2.0 mmol) and p-TsOH (20 mg) in 20 mL propionic acid were heated at 60° C. overnight, then cooled and poured into 150 mL aqueous 3 M NaOAc. A purple powder was collected by filtration, rinsed with water, and dried to give 2.15 g of dihydro-X-Rhod-5F tetramethyl ester as a purple powder.

To dihydro-X-Rhod-5F tetramethyl ester (2.1 g, 2.4 mmol) in 1:1 chloroform/methanol (80 mL) was added chloranil (1.45 g, 5.9 mmol). The solution was stirred 4 hours at room temperature then evaporated. The residue was purified by flash chromatography using chloroform/methanol/acetic acid (50:5:1) to give 3.0 g of X-Rhod-5F tetramethyl ester as a red foam.

To X-Rhod-5F tetramethyl ester (3.0 g, 2.9 mmol) in dioxane (25 mL) and methanol (25 mL) was added 1 M KOH (30 mL, 30 mmol). The solution was stirred overnight then evaporated. The residue was dissolved in 10 mL water and this added to 50 mL of 5% HCl. A precipitate was filtered and dried to give 500 mg of Compound 5 free acid as a purple powder. 100 mg of the free acid was converted to the potassium salt with aqueous KOH, followed by chromatography with water on Sephadex LH-20 to give 40 mg of Compound 5 as its potassium salt, a purple powder.

Example 33

Synthesis of Quinazolinone-Labeled BAPTA (Q-BAPTA) Compounds (Compounds 7 and 23)

Preparation of 5-Fluoro-Q-BAPTA (Compound 7): a catalytic quantity of p-toluenesulfonic acid (TsOH) was added to a solution of anthranilamide (29 mg, 0.21 mmol) and 5'-fluoro-5-formyl-4-hydroxy-BAPTA tetramethylester (128 mg, 0.21 mmol) in 10 mL dichloroethane/5 mL ethanol. The solution was refluxed overnight then cooled. Chloranil (57 mg, 0.23 mmol) was added. After 2 hours, the solution was evaporated and the residue was purified by flash chromatography using 5% methanol/chloroform to yield 50 mg of the tetramethylester of Compound 7 as a light-amber immobile oil; m/z 711 (710 calc for $C_{34}H_{34}N_4O_{12}F$).

To a green solution of the tetramethylester of compound 7 (50 mg, 0.07 mmol) in 1:1 dioxane:methanol (5 mL), was added 1 M aqueous KOH (0.56 mL, 0.56 mmol). The yellow solution was stirred overnight then evaporated. The residue was purified with water on Sephadex LH-20, generating 53 mg of compound 7 as its potassium salt as a yellow powder; m/z (positive mode) 655 (651 calculated for $C_{30}H_{23}N_4O_{12}F$).

Preparation of 5,6-Difluoro-Q-BAPTA (Compound 23): 5,6-Difluoro-4'-hydroxy-5'-formyl BAPTA tetramethylester (0.100 g, 0.163 mmol) and anthranilamide (0.022 g, 0.162 mmol) were dissolved in a mixture of methylene chloride (10 mL) and ethanol (5 mL). TsOH (5 mg) was added and the reaction mixture was refluxed for 3 hrs. Chloranil (0.044 g, 0.18 mmol) was added to the solution. The mixture was refluxed for 2 more hours and evaporated. The crude product was purified by preparative TLC using 2:1 chloroform-ethyl acetate as eluant. The main component ($R_f$=0.5) was isolated with ethyl acetate, which solution was evaporated to give 5,6-difluoro-Q-BAPTA tetramethylester as a colorless powder (0.029 g, 24%).

5,6-Difluoro-Q-BAPTA tetramethylester (0.027 g, 0.037 mmol) was dissolved in a mixture of 1 mL of methanol and 1 mL of dioxane. 1 M KOH (1 mL) was added to the solution and the reaction mixture was kept overnight at room temperature. Volatiles were evaporated, the crude product was redissolved in water and purified on a Sephadex LH-20 column, eluting with water. The product was lyophilized to give 0.021 g of 5,6-difluoro-Q-BAPTA potassium salt (Compound 23) as a yellow powder (R=$CH_2CO_2K$).

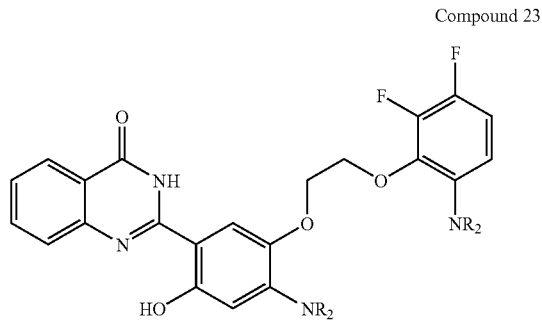

Compound 23

Example 34

Synthesis of (borapolyazaindacene BAPTA) Compounds (Compound 8 and 24)

Preparation of BODIPY FL Dye BAPTA-5F (Compound 8): To a cold solution of 5-fluoro-BAPTA tetramethylester (1.00 g, 1.82 mmol) in 9 mL acetic anhydride was added 70% nitric acid (0.15 mL, 2.3 mmol). After 10 minutes, the reaction solution was poured into 30 mL aqueous NaOAc then saturated aqueous sodium bicarbonate was added. The mixture was extracted with chloroform (2×30 mL). The extract was washed with brine, dried over sodium sulfate, and concentrated to an amber residue. This was purified by flash chromatography using ethyl acetate/hexanes to give 0.43 g of 5-nitro-5'-fluoro-BAPTA, tetramethylester as a yellow powder.

To 5-nitro-5'-fluoro-BAPTA, tetramethylester (0.43 g, 0.72 mmol) in 1:1 methanol/dioxane (10 mL) was added 1 M KOH (5.8 mL, 5.8 mmol). The solution was stirred overnight then evaporated. The residue was dissolved in 10 mL water, and the pH lowered to 2 with aqueous HCl. A precipitate was collected and dried to give 0.31 g of 5-nitro-5'-fluoro-BAPTA free acid as a yellow powder.

A solution of 5-nitro-5'-fluoro-BAPTA free acid (0.31 g, 0.58 mmol) in 30 mL methanol was shaken over 10% Pd/carbon (0.15 g) under 38 psi hydrogen gas for 6 hours, then filtered and evaporated to give 0.26 g of 5-amino-5'-fluoro-BAPTA free acid as a colorless powder. BODIPY FL dye free acid (Molecular Probes, Inc. D-2183, 27 mg, 0.09 mmol) in 5 mL anhydrous THF was treated with an oxalyl chloride (0.20 mmol) and diisopropylethylamine (DIEA, 0.20 mmol) under argon. After 15 minutes, the solution was evaporated. The residue was dissolved in 3 mL anhydrous dioxane, and this solution was slowly added to a solution of 5-amino-5'-fluoro-BAPTA free acid (50 mg, 0.10 mmol) in 5 mL water that had been pH-adjusted to pH=9.5 with sodium carbonate. This solution was stirred overnight then evaporated to near dryness. This solution was purified with water elution on Sephadex LH-20 to yield 41 mg of BODIPY FL Dye BAPTA-5F (Compound 8), sodium salt as an orange powder.

Preparation of BODIPY FL Dye-EDA-BAPTA (Compound 24)

To a solution of 5-amino-BAPTA free acid (853 mg, 1.74 mmol) in water (50 mL) and con. HCl (1.0 mL), thiophosgen (10 mL) in chloroform (50 mL) was added and virgorously stirred at rt for 8 h. The organic solvent was evaporated, and the precipitate was collected by a centrifugal. The dried precipitate was redissolved in THF (20 mL), and precipitated with hexanes (200 mL). The precipitate was collected by a centrifugal and dried to give 5-isothiocyanato-BAPTA free acid (640 mg).

The pH of a solution of BODIPY FL ethylenediamine hydrochloride salt (15 mg, 0.04 mmol, Molecular Probes) in 3 mL water was raised to 7.6 by dropwise addition of aqueous sodium bicarbonate. A solution of 5-isothiocyanato-BAPTA free acid (22 mg, 0.04 mmol) in 2 mL dioxane was added. The pH was raised to 9.5 with aqueous sodium carbonate, and the orange solution was stirred at room temperature overnight. The solution was evaporated to 2 mL, and the this solution was purified on Sephadex LH-20 using water for elution to give 17 mg of BODIPY FL-EDA-BAPTA sodium salt (Compound 24) as a fine orange powder after lyophilization ($R=CH_2CO_2Na$).

hours a solution of biotin ethylenediamine hydrobromide (66 mg, 0.18 mmol, Molecular Probes) and DIEA (0.05 mL) in 2 mL anhydrous DMF was added. After stirring overnight, the volatiles were evaporated. The residue was triturated with water (15 mL), and the resulting precipitate was collected, rinsed with water, and dried to give 0.10 g of biotin-BAPTA-5F tetramethylester as a gray powder.

To biotin-BAPTA-5F tetramethylester (0.10 g, 0.11 mmol) in 1:1 methanol/dioxane (4 mL) was added 1 M KOH (1.0 mL, 1.0 mmol). The solution was stirred overnight then evaporated. The residue was purified on Sephadex LH-20 using water, which gave biotin-BAPTA-5F (Compound 12) potassium salt as a colorless powder after lyophilization.

Preparation of Rhod-biocytin (Compound 18)

To a 0.5 M solution of 4-(succinimidyloxycarbonyl)-rhod tetramethyl ester in anhydrous THF was added 1.1 equivalent of N-t-BOC-ethylenediamine and 1.1 equivalent of DIEA. The resulting solution was stirred for 30 minutes then evaporated. The residue was purified by flash chromatography using chloroform/methanol/acetic acid. The purified carbonate was dissolved in dichloromethane and treated with trifluoroacetic acid (20 equivalents). This solution was stirred 30

Compound 24

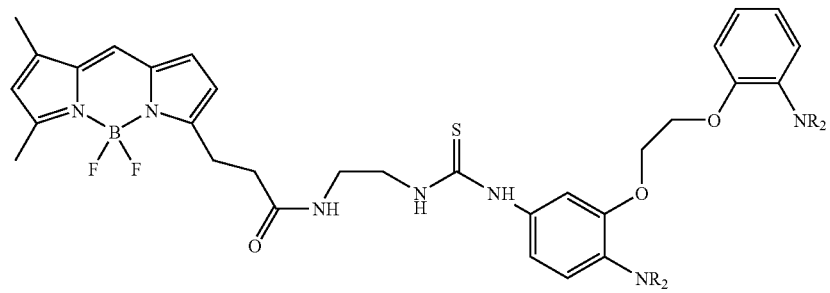

Example 35

Synthesis of Biotinylated BAPTA Compounds (Compounds 9, 12 and 18)

Preparation of Biotin-BAPTA-5F (Compound 12)

A solution of 5-nitro-5'-fluoro-BAPTA, tetramethylester was reduced by catalytic hydrogenation over 10% Pd/C in ethyl acetate. To the resulting 5-amino-5'-fluoro-BAPTA, tetramethylester (0.10 g, 0.18 mmol) in anhydrous dichloromethane/THF (4:1, 5 mL) was added glutaric anhydride (40 mg, 0.36 mmol) and catalytic DMAP. The solution was stirred overnight then evaporated. The residue was purified by flash chromatography using 10% methanol/chloroform to give 0.13 g of the glutaramide of 5-amino-5'-fluoro-BAPTA, tetramethylbester as an oil.

To the glutaramide of 5-amino-5'-fluoro-BAPTA, tetramethylester (0.18 mmol) in 5 mL anhydrous THF and 5 mL anhydrous acetonitrile was added N-hydroxysuccinimidyluronium tetrafluoroborate (108 mg, 0.36 mmol). After two minutes, then evaporated and dried to give the ethylenediamine carboxamide of 4-carboxy-rhod tetra methyl ester.

To a 0.5 M solution of the ethylenediamine carboxamide of 4-carboxy-rhod tetramethyl ester in DMF was added N-t-BOC-biocytin succinimidyl ester (1.5 equivalent, described in Wilbur et al., *Bioconjugate Chemistry*, 11: 584-98 (2000)) and DIEA (1.5 equivalent). The resulting solution was stirred at room temperature until the TLC indicated consumption of the fluorescent starting material. The volatiles were removed in vacuo, and the residue was purified by flash chromatography using chloroform/methanol/acetic acid to give N-t-BOC-rhod-biocytin tetramethyl ester.

A 0.5 M solution of N-t-BOC-rhod-biocytin tetramethyl ester in 1:1 methanol/dioxane was treated with 12 equivalents of 1 M KOH. The resulting solution was stirred overnight at room temperature then evaporated to dryness. The residue was purified on Sephadex LH-20 using water to give Compound 18 as a red powder after lyophilization ($R=CH_2CO_2K$).

Compound 18

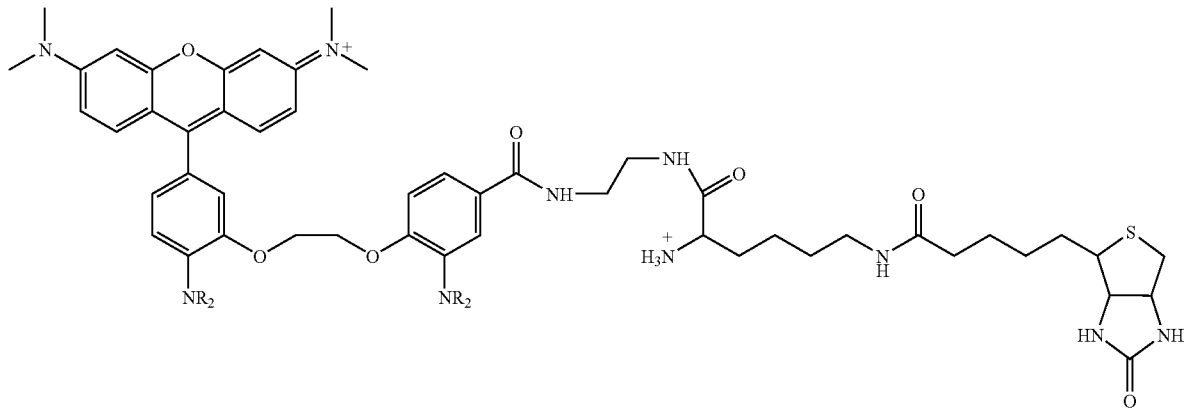

Preparation of Rhod-4-Biotin-BAPTA (Compound 9)

A suspension of (2'-nitrophenoxy)-2-chloroethane (20.15 g, 0.10 mol), methyl (4-hydroxy-3-nitro)benzoate (21.67 g, 0.11 mol), and $K_2CO_3$ (27.60 g, 0.20 mol) was stirred at 130° C. for 16 h, cooled to room temperature, and poured into ice water (1.2 L). The precipitate was filtered, washed with $H_2O$ and dried to give 32.00 g of (4'-methoxycarbonyl-2'-nitrophenoxy)-2-(2"-nitrophenoxy)ethane as a yellow solid. 4'-Methoxycarbonyl-2'-nitrophenoxy)-2-(2"-nitrophenoxy)ethane (20.0 g, 55.2 mmol) was hydrogenated over 10% Pd/C (3.0 g) in DMF (300 mL) at 40 psi for 5 h. The mixture was filtered from catalyst through Celite. The filtrate was evaporated and ether (100 mL) was added. The product was filtered and washed with ether (2×25 mL) to give 13.2 g of 1'-amino-4'-methoxycarbonylphenoxy)-2-(2"-aminophenoxy)ethane as an off-white solid.

A mixture of 2'-amino-4'-methoxycarbonylphenoxy)-2-(2"-aminophenoxy)ethane (13.20 g, 44 mmol), methanol (50 mL), dioxane (50 mL), and 1 M KOH (100 mL, 100 mmol) was stirred at 65° C. for 5 h, then overnight at room temperature. The mixture was evaporated and the residue was suspended in $H_2O$ (500 mL). Aqueous 1 M HCl was added to pH 5.0. The precipitated product was filtered, washed with $H_2O$, and dried on a filter for 4 h, then washed with ether (3×25 mL) to give 12.5 g of 2'-amino-4'-carboxy-1'-phenoxy)-2-(2"-aminophenoxy)ethane as an off-white solid.

Diphenyldiazomethane was prepared by vigorously stirring benzophenone hydrazone (6.66 g, 34 mmol) and yellow HgO (17.60 g, 80 mmol) in hexanes (200 mL) for 3 h. The mixture was filtered from inorganics, evaporated and the residue was dissolved in acetone (50 mL). This solution was added to a suspension of 2'-amino-4'-carboxy-1'-phenoxy)-2-(2"-aminophenoxy)ethane (5.76 g, 20 mmol) in acetone. The mixture was stirred for 16 h at 35° C., then the excess of diphenyldiazomethane was decomposed with AcOH (2 mL) over 2 h. The mixture was evaporated, and the crude product was purified by flash chromatography on $SiO_2$ using $CHCl_3$ as eluant to give 6.80 g of 2'-amino-4'-diphenylmethoxycarbonylphenoxy)-2-(2"-aminophenoxy)ethane as an off-white solid.

A mixture of 2'-amino-4'-diphenylmethoxycarbonylphenoxy)-2-(2"-aminophenoxy)ethane (8.28 g, 18.24 mmol), DIEA (16.3 mL, 94 mmol), methyl bromoacetate (35.3 mL, 376 mmol), and NaI (1.50 g, 10 mmol) in MeCN (400 mL) was refluxed under stirring for 70 h, cooled to room temperature and evaporated. The residue was dissolved in $CHCl_3$ (500 mL), washed with 1% AcOH (3×200 mL), $H_2O$ (200 mL), sat. NaCl (200 mL), filtered and evaporated. The residue was purified by flash chromatography on $SiO_2$ using a gradient of 30-40% EtOAc in hexanes as eluant to give 10.01 g of 4-diphenylmethoxycarbonyl-BAPTA tetramethyl ester as a white solid.

To a solution of Vilsmeier reagent made from $POCl_3$ (5 mL, 50 mmol) in DMF (35 mL) was added a solution of 4-diphenylmethoxycarbonyl-BAPTA tetramethyl ester (3.71 g, 5 mmol) in DMF (15 mL). The mixture was stirred at 40° C. for 24 h, then another portion of Vilsmeier reagent (25 mmol) was introduced and the mixture was stirred at 40° C. for 70 h. The mixture was cooled to room temperature and quickly poured into an ice-sat. $K_2CO_3$ mixture (1200 mL). After 1 h, the precipitate was filtered, washed with $H_2O$ and dried to give 3.78 g of 4-diphenylmethoxycarbonyl-5'-formyl-BAPTA tetramethyl ester as a colorless solid.

A mixture of 4-diphenylmethoxycarbonyl-5'-formyl-BAPTA tetramethyl ester (2.90 g, 3.8 mmol), m-dimethylaminophenol (1.21 g, 8.8 mmol), and TsOH (100 mg,) in propionic acid (40 mL) was stirred at 68° C. for 20 h, then cooled to room temperature and poured into 3 M NaOAc (600 mL). After 1 h, the precipitate was filtered, washed with water, and dried to give 3.70 g of 4-diphenylmethoxycarbonyl-dihydrorhod tetramethyl ester as a purple-red solid.

A mixture of 4-diphenylmethoxycarbonyl-dihydrorhod tetramethylester (2.050 g, 2.0 mmol) and powdered chloranil (0.492 g, 2.0 mmol) in $CHCl_3$ and MeOH (40 mL of each) was stirred for 2 h, filtered and evaporated. The residue was purified by flash chromatography on $SiO_2$ using a gradient 5-6.5% MeOH in $CHCl_3$/1% AcOH as eluant to give a crude product, which was re-dissolved in $CHCl_3$, filtered from $SiO_2$, and evaporated to give 0.533 g of 4-diphenylmethoxycarbonyl-rhod tetramethyl ester as a dark-purple solid.

To 4-diphenylmethoxycarbonyl-rhod tetramethyl ester (51 mg, 0.05 mmol) in dioxane (2 mL) and MeOH (1 mL) was added 1 M KOH to give pH 12.0. The mixture was stirred for 20 h, then the pH adjusted to 9.0 with 0.1 M HCl. The mixture was evaporated and the residue purified on Sephadex LH-20 using $H_2O$ as eluant. The product was lyophilized to give 26 mg of 4-carboxy-rhod tetrapotassium salt as a red-purple solid.

To 4-diphenylmethoxycarbonyl-rhod tetramethyl ester (102 mg, 0.1 mmol) in $CHCl_3$ (10 mL) was added TFA (10 mL) and the resulting mixture was stirred for 1 h then evaporated and co-evaporated with $CHCl_3$ (3×10 mL). Ether (10 mL) was added and the precipitate was filtered and washed with ether (3×10 mL) to give 82 mg of 4-carboxy-rhod tetramethyl ester as a dark purple solid.

To 4-carboxy-rhod tetramethyl ester (80 mg, 0.093 mmol) in DMF (2 mL) was added DIEA (0.35 mL, 2 mmol) and dry O-trifluoroacetyl-N-hydroxysuccinimide (TFA-SE, 225 mg, 1 mmol). The mixture was stirred for 2 h, then more TFA-SE (113 mg, 0.5 mmol) was introduced and the mixture stirred for another 16 h. The mixture was diluted with $CHCl_3$ (50 mL), washed with 1% AcOH (3×20 mL), $H_2O$ (25 mL), sat. NaCl (50 mL), filtered and evaporated. Ether (25 mL) was added and the precipitated product was filtered and washed with ether to give 86 mg of 4-(succinimidyloxycarbonyl)-rhod tetramethyl ester as a dark-purple solid.

To biotin cadaverine (34 mg, 0.077 mmol, Molecular Probes, Inc.) in DMF (1 mL) and DIEA (0.055 mL, 0.40 mmol) was added a solution of 4-(succinimidyloxycarbonyl)-rhod tetramethyl ester (36 mg, 0.038 mmol). The mixture was stirred for 3 h, diluted with $CHCl_3$ (200 mL), washed with 1% AcOH (3×150 mL), $H_2O$ (100 mL), sat. NaCl (200 mL), filtered and evaporated. The residue was purified on two preparative TLC $SiO_2$ plates, using 12% MeOH and 2.5% AcOH in $CHCl_3$ as eluant to give 38 mg of 4-(N-(5"-biotinylaminopentyl)aminocarbonyl)-rhod tetramethyl ester.

To 4-(N-(5"-biotinylaminopentyl)aminocarbonyl)-rhod tetramethyl ester (30 mg, 0.025 mmol) in MeOH (2 mL) and $H_2O$ (1 mL) was added 1 M KOH to give pH 12.0. The mixture was stirred for 20 h then adjusted to pH 8.5 with 0.1 M HCl. The mixture was evaporated and the residue purified on Sephadex LH-20 using $H_2O$ as eluant. The product was lyophilized to give 30 mg of Compound 9 (4-(N-(5"-biotinylaminopentyl)aminocarbonyl)-rhod tetrapotassium salt) as an orange-red solid.

Example 36

Synthesis of 4-(4'-(Aminophenyl)-2-ethylamino) carbonylmethyl-rhod tripotassium Salt (Compound 10)

A suspension of (2'-nitrophenoxy)-2-chloroethane (5.87 g, 29 mmol), methyl 4-hydroxy-3-nitrophenyl acetate (6.15 g, 29 mmol), and $K_2CO_3$ (8.28 g, 60 mmol) was stirred at 120° C. for 16 h, cooled to room temperature, and poured into ice water (0.6 L). The precipitate was filtered, washed with $H_2O$ and dried to give 4.49 g of (4'-methoxycarbonylmethyl-2'-nitrophenoxy)-2-(2"-nitrophenoxy)ethane as a yellow solid.

4'-(Methoxycarbonylmethyl-2'-nitrophenoxy)-2-(2"-nitrophenoxy)ethane (9.6 g, 25.5 mmol) was hydrogenated over 10% Pd/C (1.0 g) in DMF (250 mL) at 40 psi for 16 h. The mixture was filtered from catalyst through Celite. The filtrate was evaporated and the residue was purified by flash chromatography on $SiO_2$ using a gradient of 25-35% EtOAc in hexanes to give 5.53 g of (2'-amino-4'-methoxycarbonylmethylphenoxy)-2-(2"-aminophenoxy)ethane as an off-white solid.

A mixture of (2'-amino-4'-methoxycarbonylmethylphenoxy)-2-(2"-aminophenoxy)ethane (5.50 g, 17.4 mmol), methanol (40 mL), dioxane (40 mL), and 1 M KOH (35 mL, 35 mmol) was stirred at 45° C. for 1 h, then overnight at room temperature. The mixture was evaporated and the residue was suspended in $H_2O$ (100 mL). Aqueous 1 M HCl was added to pH 3.0. Precipitated product was filtered, washed with $H_2O$, and dried to give 4.59 g of (2'-amino-4'-carboxymethyl-1'-phenoxy)-2-(2"-aminophenoxy)ethane as an off-white solid.

Diphenyldiazomethane was prepared by vigorously stirring benzophenone hydrazone (2.94 g, 15 mmol) and yellow HgO (8.80 g, 40 mmol) in hexanes (70 mL) for 5 h. The mixture was filtered from inorganics, and the filtrate was evaporated and the residue was redissolved in acetone (20 mL). This solution was added to the solution of the 2'-amino-4'-carboxymethyl-1'-phenoxy)-2-(2"-aminophenoxy)ethane (3.02 g, 10 mmol) in acetone (120 mL). The resulting mixture was stirred for 16 h at 35° C., then the excess of diphenyldiazomethane was decomposed with AcOH (0.5 mL) over 2 h. The mixture was evaporated, and the crude product was purified by flash chromatography on $SiO_2$ using 1% MeOH in $CHCl_3$ as eluant to give 4.44 g of (2'-amino-4'-diphenylmethoxycarbonylmethylphenoxy)-2-(2"-aminophenoxy) ethane as an off-white solid.

A mixture of 2'-amino-4'-diphenylmethoxycarbonylmethylphenoxy)-2-(2"-aminophenoxy)ethane (2.12 g, 4.5 mmol), DIEA (4.0 mL, 23.5 mmol), methyl bromoacetate (8.8 mL, 94 mmol), and NaI (0.50 g, 4.7 mmol) in MeCN (90 mL) was refluxed for 70 h, cooled to room temperature and evaporated. The residue was dissolved in $CHCl_3$ (500 mL), washed with 1% AcOH (3×200 mL), $H_2O$ (200 mL), sat. NaCl (200 mL), filtered and evaporated. The residue was purified by flash chromatography on a $SiO_2$ column using a gradient of 30-40% EtOAc in hexanes as eluant to give 2.82 g of 4-diphenylmethoxycarbonylmethyl-BAPTA tetramethyl ester as a colorless solid.

To a solution of Vilsmeier reagent made from $POCl_3$ (1.5 mL, 30 mmol) in DMF (10 mL) was added a solution of 4-(diphenylmethoxycarbonylmethyl)-BAPTA tetramethyl ester (3.78 g, 5 mmol) in DMF (5 mL). The mixture was stirred for 24 h then quickly poured into an ice-sat. $K_2CO_3$ mixture (500 mL). The mixture was extracted with $CHCl_3$, dried over $MgSO_4$ and evaporated. The mixture of products was separated on $SiO_2$ using a gradient of 30-40% EtOAc in hexanes to give 1.65 g of aldehyde 4-(diphenylmethoxycarbonylmethyl)-5'-formyl-BAPTA tetramethyl ester as a colorless solid.

A mixture of 4-(diphenylmethoxycarbonylmethyl)-5'-formyl-BAPTA tetramethyl ester (784 mg, 1.0 mmol), m-dimethylaminophenol (301 mg, 2.2 mmol), and TsOH (20 mg, catalyst) in propionic acid (10 mL) was stirred at 65° C. for 20 h, then cooled to room temperature and poured into 3 M NaOAc (150 mL). After 1 h, the precipitate was filtered, washed with water, and dried to give 450 mg of 4-(diphenylmethoxycarbonylmethyl)-dihydrorhod tetramethyl ester as a purple-red solid.

A mixture of 4-(diphenylmethoxycarbonylmethyl)-dihydrorhod tetramethyl ester (420 mg, 0.43 mmol) and powdered chloranil (122 mg, 0.5 mmol) in $CHCl_3$ and MeOH (20 mL of each) was stirred for 3 h, filtered and evaporated. The residue was purified by flash chromatography on $SiO_2$ using a gradient of 5-7% MeOH in $CHCl_3$/0.5% AcOH as eluant to give a crude product, which was redissolved in $CHCl_3$, filtered from $SiO_2$, and evaporated to give 275 mg of 4-(diphenylmethoxycarbonylmethyl-5'-tetramethyl)-rhod tetramethyl ester as a dark-purple solid.

To a solution of 4-(diphenylmethoxycarbonylmethyl-5'-tetramethyl)-rhod tetramethyl ester (250 mg, 0.25 mmol) in CHCl$_3$ (20 mL) was added TFA (20 mL) and the resulting mixture was stirred for 1 h, then evaporated and co-evaporated with CHCl$_3$ (3×30 mL). Ether (30 ml) was added to the residue and the precipitate was filtered and washed with ether (3×10 mL) to give 200 mg of 4-carboxymethyl-rhod tetramethyl ester as a dark-purple solid.

To 4-carboxymethyl-rhod tetramethyl ester (128 mg, 0.15 mmol) in DMF (5 mL) and DIEA (0.40 mL, 2.2 mmol) was added dry TFA-SE (338 mg, 1.5 mmol). The mixture was stirred for 16 h, then a solution of 4-aminophenylethylamine (0.4 mL, 4 mmol) and DIEA (0.4 mL, 2.2. mmol) was introduced. The mixture was stirred for 2 h, diluted with CHCl$_3$ (500 mL), washed with 1% AcOH (3×100 mL), sat. NaCl (2×200 mL), filtered and evaporated. Ether (25 mL) was added to the residue, and the precipitated product was filtered and washed with ether to give 126 mg of 4-(4'-(aminophenyl)-2-ethylamino)carbonylmethyl-rhod tetramethyl ester as a dark-red solid.

To 4-(4'-(aminophenyl)-2-ethylamino)carbonylmethyl-rhod tetramethyl ester (100 mg, 0.1 mmol) in dioxane (2 mL), MeOH (2 mL) and H$_2$O (1 mL) was added 1 M KOH to give pH 12.0. The mixture was stirred for 50 h then the pH was adjusted to 9.0 with 0.1 M HCl. The mixture was evaporated and the residue was purified on Sephadex LH-20 using H$_2$O as eluant and the product lyophilized to give 21 mg of Compound 10 as an orange-red solid.

Example 37

Synthesis of BAPTA-agarose Compounds (Compounds 13 and 14)

Preparation of BAPTA-agarose (Compound 13)

A solution of 5-isothiocyanato-BAPTA free acid (65 mg, 0.12 mmol, U.S. Pat. No. 5,453,517) in 3 mL anhydrous DMF was added to a slurry of amino agarose (50% aqueous slurry, 16 μmol amine/mL, 6 mL, 96 μmole amine, Pierce) that had been diluted with 15 mL DMF. The pH was raised to 10 with DIEA (1.5 mL). The resulting light-brown mixture was stirred at room temperature for 48 hours then centrifuged. The BAPTA-agarose (compound 13) pellet was rinsed with acetone (2×) and water (2×) then suspended in water.

Preparation of BAPTA-5F-Agarose (Compound 14)

A solution of 5-amino-5'-fluoro-BAPTA free acid (0.26 g, 0.51 mmol) in 12 mL aqueous HCl was diluted with 12 mL chloroform then treated with thiophosgene (3 mL). The orange mixture was stirred at room temperature overnight then evaporated. The mixture was centrifuged, yielding a brown gum that was dried then dissolved in 2 mL anhydrous THF.

Addition of 20 mL ethyl acetate gave a precipitate, which was isolated by centrifugation to give 5-fluoro-5'-isothiocyanato-BAPTA free acid as a light gray-brown powder.

5-Fluoro-5'-isothiocyanato-BAPTA free acid (25 mg, 0.05 mmol) in 1 mL anhydrous DMF was added to 2 mL of a 50% aqueous slurry of amino agarose that had been diluted with 5 mL DMF. The pH was raised to 10 with a few drops of DIEA. The light-brown mixture was stirred at room temperature for 48 hours then centrifuged. BAPTA-5F-agarose (Compound 14) pellet was rinsed with acetone (2×) and water (2×) then suspended in water.

Example 38

Synthesis of Compound 15 (TAMRA-biotin BAPTA Compound)

A solution of BAPTA-4-isothiocyanate free acid (18 mg, 0.033 mmol) in 5 mL dioxane was added to a solution of 5-(and-6)-tetramethylrhodamine biocytin (Molecular Probes Inc., 29 mg, 0.033 mmol) in 4 mL water. The resulting pH (3.5) was raised to 10 with aqueous sodium carbonate. The resulting red solution was stirred at ambient temperature overnight, the concentrated in vacuo. The residue was purified by column chromatography on Sephadex LH-20, using water as eluant. The product was lyophilized to give TAMRA-biotin-BAPTA as 26 mg of red powder: LCMS m/2 726 (1452 calculated for C$_{73}$H$_{84}$N$_{11}$O$_{17}$S$_2$).

Example 39

Synthesis of Compound 16 (Rhodamine BAPTA Compound)

5-Formyl-5'-nitro-BAPTA tetramethyl ester (200 mg, 0.33 mmol) and 8-hydroxyjulolidine (125 mg, 0.66 mmol) in 5 mL propionic acid was heated under nitrogen at 70° C. for 1 hour, cooled to room temperature and poured into 30 mL concentrated potassium acetate solution. The mixture was extracted with chloroform then washed with brine, dried over sodium sulfate, and evaporated to a red oil that was purified by flash chromatography using ethyl acetate/hexanes to give 0.225 g of dihydro-X-Rhod-5N tetramethyl ester as a yellow foam.

To dihydro-X-Rhod-5N tetramethyl ester (0.12 g, 0.12 mmol) in 1:1 chloroform/methanol (5 mL) was added chloranil (40 mg, 0.16 mmol). The solution was stirred overnight, diluted with 50 mL chloroform, washed with brine, dried over sodium sulfate, and evaporated. The residue was purified by flash chromatography using 15% methanol/chloroform to give 63 mg of X-Rhod-5N tetramethyl ester as a purple powder.

To X-Rhod-5N tetramethyl ester (0.11 g, 0.11 mmol) in 5 mL methanol was added 2 M KOH (0.6 mL, 1.2 mmol). The solution was stirred at room temperature overnight, then evaporated. The residue was dissolved in water (5 mL) and the pH lowered to 2 with 2 M HCl. A precipitate was collected by centrifugation, dissolved in fresh aqueous KOH and precipitated with aqueous HCl. This procedure was repeated five times to give 90 mg of Compound 16 free acid as a purple powder.

Example 40

Synthesis of 4-Hydroxy-5-benzothiazolyl-BAPTA (Compound 17)

A solution of 4-hydroxy-5-formyl-5'-methyl BAPTA, tetramethylester (0.40 g, 0.68 mmol) and 2-aminothiophenol (75 mg, 0.70 mmol) in DMSO (5 mL) was heated at reflux for 15 minutes. After cooling the yellow solution was diluted with 50 mL water. A yellow precipitate was filtered and dried, then purified by flash chromatography using ethyl acetate/hexanes to give 0.22 g of 4-hydroxy-5-benzothiazolyl-BAPTA tetramethylester as a yellow foam.

To 4-hydroxy-5-benzothiazolyl-BAPTA tetramethylester (0.21 g, 0.30 mmol) in 1:1 methanol/dioxane (10 mL) was added 1 M KOH (3.0 mL, 3.0 mmol). The solution was stirred for 3 hours then evaporated. The residue was purified on Sephadex LH-20 using water as eluant to give 0.13 g of compound 17 as a yellow-green powder (R═CH$_2$CO$_2$K).

Compound 17

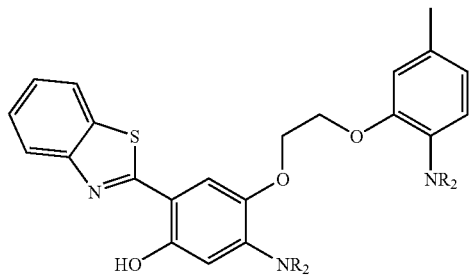

Example 41

Synthesis of 4'-Carboxymethyl-4-methoxy-rhod, Potassium Salt (COMPOUND 19)

A suspension of (4'-methoxy-2'-nitrophenoxy)-2-chloroethane (11.29 g, 48.7 mmol), methyl 4-hydroxy-3-nitrophenylacetate (10.80 g, 51.2 mmol), and K$_2$CO$_3$ (13.80 g, 100 mmol) was stirred at 130° C. for 4 h, cooled to room temperature, and poured into ice water (0.8 L), allowed to coagulate for 2 days. The precipitate was filtered, washed with H$_2$O and dried to give 15.1 g of (4'-methoxycarbonylmethyl-2'-nitrophenoxy)-2-(4"-methoxy-2"-nitrophenoxy)ethane as a yellow solid.

(4'-Methoxycarbonylmethyl-2'-nitrophenoxy)-2-(4"-methoxy-2"-nitrophenoxy)ethane (15.0 g, 43.3 mmol) was hydrogenated over 10% Pd/C (2.0 g) in CH$_2$Cl$_2$ (250 mL) at 45 psi for 16 h. The mixture was filtered through Celite. The filtrate was evaporated and the residue was treated with ether (200 mL). The precipitate was filtered and washed with ether (3×25 mL) to give 11.21 g of (2'-amino-4'-methoxycarbonylmethylphenoxy)-2-(2"-amino-4"-methoxyphenoxy)ethane as off-white solid.

A mixture of (2'-amino-4'-methoxycarbonylmethylphenoxy)-2-(2"-amino-4"-methoxyphenoxy)ethane (8.65 g, 25 mmol), methanol (80 mL), dioxane (80 mL), and 1 M KOH (50 mL, 50 mmol) was stirred at 60° C. for 1 h, then overnight at room temperature. The mixture was evaporated and the residue was suspended in H$_2$O (300 mL). Aqueous 1 M HCl was added to pH 4.0. The precipitate was filtered, washed with H$_2$O, and dried to give 6.84 g of (2'-amino-4'-carboxymethyl-1'-phenoxy)-2-(2"-amino-4"-methoxyphenoxy)ethane as off-white solid.

Diphenyldiazomethane was prepared by vigorously stirring benzophenone hydrazone (5.88 g, 30 mmol) and yellow HgO (17.60 g, 80 mmol) in hexanes (150 mL) for 6 h. The mixture was filtered from inorganics, filtrate was evaporated and the residue was re-dissolved in acetone (40 mL). This solution was added to the solution of (2'-amino-4'-carboxymethyl-1'-phenoxy)-2-(2"-amino-4"-methoxyphenoxy)ethane acid (6.64 g, 20 mmol) in acetone (200 mL). The resulting mixture was stirred for 48 h at 35° C., evaporated and the residue was suspended in CHCl$_3$. To the suspension was added AcOH (4 mL) to decompose the excess reagent and the mixture was stirred for 2 h, then evaporated, and the crude product was purified by flash chromatography on SiO$_2$ using 0.5% MeOH in CHCl$_3$ as eluant to give (2'-amino-4'-diphenylmethoxycarbonylmethylphenoxy)-2-(2"-amino-4"-methoxyphenoxy)ethane, 7.81 g (78%) as an off-white solid. A mixture of diamine (2'-amino-4'-diphenylmethoxycarbonylmethylphenoxy)-2-(2"-amino-4"-methoxyphenoxy)ethane (4.62 g, 9.3 mmol), DIEA (52 mL, 300 mmol), methyl bromoacetate (19 mL, 200 mmol), and NaI (0.75 g, 5 mmol) in MeCN (150 mL) was refluxed under stirring for 70 h, cooled to room temperature and evaporated. The residue was dissolved in CHCl$_3$ (400 mL), washed with 1% AcOH (3×200 mL), H$_2$O (200 mL), sat. NaCl (2×200 mL), filtered and evaporated. The residue was purified by flash chromatography on SiO$_2$ using a gradient of 25-40% EtOAc in hexanes as eluant to give 3.01 g of 4-diphenylmethoxycarbonylmethyl-4'-methoxy-BAPTA tetramethyl ester as a colorless solid.

To a solution of Vilsmeier reagent made from POCl$_3$ (0.28 mL, 3 mmol) in DMF (2 mL) was added a solution of 4-diphenylmethoxycarbonylmethyl-4'-methoxy-BAPTA tetramethyl ester (762 mg, 1 mmol) in DMF (2 mL). The mixture was stirred for 2 h, then was quickly poured into an ice-sat. K$_2$CO$_3$ mixture (50 mL). The mixture was extracted with CHCl$_3$ (7×20 mL), dried over MgSO$_4$ and evaporated. The mixture of products was separated by column chromatography on SiO$_2$ (4×35 cm bed) using a gradient of 30-45% EtOAc in hexanes to give 760 mg of 4-diphenylmethoxycarbonylmethyl-5'-formyl-4'-methoxy-BAPTA tetramethyl ester as a colorless solid.

A mixture of 4-diphenylmethoxycarbonylmethyl-5'-formyl-4'-methoxy-BAPTA tetramethyl ester (1.58 g, 2.0 mmol), m-dimethylaminophenol (602 mg, 4.4 mmol), and TsOH (50 mg, catalyst) in propionic acid (20 mL) was stirred at 65° C. for 20 h, then cooled to room temperature and poured into 3 M NaOAc (300 mL). After 1 h, the precipitated product was filtered, washed with water, and dried to give 2.00 g of 4-diphenylmethoxycarbonylmethyl-5'dihydrorhod tetramethyl ester as a purple-red solid.

A mixture of compound 4-diphenylmethoxycarbonylmethyl-4'-methoxy-5'-dihydrorhod tetramethyl ester (2.00 g, 1.9 mmol) and powdered chloranil (0.50 g, 2 mmol) in CHCl$_3$ and MeOH (50 mL of each) was stirred for 4 h, filtered and evaporated. The residue was purified by flash chromatography on SiO$_2$ using a gradient of 5-7% MeOH in CHCl$_3$/0.5% AcOH to give a crude product, which was redissolved in CHCl$_3$, filtered from SiO$_2$, and evaporated to give 480 mg of 4-(diphenylmethoxycarbonylmethyl)-4'-methoxy-rhod, tetramethyl ester as a dark-purple solid.

To a solution of 4-(diphenylmethoxycarbonylmethyl)-4'-methoxy-rhod, tetramethyl ester (45 mg, 0.04 mmol) in dioxane (1 mL), MeOH (2 mL) and $H_2O$ (2 mL) was added 1 M KOH to pH 12.0. The mixture was stirred for 50 h, then pH was adjusted to 9.0 with 0.1 M HCl. The mixture was evaporated and the residue was purified on Sephadex LH-20 column (2.6×90 cm bed) using $H_2O$ as eluant and lyophilized to give 12 mg of Compound 19 as a red solid ($R=CH_2CO_2K$).

Compound 19

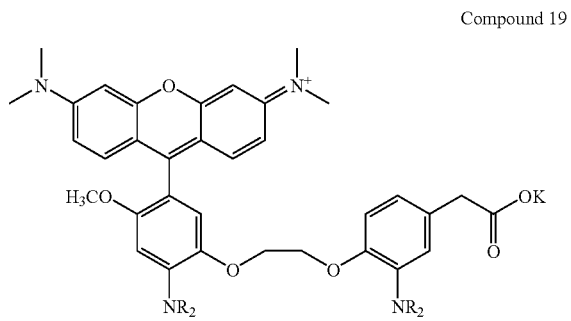

Example 42

Synthesis of Compound 20 Containing a DTPA Metal-chelating Moiety

BODIPY® TR cadaverine, Molecular Probes D-6251, 10 mg, 0.019 mmol was dissolved into a mixture of (S)-1-p-isothiocyanatobenzyldiethylenetriaminepentaacetic acid (DTPA isothiocyanate, Molecular Probes 1-24221, 10 mg, 0.019 mmol) in 2 mL water. The pH was raised to 10 with aqueous sodium carbonate. The resulting blue solution was stirred at room temperature for two days, then concentrated in vacuo. The residue was purified by column chromatography on Sephadex LH-20 using E-pure water as eluant to give 2 mg of Compound 20 as a purple powder.

Example 43

Synthesis of Compound 21 Containing a DTPA Metal-chelating Moiety

For the synthesis of carbamate 21a a solution of penta-t-butyl 1-(S)-(p-aminobenzyl)-diethylenetriaminepentaacetate (prepared according to the published procedure of Donald T. Corson & Claude F. Meares. *Bioconjugate Chem.*, 11(2): 292-299 (2000), 0.800 g, 1.03 mmol) in 20 mL of methylene chloride was added 1 mL of pyridine followed by the addition of a solution of the acid chloride of N-CBZ-6-aminohexanoic acid (0.290 g, 1.02 mmol) in 5 mL of methylene chloride. The reaction mixture was stirred overnight at room temperature and concentrated in vacuo. The residue was dissolved in 100 mL of ethyl acetate and the resulting solution was washed with 10% HCl (2×30 mL), water (30 mL), brine (30 mL) and dried over sodium sulfate. The solution was concentrated and put on a silica gel column (packed with ethyl acetate). The column was eluted with ethyl acetate to remove impurities then the desired product was eluted with 10:1 chloroform-methanol. Pure fractions were combined and the solvent evaporated to give amide 21a (0.54 g, 54%) as a viscous oil. For the synthesis of amino acid 21b, the carbamate 21a (0.700 g, 0.683 mmol) was dissolved in 10 mL of TFA. The reaction mixture is kept for 3 days at room temperature.

Volatiles were evaporated and the residue was re-evaporated twice from toluene, leaving a viscous oil. The oil was stirred with ethyl acetate until it solidified. The resulting solid was filtered and dried to give the amino acid 21 b (0.400 g, 96%).

For the synthesis of Compound 21, the amino acid 21b (0.090 g, 0.147 mmol) was suspended in 10 mL of water. The pH was adjusted to ~8 using 1 M KOH. The resulting solution was added to a solution of BODIPY® TMR-X, SE, Molecular Probes D-6117, 0.03 g, 0.049 mmol in 5 mL of DMF. The reaction mixture was stirred overnight at room temperature. The pH was monitored and adjusted to ~8 during the first 2 hrs. The solution was evaporated and the residue re-dissolved in water and purified on Sephadex LH-20 using water for elution. The combined product fractions were concentrated to ~3 mL then lyophilized to give 0.061 g of Compound 21 as a red powder.

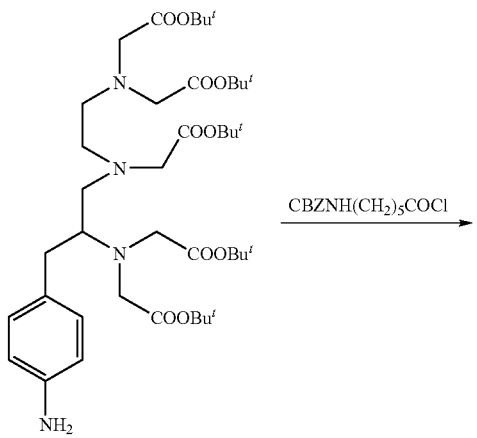

-continued
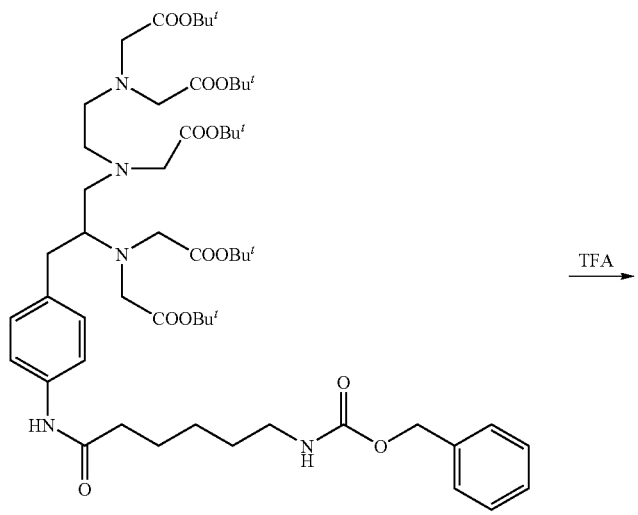
21a
TFA →
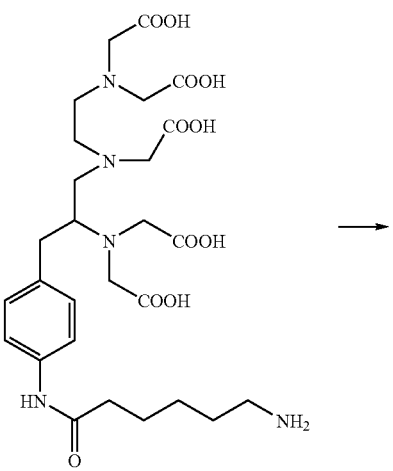
21b
→
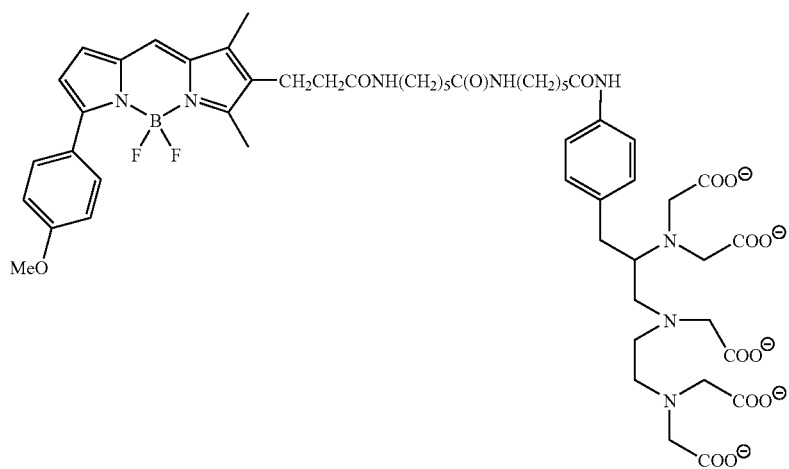
Compound 21

Example 44

Synthesis of Compound 22 Containing a DTPA Metal-chelating Moiety

BODIPY® FL EDA, Molecular Probes D-2390, 7 mg, 0.019 mmol was dissolved into a mixture of DTPA isothiocyanate, Molecular Probes 1-24221, 10 mg, 0.019 mmol in 2 mL water. The pH was raised to 10 with aqueous sodium carbonate. The resulting orange solution was stirred at room temperature for 3.5 hours, then evaporated. The residue was purified by on Sephadex LH-20 using water as eluant to give 29 mg of Compound 22 as an orange powder.

Example 45

Synthesis of Compound 25—A BAPTA-Biotin

To a solution of biotin-cadaverine (21 mg, 0.047 mmol, Molecular Probes) in 2 mL water was added 2 drops saturated sodium carbonate solution. A solution of 5-isothiocyanato-BAPTA free acid (25 mg, 0.047 mmol) in 3 mL dioxane was added. The reaction pH was raised to 9.5 with more sodium carbonate solution, and the solution was stirred overnight at ambient temperature. The volatiles were removed in vacuo and the residue was purified by chromatographpy on Sephadex LH-20 using water as eluant to give compound 25 as 40 mg of a pale brown powder (R=$CH_2CO_2Na$).

Compound 25

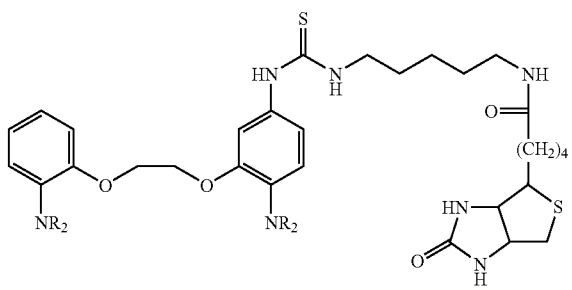

Example 46

Synthesis of Compound 26—A Rhod-BAPTA-BAPTA

To a solution of the ethylenediamine carboxamide of 4-carboxy-rhod tetramethyl ester (as in example 34, 0.04 mmol) in 1:1 water:dioxane (5 mL) was added a solution of 5-isothiocyanato-BAPTA free acid (24 mg, 0.044 mmol) in 1:1 water: dioxane (8 mL). The pH was raised to 8.5 by addition of aqueous sodium bicarbonate. The resulting red solution was stirred at ambient temperature overnight, then concentrated in vacuo and purified by column chromatography on Sephadex LH-20 using water as eluant to give the intermediate tetramethyl ester tetracarboxylate as 11 mg of red powder. To a solution of this intermediate (0.007 mmol) in 1.4 mL water was added 1 M KOH (0.07 mmol). After 3 hours the pH (13) was lowered to 9 with aqueous acetic acid, followed by concentration in vacuo. The resulting residue was purified by column chromatography on Sephadex LH-20 using water as eluant to afford compound 26 as a red powder (R=$CH_2CO_2K$).

Compound 26

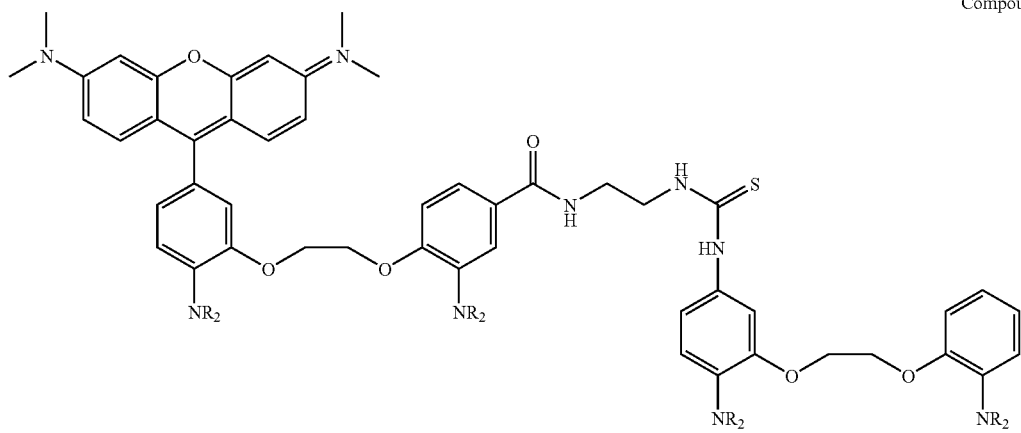

Example 47

Synthesis of Compound 27a-i

The synthesis of 27a will serve to illustrate the synthetic method used to make compounds 27a-27f. Oxalyl chloride (18 μL, 0.20 mmol) was added to a solution of 4,4-difluoro-5,7-dimethyl-4-bora-3a,4a-diaza-s-indacene-3-propionic acid (Molecular Probes B-2183, 50 mg, 0.17 mmol) in 5 mL anhydrous THF, followed by diisopropylethylamine (DIEA, 35 μL, 0.20 mmol). The resulting solution was stirred at room temperature for 15 minutes, followed by concentration in vacuo. The resulting acid chloride was dissolved in 3 mL dry dioxane. This solution was added dropwise to a solution of 27' (83 mg, 0.17 mmol, X=H) in 5 mL with stirring; the pH was maintained at 9 with sodium carbonate. The resulting cloudy orange mixture was stirred for 1 hour, whereupon silica gel TLC analysis indicated formation of 27a ($R_f$ 0.40, dioxane-isopropyl alcohol-water-ammonium hydroxide 15:58:13:14). The volatiles were removed in vacuo, and the residue purified by column chromatography on Sephadex LH-20 using water as eluant. Pure product fractions were pooled and lyophilized to give 27a as 99 mg of a fluffy orange powder (68% yield): $^1$H NMR (D$_2$O) δ 7.34 (s, 1H), 6.98-6.68 (m, 8H), 6.33 (d, J=4.0 Hz, 1H), 6.19 (s, 1H), 4.18 (m, 4H), 3.66 (s, 8H), 3.18 (t, 7.6 Hz, 2H), 2.72 (t, 7.6 Hz, 2H), 2.41 (s, 3H), 2.13 (s, 3H); LCMS (m/z) 765 (765 calcd for C$_{36}$H$_{38}$N$_5$O$_{11}$BF$_2$).

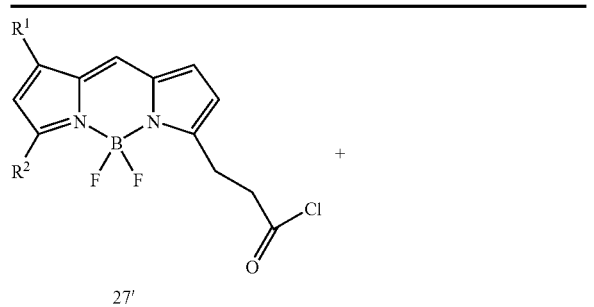

27′

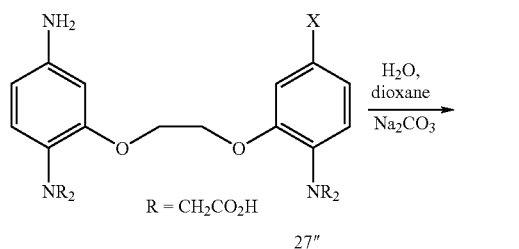

R = CH$_2$CO$_2$H

27″

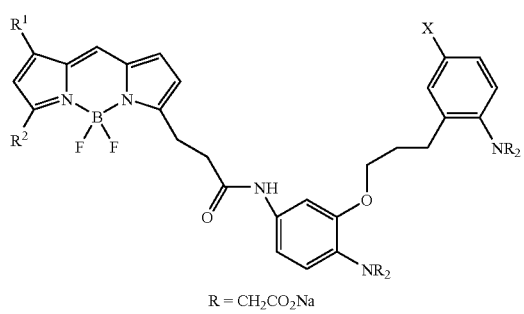

R = CH$_2$CO$_2$Na

| | R$^1$ | R$^2$ | X |
|---|---|---|---|
| 27a | CH$_3$ | CH$_3$ | H |
| 27b | Ph | Ph | H |
| 27c | H | —CH=CH—Ph | H |
| 27d | H | —(CH=CH)$_2$—Ph | H |
| 27e | H | 2-pyrrolyl | H |
| 27f | H | —CH$_2$CH$_2$CO$_2$N$_a$ | H |
| 8 | CH$_3$ | CH$_3$ | F |

Example 48

Synthesis of Compound 28 (Dansyl BAPTA)

A solution of dansyl chloride (22 mg, 0.081 mmol) in 3 mL dioxane was added to a solution of 5-amino-BAPTA (40 mg, 0.081 mmol) in 1:1 dioxane/water (10 mL) at pH 9 (maintained with sodium carbonate). The resulting solution was stirred at room temperature for 1 hour, then concentrated in vacuo. The residue was purified by column chromatography on Sephadex LH-20 using water as eluant to give Compound 28 as 40 mg of a buff powder.

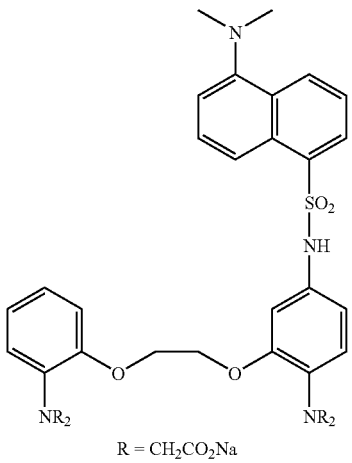

Compound 28

R = CH$_2$CO$_2$Na

Example 49

Mass Spectrometry-based Identification of Phosphoproteins from 2-D Gels

2-D gels are run according to standard protocols. All steps are performed with a volume of 500 ml/gel and 50 rpm on an orbital shaker. To remove SDS the 2-D gels are fixed in 50% MeOH, 7% HAc overnight with 1 change after one hour. The gels are washed the next day for 4×15 min in dH$_2$O before staining for 2.5-3 h with the binding solution of the present invention. To remove unspecific staining as well as to lower the background, 3 washes for 1 h each in 50 mM sodium acetate, pH 4.0, 4% acetonitrile are performed. This is followed by another wash in 50 mM NaAc, 15+% 1,2-Propanediol, pH 4.0 for another hour before imaging with 532 nm laser excitation and 580 nm emission filter. The wash is continued over night and the imaging repeated the next day.

The phosphoprotein stain is followed by SYPRO Ruby protein gel stain over night and destaining for 2-3 h in 10% MeOH, 7% HAc before imaging again. The gel is scanned with a 473 nm laser excitation and 580 nm emission filter and spots are cut out. For destaining the spots are placed into a 1.5 mL centrifuge tube and destained with 100 μL 50% MeOH, 5% HAc, 30 min, 100 μL 0.1% TFA, 30 min, 100 μL 50% MeOH/5% HOAc, 30 min, and finally dehydrated in 100 μL 100% acetonitrile (ACN), 10 min. The pieces are completely air dried before reduction and alkylation. If the proteins were already reduced and alkylated before the 2-D gel electrophoresis, the next steps can be omitted.

For the alkylation and reduction of cysteines, add enough 20 mM dithiothreitol (DTT) in 0.1 M N$_4$HCO$_3$ in order to completely cover the dried gel pieces (~50 μL). It may be necessary to add more as the gel pieces re-swell. Incubate at 56° C. for 1 hr. Remove the DTT solution and add an equal volume (50 μL) of 100 mM iodoacetamide (IAAm) in 50 mM NH$_4$HCO$_3$. Incubate at room temperature in the dark for 30 min., discard the supernatant and wash the gel pieces 2× with 100 μL 0.1 M N$_4$HCO$_3$ for 15 min. with occasional vortexing to remove excess reagents. To extract any excess reagents from the gel pieces wash with 100 μL of 0.1 M N$_4$HCO$_3$/50% ACN for 15 min with occasional shaking. Discard the supernatant and wash with 100% ACN. Discard the supernatant and completely dry the gel pieces (air).

For in gel digestion with trypsin prepare a fresh solution of 0.05 mg/ml modified trypsin (Promega) in 50 mM $NH_4HCO_3$/10% ACN. Keep on ice if not to be used immediately. Add 10 µL of the fresh trypsin solution and allow the gel pieces to soak up the trypsin solution before proceeding to the next step, i.e. 10 min. Fully re-swell the gel pieces by adding 20 µL 50 mM $NH_4HCO_3$/10% ACN ($V_{TOT}$=30 µL) and incubate overnight at 37° C.

To extraction the peptides, terminate digestion by adding 1 µL of 10% TFA; 10 min./RT. Vortex, spin, take out the supernatant and place in an 0.5 ml eppendorf tube. Add 50 µL 0.1% TFA to the pieces and incubate 30 min. Shake, spin, combine this supernatant with the first one. Add 50 µL 60% ACN/0.1% TFA, 30 min., shake, spin, and combine with first supernatant in tube. Dry the peptides in a Speed-Vac and dissolve again in 10 µL 10% ACN/0.1% TFA.

The peptide mix can be desalted and concentrated with a C18 ZipTip column from Millipore or spotted directly depending on the sample concentration. Mix 0.5 µL matrix (5 mg/ml α-cyano 4-hydroxycinnamix acid in 50% acetonitrile, 0.1% TFA) and 0.5 µL of sample on the target. Dry the spot and analyse in the mass spectrometer.

Example 50

Covalent Labeling and Detection of Phosphoproteins with Compound 34 (can also use Compound 39, Compound 36, Compound 42, and Compound 44) in Polyacrylamide Gels Purified proteins (PeppermintStick™ phosphoprotein molecular weight standards, Molecular Probes product number P33350; alpha casein; or pepsin) were separated on 13% T, 0.8% C gels by SDS-polyacrylamide gel electrophoresis. % T is the total monomer concentration expressed in grams per 100 ml. and % C is the percentage crosslinker. The 0.75 mm. thick, 6×10 cm. gels were subjected to electrophoresis using the Bio-Rad mini-Protean 3 system according to standard procedures.

Following separation of the proteins on the gel, the gel was fixed for 30 minutes in 50 ml of 50% methanol/10% acetic acid, then overnight in 100 ml of fresh fixative to ensure complete removal of the SDS. Next, the gel was rinsed two times, 10 minutes each, in 100 ml deionized water. The gel was then incubated for 90 minutes in the dark in 50 ml of 50 mM sodium acetate, pH 4, 500 mM sodium chloride, 20% acetonitrile, 1 µM gallium chloride, 1 µM Compound 34 (or Compound 36, 39, 42 or 44) dye. The gel was destained in the dark two times, 10 minutes each time, in 50 ml of 50 mM NaOAc (pH 4.0). The gel was transferred to 100 ml deionized water, and then exposed to ultraviolet light (wavelength 254 nm) by placing the gel directly on a UVP brand 3UV™ transilluminator for 2 minutes. A parallel gel, loaded, run, fixed and rinsed as described, was incubated for 90 minutes in a binding solution of the present invention containing compound 2 (See, Example 2), then destained 3×30 minutes in 50 ml of 50 mM NaOAc (pH 4.0). For both gels, the red fluorescent signal produced by the dye was visualized using the 532 nm excitation line of the SHG laser on the Fuji FLA-3000G Fluorescence Image Analyzer (Fuji Photo, Tokyo, Japan) and 580 band pass emission filter. Phosphoprotein bands were visible in both gels.

Both gels were then washed in 60 ml of 0.1 M sodium carbonate, pH11, for 1 hour to remove noncovalently bound dye. After this base treatment, the gels were rinsed in 100 ml deionized water. The gels were imaged as before. The gel stained with Compound 2 had no signal left on it. The gel incubated in Compound 34 retained fluorescence localized to the phosphoprotein bands.

Example 51

A Fluorescence Quenching Assay for Measuring Phosphorylation in Solution

Fluorescently labeled phosphotyrosine peptides were combined with Compound 2, with or without gallium. Initially, 50 µL mock kinase reactions were prepared containing 50 µM labeled peptide, 100 µM ATP and 10 mM Tris buffer, pH 7.5. Subsequently, the reactions were diluted 10 fold to a final volume of 500 µL containing 50 mM Na Acetate, pH 4.0, 15 µM Compound 2, and 15 µM $GaCl_3$. 300 µL of each reaction was transferred to a 96-well plate for analysis. The samples were excited at 488 nm, and emission scans were recorded from 500-650 nm. The results are shown in the fluorescence spectra of FIG. 12. The phosphorylated peptides are shown as follows: A, pp60-Oregon Green 488 dye (OG); B, p-Abl-OG dye; C, pp60-Alexa Fluor 488 dye (A488); D, pStat3-OG dye label. Spectra with circles represent samples without $GaCl_3$ addition, and spectra with squares represent samples with $GaCl_3$ addition. In all cases, when $GaCl_3$ is added to the reaction mixture, Oregon Green dye label and Alexa Fluor 488 dye label emission at 520 nm is significantly quenched. The results demonstrate that quenching of the 488 nm excitable compounds can be used to specifically quantitate phosphorylation of labeled compounds without interference from free ATP in solution.

Example 52

Preparation of Compound 34

To a solution of 4-(succinimidyloxycarbonyl)-rhod tetramethyl ester (30, 0.20 g, 0.18 mmol) in 3:1 THF/MeCN (20 mL) was added N-t-butoxycarbonylethylenediamine hydrochloride (43 mg, 22 mmol) and diisoproylethylamine (DIEA, 38 µL). The resulting solution was stirred overnight at room temperature (rt), then concentrated in vacuo. The residue was dissolved in 40 mL chloroform and washed with 10% citric acid (1×20 mL), dried over sodium sulfate, and concentrated to give compound 31 as 0.23 g of a red solid.

A solution of compound 31 (0.18 g, 0.18 mmol) in 20 mL dichloromethane was treated with 5 mL trifluoroacetic acid (TFA). After 2 h at room temperature the volatiles were removed in vacuo, and chloroform/toluene (1:1, 10 mL) stripped from the residue, leaving compound 32 as 0.20 g of a red solid: m/2 442.5 (885 calcd for $C_{46}H_{56}N_6O_{12}$).

A solution of compound 32 (0.18 mmol, 0.18 g) in 1:1 methanol/dioxane (8 mL) was treated with a 1 M solution of potassium hydroxide (KOH, 2.0 mL, 2.0 mmol) at rt. After stirring overnight the reaction pH was lowered to 8 with aqueous citric acid, and the volatiles removed in vacuo. The resulting red residue was purified by column chromatography on Sephadex LH-20 using water as eluant. Pure product fractions were pooled and lyophilized to give compound 33 as 0.15 g of a red powder: m/z 828 (828 calcd for $C_{42}H_{47}N_6O_{12}$).

The pH of a solution of compound 33 (30 mg, 0.03 mmol) in 5 mL water was raised to 9.6 with aqueous sodium carbonate. A solution of 4-azido-2,3,5,6-tetrafluorobenzoic acid, succinimidyl ester (Molecular Probes product 2522, 14 mg, 0.04 mmol) in 2 mL dioxane was added. After 2 h the volatiles were removed in vacuo, and the residue purified by column chromatography on Sephadex LH-20 using water as eluant. Pure product fractions were pooled and lyophilized to give compound 34 as 34 mg of a red powder: m/z 1041 (1041 calcd for $C_{49}H_{42}N_9O_{13}F_4$).

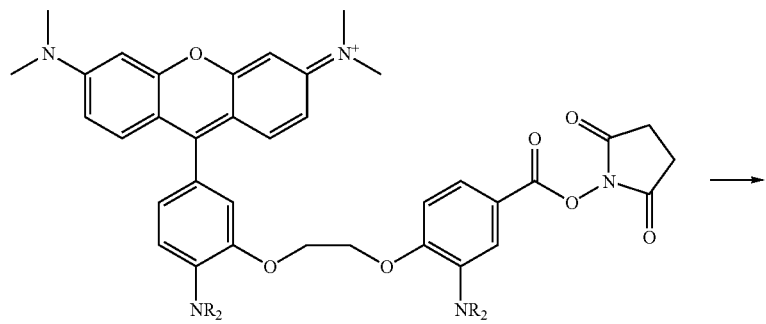
Compound 30 (R = CH₂CO₂CH₃)
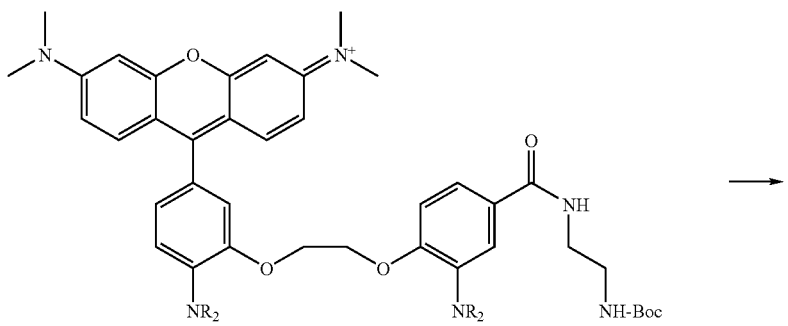
Compound 31 (R = CH₂CO₂CH₃)
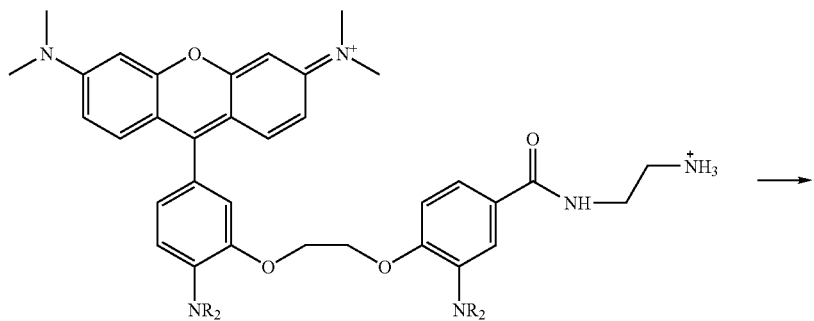
Compound 32 (R = CH₂CO₂CH₃)
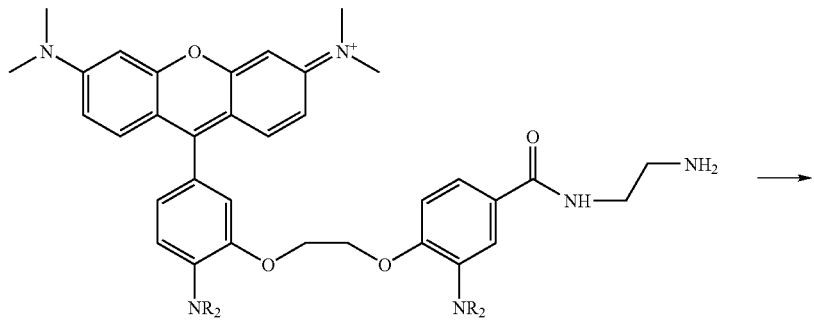
Compound 33 (R = CH₂CO₂K)

-continued

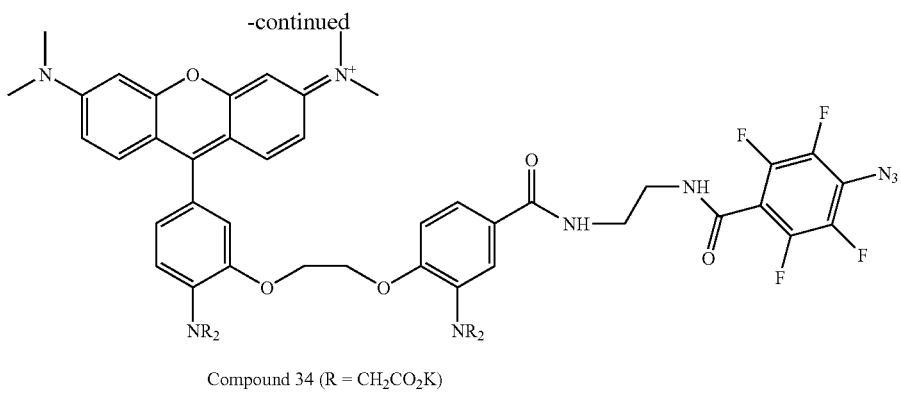

Compound 34 (R = CH₂CO₂K)

Example 53

Preparation of Compound 36

To a solution of compound 32 (0.22 g, 0.20 mmol) in 5 mL DMF was added DIEA (34 µL, 0.20 mmol) and a solution of 4-benzoylbenzoic acid, succinimidyl ester (Molecular Probes product 1577, 64 mg, 0.20 mmol) in 5 mL DMF. After stirring overnight the volatiles were removed in vacuo, giving compound 35 as a red residue that was used immediately in the next step.

To a red solution of compound 35 (~0.20 mmol) in 1:1 methanol/dioxane (6 mL) was added a 1 M solution of KOH (1.0 mL, 1.0 mmol). The resulting light brown solution was stirred at rt for 3 h, and the pH was lowered to 9.5 with aqueous citric acid. The volatiles were removed in vacuo, and the resulting red residue was purified by column chromatography on Sephadex LH-20 using water as eluant. Pure product fractions were pooled and lyophilized to give compound 36 as 125 mg of a hygroscopic red powder: m/z 1035 (1035 calcd for $C_{56}H_{51}N_6O_{14}$).

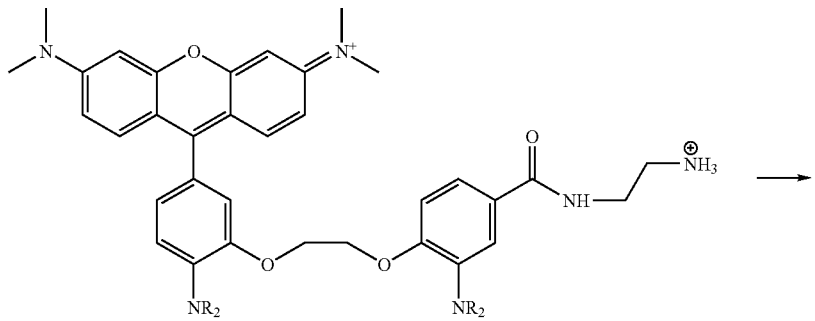

Compound 32 (R = CH₂CO₂CH₃)

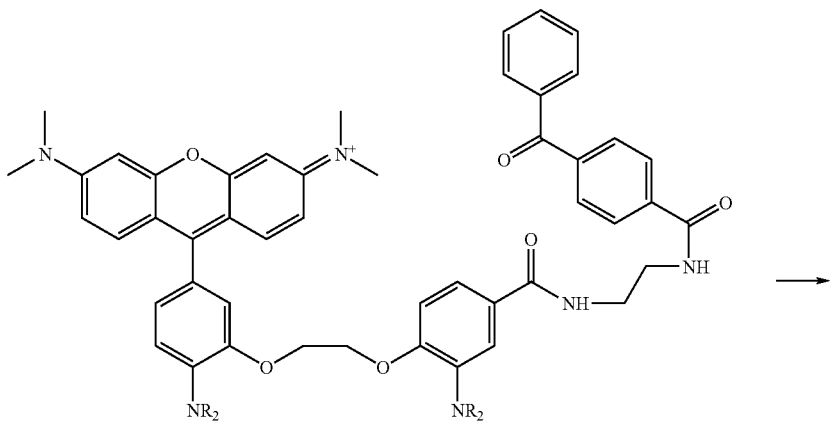

Compound 35 (R = CH₂CO₂CH₃)

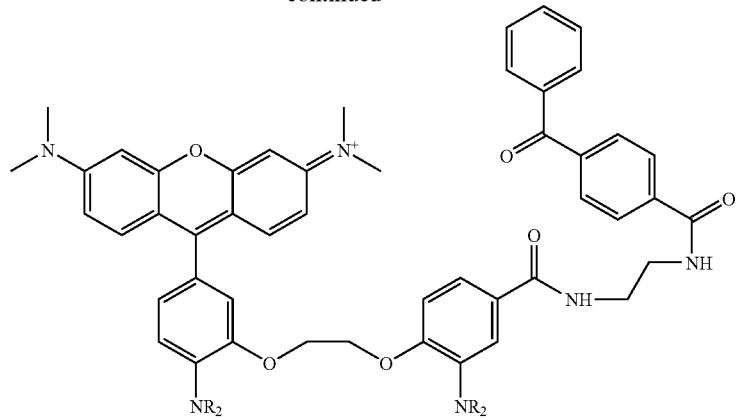

Compound 36 (R = CH₂CO₂K)

Example 54

Preparation of Compound 39

To a solution of compound 37 as its bis-trifluoroacetate salt (prepared by condensation of 2 eq of ethylenediamine with 4,4-difluoro-4-bora-3a, 4a-diaza-s-indacene-3,5-dipropionic acid (Molecular Probes product 6103)) (0.14 g, 0.22 mmol) in 10 mL water was added DIEA (35 μL, 0.20 mmol). A solution of 4-azido-2,3,5,6-tetrafluorobenzoic acid, succinimidyl ester (Molecular Probes product 2522, 73 mg, 0.22 mmol) in 8 mL dioxane was added dropwise with stirring over 10 minutes. After 1 h, the pH was lowered to 2.5 with aqueous HCl, followed by concentration in vacuo. The residue was purified by column chromatography on Sephadex LH-20 using water as eluant. Pure product fractions were pooled and lyophilized to give compound 38 as 53 mg of an orange powder.

To a solution of BAPTA isothiocyanate (Molecular Probes product 14390, 4 mg, 0.008 mmol) in 1 mL dioxane was added a solution of compound 38 (6 mg, 0.008 mmol) in 1 mL water. The reaction pH was raised to 9.3 with aqueous sodium carbonate. After 2 h the volatiles were removed in vacuo, and the residue was purified by column chromatography on Sephadex LH-20 using water as eluant. Pure product fractions were pooled and lyophilized to give compound 39 as 33 mg of a pale orange powder. Further purification was accomplished by dissolving all of compound 39 in 2 mL water. The pH was lowered to 2 with aqueous HCl. The resulting precipitate was collected by centrifugation and then suspended in 2 mL water. Dissolution was affected by addition of one drop of saturated aqueous sodium bicarbonate. The resulting solution was lyophilized to give compound 39 as 5 mg of an orange powder: m/z 1171 (1171 calcd for $C_{49}H_{45}N_{12}O_{13}BF_6S$).

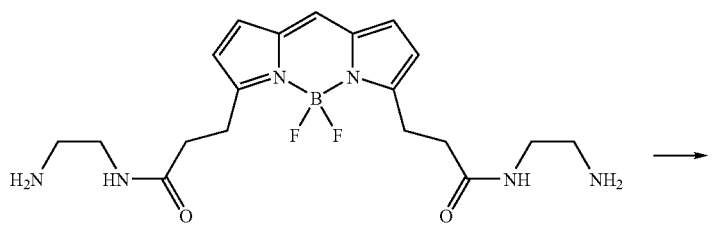

Compound 3376

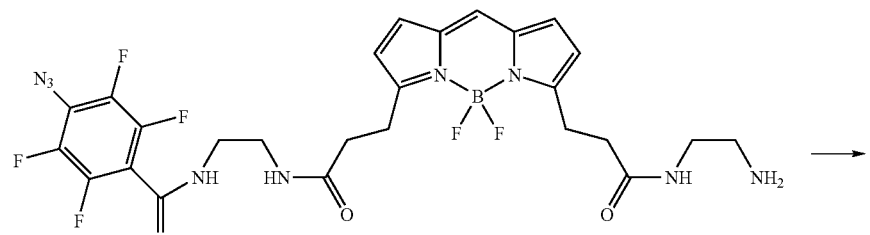

Compound 38

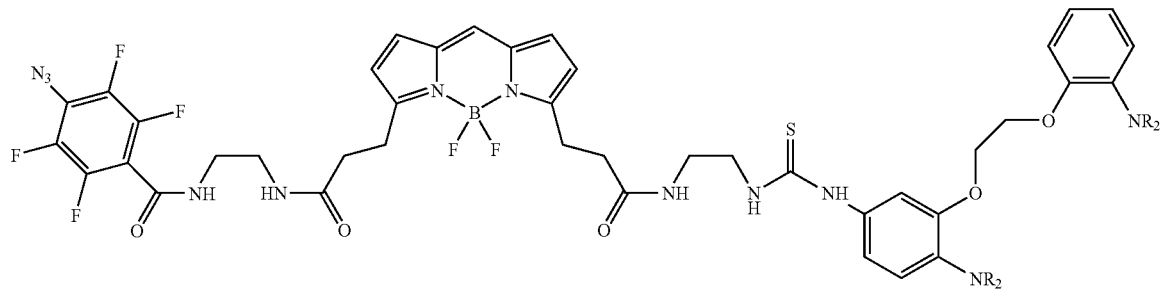

Compound 39 (R = CH₂CO₂Na)

Example 55

Preparation of Compound 42

To a solution of 4,4-difluoro-4-bora-3a,4a-diaza-s-indacene-3,5-dipropionic acid (Compound 40, Molecular Probes product 6103)) (0.10 g, 0.30 mmol) in 15 mL anhydrous acetonitrile under argon was added 1-(3-dimethylaminopropyl)-3-ethylcarbodiimide hydrochloride (EDC, 57 mg, 0.30 mmol). The resulting solution was stirred for 20 minutes, and 4-aminomethylbenzophenone (74 mg, 0.30 mmol) and DIEA (52 µL, 0.30 mmol) were added. The resulting orange mixture was stirred at rt for 5 h, then partitioned between ethyl acetate (50 mL) and 10% citric acid (40 mL). The organic layer was washed with brine (1×20 mL), dried over sodium sulfate, and concentrated to an amber residue. This residue was purified by flash chromatography on silica gel using methanol in chloroform as eluant to give compound 41 as 54 mg of an amber powder: m/z 529 (520 calcd for $C_{29}H_{26}N_3O_4BF_2$).

To a solution of compound 41 (53 mg, 0.10 mmol) in 7 mL anhydrous THF under argon was added oxalyl chloride (18 µL, 0.20 mmol) and 3 drops of DMF. The resulting mixture was stirred at rt for 20 minutes, then concentrated in vacuo. The residue was dissolved in 6 mL anhydrous dioxane, and the resulting solution was added dropwise to a solution of 5-amino-BAPTA free acid (49 mg, 0.10 mmol) in 6 mL aqueous sodium carbonate at pH 9-9.5. After stirring for 1.5 h, the reaction pH was lowered to 7.2 with aqueous citric acid, and concentrated in vacuo. The resulting residue was purified by column chromatography on Sephadex LH-20 using water as eluant. Pure product fractions were pooled and lyophilized to give compound 42 as 15 mg of an orange powder: m/z 999 (999 calcd for $C_{51}H_{45}N_6O_{13}BF_2$).

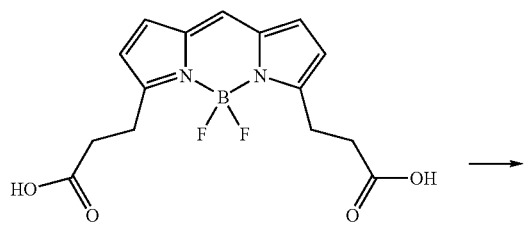

Compound 40

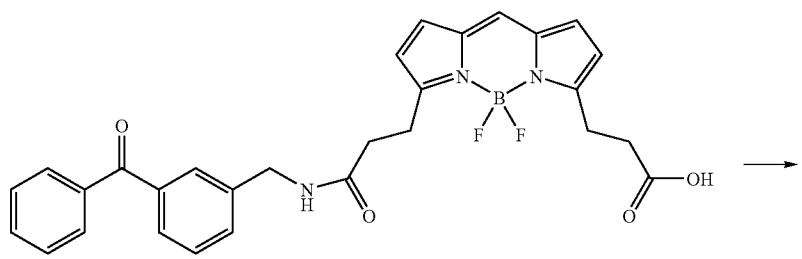

Compound 41

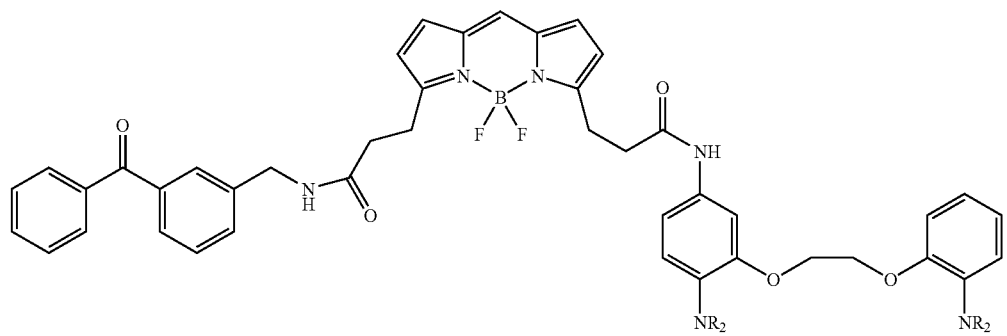

Compound 42 (R = CH₂CO₂Na)

Example 56

Preparation of Compound 44

The pH of a solution of the Compound 43 (prepared by condensing cadaverine with 4'-carboxy-fluo-4, tetramethyl ester followed by saponification) (12 mg, 0.012 mmol) in 3 mL water was raised to 10.3 with aqueous sodium carbonate. A solution of 4-benzoylbenzoic acid, succinimidyl ester (Molecular Probes product 1577, 10 mg, 0.030 mmol) in 2 mL dioxane was added. After stirring at rt overnight, the volatiles were removed in vacuo. The residue was purified by column chromatography on Sephadex LH-20 using water as eluant. Pure product fractions were pooled and lyophilized to give compound 44 as 14 mg of an orange powder: m/z 1074 (1074 calcd for $C_{56}H_{46}N_4O_{16}F_2$).

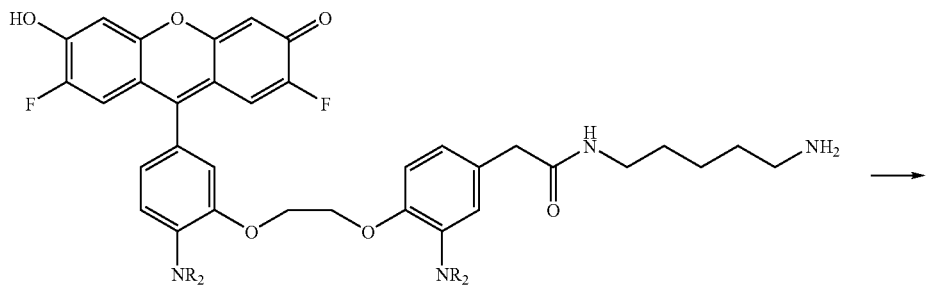

Compound 43 (R = CH₂CO₂K)

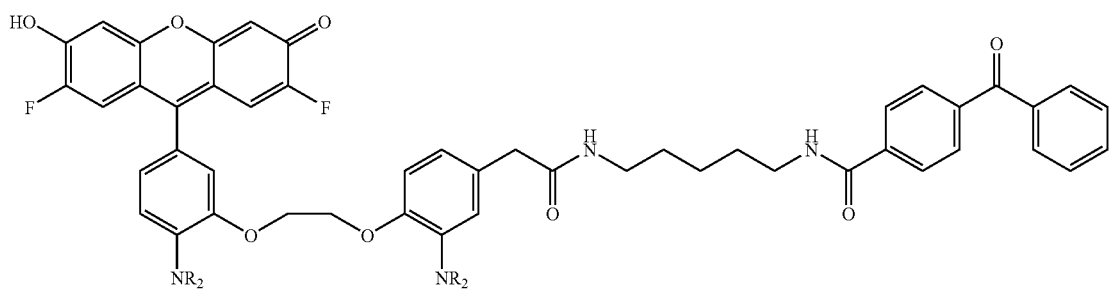

Compound 44 (R = CH₂CO₂Na)

The reagents employed in the preceding examples are commercially available or can be prepared using commercially available instrumentation, methods, or reagents known in the art or whose preparation is described in the examples. It is evident from the above description and results that the subject invention is greatly superior to presently available methods for labeling phosphorylated target molecules in a biological sample, as an unprecedented 500-1000 fold concentration range of phosphorylated target molecules can be detected. The subject invention overcomes the shortcomings of the currently used methods by allowing labeling as well as isolation of phosphorylated target molecules in a simple procedure that has increased sensitivity. It is appreciated that the methods of the present invention provide labeling of phosphorylated target molecules in solution or immobilized and that the phosphate-binding compounds can be either immobilized or in solution, allowing for identification of enzymes responsible for phosphorylation of these target molecules. The examples are not intended to provide an exhaustive description of the many different embodiments of the invention. Thus, although the foregoing invention has been described in extensive detail by way of illustration and example for purposes of clarity for understanding, those of ordinary skill in the art will readily realize that many changes and modifications can be made thereto without departing from the spirit or scope of the appended claims.

All publications and patent applications mentioned in this specification are herein incorporated by reference to the same extent as if each individual publication or patent application was specifically and individually indicated to be incorporated by reference.

What is claimed is:

1. A method for detecting a phosphorylated target molecule in a sample immobilized on a membrane, said method comprising the steps of:
   i) immobilizing said sample to a membrane;
   ii) contacting said membrane of step i) with a binding solution, wherein said binding solution comprises:
      a) phosphate-binding compound having formula (A)m(L)n(B) wherein A is a detectable chemical moiety, L is a linker, B is a metal-chelating moiety, m is an integer from 1 to 4 and n is an integer from 0 to 4;
      b) a salt comprising metal ions; and
      c) an acid;
   iii) incubating said membrane of step ii) and said binding solution for sufficient time to allow said phosphate-binding compound to associate with said phosphorylated target molecule; and,
   iv) detecting said phosphate-binding compound whereby said phosphorylated target molecule is detected,
      wherein step iii) further comprises contacting said membrane with a wash solution following contact with said binding solution, wherein said phosphorylated target molecule is selected from the group consisting of proteins, peptides, and nucleotides and wherein B of said formula (A)m(L)n(B) comprises a compound selected from the group consisting of Compound 1, 2, 3, 4, 5, 9, 10, 11 and 12 of Table 2.

2. The method according to claim 1, further comprising adding an additional detection reagent to said membrane.

3. The method according to claim 2, wherein said additional detection reagent is a staining solution specific for total proteins, a staining solution specific for glycoproteins or an antibody.

4. A method for detecting a phosphorylated target molecule in a sample immobilized on a gel, said method comprising the steps of:
   i) immobilizing said sample on a gel;
   ii) contacting said gel of step i) with a binding solution, wherein said binding solution comprises:
      a) a phosphate-binding compound having formula (A)m(L)n(B) wherein A is a detectable chemical moiety, L is a linker, B is a metal-chelating moiety, m is an integer from 1 to 4 and n is an integer from 0 to 4;
      b) a salt comprising metal ions; and,
      c) an acid;
   iii) incubating said gel of step ii) and said binding solution for sufficient time to allow said phosphate-binding compound to associate with said phosphorylated target molecule; and,
   iv) detecting said phosphate-binding compound whereby said phosphorylated target molecule is detected,
      wherein step iii) further comprises contacting said gel with a wash solution following contact with said binding solution, wherein said phosphorylated target molecules are selected from the group consisting of proteins, peptides, and nucleotides, wherein B of said formula (A)m(L)n(B) comprises a compound selected from the group consisting of Compound 1, 2, 3, 4, 5, 9, 10, 11 and 12 of Table 2.

5. A method for detecting a phosphorylated target molecule in a sample immobilized on a matrix, said method comprising the steps of:
   i) immobilizing said sample on an matrix;
   ii) contacting said matrix of step i) with a binding solution, wherein said binding solution comprises:
      a) a phosphate-binding compound having formula (A)m(L)n(B) wherein A is a detectable chemical moiety, L is a linker, B is a metal-chelating moiety, m is an integer from 1 to 4 and n is an integer from 0 to 4;
      b) a salt comprising metal ions; and,
      c) an acid;
   iii) incubating said matrix of step ii) and said binding solution for sufficient time to allow said phosphate-binding compound to associate with said phosphorylated target molecule; and,
   iv) detecting said phosphate-binding compound whereby said phosphorylated target molecule is detected,
      wherein said sample is selected from the group consisting of proteins, peptides, nucleotides, lipids, kinase substrates, phosphatase substrates, phosphate binding proteins and carbohydrates, and wherein said matrix is a polymeric gel, glass, polymeric membrane, plastic, polymeric microparticle, wherein B of said formula (A)m(L)n(B) comprises a compound selected from the group consisting of Compound 1, 2, 3, 4, 5, 9, 10, 11 and 12 of Table 2.

6. The method according to claim 5, wherein said step iii) further comprises contacting said matrix with a wash solution following contact with said binding solution.

7. The method according to claim 6, further comprising adding an additional detection reagent to said matrix.

8. The method according to claim 6, wherein said additional detection reagent is a staining solution specific for total proteins, a staining solution specific for glycoproteins or an antibody.

* * * * *